US008519222B2

(12) United States Patent
Mouradov et al.

(10) Patent No.: US 8,519,222 B2
(45) Date of Patent: Aug. 27, 2013

(54) MODIFICATION OF FLAVONOID BIOSYNTHESIS IN PLANTS

(75) Inventors: Aidyn Mouradov, Mill Park (AU); German Spangenberg, Bundoora (AU)

(73) Assignee: Agriculture Victoria Services Pty Ltd, Attwood (AU)

(*) Notice: Subject to any disclaimer, the term of this patent is extended or adjusted under 35 U.S.C. 154(b) by 0 days.

(21) Appl. No.: 13/090,850

(22) Filed: Apr. 20, 2011

(65) Prior Publication Data
US 2011/0277186 A1 Nov. 10, 2011

Related U.S. Application Data

(62) Division of application No. 11/995,791, filed as application No. PCT/AU2006/001020 on Jul. 19, 2006, now Pat. No. 7,960,608.

(30) Foreign Application Priority Data

Jul. 20, 2005 (AU) ................................ 2005903848

(51) Int. Cl.
*A01H 1/00* (2006.01)
*A01H 5/00* (2006.01)
*C12N 15/82* (2006.01)
*C07H 21/04* (2006.01)
*C07K 14/415* (2006.01)

(52) U.S. Cl.
USPC ........... 800/278; 800/279; 800/298; 435/410; 435/419; 435/320.1; 435/468; 536/23.6; 530/370

(58) Field of Classification Search
None
See application file for complete search history.

(56) References Cited

U.S. PATENT DOCUMENTS 7,622,638 B2 11/2009 Dixon et al.
2005/0182570 A1 8/2005 Geourjon et al.
2011/0093981 A9* 4/2011 La Rosa et al. ............... 800/278

FOREIGN PATENT DOCUMENTS
WO 9900501 A1 1/1999

OTHER PUBLICATIONS

Dubos et al, 2010, Trends in Plant Science, vol. 15, Issue 10, pp. 573-581.*
Blast No. 61, May 5, 2012.*
Blast No. 63, May 5, 2012.*
Yanhui et al, 2006, Plant Molecular Biology, vol. 60, pp. 107-124.*
Prouse and Campbell, Biochimica et Biophysica Acta, pp. 67-77, available online Oct. 28, 2011.*
Nesi et al, Sep. 2001, The Plant Cell, Vo. 13, pp. 2099-2114.*
Abrahams, et al., The Arabidopsis TDS4 gene encodes leucoanthocyanidin dioxygenase (LDOX) and is essential for proanthocyanidin synthesis and vacuole development, The Plant Journal, 2003, pp. 624-636, vol. 35, GenBank Accession No. AJ564262.1 and CAD91994.1.
Basic Local Alignment Search Tool Cited by US Examiner in Office Action dated Jun. 22, 2010, Query ID No. Icl 57698.
Basic Local Alignment Search Tool Cited by US Examiner in Office Action dated Jun. 22, 2010, Query ID No. Icl 71756.
Brewbaker, J.L., Cyanidin-red white clover, The Journal of Heredity, 1962, vol. 53, pp. 163-167.
Charrier, B. et al., Molecular characterization and expression of alfalfa (Medicago sativa L.) flavanone-3-hydroxylase and dihydroflavonol-4-reductase encoding genes, Plant Molecular Biology, 1995, vol. 29, pp. 773-786.
Gupta, S.B., Thin layer chromatographic separation of anthocyanins and anthocyanidins in Medicago (Papilionaceae), Journal of Chromatography, 1968, vol. 36, No. 1, pp. 115-119.
Heath, Robin et al. "Isolation and characterisation of three 4-coumarate:CoA-ligase homologue cDNAs from perennial ryegrass (*Lolium perenne*)." Journal of Plant Physiology, 2002, pp. 773-779, vol. 159.
Honda et al., "Anthocyanin biosynthetic genes are coordinately expressed during red coloration in apple skin.", Plant Physiology and Biochemistry (Paris), Nov. 2002, pp. 955-962, vol. 40, No. 11, XP002504748, ISSN: 0981-9428.
Kobayashi et al., "Myb-related genes of the Kyoho grape (*Vitis labruscana*) regulate anthocyanin biosynthesis", Planta, Oct. 1, 2002, pp. 924-933, 215, XP002966677, ISSN: 0032-0935, Springer Verlag, DE.
Noda et al., "Regulation of gene expression involved in flavonol and anthocyanin biosynthesis during petal development in lisianthus (*Eustoma grandiflorum*)", Physiologia Plantarum, Nov. 2004, pp. 305-313, vol. 122, No. 3, XP002504749, ISSN: 0031-9317.
SpTrEMBL, Accession No. P51092, Leucoanthocyanidin dioxygenase (Petunia x hybrida), 1993; Weiss, D. et al.
SpTrEMBL, Accession No. AAU12368, Anthocyanidin synthase (Fragaria x ananassa), Direct submission Oct. 31, 2004; Almeida, J.R.M. et al.
SpTrEMBL, Accession No. CAA53580, Leucoanthocyanidin dioxygenase (Vitis vinifera), 1994; Sparvoli, F. et al.
Taylor, N.L. et al., Anthocyanidin floral pigmentation in red clover, The Journal of Heredity, 1971, vol. 62, No. 1, pp. 13-15.
Xie, D-Y. et al., Molecular and biochemical analysis of two cDNA clones encoding dihydroflavonol-4-reductase from *Medicago truncatula*, Plant Physiology, Mar. 2004, vol. 134, pp. 979-994.
Xie, D-Y. et al., Anthocyanidin reductases from *Medicago truncatula* and *Arabidopsis thaliana*, Archives of Biochemistry and Biophysics, 2004, vol. 422, pp. 91-102.

(Continued)

*Primary Examiner* — Eileen B O Hara
(74) *Attorney, Agent, or Firm* — Larson & Anderson, LLC

(57) ABSTRACT

The present invention relates to nucleic acids encoding flavonoid biosynthetic enzymes, flavonoid-regulating transcription factors and a flavonoid-specific membrane transporter in plants, and the use thereof for the modification of flavonoid biosynthesis in plants. The present invention also relates to constructs and vectors including such nucleic acids, and related polypeptides. More particularly, the protein involved in flavonoid biosynthesis is selected from the group consisting of TRANSPARENT TESTA 12 (TT12), TRANSPARENT TESTA GLABRA 1 (TTG1), TRANSPARENT TESTA 2 (TT2), TRANSPARENT TESTA 8 (TT8), leucoanthocyanidin dioxygenase (LDOX), cinnamate-4-hydroxylase (C4H), 4-coumaroyl:CoA-ligase (4CL); and functionally active fragments and variants thereof.

18 Claims, 107 Drawing Sheets

(56) References Cited

OTHER PUBLICATIONS

Xie, D-Y. et al., Role of anthocyanidin reductase, encoded by BANYLUS in plant flavonoid biosynthesis, Science, Jan. 17, 2003, vol. 299, pp. 396-399.

Baudry et al., TT2, TT8, and TTG1 synergistically specify the expression of BANYULS and proanthocyanidin biosynthesis in *Arabidopsis thaliana*, The Plant Journal, 2004, pp. 366-380, vol. 36, Blackwell Scientific Publications, Oxford, GB.

Fan et al., Heterogeneous evolution of the Myc-like Anthocyanin regulatory gene and its phylogenetic utility in Cornus L. (Comaceae), Molecular Phylogenetics and Evolution, 2004, vol. 33, No. 3, pp. 580-594, vol. 33, r.

Nesi et al., The Arabidopsis TT2 Gene Encodes an R2R3 MYB Domain Protein That Acts as a Key Determinant for Proanthocyanidin Accumulation in Developing Seed, The Plant Cell, 2001, pp. 2099-2114, vol. 13, American Society of Plant Biologists, US.

Marles et al., New perspectives on proanthocyanidin biochemistry and molecular regulation, Phytochemistry, 2003, pp. 367-383, vol. 64, No. 2, Pergamon Press, GB.

\* cited by examiner

FIGURE 1

```
              *        20         *        40         *        60
WcCTa : AAAAACTAGTTGTGAGGCATATAACTATGAGCTCTATAGAAAACCAACCATTACTATTGG :  60

*        80         *       100         *       120
WcCTa : GGCTTGACTCACACTCACACATTGCAAATCTATCATCAGATACTATTGAAGAATTCTTGG : 120

*       140         *       160         *       180
WcCTa : AACATAGGCCTATTCAGTTAAGATGGTGGCTTAAACTTGTTGCTTGGGAGTCAAGGGTCC : 180

*       200         *       220         *       240
WcCTa : TATGGATACTTTCTGGTGCATCTATTATTGTCTACCTTTTCAATTACATGCTAAGCTTTG : 240

*       260         *       280         *       300
WcCTa : CTACCTTAATGTTTAGTGGACATTTAGGATCTCTTGAGCTTGCTGGTGCATCTATAGCTA : 300

*       320         *       340         *       360
WcCTa : ATGTTGGAATTCAAGGTCTTGCTTATGGAATTATGCTAGGAATGGCAAGTGCAGTGCAAA : 360

*       380         *       400         *       420
WcCTa : CTGTGTGTGGACAAGCTTATGGAGCCAAAAAATATGCAGTAATGTGCATCACATTGCAAA : 420

*       440         *       460         *       480
WcCTa : GAGCAGTAATCTTACATTTAGGAGCAGCAGTGATTCTCACATTTCTCTATTGGTTTTCTG : 480

*       500         *       520         *       540
WcCTa : GAGATTTTCTAAAAGTCATAGGACAGACAGAGAGCATAGCCGAGCAAGGTCAAGTTTTCG : 540

*       560         *       580         *       600
WcCTa : CTCGCGGTCTTATACCTCAACTCTATGCATTTGCATTGAGTTGTCCAATGCAAAGGTTTC : 600

*       620         *       640         *       660
WcCTa : TCCAAGCACAGAACATTGTTAATCCTCTTGCATATATGGCAGTTGGAGTGTTCATTCTTC : 660

*       680         *
WcCTa : ATGTGCTTGTTAGTTGGCTAGTTATCTATGTTTT : 694
```

FIGURE 2

```
                *         20        *         40        *         60
WcCTa : MSSIENQPLLLGLDSHSHIANLSSDTIEEFLEHRPIQLRWWLKLVAWESRVLWILSGASI :  60

*         80        *        100        *        120
WcCTa : IVYLFNYMLSFATLMFSGHLGSLELAGASIANVGIQGLAYGIMLGMASAVQTVCGQAYGA : 120

*        140        *        160        *        180
WcCTa : KKYAVMCITLQRAVILHLGAAVILTFLYWFSGDFLKVIGQTESIAEQGQVFARGLIPQLY : 180

*        200        *        220
WcCTa : AFALSCPMQRFLQAQNIVNPLAYMAVGVFILHVLVSWLVIYV : 222
```

FIGURE 3

```
             *        20         *        40         *        60
WcCTa1 : ------------------------------------------------TCCTATTGG :   9
WcCTa2 : ------------------ATATAACTATGAGCTCTATAGAAAACCAACCATTGCTATTGG :  42
WcCTa3 : --------TTGTGAGGCATATAACTATGAGCTCTATAGAAACC-ACCATTACTATTGG :  50
WcCTa4 : AAAAACTAGTTGTGAGGCATATAACTATGAGCTCTATAGAAAACCAACCATTACTATTGG :  60

*        80         *       100         *       120
WcCTa1 : GGCTTGACTCACACTCACACATTGCAAATCTATCATCAGATACTATTGAAGAATTCTTGG :  69
WcCTa2 : GGCTTGACTCACACTCACACATTGCAAATCTATCATCAGATACTATTGAAGAATTCTTGG : 102
WcCTa3 : GGCTTGACTCACACTCACACATTGCAAATCTATCATCAGATACTATTGAAGAATTCTTGG : 110
WcCTa4 : GGCTTGACTCACACTCACACATTGCAAATCTATCATCAGATACTATTGAAGAATTCTTGG : 120

*       140         *       160         *       180
WcCTa1 : AACATAGGCCTATTCAGTTAAGATGGTGGCTTAAACTTGTTGCTTGGGAGTCAAGGGTCC : 129
WcCTa2 : AACATAGGCCTATTCAGTTAAGATGGTGGCTTAAACTTGTTGCTTGGGAGTCAAGGGTCC : 162
WcCTa3 : AACATAGGCCTATTCAGTTAAGATGGTGGCTTAAACTTGTTGCTTGGGAGTCAAGGGTCC : 170
WcCTa4 : AACATAGGCCTATTCAGTTAAGATGGTGGCTTAAACTTGTTGCTTGGGAGTCAAGGGTCC : 180

*       200         *       220         *       240
WcCTa1 : TATGGATACTTTCTGGTGCATCTATTATTGTCTACCTTTTCAATTACATGCTAAGCTTTG : 189
WcCTa2 : TATGGATACTTTCTGGTGCATCTATTATTGTCTACCTTTTCAATTACATGCTAAGCTTTG : 222
WcCTa3 : TATGGATCCTTTCTGGTGCATCTATTATTGTCTACCTTTTCAATTACATGCTAAGCTTTG : 230
WcCTa4 : TATGGATCCTTTCTGGTGCATCTATTATTGTCTACCTTTTCAATTACATGCTAAGCTTTG : 240

*       260         *       280         *       300
WcCTa1 : CTACCTTAATGTTTAGTGGACATTTAGGATCTCTTGAGCTTGCTGGTGCATCTATAGCTA : 249
WcCTa2 : CTACCTTAATGTTTAGTGGACATTTAGGATCTCTTGAGCTTGCTGGTGCATCTATAGCTA : 282
WcCTa3 : CTACCTTAATGTTTAGTGGACATTTAGGATCTCTTGAGCTTGCTGGTGCATCTATAGCTA : 290
WcCTa4 : CTACCTTAATGTTTAGTGGACATTTAGGATCTCTAGAGCTTGCTGGTGCATCTAAAGCTA : 300

*       320         *       340         *       360
WcCTa1 : ATGTTGGAATTCAAGGTCTTGCTTATGGAATTATGCTAGGAATGGCAAGTGCAGTGCAAA : 309
WcCTa2 : ATGTTGGAATTCAAGGTCTTGCTTATGGAATTATGCTAGGAATGGCAAGTGCAGTGCAAA : 342
WcCTa3 : ATGTTGGAATTCAAGGTCTTGCTTATGGAATTATGCTAGGAATGGCAAGTGCAGTGCAAA : 350
WcCTa4 : ATGTTGGAATTCAAGGTCTTGCTTATGGAATTATGCTAGGAATGGCAAGTGCAGTGCAAA : 360

*       380         *       400         *       420
WcCTa1 : CTGTGTGTGGACAAGCTTATGGAGCCAAAAAATATGCAGTAATGTGCATCACATTGCAAA : 369
WcCTa2 : CTGTGTGTGGACAAGCTTATGGAGCCAAAAAATATGCAGTAATGTGCATCACATTGCAAA : 402
WcCTa3 : CTGTGTGTGGACAAGCTTATGGAGCCAAAAAATATGCAGTAATGTGCATCACATTGCAAA : 410
WcCTa4 : CTGTGTGTGGACAAGCTTATGGAGCCAAAAAATATGCAGTAATGTGCATCACATTGCAAA : 420

*       440         *       460         *       480
WcCTa1 : GAGCAGTAATCTTACATTTAGGAGCAGCAGTGATTCTCACATTTCTCTATTGGTTTTCTG : 429
WcCTa2 : GAGCAGTAATCTTACATTTAGGAGCAGCAGTGATTCTCACATTTCTCTATTGGTTTTCTG : 462
WcCTa3 : GAGCAGTAATCTTACATTTAGGAGCAGCAGTGATTCTCACATTTCTCTATTGGTTTTCTG : 470
WcCTa4 : GAGCAGTAATCTTACATTTAGGAGCAGCAGTGATTCTCACATTTCTCTATTGGTTTTCTG : 480
```

FIGURE 3 (cont.)

```
                    *         500         *         520         *         540
WcCTa1 : GAGATTTTCTAAAAGTCATAGGACAGACAGAGAGCATAGCCGAGCAAGGTCAAGTTTTCG : 489
WcCTa2 : GAGATTTTCTAAAAGTCATAGGACAGACAGAGAGCATAGCCGAGCAAGGTCAAGTTTTCG : 522
WcCTa3 : GAGATTTTCTAAAAGTAATAGGACAGACAGAGAGCATAGCCGAGCAAGGTCAAGTTTTCG : 530
WcCTa4 : GAGATTTTCTAAAAGTCATAGGACAGACAGAGAGCATAGCCGAGCAAGGCCAAGTTTTCG : 540

*         560         *         580         *         600
WcCTa1 : CTCGCGGTCTTATACCTCAACTC-------------------------------------  : 512
WcCTa2 : CTCGCGGTCTTATACCTCAACTCTATGCATT-----------------------------  : 553
WcCTa3 : CTCGCGGTCTTATACCTCAACTCTATGCATTTGCATTGAGTTGTCCAATGCAAAGGTTTC : 590
WcCTa4 : CTCGCGGTCTTATACCTCAACTCTATGCATTTGCATTGAGTTGTCCAATGCAAAGGTTTC : 600

*         620         *         640         *         660
WcCTa1 : ------------------------------------------------------------  :   -
WcCTa2 : ------------------------------------------------------------  :   -
WcCTa3 : TCC---------------------------------------------------------  : 593
WcCTa4 : TCCAAGCACAGAACATTGTTAATCCTCTTGCATATATGGCAGTTGGAGTGTTCATTCTTC : 660

*         680         *
WcCTa1 : ---------------------------------  :   -
WcCTa2 : ---------------------------------  :   -
WcCTa3 : ---------------------------------  :   -
WcCTa4 : ATGTGCTTGTTAGTTGGCTAGTTATCTATGTTTT  : 694
```

FIGURE 4

```
              *         20         *         40         *         60
WcCTb : TTCTCTCTTGTGTTTTTCATCAAACACCTTCTCTGCATAATTTTCTTCATCAAAAAATTC : 60

*         80         *        100         *        120
WcCTb : AAACACTCAAAAACTCAAACACCTTTCGTGCATCACCAAAAATGGAGAATTCAACTCAAG : 120

*        140         *        160         *        180
WcCTb : AATCACACATCCGATCCGAAAACTCTGTTACCTACGATTCCCCTTATCCTCTCTACGCCA : 180

*        200         *        220         *        240
WcCTb : TGGCTCTTTCTCCAAACACCAATTCACACCCACAACAACGCATCGCTGTTGGTAGTTTCA : 240

*        260         *        280         *        300
WcCTb : TCGAAGAATACACCAACCGCATCGATATCCTCAATTTCAACCCTGAGAATTTATCAATTA : 300

*        320         *        340         *        360
WcCTb : AACCTCAACCTTGACTTTCCTTGGATCATGCTTATCCACCTACCAAACTCATGTTCCATG : 360

*        380         *        400         *        420
WcCTb : CCGCAACAAATTCATCTGTGCAGAAAACCTACTACGACCTTGTAACTACTTACGGTGACT : 420

*        440         *        460         *        480
WcCTb : ATCTACGACTTTGGGAAGGTCACGAAAATTGGGGTGAGGCTCTTTCTCTTTTTAACAACA : 480

WcCTb : GC : 482
```

FIGURE 5

```
              *        20         *        40         *        60
WcCTb : MENSTQESHIRSENSVTYDSPYPLYAMALSPNTNSHPQQRIAVGSFIEEYTNRIDILNFN : 60

*
WcCTb : PENLSIKPQP : 70
```

FIGURE 6

```
             *        20         *        40         *        60
WcCTc  :  ATATACCAATAGTGCATTCTTCTTCCTATATTGTTATTACCATAAACATGGTAAGAGCTC  :   60

*        80         *       100         *       120
WcCTc  :  CTTGTTGTGAAAAAATGGGATTGAAGAGAGGTCCTTGGTCTCTTGAGGAAGATCAAATCC  :  120

*       140         *       160         *       180
WcCTc  :  TTACATCTTACATTCAAAAACATGGTAATGGCAACTGGCGTGCTCTCCCAAAGCTAGCAG  :  180

*       200         *       220         *       240
WcCTc  :  GCTTGTTAAGATGTGGAAAAAGCTGTAGACTTAGGTGGATTAACTATTTGAGACCTGATA  :  240

*       260         *       280         *       300
WcCTc  :  TCAAGAGAGGAAATTTCACAAATGAAGAAGAGGAAAATATCATTAAGCTACATGAAATGC  :  300

*       320         *       340         *       360
WcCTc  :  TTGGGAACAGGTGGTCGGCAATTGCAGCAAAATTACCAGGAAGAACGGACAATGAAATAA  :  360

*       380         *       400         *       420
WcCTc  :  AAAATGTGTGGCACACGCATTTGAAGAAGAAATTATTGAAAACAAATGAAACAAACTCAG  :  420

*       440         *       460         *       480
WcCTc  :  AAACTAAGAAAAGGGTGATCACAAAAACAAAAATCAAACGTTCTGATTCAAATTCAAGCA  :  480

*       500         *       520         *
WcCTc  :  CTATAACACAATCAGAATCAGTTTCTGCATGCACTACTAGTTCTAGTGATTTTTCAT     :  537
```

FIGURE 7

```
              *        20         *        40         *        60
WcCTc :  MVRAPCCEKMGLKRGPWSLEEDQILTSYIQKHGNGNWRALPKLAGLLRCGKSCRLRWINY :  60

*        80         *       100         *       120
WcCTc :  LRPDIKRGNFTNEEEENIIKLHEMLGNRWSAIAAKLPGRTDNEIKNVWHTHLKKKLLKTN : 120

*       140         *       160
WcCTc :  ETNSETKKRVITKTKIKRSDSNSSTITQSESVSACTTSSSDFS : 163
```

FIGURE 8

```
             *         20         *         40         *         60
WcCTc1 : ATATACCAATAGTGCATTCTTCTTCCTATATTGTTATTACCATAAACATGGTAAGAGCTCCT : 62
WcCTc2 : ATATACCAATAGTGCATTCTTCTTCCTATATTGTTATTACCATAAACATGGTAAGAGCTCCT : 62

*         80         *         100        *         120
WcCTc1 : TGTTGTGAAAAAATGGGATTGAAGAGAGGTCCTTGGTCTCTTGAGGAAGATCAAATCCTTAC : 124
WcCTc2 : TGTTGTGAAAAAATGGGATTGAAGAGAGGTCCTTGGTCTCTTGAGGAAGATCAAATCCTTAC : 124

*         140        *         160        *         180
WcCTc1 : ATCTTACATTCAAAAACATGGTAATGGCAACTGGCGTGCTCTCCCAAAGCTAGCAGGCTTGT : 186
WcCTc2 : ATCTTACATTCAAAAACATGGTAATGGCAACTGGCGTGCTCTCCCAAAGCTAGCAGGCTTGT : 186

*         200        *         220        *         240
WcCTc1 : TAAGATGTGGAAAAAGCTGTAGACTTAGGTGGATTAACTATTTGAGACCTGATATCAAGAGA : 248
WcCTc2 : TAAGATGTGGAAAAAGCTGTAGACTTAGGTGGATTAACTATTTGAGACCTGATATCAAGAGA : 248

*         260        *         280        *         300        *
WcCTc1 : GGAAATTTCACAAATGAAGAAGAGGAAAATATCATTAAGCTACATGAAATGCTTGGGAACAG : 310
WcCTc2 : GGAAATTTCACAAATGAAGAAGAGGAAAATATCATTAAGCTACATGAAATGCTTGGGAACAG : 310

320       *         340        *         360        *
WcCTc1 : GTGGTCGGCAATTGCAGCAAAATTACCAGGAAGAACGGACAATGAAATAAAAAATGTGTGGC : 372
WcCTc2 : GTGGTCGGCAATTGCAGCAAAATTACCAGGAAGAACGGACAATGAAATAAAAAATGTGTGGC : 372

380       *         400        *         420        *
WcCTc1 : ACACGCATTTGAAGAAGAAATTATTGAAAACAAATGAAACAAACTCAGAAACTAAGAAAAGG : 434
WcCTc2 : ACACGCATTTGAAGAAGAAATTATTGAAAACAAATGAAACAAACTCAGAAACTAAGAAAAGG : 434

440       *         460        *         480        *
WcCTc1 : GTGATCACAAAAACAAAAATCAAACGTTCTGATTCAAATTCAAGCACTATAACACAATCAGA : 496
WcCTc2 : GTGATCACAAAAACAAAAATCAAACGTTCTGATTCAAATTCAAGCACTATAACACAATCAGA : 496

500       *         520        *
WcCTc1 : ATCAGTTTCTGCATGCACTACTAGTTCTAGTGATT------ : 531
WcCTc2 : ATCAGTTTCTGCATGCACTACTAGTTCTAGTGATTTTTCAT : 537
```

FIGURE 9

```
              *        20         *        40         *        60
WcCTd : TTGGATTTTTATTGCAAAAATGGTGAGAGCTCCATGTTGTGAAAAAATGGGGTTGAAGAA :  60

*        80         *       100         *       120
WcCTd : AGGTCCATGGACTCAAGAAGAAGATAGAATTCTCATCAATCACATAAACACTTATGGCCA : 120

*       140         *       160         *       180
WcCTd : TTCTAATTGGCGTGCTCTTCCAAAACAAGCTGGGTTGTTAAGGTGTGGAAAAAGTTGTAG : 180

*       200         *       220         *       240
WcCTd : ATTGAGATGGGCAAATTATTTGAAACCAGATATCAAACGGGGTAATTTTACTAAAGAAGA : 240

*       260         *       280         *       300
WcCTd : AGAGGATGCAATAATCAATTTGCACCAAATGTTGGGAAATAGGTGGTCAACTATAGCAGC : 300

*       320         *       340         *       360
WcCTd : AAGATTACCAGGACGAACGGACAATGAAATAAAAAATGTATGGCACACCCACTTGAAGAA : 360

*       380         *       400         *       420
WcCTd : GAGGCTGCCACAAAACCAACAAGGCCACAACAATAGCCCAAAAAGAAATAAGAAACAAAC : 420

*       440         *       460         *       480
WcCTd : CAATTTGGACTTTGAAGCCTCCAAATCAGACCAAGATATCAAACAAGAACAAAATAATGT : 480

*       500         *       520         *       540
WcCTd : TGATGATATGCCACAATGTTCTAGTGACATGTCATACCATAATAATAGTAGCAATAGCAT : 540

WcCTd : TGCTACTAC : 549
```

FIGURE 10

```
              *        20         *        40         *        60
WcCTd : MVRAPCCEKMGLKKGPWTQEEDRILINHINTYGHSNWRALPKQAGLLRCGKSCRLRWANY :  60

*        80         *       100         *       120
WcCTd : LKPDIKRGNFTKEEEDAIINLHQMLGNRWSTIAARLPGRTDNEIKNVWHTHLKKRLPQNQ : 120

*       140         *       160         *
WcCTd : QGHNNSPKRNKKQTNLDFEASKSDQDIKQEQNNVDDMPQCSSDMSYHNNSSNSIAT     : 176
```

FIGURE 11

```
                  *        20         *        40         *        60
WcCTe : AAGCTGATGAAGGTATGAACCATGTTTTGTCAGAAAGAAGGAGAAGAGCAAAACTTAATG :  60

*        80         *       100         *       120
WcCTe : AAAGGTTTTTAACTCTTAGATCAATGGTCCCTTCAGATAGTAAGGATGACAAAGTTTCTA : 120

*       140         *       160         *       180
WcCTe : TACTAGATGATGCAATTGAATATCTTAGCAAGCTTGAGAAAAGGATAAAAGAATTAGAAG : 180

*       200         *       220         *       240
WcCTe : CTCAAAAAGAACCAATAGATATAGAGTCTAGAAGTAAAAAATCACATCATGATTTGTTGG : 240

*       260         *       280         *       300
WcCTe : AGAGGACTTGTGATGATTATTATAACAACAAAACTAACAATGGCAAGAAACCAATGATGA : 300

*       320         *       340         *       360
WcCTe : AGAAGAGGGAAATATGTGACATAGGTGAGACAAGGAGACAGATATTTTCTGATGCTTTAA : 360

*       380         *       400         *       420
WcCTe : AAGGAAGTTCTAATAGTGATGTTACTGTCAGTATGAGTGACAATGGAGTTGTGATTGAAA : 420

*       440         *       460         *       480
WcCTe : TGAAGTGTCCTTCTAGAGAAGGAAGGATATTGGAAATTATGGATGCAGTTAACAATCTCA : 480

*       500         *       520         *
WcCTe : ACATGGATTTTAATTCAGTTCAATCTACAGATTCCGATGGGAGGCTTCAT : 530
```

FIGURE 12

```
             *        20         *        40         *        60
WcCTe : ADEGMNHVLSERRRRAKLNERFLTLRSMVPSDSKDDKVSILDDAIEYLSKLEKRIKELEA :  60

*        80         *       100         *       120
WcCTe : QKEPIDIESRSKKSHHDLLERTCDDYYNNKTNNGKKPMMKKREICDIGETRRQIFSDALK : 120

*       140         *       160         *
WcCTe : GSSNSDVTVSMSDNGVVIEMKCPSREGRILEIMDAVNNLNMDFNSVQSTDSDGRLH    : 176
```

FIGURE 13

```
              *        20         *        40         *        60
WcCTf : TAGAAACTACAAAATAAAAAAAAATTATCATATAATAAAGATGGGAACCGTGGCACAAAG :  60

*        80         *       100         *       120
WcCTf : AGTTGAAAGCTTATCTTTGAGTGGAATATCATCAATTCCAAAAGAATATGTGAGACCAAA : 120

*       140         *       160         *       180
WcCTf : AGAAGAGTTAACAAACATAGGAAACATATTTGATGAAGTAAAAAAACAAGGGCCACAAGT : 180

*       200         *       220         *       240
WcCTf : TCCAACAATTGATATAAAAGAAATAAACTCTTCAGATGAAATTGTTAGAAGAAAATGTAG : 240

*       260         *       280         *       300
WcCTf : GGATAAGCTTAAGAAAGCTGCAGAGGAATGGGGTGTGATGAATTTGGTGAACCATGGTAT : 300

*       320         *       340         *       360
WcCTf : TTCTGATGAATTACTTAATCGACTTAAAAAAGTTGGTGAAACTTTTTTTGAGTTACCTGT : 360

*       380         *       400         *       420
WcCTf : TGAAGAAAAGAAAAATATGCTAATGATCAAAGTGATGGGAAGATTCAAGGGTATGGTAG : 420

*       440         *       460         *       480
WcCTf : TAAATTAGCTAATAATGCTAGTGGTCAACTTGAATGGGAAGATTATTTCTTTCATTGTAT : 480

*       500         *       520         *       540
WcCTf : TTTTCCTGAGGATAAGCGTGACTTATCTATATGGCCTAAGACTCCAGCTGATTATACTGA : 540

*       560         *       580         *       600
WcCTf : GGTCACAACAGAATATGCAAAAGAACTAAGAGGCCTAGCTAGCAAGATAATGGAAGTGTT : 600

*       620         *       640         *       660
WcCTf : ATCTCTTGAACTTGGCTTAGAAGGAGGAAGATTAGAGAAAGAAGTTGGTGGAATGGAAGA : 660

*
WcCTf : GCTTTTACTTCA : 672
```

FIGURE 14

```
             *        20         *        40         *        60
WcCTf : MGTVAQRVESLSLSGISSIPKEYVRPKEELTNIGNIFDEVKKQGPQVPTIDIKEINSSDE :  60

*        80         *       100         *       120
WcCTf : IVRRKCRDKLKKAAEEWGVMNLVNHGISDELLNRLKKVGETFFELPVEEKEKYANDQSDG : 120

*       140         *       160         *       180
WcCTf : KIQGYGSKLANNASGQLEWEDYFFHCIFPEDKRDLSIWPKTPADYTEVTTEYAKELRGLA : 180

*       200         *
WcCTf : SKIMEVLSLELGLEGGRLEKEVGGMEELLL : 210
```

FIGURE 15

```
                       *        20         *        40         *        60
05wc3FsC08 : ------------------------------------------------------------ :   -
07wc1CsC07 : ------------------------------------------------------------ :   -
05wc1WsH08 : ------------------------------------------------------------ :   -
05wc1HsC04 : ------------------------------------------------------------ :   -
07wc3GsD03 : ------------------------------------------------------------ :   -
05wc2FsB07 : --------------------------------------AGATGGGAACCGTGGCACAAAG :  22
05wc1EsE11 : -------------------------TATCATATAATAAAGATGGGAACCGTGGCACAAAG :  35
05wc3BsD09 : --------------------AAAATAAAATATAATAAAGATGGGAACCGTGGCACAAAG :  40
07wc2KsG09 : ------------------ATTAATTCAAATAATAAAATGGGAACCGTGGCACAAAG :  42
05wc3HsE05 : ----------------TAGAAAATATCATATACTAAAGATGGGAACCGTGGCACAAAG :  44
07wc1TsH04 : -------------ATAATAAGAAAATTATCATATACTAAAGATGGGAACCGTGGCACAAAG :  47
07wc3QsF06 : ------------AATAATAGAAAATAATATATAATAAAGATGGGAACCGTGGCACAAAG :  48
05wc3WsB07 : ------------ATAATACAAAATTTATCATATACTAAAGATGGGAACCGTGGCACAAAG :  48
05wc3LsD06 : TAGAAACTAAAATACATATTATATCCAATATAATATGGGAACCGTGGCACAAAG :  60
07wc1EsG08 : TAAATAATTCAAATAATAGAAAATTATCATATACTAAAGATGGGAACCGTGGCACAAAG :  60

*        80         *        100        *        120
05wc3FsC08 : -----------------------------------------------------------A :   1
07wc1CsC07 : ---------------------------------------------ATATGTGAGACCAAA :  15
05wc1WsH08 : -----------------------------------------AAGAATATGTGAGACCAAA :  19
05wc1HsC04 : ------------------------------------TTCAAAAGAATATGTGAGACCAAA :  24
07wc3GsD03 : ---TGAAAGCTTACCTTTGAGTGGAATATCATCAATTCCAAAAGAATATGTGAGACCAAA :  57
05wc2FsB07 : AGTTGAAAGCTTATCTTTGAGTGGAATATCATCAATTCCAAAAGAATATGTGAGACCAAA :  82
05wc1EsE11 : AGTTGAAAGCTTATCTTTGAGTGGAATATCATCAATTCCAAAAGAATATGTGAGACCAAA :  95
05wc3BsD09 : AGTTGAAAGCTTATCTTTGAGTGGAATATCATCAATTCCAAAAGAATATGTGAGACCAAA : 100
07wc2KsG09 : AGTTGAAAGCTTACCTTTGAGTGGAATATCATCAATTCCAAAAGAATATGTGAGACCAAA : 102
05wc3HsE05 : AGTTGAAAGCTTATCTTTGAGTGGAATATCATCAATTCCAAAAGAATATGTGAGACCAAA : 104
07wc1TsH04 : AGTTGAAAGCTTATCTTTGAGTGGAATATCATCAATTCCAAAAGAATATGTGAGACCAAA : 107
07wc3QsF06 : AGTTGAAAGCTTATCTTTGAGTGGAATATCATCAATTCCAAAAGAATATGTGAGACCAAA : 108
05wc3WsB07 : AGTTGAAAGCTTATCTTTGAGTGGAATATCATCAATTCCAAAAGAATATGTGAGACCAAA : 108
05wc3LsD06 : AGTTGAAAGCTTACCTTTGAGTGGAATATCATCAATTCCAAAAGAATATGTGAGACCAAA : 120
07wc1EsG08 : AGTTGAAAGCTTATCTTTGAGTGGAATATCATCAATTCCAAAAGAATATGTGAGACCAAA : 120

*        140        *        160        *        180
05wc3FsC08 : AGAAGAGTTAACAAACATAGGAAACATATTTGATGAAGTAAAAAAACAAGGGCCACAAGT :  61
07wc1CsC07 : AGAAGAGTTAACAAACATAGGAAACATATTTGATGAATAAAAAAACAAGGGCCACAAGT :  75
05wc1WsH08 : AGAAGAGTTAACAAACATAGGAAACATATTTGATGAAGTAAAAAAACAAGGGCCACAAGT :  79
05wc1HsC04 : AGAAGAGTTAACAAACATAGGAAACATATTTGATGAAGTAAAAAAACAAGGGCCACAAGT :  84
07wc3GsD03 : AGAAGAGTTAACAAACATAGGAAACATATTTGATGAAGAAAAAAAACAAGGGCCACAAGT : 117
05wc2FsB07 : AGAAGAGTTAACAAACATAGGAAACATATTTGATGAAGTAAAAAAACAAGGGCCACAAGT : 142
05wc1EsE11 : AGAAGAGTTAACAAACATAGGAAACATATTTGATGAAGTAAAAAAACAAGGGCCACAAGT : 155
05wc3BsD09 : AGAAGAGTTAACAAACATAGGAAACATATTTGATGAAGTAAAAAAACAAGGGCCACAAGT : 160
07wc2KsG09 : AGAAGAGTTAACAACATAGGAAACATATTTGATGAAGAAAAAAAACAAGGGCCACAAGT : 162
05wc3HsE05 : AGAAGAGTTAACAAACATAGGAAACATATTTGATGAAGAAAAAAAACAAGGGCCACAAGT : 164
07wc1TsH04 : AGAAGAGTTAACAAACATAGGAAACATATTTGATGAAGTAAAAAAACAAGGGCCACAAGT : 167
07wc3QsF06 : AGAAGAGTTAACAAACATAGGAAACATATTTGATGAAGTAAAAAAACAAGGGCCACAAGT : 168
05wc3WsB07 : AGAAGAGTTAACAAACATAGGAAACATATTTGATGAAGAAAAAAAACAAGGGCCACAAGT : 168
05wc3LsD06 : AGAAGAGTTAACAAACATAGGAAACATATTTGATGAAGAAAAAAAACAAGGGCCACAAGT : 180
07wc1EsG08 : AGAAGAGTTAACAAACATAGGAAACATATTTGATGAAGTAAAAAAACAAGGGCCACAAGT : 180
```

FIGURE 15 (cont.)

```
                    *         200         *         220         *         240
05wc3FsC08 : TCCAACAATTGATATAAAAGAAATAAACTCTTCAGATGAAATTGTTAGAAGAAAATGTAG : 121
07wc1CsC07 : TCCAACAATTGATATAAAAGAAATAAACTCTCCAGATGAAATTGTTAGAAGAAAATGTAT : 135
05wc1WsH08 : TCCAACAATTGATATAAAAGAAATAAACTCTTCAGATGAAATTGTTAGAAGAAAATGTAG : 139
05wc1HsC04 : TCCAACAATTGATATAAAAGAAATAAACTCTTCAGATGAAATTGTTAGAAGAAAATGTAG : 144
07wc3GsD03 : TCCAACAATTGATATAAAAGAAATAAACTCTCCAGATGAAATTGTTAGAAGAAATTGTAG : 177
05wc2FsB07 : TCCAACAATTGATATAAAAGAAATAAACTCTTCAGATGAAATTGTTAGAAGAAAATGTAG : 202
05wc1EsE11 : TCCAACAATTGATATAAAAGAAATAAACTCTTCAGATGAAATTGTTAGAAGAAAATGTAG : 215
05wc3BsD09 : TCCAACAATTGATATAAAAGAAATAAACTCTTCAGATGAAATTGTTAGAAGAAAATGTAG : 220
07wc2KsG09 : TCCAACAATTGATATAAAAGAAATAAACTCTTCAGATGAAATTGTTAGAAGAAAATGTAG : 222
05wc3HsE05 : TCCAACAATTGATATAAAAGAAATAAACTCTTCAGATGAAATTGTTAGAAGAAAATGTAG : 224
07wc1TsH04 : TCCAACAATTGATATAAAAGAAATAAACTCTTCAGATGAAATTGTTAGAAGAAAATGTAG : 227
07wc3QsF06 : TCCAACAATTGATATAAAAGAAATAAACTCTTCAGATGAAATTGTTAGAAGAAAATGTAG : 228
05wc3WsB07 : TCCAACAATTGATATAAAAGAAATAAACTCTTCAGATGAAATTGTTAGAA---------- : 218
05wc3LsD06 : TCCAACAATTGATATAAAAGAAATAAACTCTCCAGATGAAATTGTTAGAAGAAAATGTAG : 240
07wc1EsG08 : TCCAACAATTGATATAAAAGAAATAAACTCTTCAGATGAAATTGTTAGAAGAAAATGTAG : 240

*         260         *         280         *         300
05wc3FsC08 : GGATAAGCTTAAGAAAGCTGCAGAGGAATGGGGTGTGATGAATTTGGTGAACCATGGTAT : 181
07wc1CsC07 : GGATAAGCTTATTAAGCTGCAGAGGAATGGGGTGTGATGAATTTGGTGAACCATGGTAT : 195
05wc1WsH08 : GGATAAGCTTAAGAAAGCTGCAGAGGAATGGGGTGTGATGAATTTGGTGAACCATGGTAT : 199
05wc1HsC04 : GGATAAGCTTAAGAAAGCTGCAGAGGAATGGGGTGTGATGAATTTGGTGAACCATGGTAT : 204
07wc3GsD03 : GGATAAGCTTAAGAAAGCTGCAGAGGAATGGGGTGTGATGAATTTGGTGAACCATGGTAT : 237
05wc2FsB07 : GGATAAGCTTAAGAAAGCTGCAGAGGAATGGGGTGTGATGAATTTGGTGAACCATGGTAT : 262
05wc1EsE11 : GGATAAGCTTAAGAAAGCTGCAGAGGAATGGGGTGTGATGAATTTGGTGAACCATGGTAT : 275
05wc3BsD09 : GGATAAGCTTAAGAAAGCTGCAGAGGAATGGGGTGTGATGAATTTGGTGAACCATGGTAT : 280
07wc2KsG09 : GGATAAGCTTAAGAAAGCTGCAGAGGAATGGGGTGTGATGAATTTGGTGAACCATGGTAT : 282
05wc3HsE05 : GGATAAGCTTAAGAAAGCTGCAGAGGAATGGGGTGTGATGAATTTGGTGAACCATGGTAT : 284
07wc1TsH04 : GGATAAGCTTAAGAAAGCTGCAGAGGAATGGGGTGTGATGAATTTGGTGAACCATGGTAT : 287
07wc3QsF06 : GGATAAGCTTAAGAAAGCTGCAGAGGAATGGGGTGTGATGAATTTGGTGAACCATGGTAT : 288
05wc3WsB07 : ------------------------------------------------------------ :   -
05wc3LsD06 : GGATAAGCTTAAGAAAGCTGCAGAGGAATGGGGTGTGATGAATTTGGTGAACCATGGTAT : 300
07wc1EsG08 : GGATAAGCTTAAGAAAGCTGCAGAGGAATGGGGTGTGATGAATTTGGTGAACCATGGTAT : 300

*         320         *         340         *         360
05wc3FsC08 : TTCTGATGAATTACTTAATCGACTTAAAAAAGTTGGTGAAACTTTTTTTGAGTTACCTGT : 241
07wc1CsC07 : TTCTGATGAATTACTTAATCGACTTAAAAAAGTTGGTGAAACTTTTTTTGAGTTACCTGT : 255
05wc1WsH08 : TTCTGATGAATTACTTAATCGACTTAAAAAAGTTGGTGAAACTTTTTTTGAGTTACCTGT : 259
05wc1HsC04 : TTCTGATGAATTACTTAATCGACTTAAAAAAGTTGGTGAAACTTTTTTTGAGTTACCTGT : 264
07wc3GsD03 : TTCTGATGAATTACTTAATCGACTTAAAAAAGTTGGTGAAACTTTTTTTGAGTTACCTGT : 297
05wc2FsB07 : TTCTGATGAATTACTTAATCGACTTAAAAAAGTTGGTGAAACTTTTTTTGAGTTACCTGT : 322
05wc1EsE11 : TTCTGATGAATTACTTAATCGACTTAAAAAAGTTGGTGAAACTTTTTTTGAGTTACCTGT : 335
05wc3BsD09 : TTCTGATGAATTACTTAATCGACTTAAAAAAGTTGGTGAAACTTTTTTTGAGTTACCTGT : 340
07wc2KsG09 : TTCTGATGAATTACTTAATCGACTTAAAAAAGTTGGTGAAACTTTTTTTGAGTTACCTGT : 342
05wc3HsE05 : TTCTGATGAATTACTTAATCGACTTAAAAAAGTTGGTGAAACTTTTTTTGAGTTACCTGT : 344
07wc1TsH04 : TTCTGATGAATTACTTAATCGACTTAAAAAAGTTGGTGAAACTTTTTTTGAGTTACCTGT : 347
07wc3QsF06 : TTCTGATGAATTACTTAATCGACTTAAAAAAGTTGGTGAAACTTTTTTTGAGTTACCTGT : 348
05wc3WsB07 : ------------------------------------------------------------ :   -
05wc3LsD06 : TTCTGATGAATTACTTAATCGACTTAAAAAAGTTGGTGAAACTTTTTTTGAGTTACCTGT : 360
07wc1EsG08 : TTCTGATGAATTACTTAATCGACTTAAAAAAGTTGGTGAAACTTTTTTTGAGTTACCTGT : 360
```

FIGURE 15 (cont.)

```
                                *         380         *         400         *         420
05wc3FsC08 : TGAAGAAAAAGAAAAATATGCTAATGATCAAAGTGATGGGAAGATTCAAGGGTATGGTAG : 301
07wc1CsC07 : TGAAGAAAAAGAAAAATATGCTAATGATCAAAGTGTTGGGAAGATTCAAGGGTATGGTAG : 315
05wc1WsH08 : TGAAGAAAAAGAAAAATATGCTAATGATCAAAGTGATGGGAAGATTCAAGGGTATGGTAG : 319
05wc1HsC04 : TGAAGAAAAAGAAAAATATGCTAATGATCAAAGTGATGGGAAGATTCAAGGGTATGGTAG : 324
07wc3GsD03 : TGAAGAAAAAGAAAAATATGCTAATGATCAAAGTGTTGGGAAGATTCAAGGGTATGGTAG : 357
05wc2FsB07 : TGAAGAAAAAGAAAAATATGCTAATGATCAAAGTGATGGGAAGATTCAAGGGTATGGTAG : 382
05wc1EsE11 : TGAAGAAAAAGAAAAATATGCTAATGATCAAAGTGATGGCAAGATTCAA----------- : 384
05wc3BsD09 : TGAAGAAAAAGAAAAATATGCTAATGATCAAAGTGATGGGAAGATTCAAGGGTATGGTAG : 400
07wc2KsG09 : TGAAGAAAAAGAAAAATATGCTAATGATCAAAGTGTTGGGAAGATTCAAGGGTATGGTAG : 402
05wc3HsE05 : TGAAGAAAAAGAAAAATATGCTAATGATCAAAGTGTTGGGAAGATTCAAGGGTATGGTAG : 404
07wc1TsH04 : TGAAGAAAAAGAAAAATATGCTAATGATCAAAGTGATGGGAAGATTCAAGGGTATGGTAG : 407
07wc3QsF06 : TGAAGAAAAAGAAAAATATGCTAATGATCAAAGTGATGGGAAGATTCAAGGGTATGGTAG : 408
05wc3WsB07 : ------------------------------------------------------------ : -
05wc3LsD06 : TGAAGAAAAAGAAAAATATGCTAATGATCAAAGTGTTGGGAAGATTCAAGGGTATGGTAG : 420
07wc1EsG08 : TGAAGAAAAAGAAAAATATGCTAATGATCAAAGTGATGGGAAGATTCAAGGGTATGGTAG : 420

*         440         *         460         *         480
05wc3FsC08 : TAAATTAGCTAATAATGCTAGTGGTCAACTTGAATGGGAAGATTATTTCTTTCATTGTAT : 361
07wc1CsC07 : TAAATTAGCTAATAATGCTAGTGGTCAACTTGAATGGGAAGATTATTTCTTTCATTGTAT : 375
05wc1WsH08 : TAAATTAGCTAATAATGCTAGTGGTCAACTTGAATGGGAAGATTATTTCTTTCATTGTAT : 379
05wc1HsC04 : TAAATTAGCTAATAATGCTAGTGGTCAACTTGAATGGGAAGATTATTTCTTTCATTGTAT : 384
07wc3GsD03 : TAAATTAGCTAATAATGCTAGTGGTCAACTTGAATGGGAAGATTATTTCTTTCATTGTAT : 417
05wc2FsB07 : TAAATTAGCTAATAATGCTAGTGGTCAACTTGAATGGGAAGATTATTTCTTTCATTGTAT : 442
05wc1EsE11 : ------------------------------------------------------------ : -
05wc3BsD09 : TAAATTAGCTAATAATGCTAGTGGTCAACTTGAATGGGAAGATTATTTCTTTCATTGTAT : 460
07wc2KsG09 : TAAATTAGCTAATAATGCTAGTGGTCAACTTGAATGGGAAGATTATTTCTTTCATTGTAT : 462
05wc3HsE05 : TAAATTAGCTAATAATGCTAGTGGTCAACTTGAATGGGAAGATTATTTCTTTCATTGTAT : 464
07wc1TsH04 : TAAATTAGCTAATAATGCTAGTGGTCAACTTGAATGGGAAGATTATTTCTTTCATTGTAT : 467
07wc3QsF06 : TAAATTAGCTAATAATGCTAGTGGTCAACTTGAATGGGAAGATTATTTCTTTCATTGTAT : 468
05wc3WsB07 : ------------------------------------------------------------ : -
05wc3LsD06 : TAAATTAGCTAATAATGCTAGTGGTCAACTTGAATGGGAAGATTATTTCTTTCATTGTAT : 480
07wc1EsG08 : TAAATTAGCTAATAATGCTAGTGGTCAACTTGAATGGGAAGATTATTTCTTTCATTGTAT : 480

*         500         *         520         *         540
05wc3FsC08 : TTTTCCTGAGGATAAGCGTGACTTATCTATATGGCCTAAGACTCCAGCTGATTATACTGA : 421
07wc1CsC07 : TTTTCCTGAGGATAAGCGTGACTTATCCATATGGCCTAAGACTCCAGCTGATTATACTGA : 435
05wc1WsH08 : TTTTCCTGAGGATAAGCGTGACTTATCTATATGGCCTAAGACTCCAGCTGATTATACTGA : 439
05wc1HsC04 : TTTTCCTGAGGATAAGCGTGACTTATCTATATGGCCTAAGACTCCAGCTGATTATACTGA : 444
07wc3GsD03 : TTTTCCTGAGGATAAGCGTGACTTATCCATATGGCCTAAGACTCCAGCTGATTATACTGA : 477
05wc2FsB07 : TTTTCCTGAGGATAAGCGTGACTTATCTATATGGCCTAAGACTCCAGCTGATTATACTGA : 502
05wc1EsE11 : ------------------------------------------------------------ : -
05wc3BsD09 : TTTTCCTGAGGATAAGCGTGACTTATCTATATGGCCTAAGACTCCAGCTGATTATACTGA : 520
07wc2KsG09 : TTTTCCTGAGGATAAGCGTGACTTATCCATATGGCCTAAGACTCCTGCTGATTATACTGA : 522
05wc3HsE05 : TTTTCCTGAGGATAAGCGTGACTTATCCATATGGCCTAAGACTCCAGCTGATTATACTGA : 524
07wc1TsH04 : TTTTCCTGAGGATAAGCGTGACTTATCTATATGGCCTAAGACTCCAGCTGATTATACTGA : 527
07wc3QsF06 : TTTTCCTGAGGATAAGCGTGACTTATCTATATGGCCTAAGACTCCAGCTGATTATACTGA : 528
05wc3WsB07 : ------------------------------------------------------------ : -
05wc3LsD06 : TTTTCCTGAGGATAAGCGTGACTTATCCATATGGCCTAAGACTCCAGCTGATTATACTGA : 540
07wc1EsG08 : TTTTCCTGAGGATAAGCGTGACTTATCTATATGGCCTAAGACTCCAGCTGATTATACTGA : 540
```

FIGURE 15 (cont.)

```
                    *         560         *         580         *         600
05wc3FsC08 : GGTCACAACAGAATATGCAAAAGAACTAAGAGGCCTAGCTAGCAAGATAATGGAAGTGTT : 481
07wc1CsC07 : GGTCACAACAGAATATGCAAAAGAACTAAGAGGCCTAGCTAGCAAGATAATGGAAGTGTT : 495
05wc1WsH08 : GGTCACAACAGAATATGCAAAAGAACTAAGAGGCCTAGCTAGCAAGATAATGGAAGTGTT : 499
05wc1HsC04 : GGTCACAACAGAATATGCAAAAGAACTAAGAGGCCTAGCTAGCAAGATAATGGAAGTGTT : 504
07wc3GsD03 : GGTCACAACAGAATATGCAAAAGAACTAAGAGGCCTAGCTAGCAAGATAATGGAAGTGTT : 537
05wc2FsB07 : GGTCACAACAGAATATGCAAAAGAACTAAGAGGCCTAGCTAGCAAGATAATGGAAGTGTT : 562
05wc1EsE11 : ------------------------------------------------------------ : -
05wc3BsD09 : GGTCACAACAGAATATGCAAAAGAACTAAGAGGCCTAGCTAGCAAGATAATG-------- : 572
07wc2KsG09 : GGTCACAACAGAATATGC------------------------------------------ : 540
05wc3HsE05 : GGTCACAACAGAATATGCAAAAGAACTAAGAGGCCTAGCTAGC----------------- : 567
07wc1TsH04 : GGTCACAACAGAATATGCAAAAGAACTAAGAGGCCTAG---------------------- : 565
07wc3QsF06 : GGTCACAACAGAATATGCAAAAGAACTAAGAGGCCTAGCTAGCAAGATAATC-------- : 580
05wc3WsB07 : ------------------------------------------------------------ : -
05wc3LsD06 : GGTCACAACAGAATATGCAAAAGAACT--------------------------------- : 567
07wc1EsG08 : GGTCACAACAGAA----------------------------------------------- : 553

*         620         *         640         *         660
05wc3FsC08 : ATCTCTTGAACTTGGCTTAGAAGGAGGAAGATTAGAGAAAGAAGTTGGTGGAATGGAAGA : 541
07wc1CsC07 : ATCTCTTGAACTTGGCTTAGAA-------------------------------------- : 517
05wc1WsH08 : ATCTCTTGAACTTGGCTTAGAAGGAGGAA------------------------------- : 528
05wc1HsC04 : ATCTCTTGAACTTGGCTTAGAAGGAGGAAGATTAGAGAAAGAAGTTGGTGGAATGGAAGA : 564
07wc3GsD03 : ATCTCTTGAACTTGGCTTAGAAGGAGGAAGATTAGAGAA--------------------- : 576
05wc2FsB07 : ATCTCTTGAACT------------------------------------------------ : 574
05wc1EsE11 : ------------------------------------------------------------ : -
05wc3BsD09 : ------------------------------------------------------------ : -
07wc2KsG09 : ------------------------------------------------------------ : -
05wc3HsE05 : ------------------------------------------------------------ : -
07wc1TsH04 : ------------------------------------------------------------ : -
07wc3QsF06 : ------------------------------------------------------------ : -
05wc3WsB07 : ------------------------------------------------------------ : -
05wc3LsD06 : ------------------------------------------------------------ : -
07wc1EsG08 : ------------------------------------------------------------ : -

*
05wc3FsC08 : GC---------- : 543
07wc1CsC07 : ------------ : -
05wc1WsH08 : ------------ : -
05wc1HsC04 : GCTTTTACTTCA : 576
07wc3GsD03 : ------------ : -
05wc2FsB07 : ------------ : -
05wc1EsE11 : ------------ : -
05wc3BsD09 : ------------ : -
07wc2KsG09 : ------------ : -
05wc3HsE05 : ------------ : -
07wc1TsH04 : ------------ : -
07wc3QsF06 : ------------ : -
05wc3WsB07 : ------------ : -
05wc3LsD06 : ------------ : -
07wc1EsG08 : ------------ : -
```

FIGURE 16

```
              *        20         *        40         *        60
WcCTg : ATAGGTTGTTTACGAGGTGTAATGGTATTTACTCAAATATTTCAAATTTTTAACTAGTTA :  60

*        80         *       100         *       120
WcCTg : GATAGAATTCTCATCTTCCTCATTCTCCTTCAATTCAATTCAATTCAATGGCAGCATCAC : 120

*       140         *       160         *       180
WcCTg : AACAACAAGAAGAAATAATATTCAGGTCTAAACTTCCGGACATATACATCCCAAAACACC : 180

*       200         *       220         *       240
WcCTg : TTCCCCTCCATTCTTATTGCTTTGAAAATCTCTCCCAATTTGGTTCTCGTCCATGTCTCA : 240

*       260         *       280         *       300
WcCTg : TCAATGCACCCACCGGAAAAGTCTACACCTACCACGACGTCGAACTCACCTCTCGGAAAG : 300

*       320         *       340         *       360
WcCTg : TTGCCTCCGGTCTCAACAAATTGGGAGTCCAACAGGGTGATGTGATCATGATCCTCCTCC : 360

*       380         *       400         *       420
WcCTg : CCAATTCCCCTGAATTCGTCTTCTCCTTTCTGGCAGCTTCTTATCTCGGCGCCATAGCCA : 420

*       440         *       460         *       480
WcCTg : CAGCAGCCAATCCTTTCTTCATGGCCGCGGAGATTGGAAAGCAAGCAAAAGCCTCCAACG : 480

*       500         *       520         *       540
WcCTg : CCAAGTTGATCATAACACAGGCATGTTACTACGACAAAGTCAAGGAGTTGTTGTTGGACA : 540

*
WcCTg : ACCACAACAAG : 551
```

FIGURE 17

```
              *        20         *        40         *        60
WcCTg : MAASQQQEEIIFRSKLPDIYIPKHLPLHSYCFENLSQFGSRPCLINAPTGKVYTYHDVEL :  60

*        80         *       100         *       120
WcCTg : TSRKVASGLNKLGVQQGDVIMILLPNSPEFVFSFLAASYLGAIATAANPFFMAAEIGKQA : 120

*       140
WcCTg : KASNAKLIITQACYYDKVKELLLDNHNK : 148
```

FIGURE 18

```
                      *        20         *        40         *        60
14wc2KsH10 : ---------------------AGGTGTTTACTTGTCGTGTGGAATTCGTTCCATATTT  :  39
14wc1TsD04 : -----------GGTGTTTACTAGTCCTGTCCCAATTCGTTCCATTTTAACTAGTTA      :  48
05wc1CsE07 : ATAGGTTGTTTACTAGTTGTCTGGGAATTCGTTCCAATATTTCAACTAGTTACTTAGATA  :  60

*        80         *       100         *       120
14wc2KsH10 : GATAGTAGTTACATAGAATTCTCATCTTCCTCATTCTCCTTCAATTCAATGGCAGCATCAC  :  99
14wc1TsD04 : GATAGAATTCTCATCTTCCTCATTCTCCTTCAATTCAATTCAATGGCAGCATCAC       : 108
05wc1CsE07 : GATAGAATTCTCATCTTCCTCTTCTCCTTCAATTCAATTCAATTCAATGGCAGCATCAG   : 120

*       140         *       160         *       180
14wc2KsH10 : AACAACAAGAAGAAATAATATTCAGGTCTAAACTTCCGGACATATACATCCCAAAACACC  : 159
14wc1TsD04 : AACAACAAGAAGAAATAATATTCAGGTCTAAACTTCCAGACATATACATCCCAAAACACC  : 168
05wc1CsE07 : AACAACAAGAAGAAATAATATTCAGGTCTAAACTTCCGGACATATACATCCCAAAACACC  : 180

*       200         *       220         *       240
14wc2KsH10 : TTCCCCTCCATTCTTATTGCTTTGAAAATCTCTCCCAATTTGGTTCTCGTCCATGTCTCA  : 219
14wc1TsD04 : TTCCCCTCCATTCTTATTGCTTTGAAAATCTCTCCCAATTTGGTTCTCGTCCATGTCTCA  : 228
05wc1CsE07 : TTCCCCTCCATTCTTATTGCTTTGAAAATCTCTCCCAATTTGGTTCTCGTCCATGTCTCA  : 240

*       260         *       280         *       300
14wc2KsH10 : TCAATGCACCCACCGGAAAAGTCTACACCTACCACGACGTCGAACTCACCTCTCGGAAAG  : 279
14wc1TsD04 : TCAATGCACCCACCGGAAAAGTCTACACCTACCACGACGTCGAACTCACCTCTCGGAAAG  : 288
05wc1CsE07 : TCAATGCACCCACGGGAAAAGTCTACACCTACCACGACGTCGAACTCACCTCTCGGAAAG  : 300

*       320         *       340         *       360
14wc2KsH10 : TTGCCTCCGGTCTCAACAAATTGGGAGTCCAACAGGGTGATGTGATCATGATCCTCCTCC  : 339
14wc1TsD04 : TTGCCTCCGGTCTCAACAAATTGGGAGTCCAACAGGGTGATGTGATCATGATCCTCCTCC  : 348
05wc1CsE07 : TTGCCTCCGGTCTCAACAAATTGGGAGTCCAACAGGGTGATGTGATCATGATCCTCCTCC  : 360

*       380         *       400         *       420
14wc2KsH10 : CCAATTCCCCTGAATTCGTCTTCTCCTTTCTGGCAGCTTCTTATCTCGGCGCCATAGCCA  : 399
14wc1TsD04 : CCAATTCCCCTGAATTCGTCTTCTCCTTTCTGGCAGCTTCTTATCTCGGCGCCATAGCCA  : 408
05wc1CsE07 : CCAATTCCCCTGAATTCGTCTTCTCCTTTCTGGCAGCTTCTTATCTCGGCGCCATAGCCA  : 420

*       440         *       460         *       480
14wc2KsH10 : CAGCAGCCAATCCTTTCTTCATGGCCGCGGAGATTGGAAAGCAAGCAAAAGCCTCCAACG  : 459
14wc1TsD04 : CAGCAGCCAATCCTTTCTTCATGGCCGCGGAGATTGGAAAGCAAGCAAAAGCCTCCAACG  : 468
05wc1CsE07 : CAGCAGCCAATCCTTTCTTCATGGCCGCGGAGATTGGAAAGCAAGCAAAAGCCTCCAACG  : 480

*       500         *       520         *       540
14wc2KsH10 : CCAAGTTGATCATAACACAGGCATGTTACTACGACAAAGTCAAGGAGTTGTTGTTGGACA  : 519
14wc1TsD04 : CCAAGTTGATCATAACACAGGCATGTTACTACGACAAAGTCAAGGAGT-----------  : 516
05wc1CsE07 : CCAAGTTGATCATAACACAGGCATGTTACTACGACAAAGTCAGCAG-------------  : 526
```

FIGURE 18 (cont.)

```
14wc2KsH10 : ACCACAACAAG : 530
14wc1TsD04 : ----------- :  -
05wc1CsE07 : ----------- :  -
```

FIGURE 19

```
             *        20         *        40         *        60
WcCTh : AGTTAAGGATTTGGAAAATGTGAAGCTGGTTTTTGTGGACTCTTCACCGGAAGGAGAAAA :  60

*        80         *       100         *       120
WcCTh : NTATATGCATTTCCGTGAGCTGGCTCAAGCCGATGAGAATGAAATTGAAGAGGTAAAGAT : 120

*       140         *       160         *       180
WcCTh : AAACCCTGATGATGTGGTTGCTTTGCCATATTCTTCTGGAACAACAGGGCTACCTAAAGG : 180

*       200         *       220         *       240
WcCTh : TGTTATGCTAACACACAAAGGATTAGTGACAAGTGTAGCACAACAAGTTGGTGGTGAAAA : 240

*       260         *       280         *       300
WcCTh : TCCAAATCTATATTACCATTCTGAGGATGTCATACTATGTGTTCTTCCCATGTTTCATAT : 300

*       320         *       340         *       360
WcCTh : CTATTCACTCAACTCTGTTTTGCTCTGTGGTTTGAGAGCCAAAGCTTCCATTCTTTTAAT : 360

*       380         *       400         *       420
WcCTh : GCCAAAGTTTGATATTCATTCTTTTTTTAGCCTTGTTCATAAATACAGAGTCACTGTTGC : 420

*       440         *       460         *       480
WcCTh : TCCTGTTGTGCCACCAATTGTTTTGGCTATTTCTAAGTCACCTGAACTTGATAACTATGA : 480

*       500         *       520         *       540
WcCTh : TCTTTCATCCATAAGGATTTTGAAATCTGGTGGTGCTCCACTTGGTAAGGAACTTGAGGA : 540

*       560
WcCTh : CACTGTTAGGGCCAAATTTCCAAAAGCAA : 569
```

FIGURE 20

```
              *        20         *        40         *        60
WcCTh : VKDLENVKLVFVDSSPEGE?YMHFRELAQADENEIEEVKINPDDVVALPYSSGTTGLPKG :  59

*        80         *       100         *       120
WcCTh : VMLTHKGLVTSVAQQVGGENPNLYYHSEDVILCVLPMFHIYSLNSVLLCGLRAKASILLM : 119

*       140         *       160         *       180
WcCTh : PKFDIHSFFSLVHKYRVTVAPVVPPIVLAISKSPELDNYDLSSIRILKSGGAPLGKELED : 179

WcCTh : TVRAKFPKA : 188
```

FIGURE 21

```
               *        20         *        40         *        60
WcCTi : CGTTGCAAGAAATGCAGAGCTCAAAGTTCTTGACTCTGAAACTGGTCGCTCTCTTGGTTA :  60

*        80         *       100         *       120
WcCTi : TAATCAACCCGGTGAGATTTGCATCCGTGGCCAACAAATCATGAAAGGATATTTGAATGA : 120

*       140         *       160         *       180
WcCTi : TGAAAATGCAACAAAAACTACTATTGATGAAGAGGGTTGGCTTCATACTGGTGATGTTGG : 180

*       200         *       220         *       240
WcCTi : CTATATAGATGACAATGATGAGATTTTCATTGTTGACAGGGTGAAGGAACTCATTAAATT : 240

*       260         *       280         *       300
WcCTi : CAAAGGCTTCCAAGTGCCCCCTGCTGAACTTGAAGGCCTTCTAGTAAGCCATCCATCTAT : 300

*       320         *       340         *       360
WcCTi : TGCAGATGCAGCTGTTGTCCCGCAAAAGGATGTGGCTGCTGGTGAAGTTCCTGTTGCCTT : 360

*       380         *       400         *       420
WcCTi : TGTGGTAAGATCAAATGGACTTGATCTAACTGAAGAGGCTGTAAAGGAGTTTATAGCTAA : 420

*       440         *       460         *       480
WcCTi : ACAGGTTGTATTTTATAAGAGACTGCACAAAGTGTATTTCATTCATGCAATTCCCAAGTC : 480

*       500         *       520         *       540
WcCTi : TCCATCAGGAAAGATACTGAGGAAAGATCTCAGAGCAAAGTTAGAAAGTACCACCCAAAA : 540

*       560         *       580         *       600
WcCTi : GCCTTGAGATGCTAGAAGCTTTTTCACTTATTTTTTTTGGTCAAAATCTTCCTCATTTGT : 600

*       620         *       640
WcCTi : TCATTTGTATCCTAATATATTCTAGCTACTAGGTCTCATGC : 641
```

FIGURE 22

```
             *         20         *         40         *         60
WcCTi : VARNAELKVLDSETGRSLGYNQPGEICIRGQQIMKGYLNDENATKTTIDEEGWLHTGDVG :  60

*         80         *        100         *        120
WcCTi : YIDDNDEIFIVDRVKELIKFKGFQVPPAELEGLLVSHPSIADAAVVPQKDVAAGEVPVAF : 120

*        140         *        160         *        180
WcCTi : VVRSNGLDLTEEAVKEFIAKQVVFYKRLHKVYFIHAIPKSPSGKILRKDLRAKLESTTQK : 180

WcCTi : P : 181
```

FIGURE 23

```
              *        20         *        40         *        60
WcCTj : ACTTAAATTAATTTAAATTCCCCTTATTCCTAATATTCTCCTAACATTACCAAAATGTCA :  60

*        80         *       100         *       120
WcCTj : CCATTTCCTCCACAGCAAGAAGAATTCATATTCCGTTCCAAACTCCCAGACATTGAAATT : 120

*       140         *       160         *       180
WcCTj : CCAACAAATCTTCCATTACACTCTTATTGTTTCCAAAACCTCTCTCAATTCCATAACCGT : 180

*       200         *       220         *       240
WcCTj : CCATGTCTCATCAACGGCGACTCCGGCGAAATCTTAACATACTCCGACGTCCACCTCACC : 240

*       260         *       280         *       300
WcCTj : GTCCGCAAAATCGCCGCCGGTTTAAACACTCTCGGAATTAATCAAGGTGATGTCATCATG : 300

*       320         *       340         *       360
WcCTj : CTCGTCCTCCGTAACTCTCCTCAATTCGCACTCACTTTCCTCGGTGCCTCCTTCCGTGGC : 360

*       380         *       400         *       420
WcCTj : GCCGTCATCACCACCGCAAATCCTTTCTACACCTCATCGGAACTCGCGAAACAAGCCACA : 420

*       440         *       460         *       480
WcCTj : GCAACAAAAACTAAACTCATCGTAACTCAATCCGCATATCTAAGTAAAATCAACGATTTC : 480

*       500         *       520
WcCTj : GCTAAATTCAACAACATCAAAATCGTCTGCATAGATTCATCATC : 524
```

FIGURE 24

```
                *         20         *         40         *         60
WcCTj : MSPFPPQQEEFIFRSKLPDIEIPTNLPLHSYCFQNLSQFHNRPCLINGDSGEILTYSDVH :  60

*         80         *        100         *        120
WcCTj : LTVRKIAAGLNTLGINQGDVIMLVLRNSPQFALTFLGASFRGAVITTANPFYTSSELAKQ : 120

*        140         *
WcCTj : ATATKTKLIVTQSAYLSKINDFAKFNNIKIVCIDSS : 156
```

FIGURE 25

```
                *        20         *        40         *        60
WcCTk : TAACAACAATGGATCTACTCCTTCTTGAAAAGACTCTTTTATCCCTCTTCATCGCCGCTA :  60

*        80         *       100         *       120
WcCTk : TAATCGCAATCACAATCTCAAAACTCCGTGGAAAACGCTTCAAACTTCCACCAGGTCCAT : 120

*       140         *       160         *       180
WcCTk : TTCCAGTTCCAATTTTTGGTAATTGGCTTCAAGTTGGCGATGATCTCAACCACCGTAATT : 180

*       200         *       220         *       240
WcCTk : TAACTGATTTAGCCAAACGCTTCGGCGAAATCCTGCTTCTCCGGATGGGACAACGAAACC : 240

*       260         *       280         *       300
WcCTk : TGGTCGTTGTCTCATCACCGGAGTTAGCAAAAGAAGTCCTTCACACACAAGGTGTCGAAT : 300

*       320         *       340         *       360
WcCTk : TCGGTTCCAGAACACGGAACGTCGTATTCGACATCTTTACCGGTAAAGGACAGGACATGG : 360

*       380         *       400         *       420
WcCTk : TTTTCACCGTGTACGGTGAACATTGGCGTAAAATGAGGAGAATTATGACAGTACCATTTT : 420

*       440         *       460         *       480
WcCTk : TCACAAACAAAGTTGTTCAACAATATAGATTTGGTTGGGAATCTGAAGCTGAAAGTGTTG : 480

*       500         *       520         *       540
WcCTk : TTAATGATGTTAAGAAAAATAATGAAGCTAGTGTTGGTGGAATTGTGATTAGAAGAAGAT : 540

*       560         *       580         *
WcCTk : TACAATTGATGATGTATAATATTATGTATAGGATTATGTTTGATAGAAGATTTGAAAGT  : 599
```

FIGURE 26

```
                *         20         *         40         *         60
WcCTk : MDLLLLEKTLLSLFIAAIIAITISKLRGKRFKLPPGPFPVPIFGNWLQVGDDLNHRNLTD :  60

*         80         *        100         *        120
WcCTk : LAKRFGEILLLRMGQRNLVVVSSPELAKEVLHTQGVEFGSRTRNVVFDIFTGKGQDMVFT : 120

*        140         *        160         *        180
WcCTk : VYGEHWRKMRRIMTVPFFTNKVVQQYRFGWESEAESVVNDVKKNNEASVGGIVIRRRLQL : 180

*
WcCTk : MMYNIMYRIMFDRRFES : 197
```

FIGURE 27

```
                          *         20         *         40         *         60
05wc1LsD04 : ---------TGGATCTACTCCTTCTTGAAAAGACTCTTTTATCCCTCTTCATCGCCGCTA :  51
05wc2KsE12 : ---------TGGACCTACTCCTTCTTGAAAAGACTCTTTTATCCCTCTTCATCGCAGCAA :  51
05wc3CsG03 : ---------TGGATCTACTCCTTCTTGAAAAGACTCTTTTATCCCTCTTCATCGCCGCTA :  51
07wc3AsC10 : --------ATGGATCTACTCCTTCTTGAAAAGACTCTTTTATCCCTCTTCATCGCAGCAA :  52
14wc1CsB09 : TAACAACAATGGATCTACTCCTTCTTGAAAAGACTCTTTTATCCCTCTTCATCGCCGCTA :  60

*         80         *        100         *        120
05wc1LsD04 : TAATCGCAATCACAATCTCAAAACTCCGTGGAAAACGCTTCAAACTTCCACCAGGTCCAT : 111
05wc2KsE12 : TAATCGCAATCACAATCTCAAAACTCCGTGGAAAACGGTTCAAACTTCCACCAGGTCCAT : 111
05wc3CsG03 : TAATCGCAATCACAATCTCAAAACTCCGTGGAAAACGCTTCAAACTTCCACCAGGTCCAT : 111
07wc3AsC10 : TAATCGCAATCACAATCTCAAAACTCCGTGGAAAACGGTTCAAACTTCCACCAGGTCCAT : 112
14wc1CsB09 : TAATCGCAATCACAATCTCAAAACTCCGTGGAAAACGCTTCAAACTTCCACCAGGTCCAT : 120

*        140         *        160         *        180
05wc1LsD04 : TTCCAGTTCCAATTTTTGGTAATTGGCTTCAAGTTGGCGATGATCTCAACCACCGTAATT : 171
05wc2KsE12 : TTCCAGTTCCAATTTTTGGTAATTGGCTTCAAGTGGGCGATGATCTCAACCACCGTAACT : 171
05wc3CsG03 : TTCCAGTTCCAATTTTTGGTAATTGGCTTCAAGTTGGCGATGATCTCAACCACCGTAATT : 171
07wc3AsC10 : TTCCAGTTCCAATTTTTGGTAATTGGCTTCAAGTGGGCGATGATCTCAACCACCGTAACT : 172
14wc1CsB09 : TTCCAGTTCCAATTTTTGGTAATTGGCTTCAAGTTGGCGATGATCTCAACCACCGTAATT : 180

*        200         *        220         *        240
05wc1LsD04 : TAACTGATTTAGCCAAACGCTTCGGCGAAATCCTGCTTCTCCGGATGGGACAACGAAACC : 231
05wc2KsE12 : TAACCGATTTAGCCAAACGCTTCGGCGAAATCCTGCTACTCCGGATGGGACAACGAAACC : 231
05wc3CsG03 : TAACTGATTTAGCCAAACGCTTCGGCGAAATCCTGCTTCTCCGGATGGGACAACGAAACC : 231
07wc3AsC10 : TAACCGATTTAGCCAAACGCTTCGGCGAAATCCTGCTACTCCGGATGGGACAACGAAACC : 232
14wc1CsB09 : TAACTGATTTAGCCAAACGCTTCGGCGAAATCCTGCTTCTCCGGATGGGACAACGAAACC : 240

*        260         *        280         *        300
05wc1LsD04 : TGGTCGTTGTCTCATCACCGGAGTTAGCAAAAGAAGTCCTTCACACACAAGGTGTCGAAT : 291
05wc2KsE12 : TGGTCGTTGTCTCATCACCGGAGTTAGCAAAAGAAGTCCTTCACACACAAGGTGTCGAAT : 291
05wc3CsG03 : TGGTCGTTGTCTCATCACCGGAGTTAGCAAAAGAAGTCCTTCACACACAAGGTGTCGAAT : 291
07wc3AsC10 : TGGTCGTTGTCTCATCACCGGAGTTAGCAAAAGAAGTCCTTCACACACAAGGTGTCGAAT : 292
14wc1CsB09 : TGGTCGTTGTCTCATCACCGGAGTTAGCAAAAGAAGTCCTTCACACACAAGGTGTCGAAT : 300

*        320         *        340         *        360
05wc1LsD04 : TCGGTTCCAGAACACGGAACGTCGTATTCGACATCTTTACCGGTAAAGGACAGGACATGG : 351
05wc2KsE12 : TCGGTTCCAGAACACGGAACGTCGTATTCGACATCTTTACGGGTAAAGGACAGGACATGG : 351
05wc3CsG03 : TCGGTTCCAGAACACGGAACGTCGTATTCGACATCTTTACCGGTAAAGGACAGGACATGG : 351
07wc3AsC10 : TCGGTTCCAGAACACGGAACGTCGTATTGGACATCTTTACGGGTAAAGGACAGGACATGG : 352
14wc1CsB09 : TCGGTTCCAGAACACGGAACGTCGTATTCGACATCTTTACCGGTAAAGGACAGGACATGG : 360

*        380         *        400         *        420
05wc1LsD04 : TTTTCACCGTGTACGGTGAACATTGGCGTAAAATGAGGAGAATTATGACAGTACCATTTT : 411
05wc2KsE12 : TTTTCACCGTGTACGGTGAACATTGGCGTAAAATGAGGAGAATTATGACAGTACCATTTT : 411
05wc3CsG03 : TTTTCACCGTGTACGGTGAACATTGGCGTAAAATGAGGAGAATTATGACAGTACCATTTT : 411
07wc3AsC10 : TTTTCACCGTGTACGGTGAACATTGGCGTAAAATGAGGAGAATTATGACAGTACCATTTT : 412
14wc1CsB09 : TTTTCACCGTGTACGGTGAACATTGGCGTAAAATGAGGAGAATTATGACAGTACCATTTT : 420
```

FIGURE 27 (cont.)

```
                         *         440         *         460         *         480
05wc1LsD04 : TCACAAACAAAGTTGTTCAACAATATAGATTTGGTTGGGAATCTGAAGCTGAAAGTGTTG : 471
05wc2KsE12 : TCACAAACAAAGTTGTTCAACAATATAGATTTGGTTGGGAATCTGAAGCAGAAAGTGTTG : 471
05wc3CsG03 : TCACAAACAAAGTTGTTCAACAATATAGATTTGGTTGGGAATCTGAAGCTGAAAGTGTTG : 471
07wc3AsC10 : TCACAAACAAAGTTGTTCAACAATATAGATTTGGTTGGGAATCTGAAGCAGAAAGTGTTG : 472
14wc1CsB09 : TCACAAACAAAGTTGTTCAACAATATAGATTTGGTTGGGAATCTGAAGCTGAAAGTGTTG : 480

*         500         *         520         *         540
05wc1LsD04 : TTAATGATGTTAAGAAAAATAATGAAGCTAGTGTTGGTGGAATTGTGATTAGAAGAAGAT : 531
05wc2KsE12 : TTAATGATGCTAACAAAAATAATGAAGCTAGT---------------------------- : 503
05wc3CsG03 : TTAATGATGTTAAGAAAAATAATGAAGCTAGTGTTGGTGGAATTGTGATTAGAAGAAGAT : 531
07wc3AsC10 : TTAATGATGTTAAGAAAAATAATGAAGCTAGTGTTGGTGGAATTGTGATTAGAAGAAGAT : 532
14wc1CsB09 : TTAATGATGTTAAGAAAAATAATGAAGCTAGTGTTGGTGGAATTGTGATTAGAAGAAGAT : 540

*         560         *         580         *
05wc1LsD04 : TACAATTGATGATGTATAATATTATGTATAGGATTATGTTTGATA--------------- : 576
05wc2KsE12 : ------------------------------------------------------------ :  -
05wc3CsG03 : TACAATTGATGATGTATAATATTATGTATAGGATTATGTTTGATAGAAGATTTGAAAGT  : 590
07wc3AsC10 : TACAATTGATGATGTATAATATTATGTATAGGATTAT----------------------- : 569
14wc1CsB09 : TACAAT------------------------------------------------------ : 546
```

FIGURE 28

```
             *        20         *        40         *        60
WcCT1 : AAGTTTTGAGTATAATTATGGTGATTTTATTCCTATTTTGAGACCTTTTTTGAAAGGTTA :  60

*        80         *       100         *       120
WcCT1 : TTTGAAGGTTTGTAAAGAGGTTAAAGATCGTAGGTTGCAGCTTTTCAAAGACTATTTCGT : 120

*       140         *       160         *       180
WcCT1 : TGATGAGAGAAAGAAACTTGAAAGCACCAAGAGCACCACTAGCAATGATGGACTTAAATG : 180

*       200         *       220         *       240
WcCT1 : TGCAATTGATCACATTTTGGATGCTCAAAAGAAGGGAGAGATCAATGATGACAACGTTCT : 240

*       260         *       280         *       300
WcCT1 : TTACATTGTTGAGAACATCAAGGTTGCTGCAATTGAAACAACACTATGGTCAATTGAATG : 300

*       320         *       340         *       360
WcCT1 : GGGAATTGCTGAGCTAGTGAACCACCAAGAGATCCAAAACAAAGTAAGGGAAGAGATGGA : 360

*       380         *       400         *       420
WcCT1 : CAGAGTTCTAGGACCAGGACACCAAGTAACCGAGCCGGATCTTGAGAAGCTACCTTACCT : 420

*       440
WcCT1 : ACAAGCCGTGATCAAAGAGACAC : 443
```

FIGURE 29

```
                *          20           *          40           *          60
WcCT1 : SFEYNYGDFIPILRPFLKGYLKVCKEVKDRRLQLFKDYFVDERKKLESTKSTTSNDGLKC :  60

*          80           *         100           *         120
WcCT1 : AIDHILDAQKKGEINDDNVLYIVENIKVAAIETTLWSIEWGIAELVNHQEIQNKVREEMD : 120

*         140
WcCT1 : RVLGPGHQVTEPDLEKLPYLQAVIKET : 147
```

FIGURE 30

```
            *        20         *        40         *        60
WcCTm : AGCTTGCCGGTTATGACATCCCGGCCGAGAGCAAGATATTGGTCAACGCGTGGTGGCTTG :  60

*        80         *       100         *       120
WcCTm : CAAATAACCCGGCTCTATGGAAAAAGCCGGAGGAATTTAGGCCTGAGAGGTTCTTGGAGG : 120

*       140         *       160         *       180
WcCTm : AAGAGGCGCATGTTGAGGCTAATGGAAATGACTTTAGGTACCTTCCTTTCGGTGTCGGTA : 180

*       200         *       220         *       240
WcCTm : GAAGGAGTTGACCTGCAATTATTCTTGCTTTACCTATCCTTGGTATTACTATCGGGCGTC : 240

*       260         *       280         *
WcCTm : TTGTTCAAAATTTCCAGCTTTTGCCTGCACCCGGACAATCTAAGATTGATACTTC : 295
```

FIGURE 31

```
                 *        20         *        40         *        60
WcCTm : SLPVMTSRPRARYWSTRGGLQITRLYGKSRRNLGLRGSWRKRRMLRLMEMTLGTFLSVSV :  60

*        80         *
WcCTm : EGVDLQLFLLYLSLVLLSGVLFKISSFCLHPDNLRLIL :  98
```

FIGURE 33

```
                *         20         *         40         *         60
  : AAAAACTAGTTGTGAGGCATATAACTATGAGCTCTATAGAAAACCAACCATTACTATTGG  :   60

*         80         *        100         *        120
  : GGCTTGACTCACACTCACACATTGCAAATCTATCATCAGATACTATTGAAGAATTCTTGG  :  120

*        140         *        160         *        180
  : AACATAGGCCTATTCAGTTAAGATGGTGGCTTAAACTTGTTGCTTGGGAGTCAAGGGTCC  :  180

*        200         *        220         *        240
  : TATGGATCCTTTCTGGTGCATCTATTATTGTCTACCTTTTCAATTACATGCTAAGCTTTG  :  240

*        260         *        280         *        300
  : CTACCTTAATGTTTAGTGGACATTTAGGATCTCTAGAGCTTGCTGGTGCATCTACAGCTA  :  300

*        320         *        340         *        360
  : ATGTTGGAATTCAAGGTCTTGCTTATGGAATTATGCTAGGAATGGCAAGTGCAGTGCAAA  :  360

*        380         *        400         *        420
  : CTGTGTGTGGACAAGCTTATGGAGCCAAAAAATATGCAGTAATGTGCATCACATTGCAAA  :  420

*        440         *        460         *        480
  : GAGCAGTAATCTTACATTTAGGAGCAGCAGTGATTCTCACATTTCTCTATTGGTTTTCTG  :  480

*        500         *        520         *        540
  : GAGATTTTCTAAAAGTCATAGGACAGACAGAGAGCATAGCCGAGCAAGGCCAAGTTTTCG  :  540

*        560         *        580         *        600
  : CTCGCGGTCTTATACCTCAACTCTATGCATTTGCATTGAGTTGTCCAATGCAAAGGTTTC  :  600

*        620         *        640         *        660
  : TCCAAGCACAGAACATTGTTAATCCTCTTGCATATATGGCAGTTGGAGTGTTCATTCTTC  :  660

*        680         *        700         *        720
  : ATGTGCTTGTTAGTTGGCTAGTTATCTATGTTTTAGACTATGGACTTCTTGGTGCAGCCC  :  720

*        740         *        760         *        780
  : TTACTCTCAGCTTTTCTTGGTGGAATCTTGTCTTGTTAAATGGATTGTACATCATTCTTA  :  780

*        800         *        820         *        840
  : GCCCAAGATGCAAGGAAACTTGGACTGGCTTCTCGATCAAAGCCTTTTGCGGAATTTGGC  :  840
```

FIGURE 33 (cont.)

```
             *        860         *        880         *        900
  : CTTACTTCAAGCTCACAGCTGCTTCCGCTGTGATGTTATGCTTGGAGATATGGTACAATC :  900

*        920         *        940         *        960
  : AGGGACTAGTACTCATATCAGGGTTGCTCTCCAATCCCACAGTGGCCCTGGATTCTATTT :  960

*        980         *       1000         *       1020
  : CAATTTGCATGAATTACTTAAATTGGGATATGCAAATTGTGTTGGGTCTTGGTGCAGCAG : 1020

*       1040         *       1060         *       1080
  : CCAGTGTGCGAGTTAGCAATGAATTAGGAGCAGCTCATCCAAGAGTAGCAAAATTGTCAG : 1080

*       1100         *       1120         *       1140
  : TCTTCGTAGTGAATGGAAATAGCATCATAATTAGTGTAGTTCTCGCTGCGATTATTATGA : 1140

*       1160         *       1180         *       1200
  : TATTCCGAGTTGCTTTGAGCAAGCTTTTCACTTCTGACACTGTAGTCCTTGAAGCTGTAT : 1200

*       1220         *       1240         *       1260
  : CTGACTTGACCCCATTGCTTGCCATCTCTGTCCTCCTAAATGGCATTCAACCTATACTAT : 1260

*       1280         *       1300         *       1320
  : CTGGTGTTGCAGTTGGAAGTGGATGGCAAGCTTTGGTGGCATATGTAAACTTGGTTTGTT : 1320

*       1340         *       1360         *       1380
  : ACTATCTCATTGGTCTTCCTGTTGGGTGTGTTCTTGGCTTTAAAACTTCTTTAGGAGTAG : 1380

*       1400         *       1420         *       1440
  : CTGGTATTTGGTGGGGATTGATCCTAGGAGTTTTCATACAGACTGTTACACTAATAGTTC : 1440

*       1460         *       1480         *       1500
  : TGACTGCCAGAACAAAATGGGAAGAAGAGGTTGAAAAAGCTATTGTTCGTGTCAAAAGGG : 1500

*       1520         *       1540         *       1560
  : CTTCTGAAGATGATACCTTGGATCAACTGGTTGCCGACATATGAAGGCATTTCTCTTACT : 1560

*       1580         *       1600         *       1620
  : GTAACTTTTCTTGCAGAAATAGAAGAACACTTTAGCAGCAGATTAATAGTTTCTGAACTA : 1620

*       1640         *       1660         *       1680
  : CAAGGATAGTGATGTTGGGTTTGTTCTGATTAAGCTCAACAAATAAGCTGGATAGAGAAG : 1680
```

FIGURE 33 (cont.)

```
         *        1700         *        1720         *        1740
      : AATTGTATGATGTGGCAAGGTAGTTAGATTATGGGAGGGAATATAGGGCCATGGAGGATT : 1740

*        1760         *        1780         *        1800
      : AGAGTGAGAAACCTTTTGAATTTGTTCAGGGATTACAGGAGCTAGCTATTCTTCTGTCAT : 1800

*        1820         *        1840         *        1860
      : AGTTCCTTGTTCAATCAATAATATTATTTCCTCTTCAAAAAAAAAAAAAAAAAAAAAAAA : 1860

*
      : AAAAAAAAAAAAAAAAAAA : 1879
```

FIGURE 34

```
         *        20         *        40         *        60
: MSSIENQPLLLGLDSHSHIANLSSDTIEEFLEHRPIQLRWWLKLVAWESRVLWILSGASIIVYLFNYM :  68

*        80         *       100         *       120         *
: LSFATLMFSGHLGSLELAGASTANVGIQGLAYGIMLGMASAVQTVCGQAYGAKKYAVMCITLQRAVIL : 136

140        *       160         *       180         *       200
: HLGAAVILTFLYWFSGDFLKVIGQTESIAEQGQVFARGLIPQLYAFALSCPMQRFLQAQNIVNPLAYM : 204

*       220         *       240         *       260         *
: AVGVFILHVLVSWLVIYVLDYGLLGAALTLSFSWWNLVLLNGLYIILSPRCKETWTGFSIKAFCGIWP : 272

280         *       300         *       320         *       340
: YFKLTAASAVMLCLEIWYNQGLVLISGLLSNPTVALDSISICMNYLNWDMQIVLGLGAAASVRVSNEL : 340

*       360         *       380         *       400
: GAAHPRVAKLSVFVVNGNSIIISVVLAAIIMIFRVALSKLFTSDTVVLEAVSDLTPLLAISVLLNGIQ : 408

*       420         *       440         *       460         *
: PILSGVAVGSGWQALVAYVNLVCYYLIGLPVGCVLGFKTSLGVAGIWWGLILGVFIQTVTLIVLTART : 476

480         *       500
: KWEEEVEKAIVRVKRASEDDTLDQLVADI : 505
```

FIGURE 35
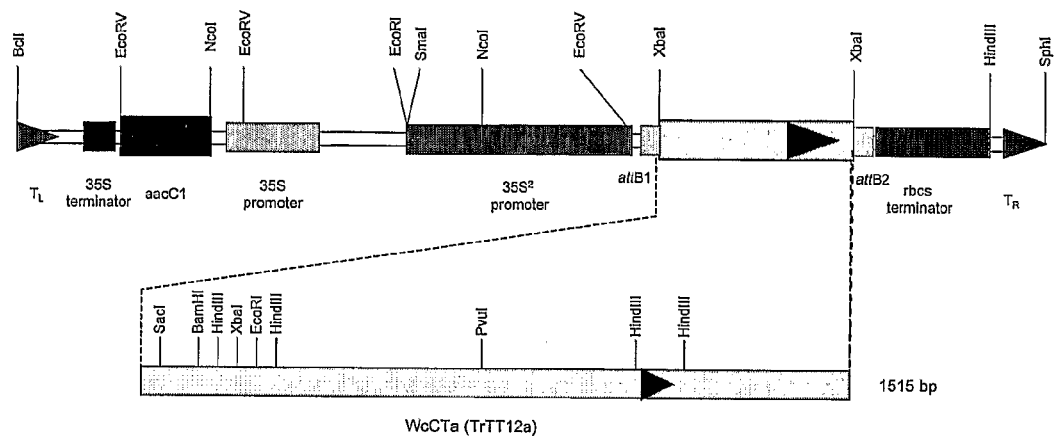
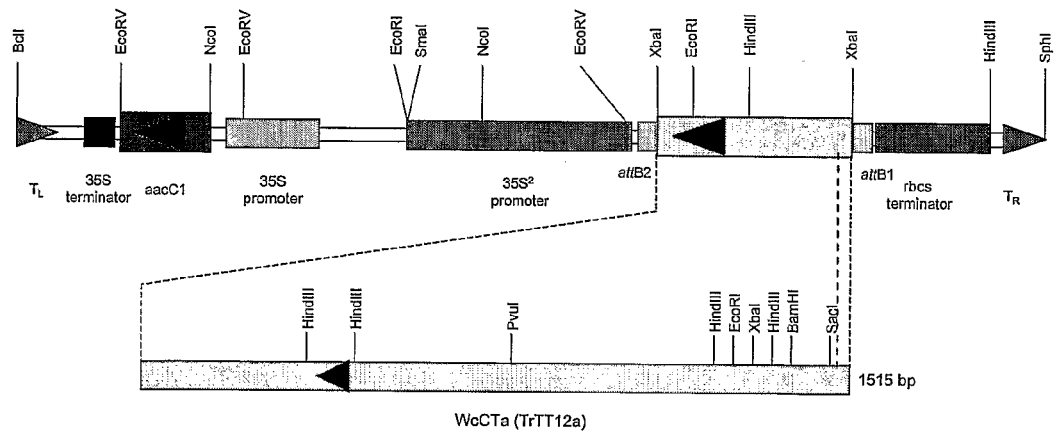

FIGURE 37

```
            *        20         *        40         *        60
: ATACTCAAGCTATGCATCCAACGCGTTGGGAGCTCTCCCATATGGTCGACCTGCAGGCGG :   60

*        80         *       100         *       120
: CCGCGAATTCACTAGTGATTAAGCAGTGGTAACAACGCAGAGTACGCGGGGGTTACCACC :  120

*       140         *       160         *       180
: TAACATTTTCCTTTCTCAGTTTCTCTCTTGTGTTTTTCATCAAACACCTTCTCTGCATAA :  180

*       200         *       220         *       240
: TTTTCTTCATCAAAAAATTCAAACACTCAAAAACTCAAACACCTTTCGTGCATCACCAAA :  240

*       260         *       280         *       300
: AATGGAGAATTCAACTCAAGAATCACACATCCGATCCGAAAACTCTGTTACCTACGATTC :  300

*       320         *       340         *       360
: CCCTTATCCTCTCTACGCCATGGCTCTTTCTCCAAACACCAATTCACACCCACAACAACG :  360

*       380         *       400         *       420
: CATCGCTGTTGGTAGTTTCATCGAAGAATACACCAACCGCATCGATATCCTCAATTTCAA :  420

*       440         *       460         *       480
: CCCTGAGAATTTATCAATTAAACCTCAACCTTNACTTTCCTTCGATCATCCTTATCCACC :  480

*       500         *       520         *       540
: TACCAAACTCATGTTCCATCCCGCAACAAATTCATCTCTCCAGAAAACCTCCTCCGACCT :  540

*       560         *       580         *       600
: TCTAGCTACTTCCGGTGACTATCTCCGTCTTTGGGAAGTTCGCGAAAATTCGGTTGAGGC :  600

*       620         *       640         *       660
: TCTTTCTCTTTTTAACAACAGCAAAACAAGTGAGTTTTGTGCTCCTTTAACGTCATTTGA :  660

*       680         *       700         *       720
: TTGGAACGAAATTGAGCCGAAACGAATTGGTACTTCAAGCATTGATACTACTTGCACAAT :  720

*       740         *       760         *       780
: TTGGGACATTGAAAGAGGCGTTGTTGAAACGCAGCTTATTGCACATGATAAAGAGGTTTA :  780

*       800         *       820         *       840
: TGACATTGCTTGGGGTGAATCGAGGGTTTTTGCTTCGGTTTCTGCTGATGGGTCTGTTAG :  840
```

FIGURE 37 (cont.)

```
         *       860         *       880         *       900
  : GATTTTTGATTTGAGGGATAAAGAGCATTCAACTATTATCTATGAGAGTCCTCAACCAGA : 900

*       920         *       940         *       960
  : TACCCCTTTGCTTCGTTTGGCTTGGAACAAGAAGGATTTGAGGTATATGGCTACAACTTT : 960

*       980         *      1000         *      1020
  : GATGGATAGTAATAAAGTTGTGATTTTGGATATTAGGTCGCCAACTACGCCTGCGGCAGA : 1020

*      1040         *      1060         *      1080
  : ATTGGAGAGACATCGTGCTGGTGTTAATGCTATTACTTGGGCTCCAAGAAGTTCTAAGCA : 1080

*      1100         *      1120         *      1140
  : TATTTGTTCTGCTGGGGATGATTCACAGGCTCTTATTTGGGAGTTGCCTACTGTGGCTGG : 1140

*      1160         *      1180         *      1200
  : TCCAAATGGGATTGATCCAATGTCTATGTATTCTGCTGGTTATGAAATTAATCAGCTTCA : 1200

*      1220         *      1240         *      1260
  : ATGGTCTGCTTCTCAGCCTGATTGGATCGCAATTGCTTTTGCTAACAAGATGCAGCTTTT : 1260

*      1280         *      1300         *      1320
  : GCGGGTTTGAGTTTTAGGTAAGGGAATAACTTGTAGATTTGGAAAACCAATTAAGCATTG : 1320

*      1340         *      1360         *      1380
  : TGGTGTTGTGACTTGTAACTCATGAGTAGTTTATTATAGTTGAACGGGACAAATTGTTTT : 1380

*      1400         *      1420         *      1440
  : ACTTCCAAAAAAAAAAAAAAAAAAAAAAAAAAAAAGTACTCTGCGTTGTTACCACTGCTT : 1440

*      1460         *      1480
  : AATCGAATTCCCGCGGCCGCCATGGCGGCCGGGAGCATGCGACGT : 1485
```

FIGURE 38

```
             *        20         *        40         *        60
: AVVTTQSTRGLPPNIFLSQFLSCVFHQTPSLHNFLHQKIQTLKNSNTFRASPKMENSTQE :  60

*        80         *       100         *       120
: SHIRSENSVTYDSPYPLYAMALSPNTNSHPQQRIAVGSFIEEYTNRIDILNFNPENLSIK : 120

*       140         *       160         *       180
: PQPLSFDHPYPPTKLMFHPATNSSLQKTSSDLLATSGDYLRLWEVRENSVEALSLFNNSK : 180

*       200         *       220         *       240
: TSEFCAPLTSFDWNEIEPKRIGTSSIDTTCTIWDIERGVVETQLIAHDKEVYDIAWGESR : 240

*       260         *       280         *       300
: VFASVSADGSVRIFDLRDKEHSTIIYESPQPDTPLLRLAWNKKDLRYMATTLMDSNKVVI : 300

*       320         *       340         *       360
: LDIRSPTTPAAELERHRAGVNAITWAPRSSKHICSAGDDSQALIWELPTVAGPNGIDPMS : 360

*       380         *
: MYSAGYEINQLQWSASQPDWIAIAFANKMQLLRV : 394
```

FIGURE 39
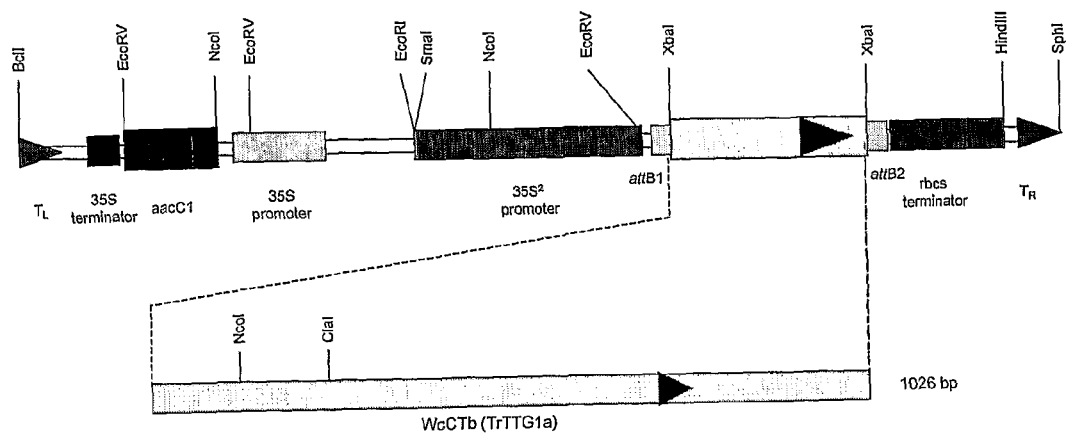
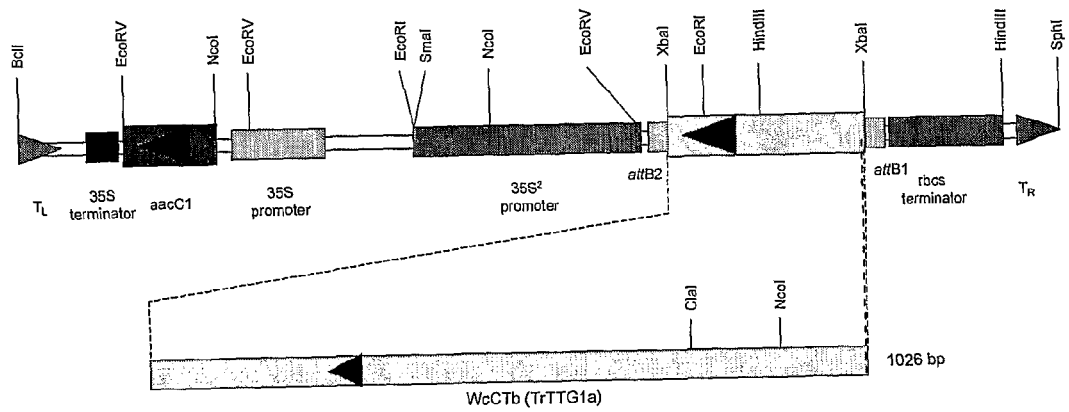

FIGURE 41

```
              *        20         *        40         *        60
   : ATATACCAATAGTGCATTCTTCTTCCTATATTGTTATTACCATAAACATGGTAAGAGCTC :   60

*        80         *       100         *       120
   : CTTGTTGTGAAAAAATGGGATTGAAGAGAGGTCCTTGGTCTCTTGAGGAAGATCAAATCC :  120

*       140         *       160         *       180
   : TTACATCTTACATTCAAAAACATGGTAATGGCAACTGGCGTGCTCTCCCAAAGCTAGCAG :  180

*       200         *       220         *       240
   : GCTTGTTAAGATGTGGAAAAAGCTGTAGACTTAGGTGGATTAACTATTTGAGACCTGATA :  240

*       260         *       280         *       300
   : TCAAGAGAGGAAATTTCACAAATGAAGAAGAGGAAAATATCATTAAGCTACATGAAATGC :  300

*       320         *       340         *       360
   : TTGGGAACAGGTGGTCGGCAATTGCAGCAAAATTACCAGGAAGAACGGACAATGAAATAA :  360

*       380         *       400         *       420
   : AAAATGTGTGGCACACGCATTTGAAGAAGAAATTATTGAAAACAAATGAAACAAACTCAG :  420

*       440         *       460         *       480
   : AAACTAAGAAAAGGGTGATCACAAAAACAAAAATCAAACGTTCTGATTCAAATTCAAGCA :  480

*       500         *       520         *       540
   : CTATAACACAATCAGAATCAGTTTCTGCATGCACTACTAGTTCTAGTGATTTTTCATCTG :  540

*       560         *       580         *       600
   : TTACGGTTGGTGAAAAAATAGATGTAAAAAGTGAAGATATTGAGTCTATGGAAGAAGAGG :  600

*       620         *       640         *       660
   : AAACAATGCCTGAAATTGATGAGAGTTTTTGGACAGAAGCAGCATTGGATGAAACTTCAA :  660

*       680         *       700         *       720
   : ATGATATGAAATCAAGTTCTTTGAATATCTCAAATGAGATAATGCCACTTCAATGCCCTT :  720

*       740         *       760         *       780
   : TAAGTAACTCTGATGAAATTTTCACACAAAATCATGATGATTATAATTCTAACTTAGATG :  780

*       800         *       820         *       840
   : ATGGCATGGATTTTTGGTATGATATATTCATTAGGACTGGAGATCAAATAGAATTGCCAG :  840
```

FIGURE 41 (cont.)

```
           *       860         *       880         *       900
     : AGTTCTAAATTTTTCCAAAAAAAGAAGTTGATGATTTAAAGTTTAGACGAGTTGGGTATC :  900

*       920         *       940         *       960
     : AAACCATCGTGTAGGTCTCACGGCTCAAATAGCGATAATTTTAGACTACTTACTCGACAG :  960

*       980         *      1000         *      1020
     : ATTGTCTCACATGGACAATGAGATTGATATTTACATCTTGGATGATATGAGTTATGTCTT : 1020

*      1040         *      1060         *      1080
     : TATCAACTGAACTATCTTTCATTATCGCATTGTAATTTCGATTTGAAAGAAATTACAAGG : 1080

*      1100         *      1120         *      1140
     : AAAGAAAAGCAGAGTATTGGGTTAATGATATGTAATCTATATCTATGTAAAAAGGAACT : 1140

*      1160         *      1180
     : ACAAGTGAAACATTGATTTTTTTTTAATATGTGTATATTGTTCCT : 1186
```

FIGURE 42

```
            *         20         *         40         *         60
: MVRAPCCEKMGLKRGPWSLEEDQILTSYIQKHGNGNWRALPKLAGLLRCGKSCRLRWINY :   60

*         80         *        100         *        120
: LRPDIKRGNFTNEEEENIIKLHEMLGNRWSAIAAKLPGRTDNEIKNVWHTHLKKKLLKTN :  120

*        140         *        160         *        180
: ETNSETKKRVITKTKIKRSDSNSSTITQSESVSACTTSSSDFSSVTVGEKIDVKSEDIES :  180

*        200         *        220         *        240
: MEEEETMPEIDESFWTEAALDETSNDMKSSSLNISNEIMPLQCPLSNSDEIFTQNHDDYN :  240

*        260
: SNLDDGMDFWYDIFIRTGDQIELPEF :  266
```

FIGURE 44

```
            *        20         *        40         *        60
: TTGGATTTTTATTGCAAAAATGGTGAGAGCTCCATGTTGTGAAAAAATGGGGTTGAAGAA :    60

*        80         *       100         *       120
: AGGTCCATGGACTCAAGAAGAAGATAGAATTCTCATCAATCACATAAACACTTATGGCCA :   120

*       140         *       160         *       180
: TTCTAATTGGCGTGCTCTTCCAAAACAAGCTGGGTTGTTAAGGTGTGGAAAAAGTTGTAG :   180

*       200         *       220         *       240
: ATTGAGATGGGCAAATTATTTGAAACCAGATATCAAACGGGGTAATTTTACTAAAGAAGA :   240

*       260         *       280         *       300
: AGAGGATGCAATAATCAATTTGCACCAAATGTTGGGAAATAGGTGGTCAACTATAGCAGC :   300

*       320         *       340         *       360
: AAGATTACCAGGACGAACGGACAATGAAATAAAAAATGTATGGCACACCCACTTGAAGAA :   360

*       380         *       400         *       420
: GAGGCTGCCACAAAACCAACAAGGCCACAACAATAGCCCAAAAAGAAATAAGAAACAAAC :   420

*       440         *       460         *       480
: CAATTTGGACTTTGAAGCCTCCAAATCAGACCAAGATATCAAACAAGAACAAAATAATGT :   480

*       500         *       520         *       540
: TGATGATATGCCACAATGTTCTAGTGACATGTCATACCATAATAATAGTAGCAATAGCAT :   540

*       560         *       580         *       600
: TGCTACTACTAATGATAATAATAATAATCTTGACATGTTCATAAATAATGATAAAGATGA :   600

*       620         *       640         *       660
: TGTTGATTCAGCAGAAAATAATCTTGCATTGGATGAAGATTTTTGGTCTGAAGTTTTGTC :   660

*       680         *       700         *       720
: ATCTGATAATTCTAGCAATGAGACAAGTGGTGGTTTTATGGATATTGGTGCTGATAATTA :   720

*       740         *       760         *       780
: TCAATTTCAAGCTTCATTTTCTCCATTAGGGACTGAAGAAGGAGTGTTTGATTCAAGTTC :   780

*       800         *       820         *       840
: ATTGAGTTTATGCCAAGATATGGACTTTTGGCATGATGTTTATGCAAGAGCTGAGGAAAT :   840
```

FIGURE 44 (cont.)

```
         *        860         *        880         *        900
:  TACTGAGTTACTTGAATTGTGATCAACTTAATTATCATTGTTATTCTTAAATTTTGACTT :  900

*        920         *        940         *        960
:  GTATTGTATGTTCATTCAATCAATGGGACGAAAATCATTTATTTTTTCCATTGTTTAGAC :  960

*        980         *       1000         *       1020
:  AAAAAAAAAAAAAAAAAAAAAAAAAAAAGTACTCTGCGTTGTTACCACTGCTTAATCACT : 1020

*       1040         *       1060         *       1080
:  AGTGAATTCGCGGCCGCCTGCAGGTCGACCATATGGGAGAGCTCCCAACGCGTTGGATGC : 1080

*       1100         *       1120         *       1140
:  ATAGCTTGAGTATTCTATAGTGTCACCTAAATAGCTTGGCGTAATCATGGTCATAGCTGT : 1140

*       1160         *       1180         *       1200
:  TTCCTGTGTGAAATTGTTATCCGCTCACAATTCCACACAACATACGAGCCGGAAGCATAA : 1200

:  AGTGTA : 1206
```

FIGURE 45

```
            *        20         *        40         *        60
: MVRAPCCEKMGLKKGPWTQEEDRILINHINTYGHSNWRALPKQAGLLRCGKSCRLRWANY :  60

*        80         *       100         *       120
: LKPDIKRGNFTKEEEDAIINLHQMLGNRWSTIAARLPGRTDNEIKNVWHTHLKKRLPQNQ : 120

*       140         *       160         *       180
: QGHNNSPKRNKKQTNLDFEASKSDQDIKQEQNNVDDMPQCSSDMSYHNNSSNSIATTNDN : 180

*       200         *       220         *       240
: NNNLDMFINNDKDDVDSAENNLALDEDFWSEVLSSDNSSNETSGGFMDIGADNYQFQASF : 240

*       260         *       280
: SPLGTEEGVFDSSSLSLCQDMDFWHDVYARAEEITELLEL : 280
```

FIGURE 46
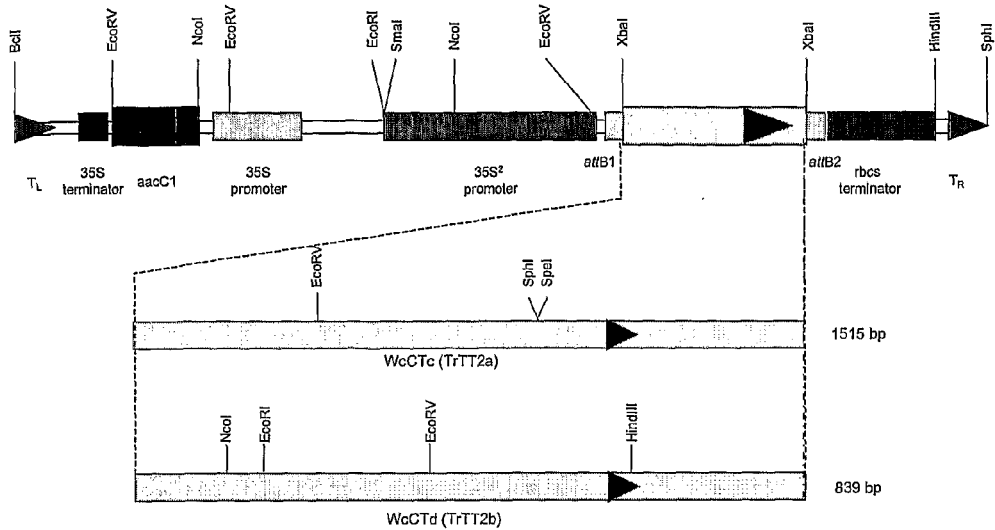
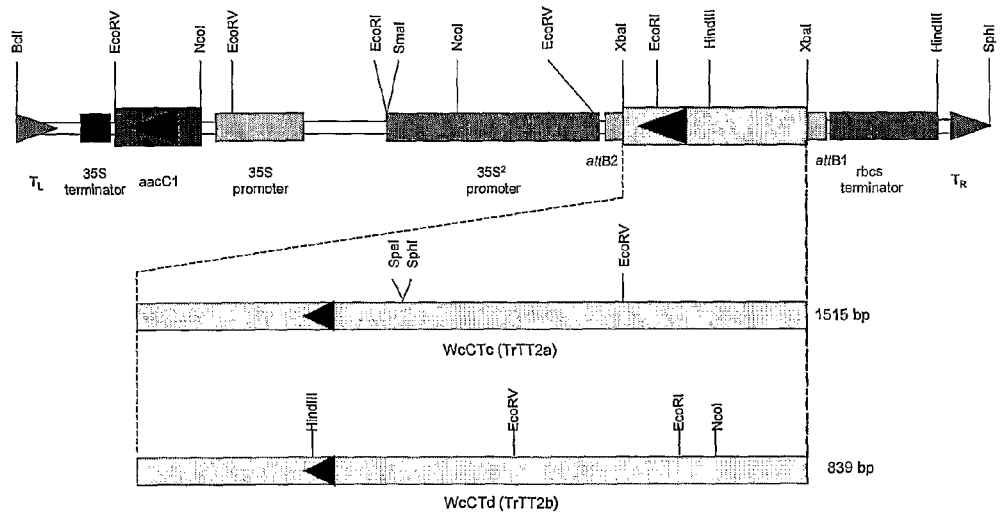

FIGURE 48

```
                  *        20         *        40         *        60
    : AAGCTGATGAAGGTATGAACCATGTTTTGTCAGAAAGAAGGAGAAGAGCAAAACTTAATG :  60

*        80         *       100         *       120
    : AAAGGTTTTTAACTCTTAGATCAATGGTCCCTTCAGATAGTAAGGATGACAAAGTTTCTA : 120

*       140         *       160         *       180
    : TACTAGATGATGCAATTGAATATCTTAGCAAGCTTGAGAAAAGGATAAAAGAATTAGAAG : 180

*       200         *       220         *       240
    : CTCAAAAAGAACCAATAGATATAGAGTCTAGAAGTAAAAAATCACATCATGATTTGTTGG : 240

*       260         *       280         *       300
    : AGAGGACTTGTGATGATTATTATAACAACAAAACTAACAATGGCAAGAAACCAATGATGA : 300

*       320         *       340         *       360
    : AGAAGAGGGAAATATGTGACATAGGTGAGACAAGGAGACAGATATTTTCTGATGCTTTAA : 360

*       380         *       400         *       420
    : AAGGAAGTTCTAATAGTGATGTTACTGTCAGTATGAGTGACAATGGAGTTGTGATTGAAA : 420

*       440         *       460         *       480
    : TGAAGTGTCCTTCTAGAGAAGGAAGGATATTGGAAATTATGGATGCAGTTAACAATCTCA : 480

*       500         *       520         *       540
    : ACATGGATTTTAATTCAGTTCAATCTACAGATTCCGATGGGAGGCTTCATGTGATCATTA : 540

*       560         *       580         *       600
    : GATCTAAGTTCAAAGGACCAGCTAATGCAACAACAAAAAGGATCAAACAAGCCCTACAAA : 600

*       620         *       640         *       660
    : AAGTGGCTTCAAAGTTTTGAATATTTGTATTTCCAAAATAAATAAAAAACATGGAGATGT : 660

*       680         *       700         *       720
    : TCAAATAAGTTCCTGCCAATTGCAGTGTGACACAGAGAGTTGAGGATATTGATTTAGTCA : 720

*       740         *       760         *       780
    : CAAGTGCAAATTCTTGGAGATATTTTTTGAAGACTTCAAGTTAGTCTTTGAGCAATAATA : 780

*       800         *       820         *       840
    : ACTCTTGGTGATGTAACATGGACATTTGTTTCATTACTTGTAAATGGGTAGATAGATTTA : 840
```

FIGURE 48(cont.)

```
        *         860         *         880         *         900
   : GTTGACATTTATACTCAATTAATTAGCCAAAAAAAAAAAAAAAAAAAAAAAAAAAAAAAA : 900

*         920         *         940         *
   : AAAAAAAAAAAAAAAAAAAAAAAATTAAAAAAAAAAAAAAAAAAAAAAAAAAAAAA : 956
```

FIGURE 49

```
            *        20         *        40         *        60
: MNHVLSERRRRAKLNERFLTLRSMVPSDSKDDKVSILDDAIEYLSKLEKRIKELEAQKEP :  60

*        80         *       100         *       120
: IDIESRSKKSHHDLLERTCDDYYNNKTNNGKKPMMKKREICDIGETRRQIFSDALKGSSN : 120

*       140         *       160         *       180
: SDVTVSMSDNGVVIEMKCPSREGRILEIMDAVNNLNMDFNSVQSTDSDGRLHVIIRSKFK : 180

*       200
: GPANATTKRIKQALQKVASKF : 201
```

FIGURE 52

```
                *        20         *        40         *        60
  : CGACGTCGCATGCTCCCGGCCGCCATGGCGGCCGCGGGAATTCGATTAAGCAGTGGTAAC :    60

*        80         *       100         *       120
  : AACGCAGAGTACGCGGGGATGGGAGCCGTGGCACAAAGAGTTGAAAGCTTAGCTTTGAGT :   120

*       140         *       160         *       180
  : GGAATATCATCAATTCCAAAAGAATATGTGAGACCAAAAGAAGAGTTAATAAACATAGGA :   180

*       200         *       220         *       240
  : AACATATTTGATGAAGAAAAAAACAAGGGCCACAAGTTCCAACAATTGATATAAAAGAA :    240

*       260         *       280         *       300
  : ATAAACTCTACAGATGAAATTGTTAGAAGAAAATGTAGGGATAAGCTTAAGAAAGCTGCA :   300

*       320         *       340         *       360
  : GAGGAATGGGGTGTGATGAATTTGGTGAATCATGGTATTTCTGATGAATTACTTAATCGA :   360

*       380         *       400         *       420
  : CTTAAAAAAGTTGGTGAAACTTTTTTTGAGTTACCTGTTGAAGAAAAGAAAAATATGCT :    420

*       440         *       460         *       480
  : AATGATCAAAGTGTTGGGAAGATTCAAGGGTATGGTAGTAAATTAGCTAATAATGCTAGT :   480

*       500         *       520         *       540
  : GGTCAACTTGAATGGGAAGATTATTTCTTTCATTGTATTTTTCCTGAGGATAAGCGTGAC :   540

*       560         *       580         *       600
  : TTATCCATATGGCCTAAGACTCCAGCTGATTATACTGAGGTCACAACAGAATATGCAAAA :   600

*       620         *       640         *       660
  : GAACTAAGAGGCCTAGCTAGCAAGATAATGGAAGTGTTATCTCTTGAACTTGGCTTAGAA :   660

*       680         *       700         *       720
  : GGAGGAAGATTAGAGAAAGAAGTTGGTGGAATGGAAGAGCTTTTACTTCAAATGAAAATC :   720

*       740         *       760         *       780
  : AACTATTACCCAATTTGCCCTCAGCCAGAACTAGCACTTGGAGTTGAAGCTCATACAGAT :   780

*       800         *       820         *       840
  : ATAAGTTCACTTACTTTCCTTCTCCACAACATGGTGCCAGGTTTGCAACTTTTTTATGAG :   840
```

FIGURE 52 (cont.)

```
              *       860         *       880         *       900
: GGTAAATGGGTCACAGCAAAATGTGTACCTGGTTCAATTCTAATGCATATTGGTGATACA  :  900

*       920         *       940         *       960
: ATTGAGATTCTTAGCAATGGAAAATACAAAAGTATCCTTCACCGTGGATTGGTTAATAAG  :  960

*       980         *      1000         *      1020
: GAAAAAGTTAGAATATCTTGGGCAGTGTTTTGTGAACCACCTAAAGAGAAAATTATTCTT  : 1020

*      1040         *      1060         *      1080
: AAGCCACTTCCTGAACTTGTTACTGAGATCGAACCAGCACGTTTTCCGCCTCGTACTTTT  : 1080

*      1100         *      1120         *      1140
: GCTCAGCATATTCATCACAAACTTTTTAGGAAGAGTGAGGAAGAGAAGAAGGATGATCCT  : 1140

*      1160         *      1180         *      1200
: AAAAAATGAGTGTCTCATAAGTCATAATTCAGCTGACATTGTATCACATTTTTCGTATCT  : 1200

*      1220         *      1240         *      1260
: ATATTAGCCTATGAACTTTTGTGTGTGTAAGTGGAATAATAGGCTATGCAGCCTAAATTT  : 1260

*      1280         *      1300         *      1320
: GTTGTATGTTTTAAAAAAAACTATGTAAGTCATGTTTTTAGATTTGATTTGATTTATCTT  : 1320

*      1340         *      1360         *      1380
: ATTCAGTTGGTATTTAGAGGAAGCGAGTCTTAGTAATCGGACGCTACATGAGAAATGGAC  : 1380

*      1400         *      1420         *      1440
: TTGAACTCTAAAAAAAAAAAAAAAAAAAAAAAAAAAAGTACTCTGCGTTGTTACCACTG  : 1440

*      1460         *      1480         *      1500
: CTTAATCACTAGTGAATTCGCGGCCGCCTGCAGGTCGACCATATGGGAGAGCTCCCAACG  : 1500

*      1520         *      1540         *      1560
: CGTTGGATGCATAGCTTGAGTATTCTATAGTGTCACCTAAATAGCTTGGCGTAATCATGG  : 1560

*      1580         *      1600         *      1620
: TCATAGCTGTTTCCTGTGTGAAATTGTTATCCGCTCACAATTCCACACAACATACGAGCC  : 1620

*      1640         *      1660         *      1680
: GGAAGCATAAAGTGTAAAGCCTGGGGTGCCTAATGAGTGAGCTAACTCACATTAATTGCG  : 1680
```

FIGURE 52 (cont.)

```
           *       1700         *      1720         *      1740
: TTGCGCTCACTGCCCGCTTTCCAGTCGGGAAACCTGTCGTGCCAGCTGCATTAATGAATC : 1740

*       1760         *      1780         *
: GGCCAACGCGCGGGGAGAGGCGGTTTGCGTATTGGGCGCTCTTCCGCTTC : 1790
```

FIGURE 53

```
              *        20         *        40         *        60
: MAAAGIRLSSGNNAEYAGMGAVAQRVESLALSGISSIPKEYVRPKEELINIGNIFDEEKK :  60

*        80         *       100         *       120
: QGPQVPTIDIKEINSTDEIVRRKCRDKLKKAAEEWGVMNLVNHGISDELLNRLKKVGETF : 120

*       140         *       160         *       180
: FELPVEEKEKYANDQSVGKIQGYGSKLANNASGQLEWEDYFFHCIFPEDKRDLSIWPKTP : 180

*       200         *       220         *       240
: ADYTEVTTEYAKELRGLASKIMEVLSLELGLEGGRLEKEVGGMEELLLQMKINYYPICPQ : 240

*       260         *       280         *       300
: PELALGVEAHTDISSLTFLLHNMVPGLQLFYEGKWVTAKCVPGSILMHIGDTIEILSNGK : 300

*       320         *       340         *       360
: YKSILHRGLVNKEKVRISWAVFCEPPKEKIILKPLPELVTEIEPARFPPRTFAQHIHHKL : 360

*
: FRKSEEEKKDDPKK : 374
```

FIGURE 54
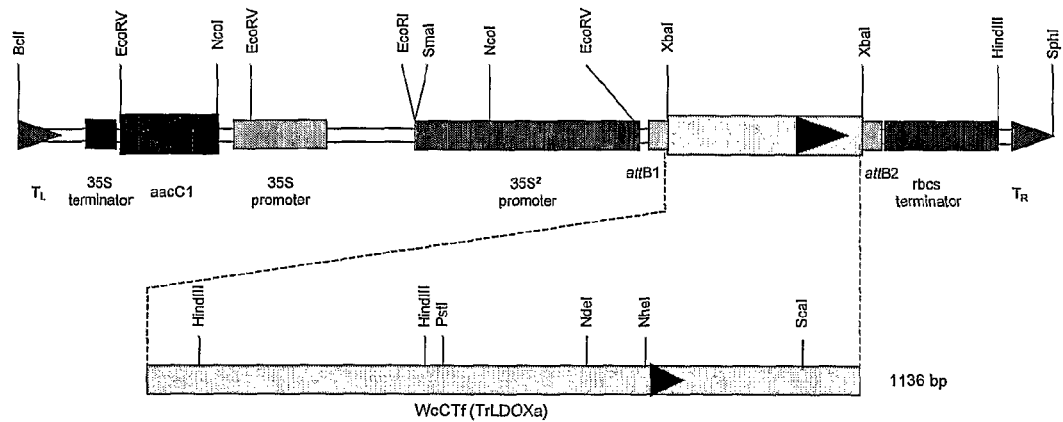
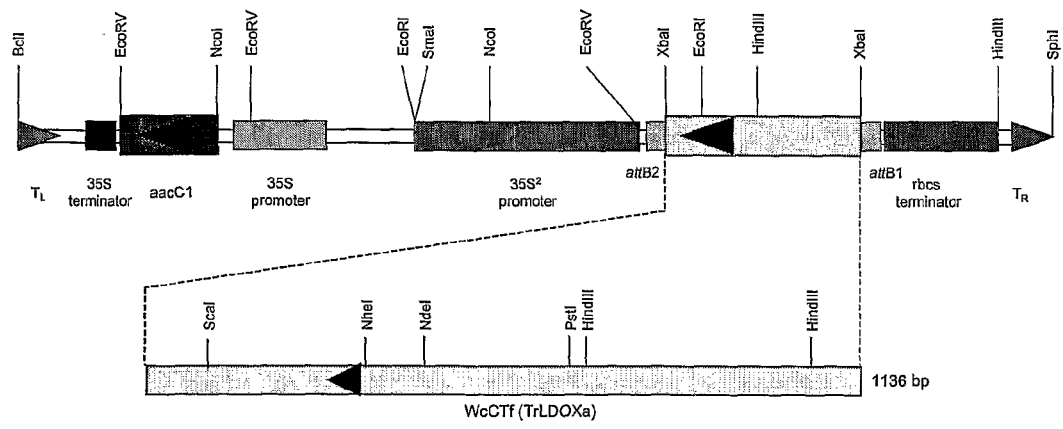

FIGURE 56

```
              *         20         *         40         *         60
: AGGTTGTTTACTAGTCGTGTCGGAATTCCTTCCATATTTCAACTAGTTAGATAGAATTCT :    60

*         80         *        100         *        120
: CATCTTCCTCATTCTCCTTCAATTCAATGGCAGCATCACAACAACAAGAAGAAATAATAT :   120

*        140         *        160         *        180
: TCAGGTCTAAACTTCCGGACATATACATCCCAAAACACCTTCCCCTCCATTCTTATTGCT :   180

*        200         *        220         *        240
: TTGAAAATCTCTCCCAATTTGGTTCTCGTCCATGTCTCATCAATGCACCCACCGGAAAAG :   240

*        260         *        280         *        300
: TCTACACCTACCACGACGTCGAACTCACCTCTCGGAAAGTTGCCTCCGGTCTCAACAAAT :   300

*        320         *        340         *        360
: TGGGAGTCCAACAGGGTGATGTGATCATGATCCTCCTCCCCAATTCCCCTGAATTCGTCT :   360

*        380         *        400         *        420
: TCTCCTTTCTGGCAGCTTCTTATCTCGGCGCCATAGCCACAGCAGCCAATCCTTTCTTCA :   420

*        440         *        460         *        480
: TGGCCGCGGAGATTGGAAAGCAAGCAAAAGCCTCCAACGCCAAGTTGATCATAACACAGG :   480

*        500         *        520         *        540
: CATGTTACTACGACAAAGTCAAGGAGTTGTTGTTGGACAACCACAACAAGAAGAAGAAGA :   540

*        560         *        580         *        600
: AGTTGGTGCTCATAGACTCTCTCCCTCCCTCTACCACCACCACAGAAGAAGAAGAAGATG :   600

*        620         *        640         *        660
: GTAATCATGTTCATTTCTCGACACTGATCGATGCTGACGAGAAGGAATTGCCGGCGGATG :   660

*        680         *        700         *        720
: TGAAGATCGACCCTGAAGATGTGGTGGCACTTCCCTATTCATCGGGGACAACGGGTCTGC :   720

*        740         *        760         *        780
: CAAAAGGGGTGATGTTAACACACAAGGGATTGGTGAGCAGCATAGCGCAGCAGGTGGATG :   780

*        800         *        820         *        840
: GAGAGAATCCAAATCTATGTTACAGCAGTGAAGATGTGATACTGTGTGTGCTTCCTCTGT :   840

*        860         *        880         *        900
: TTCACATATACTCTCTAAATTCTGTTTTGCTATGTGGACTGAGAGCGAAGGCAAGTATAC :   900
```

FIGURE 56 (cont.)

```
              *         920         *         940         *         960
:   TTTTGATGCCAAAATTCGACATAAATGGTTTCTTGAGTCTTGTGAACAAACATGGAGTTA  :   960

*         980         *        1000         *        1020
:   CAGTTGCACCGGTAGTTCCTCCGATAGTGTTGGCGATTGCAAAGTCGCCGGATCTTAACA  :  1020

*        1040         *        1060         *        1080
:   AATATGATCTGCCTTCAATAAGGATATTGAAATCAGGAGGTGCTCCACTCGGCAAAGAAC  :  1080

*        1100         *        1120         *        1140
:   TTGAAGACACTGTTAGGAACAAATTTCCCAAAGTAATACTTGGACAGGGATACGGAATGA  :  1140

*        1160         *        1180         *        1200
:   CTGAGGCAGGGCCAGTGTTAACAATGAGCTTAGCATTTGCTAAAGAAGCAGTGAATGTGA  :  1200

*        1220         *        1240         *        1260
:   AGCCGGGTGCGTGTGGAACAGTTGTAAGAAATGCAGAGATGAAGATTGTGGATCCTGAAA  :  1260

*        1280         *        1300         *        1320
:   GTGGTAATTCTTTACCTAGAAACCAATCTGGTGAAATCTGCATAAGAGGAGACCAGATCA  :  1320

*        1340         *        1360         *        1380
:   TGAAAGGTTATCTAAATGATGTGGAGGCAACTGAGAGAACGATTGACAAAGAAGGTTGGT  :  1380

*        1400         *        1420         *        1440
:   TGCATACAGGTGATATTGGGTATATTGACGATGACGATGAGTTATTCATTGTTGATAGAT  :  1440

*        1460         *        1480         *        1500
:   TGAAGGAATTGATCAAATACAAAGGATTTCAAGTTGCTCCAGCTGAACTTGAAGCTCTTC  :  1500

*        1520         *        1540         *        1560
:   TTCTTTCTCATCCCAAAATCTCTGATGCTGCTGTTGTCCCAATGAAGGATGAAGCCGCCG  :  1560

*        1580         *        1600         *        1620
:   GAGAGGTACCTGTTGCATTTGTTGTGGGATCAAATGGTCACACTGACTTAACCGAGGATG  :  1620

*        1640         *        1660         *        1680
:   AAATTAAGCACTTTATCTCCAAACAGGTGGTGTTTTACAAAAGAATAAGTCGAGTATTCT  :  1680

*        1700         *        1720         *        1740
:   TCATTGATGCAATTCCCAAGTCACCTTCAGGCAAAATATTGCGTAAGGATCTCAGAGCAA  :  1740
```

FIGURE 56 (cont.)

```
      *      1760       *      1780       *      1800
: AGTTAGCAGCAGAATAAGCTGTTCCAAATTGATCATCACTTTCACATCTTATTTCTCAAC : 1800

*      1820       *      1840       *      1860
: CATATGTATTATATAAGTTACAAGCTTGTGTTGTGTGTTCTTTTCATCTTATTTTACAAT : 1860

*      1880       *      1900       *      1920
: TATTCTGTAAAATCATTCAATCCCGATCTAACTTTCATTTCTATCATCATGTACTCAAAA : 1920

*      1940       *      1960       *      1980
: TATTATTTTTACTAAAACAAATGCACTTCTTTGTTTTTTTTTAAAAAAAAAAAAAAAAAA : 1980

*      2000       *      2020       *      2040
: AAAAAAAAAAAAAAAAAAAAAAAAAAAAAAAAAAAAAAAAAAAAAAAAAAAAAAAAAAAA : 2040

*      2060       *      2080       *
: AAAAAAAAAAAAAATATAAAAAAAAAAAAAAAAAAAAAAAAAAAAAA : 2090
```

FIGURE 57

```
              *        20         *        40         *        60
: MAASQQQEEIIFRSKLPDIYIPKHLPLHSYCFENLSQFGSRPCLINAPTGKVYTYHDVEL  :  60

*        80         *       100         *       120
: TSRKVASGLNKLGVQQGDVIMILLPNSPEFVFSFLAASYLGAIATAANPFFMAAEIGKQA  : 120

*       140         *       160         *       180
: KASNAKLIITQACYYDKVKELLLDNHNKKKKKLVLIDSLPPSTTTTEEEEDGNHVHFSTL  : 180

*       200         *       220         *       240
: IDADEKELPADVKIDPEDVVALPYSSGTTGLPKGVMLTHKGLVSSIAQQVDGENPNLCYS  : 240

*       260         *       280         *       300
: SEDVILCVLPLFHIYSLNSVLLCGLRAKASILLMPKFDINGFLSLVNKHGVTVAPVVPPI  : 300

*       320         *       340         *       360
: VLAIAKSPDLNKYDLPSIRILKSGGAPLGKELEDTVRNKFPKVILGQGYGMTEAGPVLTM  : 360

*       380         *       400         *       420
: SLAFAKEAVNVKPGACGTVVRNAEMKIVDPESGNSLPRNQSGEICIRGDQIMKGYLNDVE  : 420

*       440         *       460         *       480
: ATERTIDKEGWLHTGDIGYIDDDDELFIVDRLKELIKYKGFQVAPAELEALLLSHPKISD  : 480

*       500         *       520         *       540
: AAVVPMKDEAAGEVPVAFVVGSNGHTDLTEDEIKHFISKQVVFYKRISRVFFIDAIPKSP  : 540

*
: SGKILRKDLRAKLAAE                                             : 556
```

FIGURE 59

```
              *        20         *        40         *        60
: CCGACGTCGCATGCTCCCGGCCGCCATGGCGGCCGCGGGAATTCGATTAAGCAGTGGTAA :   60

*        80         *       100         *       120
: CAACGCAGAGTACGCGGGAACACAAGGTTGTTACTATGACAAAGTTAAGGATTTGGAAAA :  120

*       140         *       160         *       180
: TGTGAAGCTGGTTTTTGTGGACTCTTCACCGGAAGGAGAAAATCATATGCATTTCCGTGA :  180

*       200         *       220         *       240
: GCTGGCTCAAGCCGATGAGAATGAAATTGAAGAGGTAAAGATAAACCCTGATGATGTGGT :  240

*       260         *       280         *       300
: TGCTTTGCCATATTCTTCTGGAACAACAGGGCTACCTAAAGGTGTTATGCTAACACACAA :  300

*       320         *       340         *       360
: AGGATTAGTGACAAGTGTAGCACAACAAGTTGGTGGTGAAAATCCAAATCTATATTACCA :  360

*       380         *       400         *       420
: TTCTGAGGATGTCATACTATGTGTTCTTCCCATGTTTCATATCTATTCACTCAACTCTGT :  420

*       440         *       460         *       480
: TTTGCTCTGTGGTTTGAGAGCCAAAGCTTCCATTCTTTTAATGCCAAAGTTTGATATTCA :  480

*       500         *       520         *       540
: TTCTTTTTTTAGCCTTGTTCATAAATACAGAGTCACTGTTGCTCCTGTTGTGCCACCAAT :  540

*       560         *       580         *       600
: TGTTTTGGCTATTTCTAAGTCACCTGAACTTGATAACTATGATCTTTCATCCATAAGGAT :  600

*       620         *       640         *       660
: TTTGAAATCTGGTGGTGCTCCACTTGGTAAGGAACTTGAGGACACTGTTAGGGCCAAATT :  660

*       680         *       700         *       720
: TCCAAAAGCAAAACTTGGACAAGGATATGGGATGACTGAGGCTGGTCCAGTTTTAACAAT :  720

*       740         *       760         *       780
: GTGTTTGTCATTTGCAAAAGTGCCAATAGATGTTAAACCGGGTGCATGTGGAACTGTTGT :  780

*       800         *       820         *       840
: AAGAAATGCTCAGATCAAAATTGTTGATCCTGAAAATGATTCTTCTTTGCCTCGTAATCA :  840

*       860         *       880         *       900
: ACCTGGTGAAATTTGTATTAGAGGAGACCAAATCATGAAAGGTTATCTAAACGACCCAGA :  900
```

FIGURE 59 (cont.)

```
              *         920         *         940         *         960
 : AGCAACAGGGAGAACAATAGACAAAGAAGGTTGGTTGCACACAGGTGACATTGGTTACAT :  960

*         980         *        1000         *        1020
 : TGACAATGATGATGAATTGTTCATAGTGGATAGGCTTAAAGAATTGATTAAATACAAAGG : 1020

*        1040         *        1060         *        1080
 : TTTTCAAGTTGCTCCAGCTGAACTTGAAGCCATTATTCTTTCACATCCCAATATCTCTGA : 1080

*        1100         *        1120         *        1140
 : TGTTGCTGTCGTCCCAATGCTGGATGAAGCTGCTGGTGAGGTCCCAGTTGCATTTGTTGT : 1140

*        1160         *        1180         *        1200
 : GAGATCAAATGGAAGTATCGACACAACTGAGGATGAAATTAAGAAGTTTGTCTCCAAACA : 1200

*        1220         *        1240         *        1260
 : GGTGGTATTTTACAAAAGAATAAACAGAGTATTCTTCATTGATGCCATTCCCAAGTCACC : 1260

*        1280         *        1300         *        1320
 : CTCAGGCAAAATATTAAGAAAGGACCTAAGGGCTAAGCTTGCAGCTGGTGTTCCAACAAA : 1320

*        1340         *        1360         *        1380
 : TTAAACAATCCATTTATTATTTATTTTTCATGTATTTTTTATTCACAGCCTGTTCCAAA  : 1380

*        1400         *        1420         *        1440
 : TTCAACAGCTCAATCAATTTCAGACCTTATTTTTAATTATTAGAAAAAAAAAAAAAAAAA : 1440

*        1460
 : AAAAAAAAAAAAAGTACTCTGCGTGTGT : 1467
```

FIGURE 60

```
              *        20         *        40         *        60
: MAAAGIRLSSGNNAEYAGTQGCYYDKVKDLENVKLVFVDSSPEGENHMHFRELAQADENE :  60

*        80         *       100         *       120
: IEEVKINPDDVVALPYSSGTTGLPKGVMLTHKGLVTSVAQQVGGENPNLYYHSEDVILCV : 120

*       140         *       160         *       180
: LPMFHIYSLNSVLLCGLRAKASILLMPKFDIHSFFSLVHKYRVTVAPVVPPIVLAISKSP : 180

*       200         *       220         *       240
: ELDNYDLSSIRILKSGGAPLGKELEDTVRAKFPKAKLGQGYGMTEAGPVLTMCLSFAKVP : 240

*       260         *       280         *       300
: IDVKPGACGTVVRNAQIKIVDPENDSSLPRNQPGEICIRGDQIMKGYLNDPEATGRTIDK : 300

*       320         *       340         *       360
: EGWLHTGDIGYIDNDDELFIVDRLKELIKYKGFQVAPAELEAIILSHPNISDVAVVPMLD : 360

*       380         *       400         *       420
: EAAGEVPVAFVVRSNGSIDTTEDEIKKFVSKQVVFYKRINRVFFIDAIPKSPSGKILRKD : 420

*
: LRAKLAAGVPTN : 432
```

FIGURE 62

```
              *        20         *        40         *        60
: CGACGTCGCATGCTCCCGGCCGCCATGGCGGCCGCGGGAATTCGATTAAGCAGTGGTAAC :  60

*        80         *       100         *       120
: AACGCAGAGTACGCGGGNGGTTCATGTGGAACCGTTGCAAGAAATGCAGAGCTCAAAGTT : 120

*       140         *       160         *       180
: CTTGACTCTGAAACTGGTCGCTCTCTTGGTTATAATCAACCCGGTGAGATTTGCATCCGT : 180

*       200         *       220         *       240
: GGCCAACAAATCATGAAAGGATATTTGAATGATGAAAATGCAACAAAAACTACTATTGAT : 240

*       260         *       280         *       300
: GAAGAGGGTTGGCTTCATACTGGTGATGTTGGCTATATAGATGACAATGATGAGATTTTC : 300

*       320         *       340         *       360
: ATTGTTGACAGGGTGAAGGAACTCATTAAATTCAAAGGCTTCCAAGTGCCCCCTGCTGAA : 360

*       380         *       400         *       420
: CTTGAAGGCCTTCTAGTAAGCCATCCATCTATTGCAGATGCAGCTGTTGTCCCGCAAAAG : 420

*       440         *       460         *       480
: GATGTGGCTGCTGGTGAAGTTCCTGTTGCCTTTGTGGTAAGATCAAATGGACTTGATCTA : 480

*       500         *       520         *       540
: ACTGAAGAGGCTGTAAAGGAGTTTATAGCTAAACAGGTTGTATTTTATAAGAGACTGCAC : 540

*       560         *       580         *       600
: AAAGTGTATTTCATTCATGCAATTCCCAAGTCTCCATCAGGAAAGATACTGAGGAAAGAT : 600

*       620         *       640         *       660
: CTCAGAGCAAAGTTAGAAAGTACCACCCAAAAGCCTTGAGATGCTAGAAGCTTTTTCACT : 660

*       680         *       700         *       720
: TATTTTTTTGGTCAAAATCTTCCTCATTTGTTCATTTGTATCCTAATATATTCTAGCTA : 720

*       740         *       760         *       780
: CTAGGTCTCATGCTTAATTTATGTATTGATAATATATATAAGGTATAAAGTCAATATATC : 780
```

FIGURE 62 (cont.)

```
         *         800         *         820         *         840
      : CATGGTGAAGTTGTATGTACAAATGCTCCATTGTGTATTTTTAAGCCAATTGCCTAAGCA : 840

*         860         *         880         *         900
      : GTTCTCTGGTTTGTTGTGCTTGTAATGTGATTTGGGAAACAGTATTGTTACTATCAATCT : 900

*         920         *         940         *         960
      : ATGTAGTTCTTTTCATCATATAAAAAAAAAAAAAAAAAAAAAAAAAAAAAAAAAAAAAAA : 960

*         980         *
      : AAAAAAAAAAAAAAAAAAAAAAAAAAAAAAA : 991
```

FIGURE 63

```
              *        20         *        40         *        60
: MAAAGIRLSSGNNAEYAXGSCGTVARNAELKVLDSETGRSLGYNQPGEICIRGQQIMKGY :  60

*        80         *       100         *       120
: LNDENATKTTIDEEGWLHTGDVGYIDDNDEIFIVDRVKELIKFKGFQVPPAELEGLLVSH : 120

*       140         *       160         *       180
: PSIADAAVVPQKDVAAGEVPVAFVVRSNGLDLTEEAVKEFIAKQVVFYKRLHKVYFIHAI : 180

*       200
: PKSPSGKILRKDLRAKLESTTQKP : 204
```

FIGURE 65

```
             *        20         *        40         *        60
 : CGACGTCGCATGCTCCCGGCCGCCATGGCGGCCGCGGGAATTCGATTAAGCAGTGGTAAC :    60

*        80         *       100         *       120
 : AACGCAGAGTACGCGGGGAAACTTAGCTAACTTAAATTAATTTAATTCCCCTTATTCCTA :   120

*       140         *       160         *       180
 : ATATTCTCCTAACATTACCAAAATGTCACCATTTCCTCCACAGCAAGAAGAATTCATATT :   180

*       200         *       220         *       240
 : CCGTTCCAAACTCCCAGACATTGAAATTCCAACAAATCTTCCATTACACTCTTATTGTTT :   240

*       260         *       280         *       300
 : CCAAAACCTCTCTCAATTCCATAACCGTCCATGTCTCATCAACGGCGACTCCGGCGAAAT :   300

*       320         *       340         *       360
 : CTTAACATACTCCGACGTCCACCTCACCGTCCGCAAAATCGCCGCCGGTTTAAACACTCT :   360

*       380         *       400         *       420
 : CGGAATTAATCAAGGTGATGTCATCATGCTCGTCCTCCGTAACTCTCCTCAATTCGCACT :   420

*       440         *       460         *       480
 : CACTTTCCTCGGTGCCTCCTTCCGTGGCGCCGTCATCACCACCGCAAATCCTTTCTACAC :   480

*       500         *       520         *       540
 : CTCATCGGAACTCGCGAAACAAGCCACAGCAACAAAAACTAAACTCATCGTAACTCAATC :   540

*       560         *       580         *       600
 : CGCATATCTAAGTAAAATCAACGATTTCGCTAAATTCAACAACATCAAAATCGTCTGCAT :   600

*       620         *       640         *       660
 : AGATTCATCATCGTCGCCGTCGTCGGAAGAAGATGCCACCGGCGTTGTGGATTTTTCAGT :   660

*       680         *       700         *       720
 : TTTAACAAATGCTGATGAAAACGATTTACCAGATGTTAAACTAACGCCTAACGACATCGT :   720

*       740         *       760         *       780
 : TGCGTTACCGTTTTCTTCGGGAACTTCAGGACTTCCAAAAGGCGTTATGTTAACACATGA :   780

*       800         *       820         *       840
 : AAATTTAGTTACAACTATATCACAGTTAGTTGACGGTGAAAATCCACATCAATACACTAA :   840
```

FIGURE 65 (cont.)

```
             *        860         *        880         *        900
  : CGGCGAGGATGTGTTACTCTGTGTGTTACCTATGTTTCATATCTATGCACTCAATTCAAT :  900

*        920         *        940         *        960
  : ATTACTATGTGGAATTCGTTGTGGTGCTGCGGTTTTAATTGTGGAAAAATTTGAGATTAA :  960

*        980         *       1000         *       1020
  : AACGTTATTGGAACTTATTGAAAAGTTTAAAGTGACGGTAGCGTCGTTTGTGCCACCAAT : 1020

*       1040         *       1060         *       1080
  : TGTTTTGGCGTTGGTAAAAAGTGGTGAATCAAATAAATATGATTTGTCGTCTATTAGAGC : 1080

*       1100         *       1120         *       1140
  : GATGATTACTGGTGCAGCACCTATGGGAATGGAACTTGAACAAGCTGTAAAGGATAGATT : 1140

*       1160         *       1180         *       1200
  : GCCACATACAGTACTTGGTCAGGGATACGGCATGACAGAGGCAGGACCACTATCAATTAG : 1200

*       1220         *       1240         *       1260
  : CCTTGCATTTGCAAAGGAACCATTCAGAACAAAACCTGGTGCATGTGGCACCGTCGTAAG : 1260

*       1280         *       1300         *       1320
  : AAACGCCGAGATGAAAATCGTTGATACAGAGACTGGTGTTTCTCTTCCTAGAAACAAAGC : 1320

*       1340         *       1360         *       1380
  : TGGTGAAATTTGCATTAGAGGCACAAAGGTTATGAAAGGATACCTAAATGATCCCGAGGC : 1380

*       1400         *       1420         *       1440
  : GACAAAGAGAACTATAGACGAAGAGGGATGGCTACACACGGGTGACATTGGTTTGATTGA : 1440

*       1460         *       1480         *       1500
  : CGATGATGATGAACTCTTCATCGTTGATCGATTAAAAGAATTGATCAAATACAAAGGATA : 1500

*       1520         *       1540         *       1560
  : CCAAGTAGCTCCTGCTGAGCTCGAAGCATTGTTAATTTCACACTCGAACATTTCTGATGC : 1560

*       1580         *       1600         *       1620
  : TGCTGTTGTACCATTGAAAGATGAAGTTGCTGGAGAATTACCGGTTGCATTTGTTGTAAG : 1620
```

FIGURE 65 (cont.)

```
              *      1640         *      1660         *      1680
 : ATCAAACGGTTCAAAGATCAGTGAAGATGAAATCAAGCAATACATTTCACAACAGGTTGT : 1680

*      1700         *      1720         *      1740
 : ATTTTACAAGAGAATAAACAGAGTTTATTTCACAGACACAATTCCTAAAGCGGCCTCTGG : 1740

*      1760         *      1780         *      1800
 : CAAAATTCTCCGAAAGAAATTAACCGCAAGACTTAACGAAGGTTTGGTGGTGGCCACTTA : 1800

*      1820         *      1840         *      1860
 : ATTATGTTCGTGTGTGTGACAAAGACGAACGAATTACACTACCTGCATATGCAAATGCAG : 1860

*      1880         *      1900         *      1920
 : CAGCATGAATGGATACAAAATATTCTTAAACAATACAAGTATTGTGTGTTCTGTCACTTC : 1920

*      1940         *      1960         *      1980
 : TGTGCAATATTTGTTTCTCTGTGTGCAAATTCTTTCTCTGCAATGCGGCTTCTGCTGTGG : 1980

*      2000         *      2020         *      2040
 : GTATTGGATCATCAATGCGCGCGGCTTCTTTCTGTGATTAAAAAATAATAATGCCGTGTT : 2040

*      2060         *      2080         *      2100
 : AATCCTACTAGGTAGGCCTATTCGTTCGCTTCTTTTTAGGGGATTATTCACTACTTATTG : 2100

*      2120         *      2140         *      2160
 : ATAGAAGATGTTTAAGACAGCCTTTTCTTTCTCTATAAGAAAAAAATTCAGGTACTGTAT : 2160

*      2180         *      2200         *      2220
 : TAAGTCTTTTTTCGTCAACTGTGTAATGTGACATTTCATTTTTGATGAACAAATGCCACA : 2220

*      2240         *      2260         *      2280
 : GAACATTAAATCAAGTGTCCAACAAAACAATTCACTGCTATTTAGATGTAATATATAGTG : 2280

*      2300         *      2320         *      2340
 : TTCCTGCAAACCGTGTTTAATCAATTTTTTTAGTAAAATTGTCAAGTCTTTTGACAATAT : 2340

*      2360         *      2380         *      2400
 : TATTGCAAATTTTAATCTATATGTAAAAATCTTAAGCGATACAATACTCATTTTAAAGCT : 2400
```

FIGURE 65 (cont.)

```
              *        2420         *        2440         *        2460
: AAGAGAATGATAATAAGATAAGATAGAATGAAATTCATACAAAAAAAAAAAAAAAAAAAA : 2460

*        2480         *        2500         *        2520
: AAAAAAAAAGTACTCTGCGTTGTTACCACTGCTTAATCACTAGTGAATTCGCGGCCGCCT : 2520

*        2540         *        2560         *        2580
: GCAGGTCGACCATATGGGAGAGCTCCCAACGCGTTGGATGCATAGCTTGAGTATTCTATA : 2580

*        2600         *        2620         *        2640
: GTGTCACCTAAATAGCTTGGCGTAATCATGGTCATAGCTGTTTCCTGTGTGAAATTGTTA : 2640

*        2660         *        2680         *        2700
: TCCGCTCACAATTCCACACAACATACGAGCCGGAAGCATAAAGTGTAAAGCCTGGGGTGC : 2700

*        2720         *        2740         *        2760
: CTAATGAGTGAGCTAACTCACATTAATTGCGTTGCGCTCACTGCCCGCTTTCCAGTCGGG : 2760

*        2780         *        2800         *        2820
: AAACCTGTCGTGCCAGCTGCATTAATGAATCGGCCAACGCGCGGGGAGAGGCGGTTTGCG : 2820

*
: TATTGGGCGCTCT : 2833
```

FIGURE 66

```
              *        20         *        40         *        60
 : MSPFPPQQEEFIFRSKLPDIEIPTNLPLHSYCFQNLSQFHNRPCLINGDSGEILTYSDVH  :  60

*        80         *       100         *       120
 : LTVRKIAAGLNTLGINQGDVIMLVLRNSPQFALTFLGASFRGAVITTANPFYTSSELAKQ  : 120

*       140         *       160         *       180
 : ATATKTKLIVTQSAYLSKINDFAKFNNIKIVCIDSSSSPSSEEDATGVVDFSVLTNADEN  : 180

*       200         *       220         *       240
 : DLPDVKLTPNDIVALPFSSGTSGLPKGVMLTHENLVTTISQLVDGENPHQYTNGEDVLLC  : 240

*       260         *       280         *       300
 : VLPMFHIYALNSILLCGIRCGAAVLIVEKFEIKTLLELIEKFKVTVASFVPPIVLALVKS  : 300

*       320         *       340         *       360
 : GESNKYDLSSIRAMITGAAPMGMELEQAVKDRLPHTVLGQGYGMTEAGPLSISLAFAKEP  : 360

*       380         *       400         *       420
 : FRTKPGACGTVVRNAEMKIVDTETGVSLPRNKAGEICIRGTKVMKGYLNDPEATKRTIDE  : 420

*       440         *       460         *       480
 : EGWLHTGDIGLIDDDDELFIVDRLKELIKYKGYQVAPAELEALLISHSNISDAAVVPLKD  : 480

*       500         *       520         *       540
 : EVAGELPVAFVVRSNGSKISEDEIKQYISQQVVFYKRINRVYFTDTIPKAASGKILRKKL  : 540

*       560         *       580         *       600
 : TARLNEGLVVATLCSCVQRRTNYTTCICKCSSMNGYKIFLNNTSIVCSVTSVQYLFLCVQ  : 600

*       620
 : ILSLQCGFCCGYWIINARGFFL  : 622
```

FIGURE 70

```
              *        20         *        40         *        60
   : CGTCGCATGCTCCCGGCCGCCATGGCGGCCGCGGGAATTCGATTAAGCAGTGGTAACAAC :   60

*        80         *       100         *       120
   : GCAGAGTACGCGGGGAATTAACATCTCCACAACCACAATAACAATAACAACAATGGATCT :  120

*       140         *       160         *       180
   : ACTCCTTCTTGAAAAGACTCTTTTATCCCTCTTCATCGCCGCTATAATCGCAATCACAAT :  180

*       200         *       220         *       240
   : CTCAAAACTCCGTGGAAAACGCTTCAAACTTCCACCAGGTCCATTTCCAGTTCCAATTTT :  240

*       260         *       280         *       300
   : TGGTAATTGGCTTCAAGTTGGCGATGATCTCAACCACCGTAATTTAACTGATTTAGCCAA :  300

*       320         *       340         *       360
   : ACGCTTCGGCGAAATCCTGCTTCTCCGGATGGGACAACGAAACCTGGTCGTTGTCTCATC :  360

*       380         *       400         *       420
   : ACCGGAGTTAGCAAAAGAAGTCCTTCACACACAAGGTGTCGAATTCGGTTCCAGAACACG :  420

*       440         *       460         *       480
   : GAACGTCGTATTCGACATCTTTACCGGTAAAGGACAGGACATGGTTTTCACCGTGTACGG :  480

*       500         *       520         *       540
   : TGAACATTGGCGTAAAATGAGGAGAATTATGACAGTACCATTTTTCACAAACAAAGTTGT :  540

*       560         *       580         *       600
   : TCAACAATATAGATTTGGTTGGGAATCTGAAGCTGAAAGTGTTGTTAATGATGTTAAGAA :  600

*       620         *       640         *       660
   : AAATAATGAAGCTAGTGTTGGTGGAATTGTGATTAGAAGAAGATTACAATTGATGATGTA :  660

*       680         *       700         *       720
   : TAATATTATGTATAGGATTATGTTTGATAGAAGATTTGAAAGTGAAGAAGATCCTTTGTT :  720

*       740         *       760         *       780
   : TGTGAAATTGAAAGCTTTGAATGGTGAAAGGAGTCGTTTAGCTCAAAGTTTTGAGTATAA :  780

*       800         *       820         *       840
   : TTATGGTGATTTTATTCCAATTTTGAGACCTTTTTTGAAAGGTTATTTGAAGGTTTGTAA :  840

*       860         *       880         *       900
   : AGAGGTTAAGGATCGTAGGTTGCAGCTTTTCAAAGACTATTTCGTTGATGAGAGAAAGAA :  900
```

FIGURE 70 (cont.)

```
              *       920         *       940         *       960
 : GCTTGAAAGTACCAAGAGCACCACTAGCAATGATGGACTTAAATGTGCTATTGATCACAT :  960

*       980         *      1000         *      1020
 : TTTGGATGCTCAAAAGAAAGGAGAGATCAATGATGACAACGTTCTTTACATTGTCGAGAA : 1020

*      1040         *      1060         *      1080
 : CATCAATGTTGCTGCAATTGAAACAACACTATGGTCAATTGAATGGGGAATTGCTGAGCT : 1080

*      1100         *      1120         *      1140
 : AGTGAACCACCAAGGGATCCAAAACAAAGTAAGGGAAGAGATGGACAGAGTTCTAGGACC : 1140

*      1160         *      1180         *      1200
 : AGGACACCAAGTAACCGAGCCGGATCTTCAGAAGCTACCTTACCTACAAGCCGTGATCAA : 1200

*      1220         *      1240         *      1260
 : AGAGACACTTCGTCTACGAATGGCAATTCCACTCCTCGTCCCACACATGAACCTTCATGA : 1260

*      1280         *      1300         *      1320
 : TGCAAAGCTTGCCGGTTATGACATCCCGGCCGAGAGCAAGATATTGGTCAACGCGTGGTG : 1320

*      1340         *      1360         *      1380
 : GCTTGCAAATAACCCGGCTCTATGGAAAAATCCAGAGGAATTTAGGCCTGAGAGGTTCTT : 1380

*      1400         *      1420         *      1440
 : GGAGGAAGAGGCGCATGTTGAGGCTAATGGAAATGACTTTAGGTACCTTCCTTTCGGTGT : 1440

*      1460         *      1480         *      1500
 : TGGTAGAAGGAGTTGTCCTGGAATTATTCTTGCTTTACCTATCCTTGGTATTACTATCGG : 1500

*      1520         *      1540         *      1560
 : GCGTCTTGTTCAGAATTTCGAGCTTTTGCCTCCACCCGGACAATCTAAGATTGATACTTC : 1560

*      1580         *      1600         *      1620
 : CGAGAAAGGAGGACAGTTTAGTTTGCACATACTCAAACATTCCACCATTGTTGCTAAGCC : 1620

*      1640         *      1660         *      1680
 : AAGATCATTTTAATTAGTATTCACACTAATACCCTTTATTTGTTTTACTTTACTTTGTGT : 1680

*      1700         *      1720         *      1740
 : AATGCATTTTAATGATTCATAATGTGGGAATGTTATTAAAATGTCTTAGGTGAATAATGT : 1740
```

FIGURE 70 (cont.)

```
          *       1760        *       1780         *       1800
: TGTTGTTTTGTGCTTGTCCCATGTATAAATCTTTTGAACTTTAAGTAATGGTTTTGAGAT : 1800

*       1820        *       1840         *       1860
: GATTTTGTAACAACACTTGTCCCTTATATTCTCTTGATTGATTAATAGTTTGTTGTCCTG : 1860

*       1880        *       1900         *       1920
: AAAAAAAAAAAAAAAAAAAAAAAAAAAAAAAAAAAAAAAAAAAAAAAAAAAAAAAAAAAA : 1920

*       1940        *       1960         *       1980
: AAAAAAAAAAAAAAAAAAAAAAAAAAAAAAAAAAAAAAAAAAAAAAAAAAAAAAAAAAAA : 1980

*       2000        *       2020         *       2040
: AAAAAAAAAAAAAAAAAACAAAAAAAAAAAAAAAAAAAAAAAAAAAAAAGTACTCTGCGTT : 2040

*       2060        *       2080         *       2100
: GTTACCACTGCTTAATCACTAGTGAATTCGCGGCCGCCTGCAGGTGGGCCATATGGGAGA : 2100

*       2120        *       2140         *
: GCTCCCAACGCGTTGGATGCATAGCTTGAGTATTCTATTAGTGTCAACCCCC : 2152
```

FIGURE 71

```
            *        20         *        40         *        60
: MDLLLLEKTLLSLFIAAIIAITISKLRGKRFKLPPGPFPVPIFGNWLQVGDDLNHRNLTD :  60

*        80         *       100         *       120
: LAKRFGEILLLRMGQRNLVVVSSPELAKEVLHTQGVEFGSRTRNVVFDIFTGKGQDMVFT : 120

*       140         *       160         *       180
: VYGEHWRKMRRIMTVPFFTNKVVQQYRFGWESEAESVVNDVKKNNEASVGGIVIRRRLQL : 180

*       200         *       220         *       240
: MMYNIMYRIMFDRRFESEEDPLFVKLKALNGERSRLAQSFEYNYGDFIPILRPFLKGYLK : 240

*       260         *       280         *       300
: VCKEVKDRRLQLFKDYFVDERKKLESTKSTTSNDGLKCAIDHILDAQKKGEINDDNVLYI : 300

*       320         *       340         *       360
: VENINVAAIETTLWSIEWGIAELVNHQGIQNKVREEMDRVLGPGHQVTEPDLQKLPYLQA : 360

*       380         *       400         *       420
: VIKETLRLRMAIPLLVPHMNLHDAKLAGYDIPAESKILVNAWWLANNPALWKNPEEFRPE : 420

*       440         *       460         *       480
: RFLEEEAHVEANGNDFRYLPFGVGRRSCPGIILALPILGITIGRLVQNFELLPPPGQSKI : 480

*       500
: DTSEKGGQFSLHILKHSTIVAKPRSF : 506
```

FIGURE 74

```
              *        20         *        40         *        60
: TACTCAAGCTATGCATCCAACGCGTTGGGAGCTCTCCCATATGGTCGATCTGCAGGCGGC  :   60

*        80         *       100         *       120
: CGCGAATTCACTAGTGATTAAGCAGTGGTAACAACGCAGAGTACGCGGGGGAGTCGTTTG  :  120

*       140         *       160         *       180
: GCACAAAGTTTTGAGTATAATTATGGTGATTTTATTCCTATTTTGAGACCTTTTTTGAAA  :  180

*       200         *       220         *       240
: GGTTATTTGAAGGTTTGTAAAGAGGTTAAAGATCGTAGGTTGCAGCTTTTCAAAGACTAT  :  240

*       260         *       280         *       300
: TTCGTTGATGAGAGAAAGAAACTTGAAAGCACCAAGAGCACCACTAGCAATGATGGACTT  :  300

*       320         *       340         *       360
: AAATGTGCAATTGATCACATTTTGGATGCTCAAAAGAAGGGAGAGATCAATGATGACAAC  :  360

*       380         *       400         *       420
: GTTCTTTACATTGTTGAGAACATCAAGGTTGCTGCAATTGAAACAACACTATGGTCAATT  :  420

*       440         *       460         *       480
: GAATGGGGAATTGCTGAGCTAGTGAACCACCAAGAGATCCAAAACAAAGTAAGGGAAGAG  :  480

*       500         *       520         *       540
: ATGGACAGAGTTCTAGGACCAGGACACCAAGTAACCGAGCCGGATCTTCAGAAGCTACCT  :  540

*       560         *       580         *       600
: TACCTACAAGCCGTGATCAAAGAGACACTTCGTCTTCGAATGGCAATCCCACTCCTCGTC  :  600

*       620         *       640         *       660
: CCACACATGAACCTTCATGATGCAAAGCTTGCCGGTTATGACATCCCGGCCGAGAGCAAG  :  660

*       680         *       700         *       720
: ATATTGGTCAATGCTTGGTGGCTTGCAAATAACCCGGCTTTGTGGAAAAAGCCGGAGGAA  :  720

*       740         *       760         *       780
: TTTAGGCCAGAGGGGTTCTTGGAGGAAGAGGCGCATGTTGAGGCTAATGGAAATGACTTT  :  780

*       800         *       820         *       840
: AGGTACCTTCCTTTCGGTGTTGGTAGAAGGAGTTGTCCTGGAATTATTCTTGCTTTACCT  :  840
```

FIGURE 74 (cont.)

```
              *         860         *         880         *         900
  : ATCCTTGGTATTACTATCGGGCGTCTTGTTCAGAATTTCGAGCTTTTGCCTCCACCCGGA :  900

*         920         *         940         *         960
  : CAATCTAAGATTGATACTTCTGAGAAAGGAGGACAGTTTAGTTTGCACATACTCAAACAT :  960

*         980         *        1000         *        1020
  : TCCACCATTGTTGCTAAGCCAAGATCATTTTAATTAGTATTCACACTAATACCCTTTATT : 1020

*        1040         *        1060         *        1080
  : TGTTATAAAAAAAAAAAAAAAAAAAAAAAAAAAAAAAAGTACTCTGCGTTGTTACCACTG : 1080

*        1100         *        1120         *        1140
  : CTTAATCGAATTCCCGCGGCCGCCATGGCGGCCGGGAGCATGCGACGTCGGGCCCAATTC : 1140

*        1160         *        1180         *        1200
  : GCCCTATAGTGAGTCGTATTACAATTCACTGGCCGTCGTTTTACAACGTCGTGACTGGGA : 1200

*        1220         *
  : AAACCCTGGCGTTACCCAACTTAATCGCCTTGCA : 1234
```

FIGURE 75

```
            *        20         *        40         *        60
: AVVTTQSTRGSRLAQSFEYNYGDFIPILRPFLKGYLKVCKEVKDRRLQLFKDYFVDERKK :  60

*        80         *       100         *       120
: LESTKSTTSNDGLKCAIDHILDAQKKGEINDDNVLYIVENIKVAAIETTLWSIEWGIAEL : 120

*       140         *       160         *       180
: VNHQEIQNKVREEMDRVLGPGHQVTEPDLQKLPYLQAVIKETLRLRMAIPLLVPHMNLHD : 180

*       200         *       220         *       240
: AKLAGYDIPAESKILVNAWWLANNPALWKKPEEFRPEGFLEEEAHVEANGNDFRYLPFGV : 240

*       260         *       280         *       300
: GRRSCPGIILALPILGITIGRLVQNFELLPPPGQSKIDTSEKGGQFSLHILKHSTIVAKP : 300

: RSF : 303
```

FIGURE 77

```
            *        20         *        40         *        60
:  GCCCGACGTCGCATGCTCCCGGCCGCCATGGCGGCCGCGGGAATTCGATTAATTCAGTGG  :  60

*        80         *       100         *       120
:  TAACAACGCAGAGTACGCGGGACATGAACCTTCATGATGCAAAGCTTGCCGGTTATGACA  :  120

*       140         *       160         *       180
:  TCCCGGCCGAGAGCAAGATATTGGTCAACGCGTGGTGGCTTGCAAATAACCCGGCTCTAT  :  180

*       200         *       220         *       240
:  GGAAAAAGCCGGAGGAATTTAGGCCTGAGAGGTTCTTGGAGGAAGAGGCGCATGTTGAGG  :  240

*       260         *       280         *       300
:  CTAATGGAAATGACTTTAGGTACCTTCCTTTCGGTGTTGGTAGAAGGAGTTGTCCTGGAA  :  300

*       320         *       340         *       360
:  TTATTCTTGCTTTACCTATCCTTGGTATTACTATCGGGCGTCTTGTTCAGAATTTCGAGC  :  360

*       380         *       400         *       420
:  TTTTGCCTCCACCCGGACAATCTAAGATTGATACTTCCGAGAAAGGAGGACAATTTAGTT  :  420

*       440         *       460         *       480
:  TGCACATACTCAAACATTCCACCATTGTTGCTAAGCCAAGATCATTTTAATTAGTATTCA  :  480

*       500         *       520         *       540
:  CACTAATACCCTTTATTTGTTTTACTTTACTTTGTGTAATGCATTTTAATGATTCATAAT  :  540

*       560         *       580         *       600
:  GTGGGAATGTTATTAAAATGTCTTAGGTGAATAATGTTGTTGTTTTGTGCTTGTCCCATG  :  600

*       620         *       640         *       660
:  TATAAATCTTTTGAACTTTTAAGTAATGGTTTTGAGATGATTTTGTAACAAAAAAAAAAA  :  660

*       680         *       700         *       720
:  AAAAAAAAAAAAAAAAAAAAAAAAAAAAAAAAAAAAGAAAAAAAAAAAAAAAAAAAAAAA  :  720

*       740
:  AAAAAAGTACCCTGGGTTGTTACC  :  744
```

FIGURE 78

```
            *        20         *        40         *        60
: PTSHAPGRHGGRGNSINSVVTTQSTRDMNLHDAKLAGYDIPAESKILVNAWWLANNPALW :  60

*        80         *       100         *       120
: KKPEEFRPERFLEEEAHVEANGNDFRYLPFGVGRRSCPGIILALPILGITIGRLVQNFEL : 120

*       140         *
: LPPPGQSKIDTSEKGGQFSLHILKHSTIVAKPRSF : 155
```

FIGURE 82
A
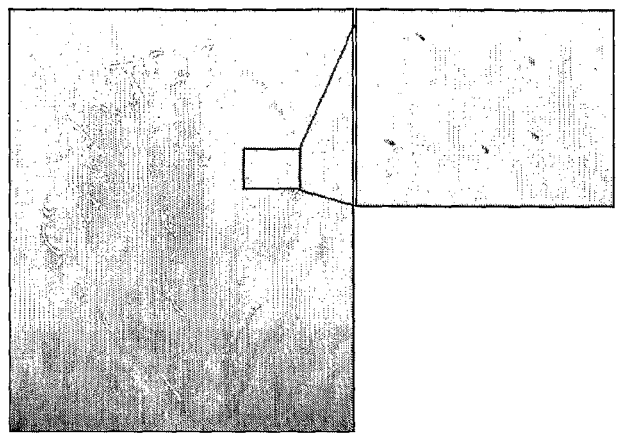
B
C
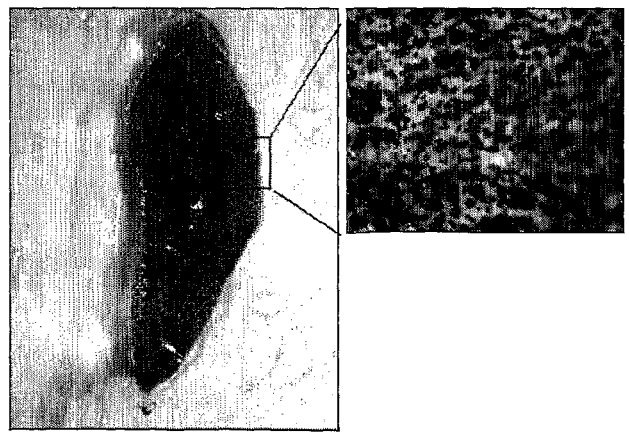

MODIFICATION OF FLAVONOID BIOSYNTHESIS IN PLANTS

The present invention relates generally to nucleic acid fragments and their encoded amino acid sequences for flavonoid biosynthetic enzymes in plants, and the use thereof for the modification of flavonoid biosynthesis in plants.

Flavonoids constitute a relatively diverse family of aromatic molecules that are derived from phenylalanine and malonyl-coenzyme A (CoA, via the fatty acid pathway). These compounds include six major subgroups that are found in most higher plants: the chalcones, flavones, flavonols, flavandiols, anthocyanins and condensed tannins (or proanthocyanidins). A seventh group, the aurones, is widespread, but not ubiquitous.

Some plant species also synthesize specialised forms of flavonoids, such as the isoflavonoids that are found in legumes and a small number of non-legume plants. Similarly, sorghum and maize are among the few species known to synthesize 3-deoxyanthocyanins (or phlobaphenes in the polymerised form). The stilbenes, which are closely related to flavonoids, are synthesised by another group of unrelated species that includes grape, peanut and pine.

Besides providing pigmentation to flowers, fruits, seeds, and leaves, flavonoids also have key roles in signalling between plants and microbes, in male fertility of some species, in defense as antimicrobial agents and feeding deterrents, and in UV protection.

Flavonoids also have significant activities when ingested by animals, and there is great interest in their potential health benefits, particularly for compounds such as isoflavonoids, which have been linked to anticancer benefits, and stilbenes that are believed to contribute to reduced heart disease.

The major branch pathways of flavonoid biosynthesis start with general phenylpropanoid metabolism and lead to the nine major subgroups: the colorless chalcones, aurones, isoflavonoids, flavones, flavonols, flavandiols, anthocyanins, condensed tannins, and phlobaphene pigments. The enzyme phenylalanine ammonia-lyase (PAL) of the general phenylpropanoid pathway will lead to the production of cinnamic acid. Cinnamate-4-hydroxylase (C4H) will produce p-coumaric acid which will be converted through the action of 4-coumaroyl:CoA-ligase (4CL) to the production of 4-coumaroyl-CoA and malonyl-CoA.

In the phenylpropanoid pathway, chalcone synthase (CHS) uses malonyl CoA and 4-coumaryl CoA as substrates. Chalcone reductase (CHR) balances the production of 5-hydroxy- or 5-deoxyflavonoids. The next enzyme, chalcone isomerase (CHI) catalyses ring closure to form a flavanone, but the reaction can also occur spontaneously. Further enzymes in the pathway are: flavanone 3-hydroxylase (F3H), dihydroflavonol 4-reductase (DFR), flavonoid 3'-hydroxylase (F3'H) and flavonoid 3',5' hydroxylase (F3'5'H).

In the branch of the phenylpropanoid pathway that is specific to condensed tannin and anthocyanin production, leucoanthocyanidins can be reduced to catechins by leucoanthocyanidin reductase (LAR) or to anthocyanidins by leucoanthocyanidin dioxygenase (LDOX). Anthocyanidins can be converted to anthocyanins by the addition of sugar groups, or to epicatechins by anthocyanidin reductase (ANR), encoded by the BANYULS gene. Catechins and epicatechins are the subunits of condensed tannins (CTs), which in Arabidopsis are thought to be transported into the vacuole by a multidrug secondary transporter-like protein, TRANSPARENT TESTA 12 (TT12), and polymerised by an unknown mechanism.

Enzymes in the flavonoid pathway have been found to be controlled by a range of transcription factors in *Arabidopsis*, maize and petunia. In *Arabidopsis*, condensed tannin biosynthesis requires the function of TRANSPARENT TESTA 2 (TT2), a myb family factor, TRANSPARENT TESTA 8 (TT8), a myc family factor and TRANSPARENT TESTA GLABRA 1 (TTG1), a WD40 family factor, among other transcription factors. These three proteins are thought to form a transcription complex that coordinately activates multiple flavonoid pathway enzymes in order to promote condensed tannin production in *Arabidopsis* seeds. Other myc and myb family transcription factors regulate distinct parts of the flavonoid pathway in maize, petunia and other plant species.

While nucleic acid sequences encoding some flavonoid biosynthetic enzymes have been isolated for certain species of plants, for example certain C4H, 4CL, LDOX, TT12-like transporters and TT8-like, TT4-like and TTG1-like transcription factors, there remains a need for materials useful in modifying flavonoid biosynthesis; in modifying protein binding, metal chelation, anti-oxidation, and UV-light absorption; in modifying plant pigment production; in modifying plant defense to biotic stresses such as viruses, microorganisms, insects, fungal pathogens; in modifying forage quality, for example by disrupting protein foam and conferring protection from rumen pasture bloat, particularly in forage legumes and grasses, including alfalfa, medics, clovers, ryegrasses and fescues. There is also a need for methods of using such materials.

It is an object of the present invention to overcome, or at least alleviate, one or more of the difficulties or deficiencies associated with the prior art or to assist in meeting the needs stated above.

In one aspect, the present invention provides a substantially purified or isolated nucleic acid or nucleic acid fragment encoding a flavonoid biosynthesis-regulating transcription factor selected from the group consisting of TRANSPARENT TESTA GLABRA 1 (TTG1), TRANSPARENT TESTA 2 (TT2), and TRANSPARENT TESTA 8 (TT8); a flavonoid biosynthetic enzyme selected from the group consisting of leucoanthocyanidin dioxygenase (LDOX), cinnamate-4-hydroxylase (C4H) and 4-coumaroyl:CoA-ligase (4CL); and a flavonoid transporter TRANSPARENT TESTA 12 (TT12); from a clover (*Trifolium*), medic (*Medicago*), ryegrass (*Lolium*) or fescue (*Festuca*) species; or a functionally active fragment or variant thereof. The present invention further provides substantially purified or isolated nucleic acids or nucleic acid fragments complementary and antisense to the nucleic acids or nucleic acid fragments of the present invention.

The present invention also provides substantially purified or isolated nucleic acids or nucleic acid fragments encoding amino acid sequences for a class of proteins which are related to C4H, 4CL, LDOX, TT12, TT2, TT8 and TTG1, or functionally active fragments or variants thereof. Such proteins are referred to herein as C4H-like, 4CL-like, LDOX-like, TT12-like, TT2-like, TT8-like and TTG1-like, respectively. Proteins are related in that either one of both of the following criteria apply: (i) the genes which encode these proteins are expressed in a similar manner to C4H, 4CL, LDOX, TT12, TT2, TT8 or TTG1, and (ii) the polypeptides have similar functional activity to C4H, 4CL, LDOX, TT12, TT2, TT8 and TTG1. In a preferred embodiment, the related proteins are at least 70%, preferably at least 80%, more preferably at least 90% homologous to C4H, 4CL, LDOX, TT12, TT2, TT8 or TTG1. Also provided are substantially isolated nucleic acids or nucleic acid fragments complementary and antisense to C4H-like, 4CL-like, LDOX-like, TT12-like, TT2-like, TT8-like and TTG1-like-encoding nucleic acid fragments.

The individual or simultaneous enhancement or otherwise manipulation of the expression of C4H, 4CL, LDOX, TT12, TT2, TT8, TTG1 or -like polypeptides in plants may enhance or otherwise alter flavonoid biosynthesis; may enhance or otherwise alter the plant capacity for protein binding, metal chelation, anti-oxidation, and UV-light absorption; may enhance or reduce or otherwise alter plant pigment production.

The individual or simultaneous enhancement or otherwise manipulation of the expression of C4H, 4CL, LDOX, TT12, TT2, TT8, TTG1 or -like polypeptides in plants has significant consequences for a range of applications in, for example, plant production and plant protection. For example, it has applications in increasing plant tolerance and plant defense to biotic stresses such as viruses, microorganisms, insects and fungal pathogens; in improving plant forage quality, for example by disrupting protein foam and in conferring protection from rumen pasture bloat; in reducing digestion rates in the rumen and reducing parasitic load; in the production of plant compounds leading to health benefits, such as isoflavonoids, which have been linked to anticancer benefits, and stilbenes that are believed to contribute to reduced heart disease.

White clover expresses multiple isoforms of 4CL and C4H. Co-ordinate expression of genes encoding isoforms of 4CL, PAL and C4H that are involved in the production of specific flavonoids, such as CTs, may allow the production of various flavonoids to be regulated independently by cell-specific factors and the circadian clock. Hence, the identification of CT-specific isoforms of enzymes located early in the phenylpropanoid pathway is an important step towards modification of this pathway in forage legumes.

Methods for the manipulation of C4H, 4CL, LDOX, TT12, TT2, TT8, TTG1 or like gene activities in plants, including legumes such as clovers (*Trifolium* species), lucerne (*Medicago sativa*) and grass species such as ryegrasses (*Lolium* species) and fescues (*Festuca* species) may facilitate the production of, for example, forage legumes and forage grasses and other crops with enhanced tolerance to biotic stresses such as viruses, microorganisms, insects and fungal pathogens; altered pigmentation in flowers; forage legumes with enhanced herbage quality and bloat-safety; crops with enhanced isoflavonoid content leading to health benefits.

The use of transcription factors to modify multiple product-specific enzymes in the flavonoid pathway may be a useful alternative strategy to cloning genes encoding many enzymes and modifying their expression in transgenic plants.

The clover (*Trifolium*), medic (*Medicago*), ryegrass (*Lolium*) or fescue (*Festuca*) species may be of any suitable type, including white clover (*Trifolium repens*), red clover (*Trifolium pretense*), subterranean clover (*Trifolium subterraneum*), alfalfa (*Medicago sativa*), Italian or annual ryegrass (*Lolium multiflorum*), perennial ryegrass (*Lolium perenne*), tall fescue (*Festuca arundinacea*), meadow fescue (*Festuca pratensis*) and red fescue (*Festuca rubra*). Preferably the species is a clover or a ryegrass, more preferably white clover (*T. repens*) or perennial ryegrass (*L. perenne*). White clover (*Trifolium repens* L.) and perennial ryegrass (*Lolium perenne* L.) are key pasture legumes and grasses, respectively, in temperate climates throughout the world. Perennial ryegrass is also an important turf grass.

Nucleic acids according to the invention may be full-length genes or part thereof, and are also referred to as "nucleic acid fragments" and "nucleotide sequences" in this specification. For convenience, the expression "nucleic acid or nucleic acid fragment" is used to cover all of these.

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

Such nucleic acids or nucleic acid fragments could be assembled to form a consensus contig. As used herein, the term "consensus contig" refers to a nucleotide sequence that is assembled from two or more constituent nucleotide sequences that share common or overlapping regions of sequence homology. For example, the nucleotide sequence of two or more nucleic acids or nucleic acid fragments can be compared and aligned in order to identify common or overlapping sequences. Where common or overlapping sequences exist between two or more nucleic acids or nucleic acid fragments, the sequences (and thus their corresponding nucleic acids or nucleic acid fragments) can be assembled into a single contiguous nucleotide sequence.

In a preferred embodiment of this aspect of the invention, the substantially purified or isolated nucleic acid or nucleic acid fragment encoding a TT12 or TT12-like protein or complementary or antisense to a sequence encoding a TT12 or TT12-like protein includes a nucleotide sequence selected from the group consisting of (a) the sequences shown in FIGS. 1 and 33 hereto; (b) the complement of the sequences recited in (a); (c) sequences antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encoding a TTG1 or TTG1-like protein or complementary or antisense to a sequence encoding a TTG1 or TTG1-like protein includes a nucleotide sequence selected from the group consisting of (a) the sequences shown in FIGS. 4 and 37 hereto; (b) the complement of the sequences recited in (a); (c) the sequence antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encoding an TT2 or TT2-like protein or complementary or antisense to a sequence encoding a TT2 or TT2-like protein includes a nucleotide sequence selected from the group consisting of (a) sequences shown in FIGS. 6, 9, 41 and 44 hereto; (b) complements of the sequences recited in (a); (c) sequences antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encoding a TT8 or TT8-like protein or complementary or antisense to a sequence encoding a TT8 or TT8-like protein includes a nucleotide sequence selected from the group consisting of (a) the sequences shown in FIGS. 11 and 48 hereto; (b) the complement of the sequences recited in (a); (c) the sequences antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encoding a LDOX or LDOX-like protein or complementary or antisense to a sequence encoding a LDOX or LDOX-like protein includes a nucleotide sequence selected from the group consisting of (a) the sequences shown in FIGS. 13 and 52 hereto; (b) the complement of the sequences recited in (a); (c) sequences antisense to the sequences recited in (a) and (b); and (d) functionally active fragments and variants of the sequences recited in (a), (b) and (c).

In a still further preferred embodiment of this aspect of the invention, the substantially purified or isolated nucleic acid or nucleic acid fragment encoding a 4CL or 4CL-like protein or complementary or antisense to a sequence encoding a 4CL or 4CL-like protein includes a nucleotide sequence selected from the group consisting of (a) sequences shown in FIGS. 16, 19, 21, 23, 56, 59, 62 and 65 hereto; (b) complements of the sequences recited in (a); (c) sequences antisense to the sequences recited in (a) and (b); and (d) functionally active fragments and variants of the sequences recited in (a), (b) and (c).

In a further preferred embodiment of this aspect of the invention, the substantially purified or isolated nucleic acid or nucleic acid fragment encoding a C4H or C4H-like protein or complementary or antisense to a sequence encoding a C4H or C4H-like protein includes a nucleotide sequence selected from the group consisting of (a) sequences shown in FIGS. 25, 28, 30, 70, 74 and 77 hereto; (b) complements of the sequences recited in (a); (c) sequences antisense to the sequences recited in (a) and (b); and (d) functionally active fragments and variants of the sequences recited in (a), (b) and (c).

By "functionally active" in relation to nucleic acids it is meant that the fragment or variant (such as an analogue, derivative or mutant) encodes a polypeptide, which is capable of modifying flavonoid biosynthesis; in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 75% identity to the relevant part of the above mentioned nucleotide sequence, more preferably at least approximately 80% identity, more preferably at least approximately 90% identity, most preferably at least approximately 95% identity. Such functionally active variants and fragments include, for example, those having nucleic acid changes which result in conservative amino acid substitutions of one or more residues in the corresponding amino acid sequence. Preferably the fragment has a size of at least 30 nucleotides, more preferably at least 45 nucleotides, most preferably at least 60 nucleotides.

It will also be understood that the term "comprises" (or its grammatical variants) as used in this specification is equivalent to the term "includes" and should not be taken as excluding the presence of other elements or features.

Nucleic acids or nucleic acid fragments encoding at least a portion of several C4Hs, 4CLs, LDOXs, and candidate TT12, TT2, TT8 and TTG1 orthologs have been isolated and identified. The nucleic acids or nucleic acid fragments of the present invention may be used to isolate cDNAs and genes encoding homologous proteins from the same or other plant species. Isolation of homologous genes can be isolated using sequence-dependent protocols, such as methods of nucleic acid hybridisation, and methods of DNA and RNA amplification as exemplified by various uses of nucleic acid amplification technologies (e.g. polymerase chain reaction, ligase chain reaction).

For example, genes encoding other C4H or C4H-like, 4CL or 4CL-like, LDOX or LDOX-like, TT12-like, TT2-like, TT8-like, TTG1-like proteins, either as cDNAs or genomic DNAs, may be isolated directly by using all or a portion of the nucleic acids or nucleic acid fragments of the present invention as hybridisation probes to screen libraries from the desired plant. Specific oligonucleotide probes based upon the nucleic acid sequences of the present invention may be designed and synthesized. Moreover, the entire sequences may be used directly to synthesize DNA probes by methods such as random primer DNA labelling, nick translation, or end-labelling techniques, or RNA probes using available in vitro transcription systems. In addition, specific primers may be designed and used to amplify a part or all of the sequences of the present invention. The resulting amplification products may be labelled directly during amplification reactions or labelled after amplification reactions, and used as probes to isolate full-length cDNA or genomic fragments under conditions of appropriate stringency.

In addition, short segments of the nucleic acids or nucleic acid fragments of the present invention may be used in protocols to amplify longer nucleic acids or nucleic acid fragments encoding homologous genes from DNA or RNA. For example, polymerase chain reaction may be performed on a library of cloned nucleic acid fragments wherein the sequence of one primer is derived from the nucleic acid sequences of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol (Frohman et al. (1988) *Proc. Natl. Acad. Sci. USA* 85:8998, the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments may be isolated (Ohara et al. (1989) *Proc. Natl. Acad Sci USA* 86:5673; Loh et al. (1989) *Science* 243:217, the entire disclosures of which are incorporated herein by reference). Products generated by the 3' and 5' RACE procedures may be combined to generate full-length cDNAs.

In a second aspect of the present invention there is provided a substantially purified or isolated polypeptide from a clover (*Trifolium*), medic (*Medicago*), ryegrass (*Lolium*) or fescue (*Festuca*) species, selected from the group consisting of C4H and C4H-like, 4CL and 4CL-like, LDOX and LDOX-like, TT12 and TT12-like, TT2 and TT2-like, TT8 and TT8-like and TTG1 and TTG1-like proteins; and functionally active fragments and variants thereof.

The clover (*Trifolium*), medic (*Medicago*), ryegrass (*Lolium*) or fescue (*Festuca*) species may be of any suitable type, including white clover (*Trifolium repens*), red clover (*Trifolium pratense*), subterranean clover (*Trifolium subterraneum*), alfalfa (*Medicago sativa*), Italian or annual ryegrass (*Lolium multiflorum*), perennial ryegrass (*Lolium perenne*), tall fescue (*Festuca arundinacea*), meadow fescue (*Festuca pratensis*) and red fescue (*Festuca rubra*). In particular, the species may be a clover or a ryegrass, more particularly white clover (*T. repens*) or perennial ryegrass (*L. perenne*).

In a preferred embodiment of this aspect of the invention, the substantially purified or isolated TT12 or TT12-like polypeptide includes an amino acid sequence selected from the group consisting of the sequences shown in FIGS. 2 and 34 hereto, and functionally active fragments and variants thereof.

In a further preferred embodiment of this aspect of the invention, the substantially purified or isolated TTG1 or TTG1-like polypeptide includes an amino acid sequence selected from the group consisting of the sequences shown in FIGS. 5 and 38 hereto, and functionally active fragments and variants thereof.

In a further preferred embodiment of this aspect of the invention, the substantially purified or isolated TT2 or TT2-like polypeptide includes an amino acid sequence selected from the group consisting of the sequences shown in FIGS. 7, 10, 42 and 45 hereto, and functionally active fragments and variants thereof.

In a still further preferred embodiment of this aspect of the invention, the substantially purified or isolated TT8 or TT8-like polypeptide includes an amino acid sequence selected from the group consisting of the sequences shown in FIGS. 12 and 49 hereto, and functionally active fragments and variants thereof.

In a still further preferred embodiment of this aspect of the invention, the substantially purified or isolated LDOX or LDOX-like polypeptide includes an amino acid sequence selected from the group consisting of the sequences shown in FIGS. 14 and 53 hereto, and functionally active fragments and variants thereof.

In a still further preferred embodiment of this aspect of the invention, the substantially purified or isolated 4CL or 4CL-like polypeptide includes an amino acid sequence selected from the group consisting of the sequences shown in FIGS. 17, 20, 22, 24, 57, 60, 63 and 66 hereto, and functionally active fragments and variants thereof.

In a still further preferred embodiment of this aspect of the invention, the substantially purified or isolated C4H or C4H-like polypeptide includes an amino acid sequence selected from the group consisting of the sequences shown in FIGS. 26, 29, 31, 71, 75 and 78 hereto, and functionally active fragments and variants thereof.

By "functionally active" in relation to polypeptides it is meant that the fragment or variant has one or more of the biological properties of the proteins TT12, TT12-like, TTG1, TTG1-like, TT2, TT2-like, TT8, TT8-like, LDOX, LDOX-like, 4CL, 4CL-like, C4H, C4H-like, respectively. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the above mentioned amino acid sequence, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

In a further embodiment of this aspect of the invention, there is provided a polypeptide recombinantly produced from a nucleic acid or nucleic acid fragment according to the present invention.

Availability of the nucleotide sequences of the present invention and deduced amino acid sequences facilitates immunological screening of cDNA expression libraries. Synthetic peptides representing portions of the instant amino acid sequences may be synthesized. These peptides may be used to immunise animals to produce polyclonal or monoclonal antibodies with specificity for peptides and/or proteins including the amino acid sequences. These antibodies may be then used to screen cDNA expression libraries to isolate full-length cDNA clones of interest.

A genotype is the genetic constitution of an individual or group. Variations in genotype are important in commercial breeding programs, in determining parentage, in diagnostics and fingerprinting, and the like. Genotypes can be readily described in terms of genetic markers. A genetic marker identifies a specific region or locus in the genome. The more genetic markers, the finer defined is the genotype. A genetic marker becomes particularly useful when it is allelic between organisms because it then may serve to unambiguously identify an individual. Furthermore, a genetic marker becomes particularly useful when it is based on nucleic acid sequence information that can unambiguously establish a genotype of an individual and when the function encoded by such nucleic acid is known and is associated with a specific trait. Such nucleic acids and/or nucleotide sequence information including single nucleotide polymorphisms (SNPs), variations in single nucleotides between allelic forms of such nucleotide sequence, may be used as perfect markers or candidate genes for the given trait.

Applicants have identified a number of SNPs of the nucleic acids or nucleic acid fragments of the present invention. These are indicated (marked with grey on the black background) in the figures that show multiple alignments of nucleotide sequences of nucleic acid fragments contributing to consensus contig sequences. See for example, FIGS. 3, 15, 18 and 27 hereto.

Accordingly, in a further aspect of the present invention, there is provided a substantially purified or isolated nucleic acid or nucleic acid fragment including a single nucleotide polymorphism (SNP) from a nucleic acid or nucleic acid fragment according to the present invention, for example a SNP from a nucleic acid sequence shown in FIGS. 3, 15, 18 and 27 hereto; or complements or sequences antisense thereto, and functionally active fragments and variants thereof.

In a still further aspect of the present invention there is provided a method of isolating a nucleic acid or nucleic acid fragment of the present invention including a SNP, said method including sequencing nucleic acid fragments from a nucleic acid library.

The nucleic acid library may be of any suitable type and is preferably a cDNA library.

The nucleic acid or nucleic acid fragment may be isolated from a recombinant plasmid or may be amplified, for example using polymerase chain reaction.

The sequencing may be performed by techniques known to those skilled in the art.

In a still further aspect of the present invention, there is provided use of the nucleic acids or nucleic acid fragments of the present invention including SNPs, and/or nucleotide sequence information thereof, as molecular genetic markers.

In a still further aspect of the present invention there is provided use of a nucleic acid or nucleic acid fragment of the present invention, and/or nucleotide sequence information thereof, as a molecular genetic marker.

More particularly, nucleic acids or nucleic acid fragments according to the present invention and/or nucleotide sequence information thereof may be used as a molecular genetic marker for quantitative trait loci (QTL) tagging, QTL mapping, DNA fingerprinting and in marker assisted selection, particularly in clovers, alfalfa, ryegrasses and fescues.

Even more particularly, nucleic acids or nucleic acid fragments according to the present invention and/or nucleotide sequence information thereof may be used as molecular genetic markers in plant improvement in relation to plant tolerance to biotic stresses such as viruses, microorganisms, insects, fungal pathogens; in relation to forage quality; in relation to bloat safety; in relation to condensed tannin content; in relation to plant pigmentation. Even more particularly, sequence information revealing SNPs in allelic variants of the nucleic acids or nucleic acid fragments of the present invention and/or nucleotide sequence information thereof may be used as molecular genetic markers for QTL tagging and mapping and in marker assisted selection, particularly in clovers, alfalfa, ryegrasses and fescues.

In a still further aspect of the present invention there is provided a construct including a nucleic acid or nucleic acid fragment according to the present invention.

The term "construct" as used herein refers to an artificially assembled or isolated nucleic acid molecule, which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

In a still further aspect of the present invention there is provided a vector including a nucleic acid or nucleic acid fragment according to the present invention.

The term "vector" as used herein encompasses both cloning and expression vectors. Vectors are often recombinant molecules containing nucleic acid molecules from several sources.

In a preferred embodiment of this aspect of the invention, the vector may include a regulatory element such as a promoter, a nucleic acid or nucleic acid fragment according to the present invention and a terminator; said regulatory element, nucleic acid or nucleic acid fragment and terminator being operatively linked.

By "operatively linked" is meant that said regulatory element is capable of causing expression of said nucleic acid or nucleic acid fragment in a plant cell and said terminator is capable of terminating expression of said nucleic acid or nucleic acid fragment in a plant cell. Preferably, said regulatory element is upstream of said nucleic acid or nucleic acid fragment and said terminator is downstream of said nucleic acid or nucleic acid fragment.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable constitutive promoters include the Cauliflower Mosaic Virus 35S (CaMV 35S) promoter, the maize Ubiquitin promoter, and the rice Actin promoter.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid or nucleic acid fragment of the present invention and the terminator, may include further elements necessary for expression of the nucleic acid or nucleic acid fragment, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and western blot hybridisation analyses.

Those skilled in the art will appreciate that the various components of the vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

The vectors of the present invention may be incorporated into a variety of plants, including monocotyledons (such as grasses from the genera *Lolium, Festuca, Paspalum, Pennisetum, Panicum* and other forage and turfgrasses, corn, oat, sugarcane, wheat and barley), dicotyledons (such as *arabidopsis*, tobacco, clovers, medics, eucalyptus, potato, sugarbeet, canola, soybean, chickpea) and gymnosperms.

In a preferred embodiment, the vectors may be used to transform monocotyledons, preferably grass species such as ryegrasses (*Lolium* species) and fescues (*Festuca* species), more preferably perennial ryegrass, including forage- and turf-type cultivars. In an alternate preferred embodiment, the vectors may be used to transform dicotyledons, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and alfalfa (*Medicago sativa*). Clovers, alfalfa and medics are key pasture legumes in temperate climates throughout the world.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a vector or construct, nucleic acid or nucleic acid fragment of the present invention.

The plant cell, plant, plant seed or other plant part may be from any suitable species, including monocotyledons, dicotyledons and gymnosperms. In a preferred embodiment the plant cell, plant, plant seed or other plant part may be from a monocotyledon, preferably a grass species, more preferably a ryegrass (*Lolium* species) or fescue (*Festuca* species), more preferably perennial ryegrass, including both forage- and turf-type cultivars. In an alternate preferred embodiment the plant cell, plant, plant seed or other plant part may be from a dicotyledon, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and alfalfa (*Medicago sativa*).

The present invention also provides a plant, plant seed or other plant part, or a plant extract derived from a plant cell of the present invention.

The present invention also provides a plant, plant seed or other plant part, or a plant extract derived from a plant of the present invention.

Using the methods and materials of the present invention, flavonoid biosynthesis may be increased or decreased. It may be increased, for example by incorporating additional copies of a sense nucleic acid of the present invention. It may be decreased, for example, by incorporating an antisense nucleic acid or dsRNA or small interfering RNA (siRNA) derived from the nucleotide sequences of the present invention. In addition, the number of copies of genes encoding different enzymes involved in flavonoid biosynthesis may be manipulated to modify flavonoid biosynthesis, protein binding, metal chelation, anti oxidation, UV light absorption, plant pigment production, plant defense to biotic stresses and modifying forage quality.

In a further aspect of the present invention there is provided a method of modifying flavonoid biosynthesis; of modifying protein binding, metal chelation, anti-oxidation, and UV-light absorption; of modifying plant pigment production; of modifying plant defense to biotic stresses such as viruses, microorganisms, insects, fungal pathogens; of modifying forage quality by disrupting protein foam and conferring protection from rumen pasture bloat, said method including introducing into said plant an effective amount of a nucleic acid or nucleic acid fragment and/or a vector according to the present invention.

By "an effective amount" it is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

Using the methods and materials of the present invention, flavonoid biosynthesis, protein binding, metal chelation, anti-oxidation, UV-light absorption, tolerance to biotic stresses such as viruses, microorganisms, insects and fungal pathogens; pigmentation in for example flowers and leaves; herbage quality and bloat-safety; isoflavonoid content leading to health benefits, may be increased or otherwise altered, for example by incorporating additional copies of a sense nucleic acid or nucleic acid fragment of the present invention. They may be decreased or otherwise altered, for example by incorporating an antisense nucleic acid or nucleic acid fragment of the present invention.

Documents cited in this specification are for reference purposes only and their inclusion is not acknowledgment that they form part of the common general knowledge in the relevant art.

The present invention will now be more fully described with reference to the accompanying Examples and drawings. It should be understood, however, that the description following is illustrative only and should not be taken in any way as a restriction on the generality of the invention described above.

IN THE FIGURES

FIG. 1 shows the consensus nucleotide sequence of WcCTa (TrTT12a) (SEQ ID No: 1).

FIG. 2 shows the deduced amino acid sequence of WcCTa (TrTT12a) (SEQ ID No: 2).

FIG. 3 shows the nucleotide sequences of nucleic acid fragments contributing to the consensus sequence of WcCTa (TrTT12a) (SEQ ID Nos: 3 to 6).

FIG. 4 shows the nucleotide sequence of WcCTb (TrTTG1a) (SEQ ID No: 7).

FIG. 5 shows the deduced amino acid sequence of WcCTb (TrTTG1a) (SEQ ID No: 8).

FIG. 6 shows the consensus nucleotide sequence of WcCTc (TrTT2a) (SEQ ID No: 9).

FIG. 7 shows the deduced amino acid sequence of WcCTc (TrTT2a) (SEQ ID No: 10).

FIG. 8 shows the nucleotide sequences of nucleic acid fragments contributing to the consensus sequence of WcCTc (TrTT2b) (SEQ ID Nos: 11 and 12).

FIG. 9 shows the nucleotide sequence of WcCTd (TrTT2b) (SEQ ID No: 13).

FIG. 10 shows the deduced amino acid sequence of WcCTd (TrTT2b) (SEQ ID No: 14).

FIG. 11 shows the nucleotide sequence of WcCTe (TrTT8a) (SEQ ID No: 15).

FIG. 12 shows the deduced amino acid sequence of WcCTe (TrTT8a) (SEQ ID No: 16).

FIG. 13 shows the consensus nucleotide sequence of WcCTf (TrLDOXa) (SEQ ID No: 17).

FIG. 14 shows the deduced amino acid sequence of WcCTf (TrLDOXa) (SEQ ID No: 18).

FIG. 15 shows the nucleotide sequences of nucleic acid fragments contributing to the consensus sequence of WcCTf (TrLDOXa) (SEQ ID Nos: 19 to 33).

FIG. 16 shows the consensus nucleotide sequence of WcCTg (Tr4CLa) (SEQ ID No: 34).

FIG. 17 shows the deduced amino acid sequence of WcCTg (Tr4CLa) (SEQ ID No: 35).

FIG. 18 shows the nucleotide sequences of nucleic acid fragments contributing to the consensus sequence of WcCTg (Tr4CLa) (SEQ ID Nos: 36 to 38).

FIG. 19 shows the nucleotide sequence of WcCTh (Tr4CLb) (SEQ ID No: 39).

FIG. 20 shows the deduced amino acid sequence of WcCTh (Tr4CLb) (SEQ ID No: 40).

FIG. 21 shows the nucleotide sequence of WcCTi (Tr4CLc) (SEQ ID No: 41).

FIG. 22 shows the deduced amino acid sequence of WcCTi (Tr4CLc) (SEQ ID No: 42).

FIG. 23 shows the nucleotide sequence of WcCTj (Tr4CLd) (SEQ ID No: 43).

FIG. 24 shows the deduced amino acid sequence of WcCTj (Tr4CLd) (SEQ ID No: 44).

FIG. 25 shows the consensus nucleotide sequence of WcCTk (TrC4Ha) (SEQ ID No: 45).

FIG. 26 shows the deduced amino acid sequence of WcCTk (TrC4Ha) (SEQ ID No: 46).

FIG. 27 shows the nucleotide sequences of nucleic acid fragments contributing to the consensus sequence of WcCTk (TrC4Ha) (SEQ ID Nos: 47 to 51).

FIG. 28 shows the nucleotide sequence of WcCTl (TrC4Hb) (SEQ ID No: 52).

FIG. 29 shows the deduced amino acid sequence of WcCTl (TrC4Hb) (SEQ ID No: 53).

FIG. 30 shows the nucleotide sequence of WcCTm (TrC4Hc) (SEQ ID No: 54).

FIG. 31 shows the deduced amino acid sequence of WcCTm (TrC4Hc) (SEQ ID No: 55).

FIG. 33 shows the full nucleotide sequence of the white clover WcCTa (TrTT12a) cDNA (SEQ ID No: 56).

FIG. 34 shows the deduced amino acid sequence of white clover WcCTa (TrTT12a) cDNA (SEQ ID No: 57).

FIG. 35 shows plasmid maps of the cDNA encoding white clover WcCTa (TrTT12a) in the sense and antisense orientations in the pPZP221 binary transformation vector

FIG. 37 shows the full nucleotide sequence of the white clover WcCTb (TrTTG1a) cDNA (SEQ ID No: 58).

FIG. 38 shows the deduced amino acid sequence of the white clover WcCTb (TrTTG1a) cDNA (SEQ ID No: 59).

FIG. 39 shows plasmid maps of the cDNA encoding white clover WcCTb (TrTTG1a) in the sense and antisense orientations in the pPZP221 binary transformation vector

FIG. 41 shows the full nucleotide sequence of the white clover WcCTc (TrTT2a) cDNA (SEQ ID No: 60).

FIG. 42 shows the deduced amino acid sequence of the white clover WcCTc (TrTT2a) cDNA (SEQ ID No: 61).

FIG. 44 shows the full nucleotide sequence of the white clover WcCTd (TrTT2b) cDNA (SEQ ID No: 62).

FIG. 45 shows the deduced amino acid sequence of the white clover WcCTd (TrTT2b) cDNA (SEQ ID No: 63).

FIG. 46 shows plasmid maps of the cDNAs encoding white clover WcCTc (TrTT2a) and WcCTd (TrTT2b) in the sense and antisense orientations in the pPZP221 binary transformation vector

FIG. 48 shows the full nucleotide sequence of the white clover WcCTe (TrTT8a) cDNA (SEQ ID No: 64).

FIG. 49 shows the deduced amino acid sequence of the white clover WcCTe (TrTT8a) cDNA (SEQ ID No: 65).

FIG. 52 shows the full nucleotide sequence of the white clover WcCTf (TrLDOXa) cDNA (SEQ ID No: 66).

FIG. 53 shows the deduced amino acid sequence of the white clover WcCTf (TrLDOXa) cDNA (SEQ ID No: 67).

FIG. 54 shows plasmid maps of the cDNA encoding white clover WcCTf (TrLDOXa) in the sense and antisense orientations in the pPZP221 binary transformation vector

FIG. 56 shows the full nucleotide sequence of the white clover WcCTg (Tr4CLa) cDNA (SEQ ID No: 68).

FIG. 57 shows the deduced amino acid sequence of the white clover WcCTg (Tr4CLa) cDNA (SEQ ID No: 69).

FIG. 59 shows the full nucleotide sequence of the white clover WcCTh (Tr4CLb) cDNA (SEQ ID No: 70).

FIG. 60 shows the deduced amino acid sequence of the white clover WcCTh (Tr4CLb) cDNA (SEQ ID No: 71).

FIG. 62 shows the full nucleotide sequence of the white clover WcCTi (Tr4CLc) cDNA (SEQ ID No: 72).

FIG. 63 shows the deduced amino acid sequence of the white clover WcCTi (Tr4CLc) cDNA (SEQ ID No: 73).

FIG. 65 shows the full nucleotide sequence of the white clover WcCTj (Tr4CLd) cDNA (SEQ ID No: 74).

FIG. 66 shows the deduced amino acid sequence of the white clover WcCTj (Tr4CLd) cDNA (SEQ ID No: 75).

Figure 32:
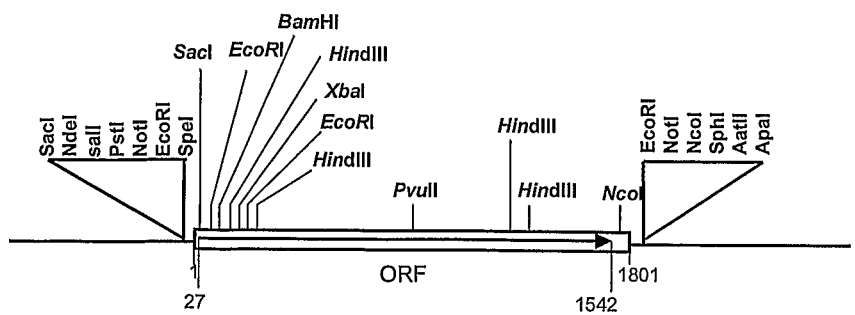
FIG. 32 shows a plasmid map of the cDNA encoding white clover WcCTa (TrTT12a).
Figure 36:
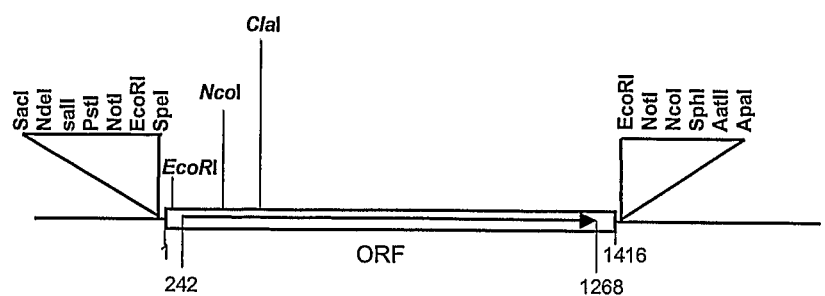
FIG. 36 shows a plasmid map of the cDNA encoding white clover WcCTb (TrTTG1a).
Figure 40:
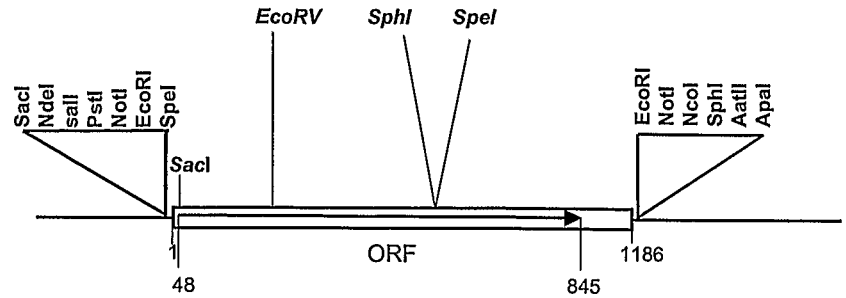
FIG. 40 shows a plasmid map of the cDNA encoding white clover WcCTc (TrTT2a).
Figure 43:
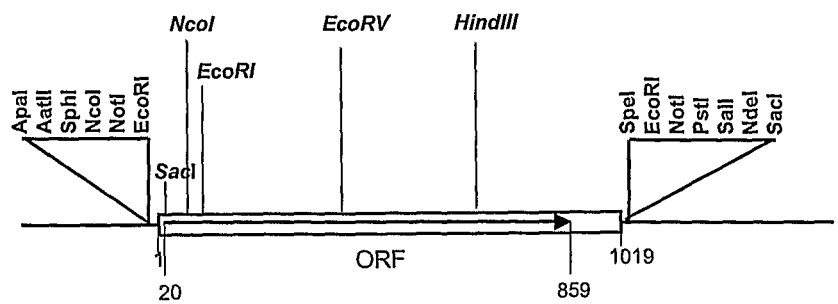
FIG. 43 shows a plasmid map of the cDNA encoding white clover WcCTd (TrTT2b).
Figure 47:
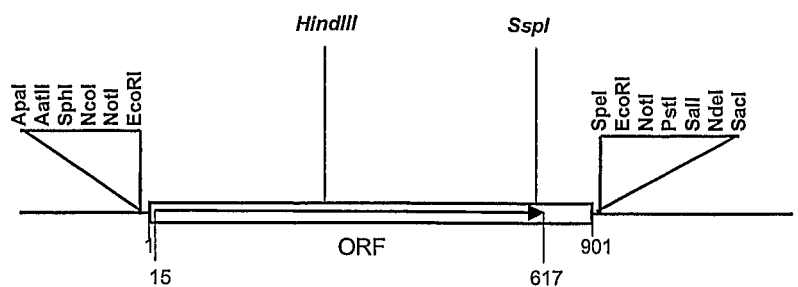
FIG. 47 shows a plasmid map of the cDNA encoding white clover WcCTe (TrTT8a).
Figure 50:
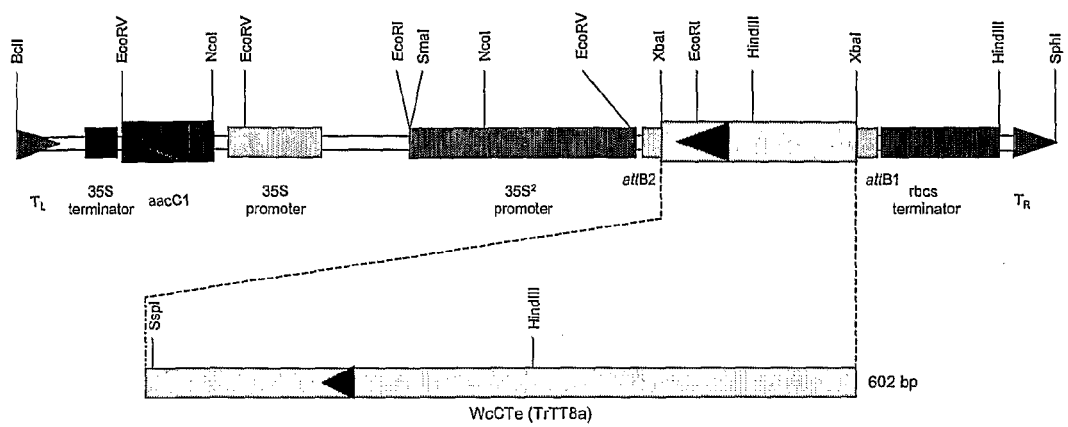
FIG. 50 shows a plasmid map of the cDNA encoding white clover WcCTe (TrTT8a) in the antisense orientation in the pPZP221 binary transformation vector
Figure 51:
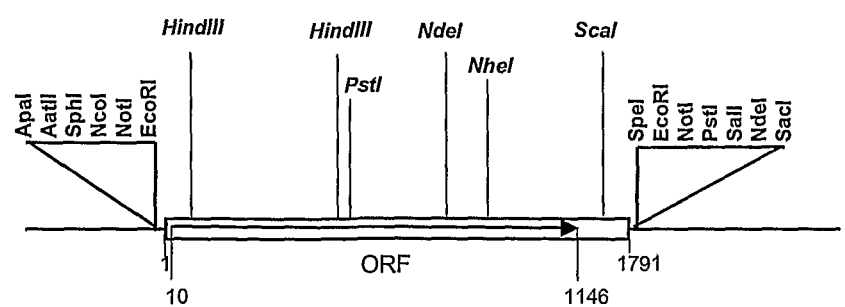
FIG. 51 shows a plasmid map of the cDNA encoding white clover WcCTf (TrLDOXa).
Figure 55:
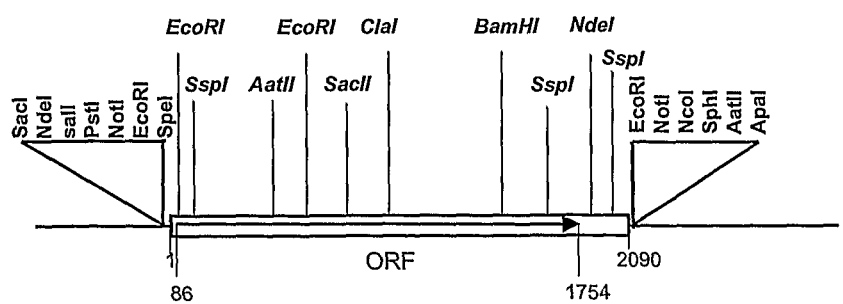
FIG. 55 shows a plasmid map of the cDNA encoding white clover WcCTg (Tr4CLa).
Figure 58:
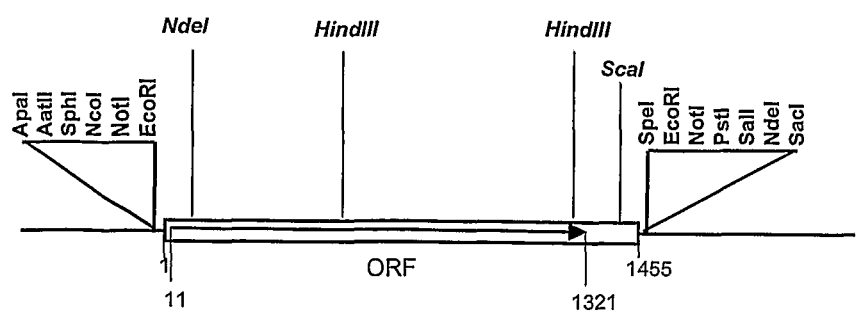
FIG. 58 shows a plasmid map of the cDNA encoding white clover WcCTh (Tr4CLb).
Figure 61:
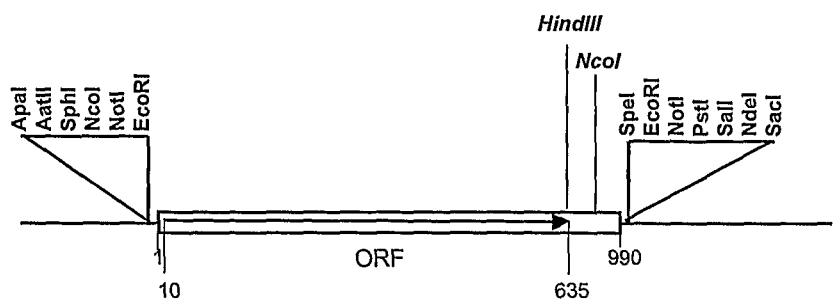
FIG. 61 shows a plasmid map of the cDNA encoding white clover WcCTi (Tr4CLc).
Figure 64:
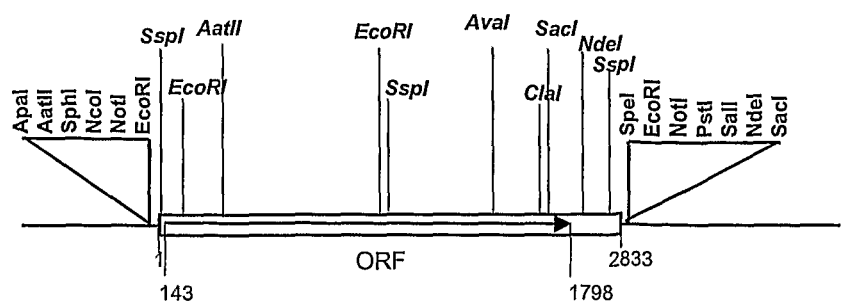
FIG. 64 shows a plasmid map of the cDNA encoding white clover WcCTj (Tr4CLd).
Figure 67:
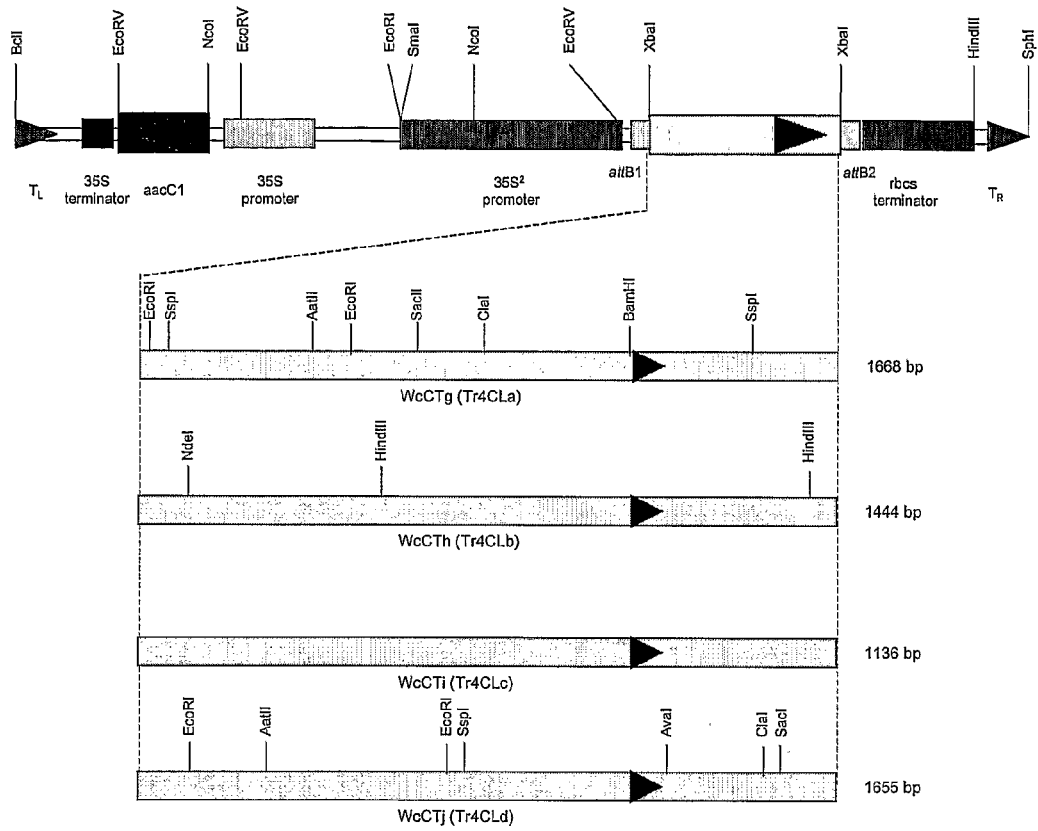
Figure 68:
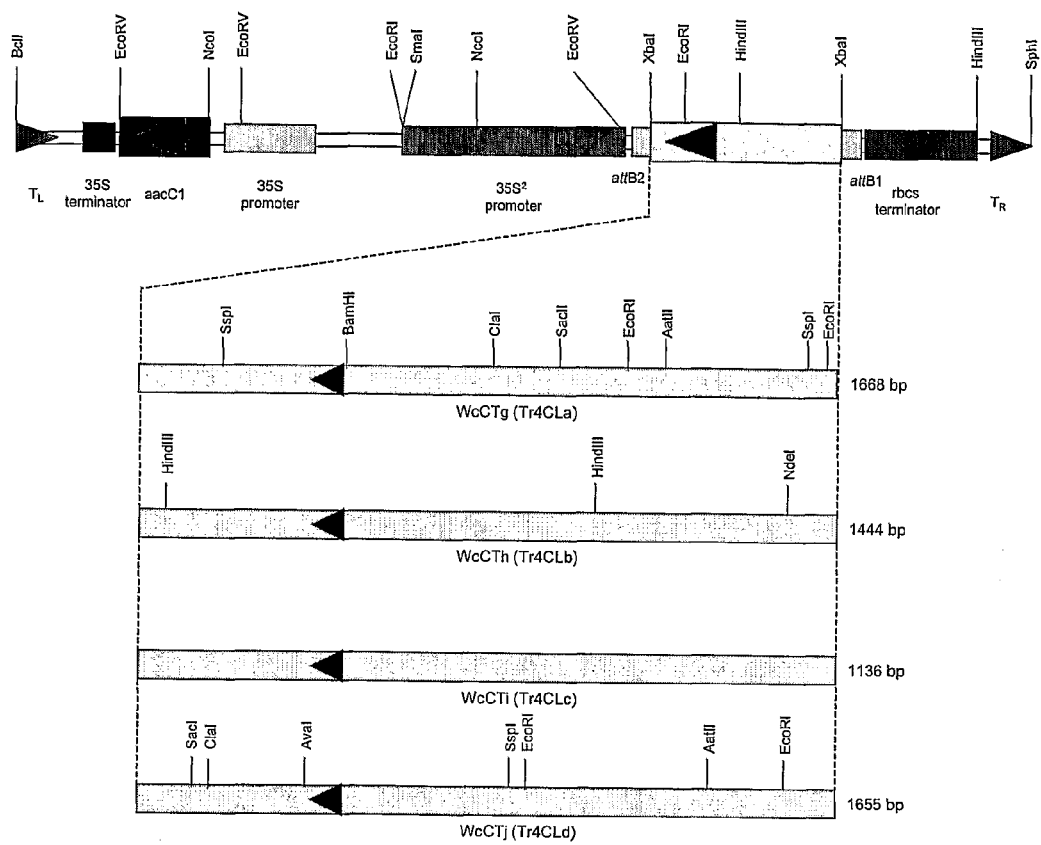
Figure 69:
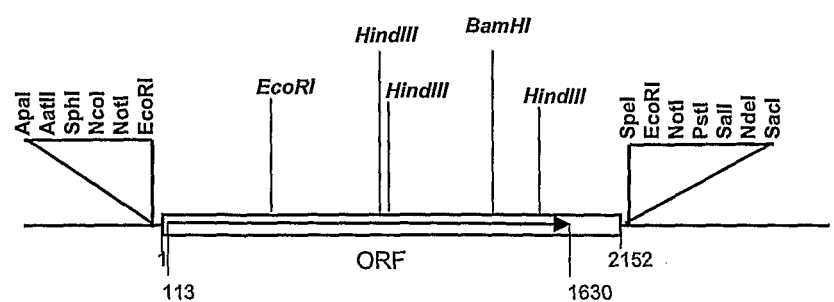

FIG. 67 shows plasmid maps of the cDNAs encoding white clover WcCTg (Tr4CLa), WcCTh (Tr4CLb), WcCTi (Tr4CLc) and WcCTj (Tr4CLd) in the sense orientation in the pPZP221 binary transformation vector FIG. 68 shows plasmid maps of the cDNAs encoding white WcCTg (Tr4CLa), WcCTh (Tr4CLb), WcCTi (Tr4CLc) and WcCTj (Tr4CLd) in the antisense orientation in the pPZP221 binary transformation vector FIG. 69 shows a plasmid map of the cDNA encoding white clover WcCTk (TrC4Ha).

FIG. 70 shows the full nucleotide sequence of the white clover WcCTk (TrC4Ha) cDNA (SEQ ID No: 76).

FIG. 71 shows the deduced amino acid sequence of the white clover WcCTk (TrC4Ha) cDNA (SEQ ID No: 77).

Figure 72:
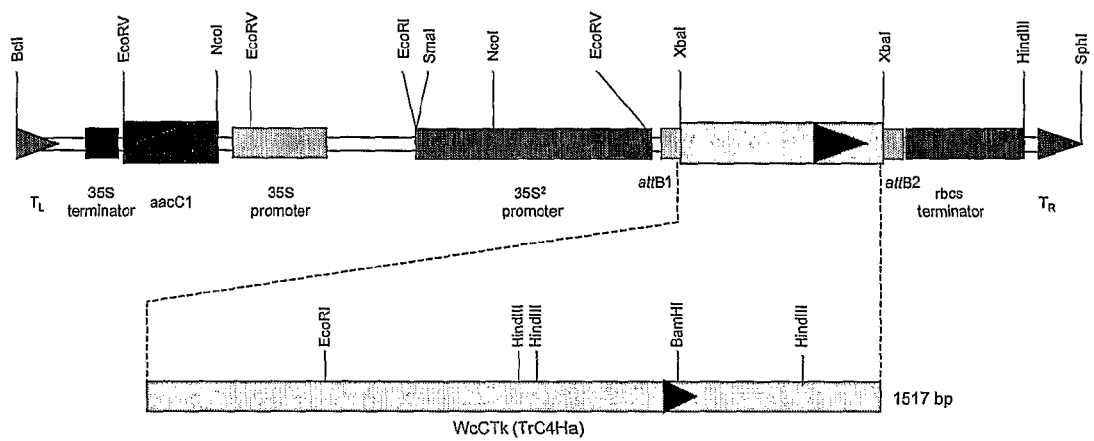
Figure 73:
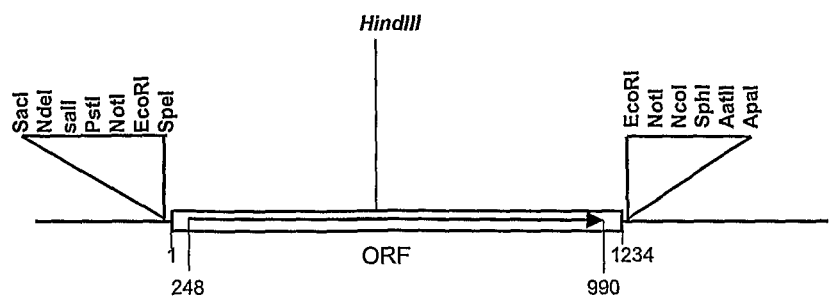

FIG. 72 shows a plasmid map of the cDNA encoding white clover WcCTk (TrC4Ha) in the sense orientation in the pPZP221 binary transformation vector FIG. 73 shows a plasmid map of the cDNA encoding white clover WcCTl (TrC4Hb).

FIG. 74 shows the full nucleotide sequence of the white clover WcCTl (TrC4Hb) cDNA (SEQ ID No: 78).

FIG. 75 shows the deduced amino acid sequence of the white clover WcCTl (TrC4Hb) cDNA (SEQ ID No: 79).

Figure 76:
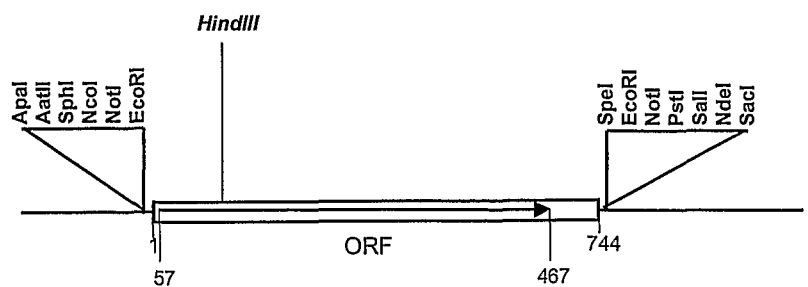

FIG. 76 shows a plasmid map of the cDNA encoding white clover WcCTm (TrC4Hc).

FIG. 77 shows the full nucleotide sequence of the white clover WcCTm (TrC4Hc) cDNA (SEQ ID No: 80).

FIG. 78 shows the deduced amino acid sequence of the white clover WcCTm (TrC4Hc) cDNA (SEQ ID No. 81)

Figure 79:
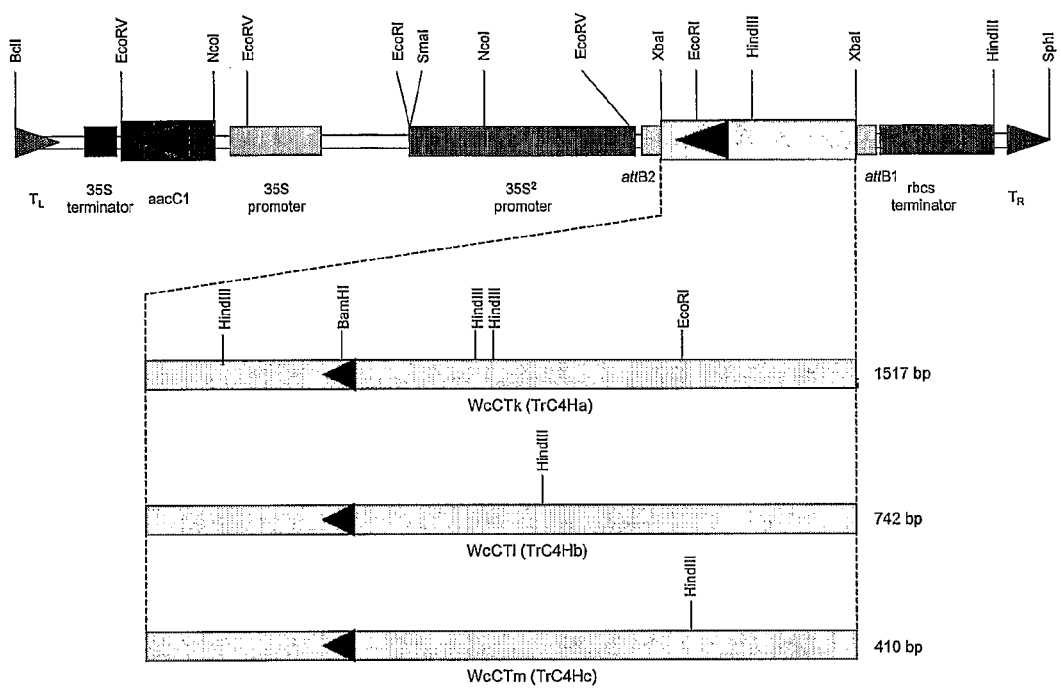
Figure 80:
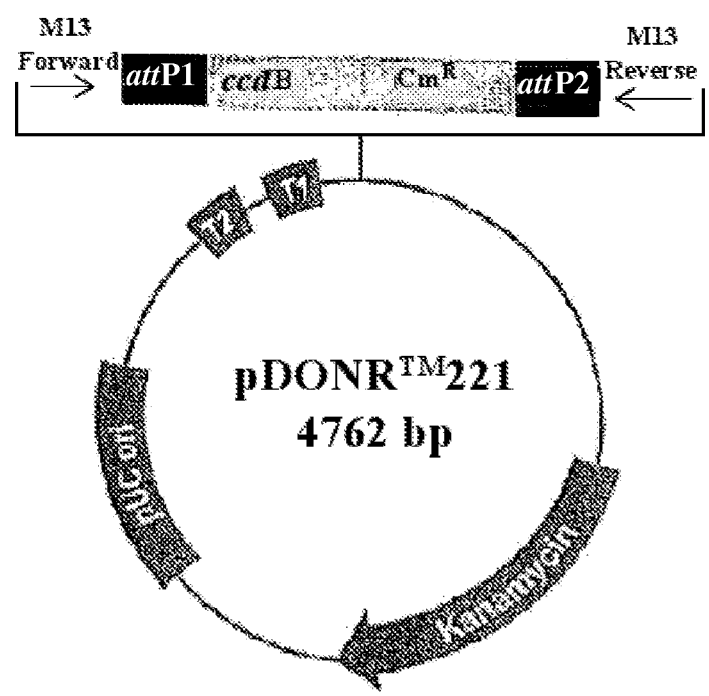

FIG. 79 shows plasmid maps of the cDNAs encoding white clover WcCTk (TrC4Ha), WcCTl (TrC4Hb) and WcCTm (TrC4Hc) in the antisense orientation in the pPZP221 binary transformation vector FIG. 80 shows a plasmid map of the pDONR221 GATE-WAY entry vector (Invitrogen, Carlsbad, USA).

Figure 81:
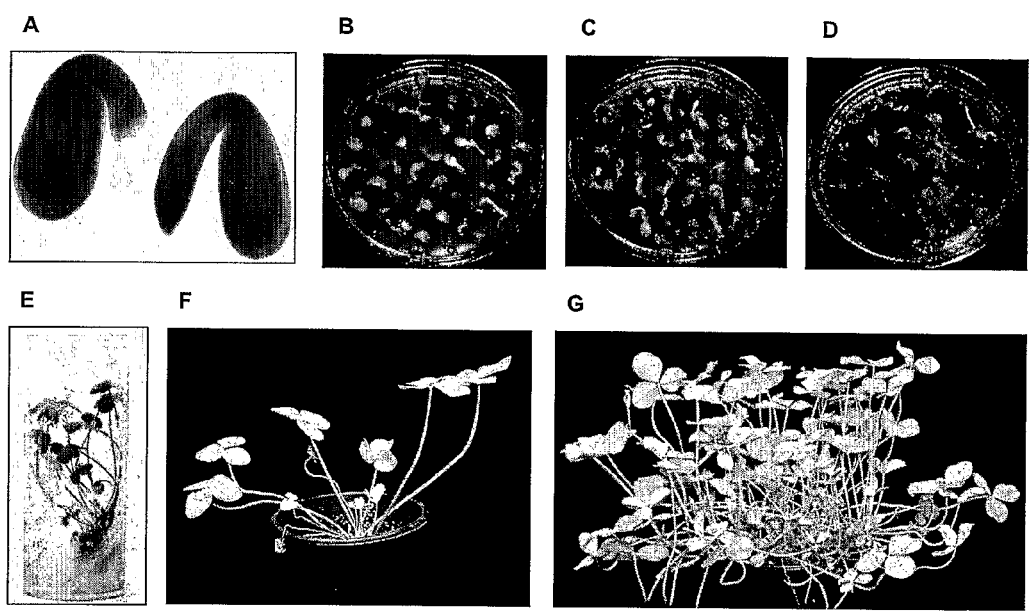

FIG. 81 shows the steps of selection during Agrobacterium-mediated transformation of white clover cotyledons. Cotyledonary explants are extracted from imbibed seeds (A), cocultivated with Agrobacterium tumefaciens strain containing the binary transformation vector and subjected to a series of 2-week selective steps on tissue culture plates (B, C and D). Shoots are excised and grown on root-inducing media in tissue culture vessels (E). Finally, transgenic white clover plantlets are transferred to glasshouse conditions (F and G), allowing molecular and phenotypic analyses to take place.

FIG. 82 shows 4-dimethylaminocinnemaldehyde (DMACA) staining patterns in Trifolium repens (cv 'Mink') leaf (A) and inflorescence (B) tissue and in Lotus corniculatus (cv 'Draco') leaf tissue (C).

Figure 83:
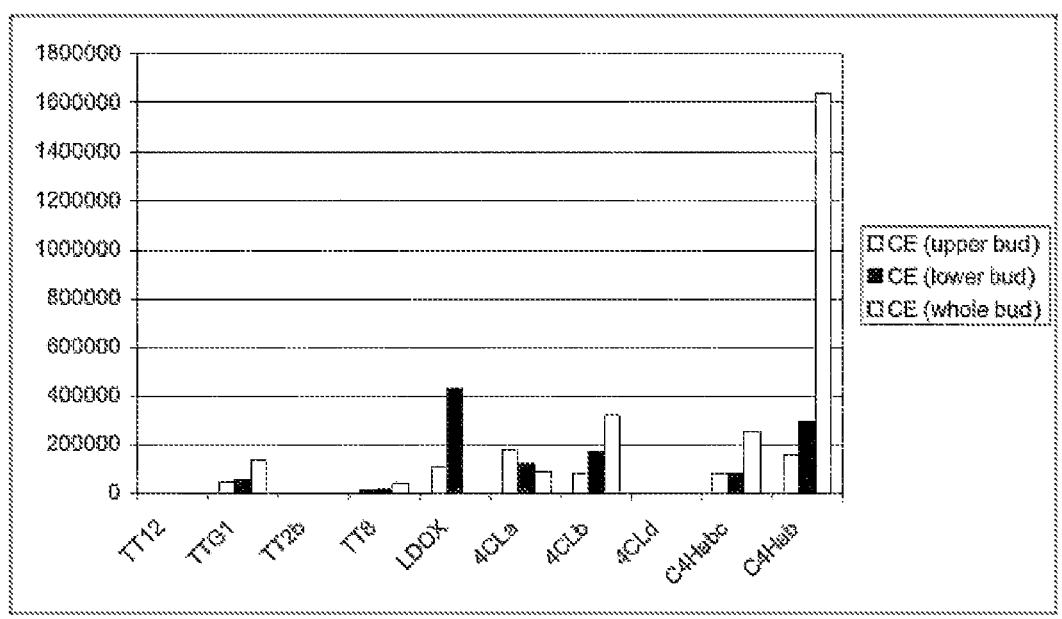

FIG. 83 shows the results of real-time RT-PCR analysis of white clover homologues of TT12, TTG1, TT2, TT8, LDOX, 4CL and C4H in upper and lower halves of white clover (cv Mink) buds as well as whole buds. More particularly, FIG. 83 shows comparative expression of flavonoid-related genes relative to a histone control gene. Complementary DNA from white clover (cv Mink) upper, lower and whole buds was tested by real-time RT-PCT using SYBR Green chemistry, primer sets designed using cDNA clones of flavonoid-related genes (Table 3) and the δδCT method of analysis. TT12, TTG1, TT2b, TT8, LDOX, 4Cla, 4CLb, 4CLd, C4Ha, C4Hb and C4Hc correspond to WcCTa, WcCTb, WcCTd, WcCTe, WcCTf, WcCTg, WcCTh, WcCTj, WcCTK, WcCT1, and WcCTM respectively.

EXAMPLE 1

Preparation of cDNA Libraries, Isolation and Sequencing of cDNAs Coding for TT12-Like, TTG1-Like, TT2-Like, TT8-Like, LDOX, LDOX-Like, 4CL, 4CL-Like, C4H and C4H-Like Proteins from White Clover (Trifolium repens)

cDNA libraries representing mRNAs from various organs and tissues of white clover (Trifolium repens) were prepared. The characteristics of the white clover libraries, respectively, are described below (Tables 1 and 2).

TABLE 1 cDNA libraries from white clover (Trifolium repens)

| Library | Organ/Tissue |
| --- | --- |
| 01wc | Whole seedling, light grown |
| 02wc | Nodulated root 3, 5, 10, 14, 21 &28 day old seedling |
| 03wc | Nodules pinched off roots of 42 day old rhizobium inoculated plants |
| 04wc | Cut leaf and stem collected after 0, 1, 4, 6 &14 h after cutting |
| 05wc | Inflorescences: <50% open, not fully open and fully open |

TABLE 1-continued cDNA libraries from white clover (Trifolium repens)

| Library | Organ/Tissue |
| --- | --- |
| 06wc | Dark grown etiolated |
| 07wc | Inflorescence - very early stages, stem elongation, <15 petals, 15-20 petals |
| 08wc | seed frozen at −80° C., imbibed in dark overnight at 10° C. |
| 09wc | Drought stressed plants |
| 10wc | AMV infected leaf |
| 11wc | WCMV infected leaf |
| 12wc | Phophorus starved plants |
| 13wc | Vegetative stolon tip |
| 14wc | stolon root initials |
| 15wc | Senescing stolon |
| 16wc | Senescing leaf |

The cDNA libraries may be prepared by any of many methods available. For example, total RNA may be isolated using the Trizol method (Gibco-BRL, USA) or the RNeasy Plant Mini kit (Qiagen, Germany), following the manufacturers' instructions. cDNAs may be generated using the SMART PCR cDNA synthesis kit (Clontech, USA), cDNAs may be amplified by long distance polymerase chain reaction using the Advantage 2 PCR Enzyme system (Clontech, USA), cDNAs may be cleaned using the GeneClean spin column (Bio 101, USA), tailed and size fractionated, according to the protocol provided by Clontech. The cDNAs may be introduced into the pGEM-T Easy Vector system 1 (Promega, USA) according to the protocol provided by Promega. The cDNAs in the pGEM-T Easy plasmid vector are transfected into Escherichia coli Epicurian coli XL10-Gold ultra competent cells (Stratagene, USA) according to the protocol provided by Stratagene.

Alternatively, the cDNAs may be introduced into plasmid vectors for first preparing the cDNA libraries in Uni-ZAP XR vectors according to the manufacturer's protocol (Stratagene Cloning Systems, La Jolla, Calif., USA). The Uni-ZAP XR libraries are converted into plasmid libraries according to the protocol provided by Stratagene. Upon conversion, cDNA inserts will be contained in the plasmid vector pBluescript. In addition, the cDNAs may be introduced directly into precut pBluescript II SK(+) vectors (Stratagene) using T4 DNA ligase (New England Biolabs), followed by transfection into E. coli DH10B cells according to the manufacturer's protocol (GIBCO BRL Products).

Once the cDNA inserts are in plasmid vectors, plasmid DNAs are prepared from randomly picked bacterial colonies containing recombinant plasmids, or the insert cDNA sequences are amplified via polymerase chain reaction using primers specific for vector sequences flanking the inserted cDNA sequences. Plasmid DNA preparation may be performed robotically using the Qiagen QiaPrep Turbo kit (Qiagen, Germany) according to the protocol provided by Qiagen. Amplified insert DNAs are sequenced in dye-terminator sequencing reactions to generate partial cDNA sequences (expressed sequence tags or "ESTs"). The resulting ESTs are analyzed using an Applied Biosystems ABI 3700 sequence analyser.

EXAMPLE 2

DNA Sequence Analyses

The cDNA clones encoding TT12, TT12-like, TTG1, TTG1-like, TT8, TT8-like, TT2, TT2-like, LDOX, LDOX-like, 4CL, 4CL-like, C4H and C4H-like proteins were identified by conducting BLAST (Basic Local Alignment Search Tool; Altschul et al. (1993) *J. Mol. Biol.* 215:403-410) searches. The cDNA sequences obtained were analysed for similarity to all publicly available DNA sequences contained in the eBioinformatics nucleotide database using the BLASTN algorithm provided by the National Center for Biotechnology Information (NCBI). The DNA sequences were translated in all reading frames and compared for similarity to all publicly available protein sequences contained in the SWISS-PROT protein sequence database using BLASTx algorithm (v 2.0.1) (Gish and States (1993) *Nature Genetics* 3:266-272) provided by the NCBI.

The cDNA sequences obtained and identified were then used to identify additional identical and/or overlapping cDNA sequences generated using the BLASTN algorithm. The identical and/or overlapping sequences were subjected to a multiple alignment using the CLUSTALw algorithm, and to generate a consensus contig sequence derived from this multiple sequence alignment. The consensus contig sequence was then used as a query for a search against the SWISS-PROT protein sequence database using the BLASTx algorithm to confirm the initial identification.

EXAMPLE 3

Identification and Full-Length Sequencing of cDNAs Encoding White Clover TT12, TTG1, TT2, TT8, LDOX, 4CL and C4H Proteins To fully characterise for the purposes of the generation of probes for hybridisation experiments and the generation of transformation vectors, a set of cDNAs encoding white clover TT12, TTG1, TT2, TT8, LDOX, 4CL and C4H proteins was identified and fully sequenced.

Full-length or partial cDNAs were identified from our EST sequence database using relevant published sequences (NCBI databank) as queries for BLAST searches. Full-length cDNAs were identified by alignment of the query and hit sequences using Sequencher (Gene Codes Corp., Ann Arbor, Mich. 48108, USA). The original cDNA in the pGEM-T easy vector was then used to transform chemically competent DH5 alpha cells (Invitrogen, Carlsbad, USA). At least two colonies per transformation were picked for initial sequencing with M13F and M13R primers. The resulting sequences were aligned with the original EST sequence using Sequencher to confirm identity and one of the two clones was picked for full-length sequencing, usually the one with the best initial sequencing result.

Sequencing was completed by primer walking, i.e. oligonucleotide primers were designed to the initial sequence and used for further sequencing from the 5' end. The sequences of the oligonucleotide primers are shown in Table 2. In most instances, an extended poly-A tail necessitated the sequencing of the cDNA to be completed from the 5' end.

Contigs were then assembled in Sequencher. The contigs include at least the 5' end of the original EST sequence and extend to at least the poly-A tail at the 3' end of the cDNA.

Plasmid maps and the full or partial cDNA sequences of white clover TT12, TTG1, TT2, TT8, LDOX, 4CL and C4H genes in the pGEM-T Easy vector were obtained (FIGS. 32, 33, 36, 37, 40, 41, 43, 44, 47, 48, 51, 52, 55, 56, 58, 59, 61, 62, 64, 65, 69, 70, 73, 74, 76, 77).

TABLE 2

List of primers used for sequencing of the full-length cDNAs

| gene name | clone ID | sequencing primer | primer sequence (5'>3') | Seq. ID No. |
|---|---|---|---|---|
| WcCTa (TrTT12a) | 05wc1CsD12 | 05wc1CsD12.f | GCATTTGCATTGAG TTGTC | 82 |
|  |  | 05wc1CsD12.f2 | AGCCAGTGTGCGAG TTAG | 83 |
|  |  | 05wc1CsD12.f3 | AATTGTCAGTCTTC GTAGTG | 84 |
|  |  | 05wc1CsD12.r1 | ACAACGAAGTATGA CAGAAG | 85 |
| WcCTb (TrTTG1a) | 10wc1CsD0710wc1CsD07.f |  | GCATCGCTGTTGGT AGTT | 86 |
|  |  | 10wc1CsD07.r1 | CAACGCCTCTTTCA ATGTC | 87 |
|  |  | 10wc1CsD07.f2 | TACCCCTTTGCTTC GTTTG | 88 |
| WcCTc (TrTT2a) | 14wc1LsB0514wc1LsB05.f1 |  | CACACGCATTTGAA GAAG | 89 |
| WcCTd (TrTT2b) | 04wc1EsE1104wc1EsE11.f1 |  | AACCAACAAGGCCA CAAC | 90 |
| WcCTe (TrTT8a) | 06wc2DsD0406wc2DsD04.f1 |  | ATAGGTGAGACAAG GAGACAGA | 91 |
| WcCTf (TrLDOXa) | 07wc3GsD0307wc3GsD03.f1 |  | GCCTAAGACTCCAG CTGA | 92 |
|  |  | 07wc3GsD03.r1 | TCCCATTCAAGTTG ACCAC | 93 |
|  |  | 07wc3GsD03.f2 | AACAAGGGCCACAA GTTC | 94 |
|  |  | 07wc3GsD03.f3 | TCTTGGGCAGTGTT TTGTG | 95 |
| WcCTg (Tr4Cla) | 14wc2KsH1014wc2KsH10.f1 |  | CAGCAGCCAATCCT TTCTTC | 96 |
|  |  | 14wc2KsH10.f2 | AGTCCAACAGGGTG ATGT | 97 |
|  |  | 14wc2KsH10.f3 | GTAGTTCCTCCGAT AGTGT | 98 |
|  |  | 14wc2KsH10.f4 | TCTGATGCTGCTGT TGTC | 99 |
| WcCTh (Tr4CLb) | 13wc1DsH0713wc1DsH07.f1 |  | TTGGTAAGGAACTT GAGGACA | 100 |
|  |  | 13wc1DsH07.f2 | CAAAAGCCTCCAAT GCTAAG | 101 |
| WcCTi (Tr4CLc) | 16wc1NsB1116wc1NsB11.f1 |  | GAAGAGGCTGTAAA GGAG | 102 |
| WcCTj (Tr4CLd) | 12wc1CsA1112wc1CsA11.f1 |  | ACTCATCGTAACTC AATCC | 103 |
|  |  | 12wc1CsA11.f2 | GCGTTGGTAAAAAG TGGTG | 104 |
|  |  | 12wc1CsA11.f3 | TTTCGATGCTGCTG TTGT | 105 |
|  |  | 12wc1CsA11.f4 | GCCTATTCGTTCGC TTCT | 106 |
| WcCTk (TrC4Ha) | 14wc2CsB0914wc2CsB09.f1 |  | TACGGTGAACATTG GCGT | 107 |
|  |  | 14wc2CsB09.f2 | GATGCTCAAAAGAA AGGAGAG | 108 |
|  |  | 14wc2CsB09.f3 | ATCGGGCGTCTTGT TCAG | 109 |
| WcCTl (TrC4Hb) | 11wc1OsE0411wc1OsE04.f1 |  | AGGACCAGGACACC AAGTA | 110 |
| WcCTm (TrC4Hc) | 06wc1OsE1206wc1OsE12.f1 (810) |  | TAACCCGGCTCTAT GGAA | 111 |

EXAMPLE 4

Development of Binary Transformation Vectors Containing Chimeric Genes with cDNA Sequences from White Clover TT12a, TrTTG1, TrTT2a, TrTT2b, TrTT8a, TrLDOXa, Tr4CLa, Tr4CLb, Tr4Clc Tr4CLd, TrC4Ha, TrC4Hb and TrC4Hc To alter the expression of the proteins involved in flavonoid biosynthesis, protein binding, metal chelation, anti-oxidation, UV-light absorption, tolerance to biotic stresses such as viruses, micro-organisms, insects and fungal pathogens; pigmentation in for example flowers and leaves; herbage quality and bloat-safety and isoflavonoid content leading to health benefits, white clover TT12a, TTG1, TT2a, TT2b, TT8a, LDOXa, 4CLa, 4CLb, 4Clc 4CLd, C4Ha, C4Hb and C4Hc through antisense and/or sense suppression technology and for over-expression of these key proteins in transgenic plants, a set of sense and antisense binary transformation vectors was produced.

cDNA fragments were generated by high fidelity PCR using the original pGEM-T Easy plasmid cDNA as a template. The primers used (Table 3) contained attB1 and attB2 GATEWAY® recombination sites for directional cloning into the target vector. After PCR amplification and purification of the products, the cDNA fragments were cloned into the recombination site of the pDONR221™ vector (FIG. 80) using BP GATEWAY® technology (Invitrogen, Carlsbad, USA). vector The pPZP221 binary vector (Hajdukiewicz et al., 1994) was modified to contain the $35S^2$ cassette from pKYLX71:35 $S^2$ as follows. pKYLX71:35 $S^2$ was cut with ClaI. The 5' overhang was filled in using Klenow and the blunt end was A-tailed with Taq polymerase. After cutting with EcoRI, the 2 kb fragment with an EcoRI-compatible and a 3'-A tail was gel-purified. pPZP221 was cut with HindIII and the resulting 5' overhang filled in and T-tailed with Taq polymerase. The remainder of the original pPZP221 multi-cloning site was removed by digestion with EcoRI, and the expression cassette cloned into the EcoRI site and the 3' T overhang restoring the HindIII site. This binary vector contains between the left and right border the plant selectable marker gene aaaC1 under the control of the 35S promoter and 35S terminator and the pKYLX71:35 $S^2$-derived expression cassette with a CaMV 35S promoter with a duplicated enhancer region and an rbcS terminator. This vector was GATEWAY®-enabled by digesting it with XbaI and blunt-ended using Klenow DNA polymerase, allowing the RfA recombination cassette to be cloned in the sense or antisense orientation between the enhanced 35S promoter and the rbcS terminator.

The orientation of the constructs (sense or antisense) was checked by restriction enzyme digestion and sequencing. Transformation vectors containing chimeric genes using full-length open reading frame cDNAs encoding white clover TT12a, TTG1, TT2a, TT2b, TT8a, LDOXa, 4CLa, Tr4CLb, 4Clc 4CLd, C4Ha, C4Hb and C4Hc proteins in sense and antisense orientations under the control of the CaMV $35S^2$ promoter were generated (FIGS. 35, 39, 46, 50, 54, 67, 68, 72 and 79).

TABLE 3

List of primers used to PCR-amplify the open reading frames of flavonoid-related genes from white clover

| gene name | clone ID | primer | primer sequence (5'->3') | SEQ. ID NO. |
|---|---|---|---|---|
| WcCTa (TrTT12a) | 05wc1CsD1205wc1CsD12GW.f | GGGGACAAGTTTGTACAAAAAAGCAGGCTTCATGAGCTCTATAGAAAACCAACC | | 112 |
| WcCTa (TrTT12a) | 05wc1CsD1205wc1CsD12GW.r | GGGGACCACTTTGTACAAGAAAGCTGGGTCTCATATGTCGGCAACCAGTTGATCC | | 113 |
| WcCTb (TrTTG1a) | 10wc1CsD0710wc1CsD07GW.f | GGGGACAAGTTTGTACAAAAAAGCAGGCTTCATGGAGAATTCAACTCAAGAATCACAC | | 114 |
| WcCTb (TrTT2a) | 10wc1CsD0710wc1CsD07GW.r | GGGGACCACTTTGTACAAGAAAGCTGGGTCTCAAACCCGCAAAAGCTGCATCTTG | | 115 |
| WcCTc (TrTT2a) | 14wc1LsB0514wc1LsB05GW.f | GGGGACAAGTTTGTACAAAAAAGCAGGCTTCATGGTAAGAGCTCCTTGTTGTGA | | 116 |
| WcCTc (TrTT2a) | 14wc1LsB0514wc1LsB05GW.r | GGGGACCACTTTGTACAAGAAAGCTGGGTCTTAGAACTCTGGCAATTCTATTTGATC | | 117 |
| WcCTd (TrTT2b) | 04wc1EsE1104wc1EsE11GW.f | GGGGACAAGTTTGTACAAAAAAGCAGGCTTCATGGTGAGAGCTCCATGTTGTGA | | 118 |
| WcCTd (TrTT2b) | 04wc1EsE1104wc1EsE11GW.r | GGGGACCACTTTGTACAAGAAAGCTGGGTCTCACAATTCAAGTAACTCAGTAATTTCC | | 119 |
| WcCTe* (TrTT8a) | 06wc2DsD0406wc2DsD04GW.f | GGGGACAAGTTTGTACAAAAAAGCAGGCTTCATGAACCATGTTTTGTCAGAAAGAAGG | | 120 |
| WcCTe* (TrTT8a) | 06wc2DsD0406wc2DsD04GW.r | GGGGACCACTTTGTACAAGAAAGCTGGGTCTCAAAACTTTGAAGCCACTTTTTGTAGG | | 121 |
| WcCTf (TrLDOXa) | 07wc3GsD0307wc3GsD03GW.f | GGGGACAAGTTTGTACAAAAAAGCAGGCTTCATGGGAGCCGTGGCACAAAGAGTTG | | 122 |
| WcCTf (TrLDOXa) | 07wc3GsD0307wc3GsD03GW.r | GGGGACCACTTTGTACAAGAAAGCTGGGTCTCATTTTTTAGGATCATCCTTCTTCTC | | 123 |

TABLE 3-continued

List of primers used to PCR-amplify the open reading frames of flavonoid-related genes from white clover

| gene name | clone ID | primer | primer sequence (5'->3' | SEQ. ID NO. |
|---|---|---|---|---|
| WcCTg (Tr4CLa) | 14wc2KsH1014wc2KsH10GW.f | | GGGGACAAGTTTGTACAAAAAAGCAGGCTT CATGGCGGCCGCGGGAATTCGATTAAGC | 124 |
| WcCTg (Tr4CLa) | 14wc2KsH1014wc2KsH10GW.r | | GGGGACCACTTTGTACAAGAAAGCTGGGTC TTATTCTGCTGCTAACTTTGCTCTGAG | 125 |
| WcCTh (Tr4CLb) | 13wc1DsH0713wc1DsH07GW.f | | GGGGACAAGTTTGTACAAAAAAGCAGGCTT CATGGCGGCCGCGGGAATTCGATTAAGC | 126 |
| WcCTh (Tr4CLb) | 13wc1DsH0713wc1DsH07GW.r | | GGGGACCACTTTGTACAAGAAAGCTGGGTC TTAATTTGTTGGAACACCAGCTGC | 127 |
| WcCTi (Tr4CLc) | 16wc1NsB1116wc1NsB11GW.f | | GGGGACAAGTTTGTACAAAAAAGCAGGCTT CATGGCGGCCGCGGGAATTCGATTAAGC | 128 |
| WcCTi (Tr4CLc) | 16wc1NsB1116wc1NsB11GW.r | | GGGGACCACTTTGTACAAGAAAGCTGGGTC TCAAGGCTTTTGGGTGGTACTTTCTAAC | 129 |
| WcCTj (Tr4CLd) | 12wc1CsA1112wc1CsA11GW.f | | GGGGACAAGTTTGTACAAAAAAGCAGGCTT CATGTCACCATTTCCTCCACAGCAAG | 130 |
| WcCTj (Tr4CLd) | 12wc1CsA1112wc1CsA11GW.r | | GGGGACCACTTTGTACAAGAAAGCTGGGTC TTAAGTGGCCACCACCAAACCTTCG | 131 |
| WcCTk (TrC4Ha) | 14wc2CsB0914wc2CsB09GW.f | | GGGGACAAGTTTGTACAAAAAAGCAGGCTT CATGGATCTACTCCTTCTTGAAAAGACTC | 132 |
| WcCTk (TrC4Ha) | 14wc2CsB0914wc2CsB09GW.r | | GGGGACCACTTTGTACAAGAAAGCTGGGTC TTAAAATGATCTTGGCTTAGCAACAATG | 133 |
| WcCTl* (TrC4Hb) | 11wc1OsE0411wc1OsE04GW.f | | GGGGACAAGTTTGTACAAAAAAGCAGGCTT CGCAGTGGTAACAACGCAGAGTACGC | 134 |
| WcCTl* (TrC4Hb) | 11wc1OsE0411wc1OsE04GW.r | | GGGGACCACTTTGTACAAGAAAGCTGGGTC TTAAAATGATCTTGGCTTAGCAACAATG | 135 |
| WcCTm* (TrC4Hc) | 06wc1OsE1206wc1OsE12GW.f | | GGGGACAAGTTTGTACAAAAAAGCAGGCTT CCCGACGTCGCATGCTCCCGGC | 136 |
| WcCTm* (TrC4Hc) | 06wc1OsE1206wc1OsE12GW.r | | GGGGACCACTTTGTACAAGAAAGCTGGGTC TTAAAATGATCTTGGCTTAGCAACAATG | 137 |

EXAMPLE 5

Production and Analysis of Transgenic White Clover Plants Carrying Chimeric White Clover TT12a, TTG1, TT2a, TT2b, TT8a, LDOXa, 4CLa, 4CLb, 4Clc 4CLd, C4Ha, C4Hb and C4Hc Genes Involved in Flavonoid Biosynthesis A set of transgenic white clover plants carrying white clover genes involved in flavonoid biosynthesis, protein binding, metal chelation, anti-oxidation, UV-light absorption, tolerance to biotic stresses such as viruses, micro-organisms, insects and fungal pathogens; pigmentation in for example flowers and leaves; herbage quality and bloat-safety and isoflavonoid content leading to health benefits, were produced.

pPZP221-based transformation vectors with WcCTa (TrTT12a), WcCTb (TrTTG1), WcCTc (TrTT2a), WcCTd (TrTT2b), WcCTe (TrTT8a), WcCTf (TrLDOXa), WcCTg (Tr4Cla), WcCTh (Tr4CLb), WcCTi (Tr4Clc) WcCTj (Tr4CLd), WcCTk (TrC4Ha), WcCTl (TrC4Hb) and WcCTm (TrC4Hc) cDNAs comprising the full open reading frame sequences in sense and antisense orientations under the control of the CaMV 35S promoter with duplicated enhancer region ($35S^2$) were generated as detailed in Example 4.

*Agrobacterium*-mediated gene transfer experiments were performed using these transformation vectors.

The production of transgenic white clover plants carrying the white clover WcCTa (TrTT12a), WcCTb (TrTTG1), WcCTc (TrTT2a), WcCTd (TrTT2b), WcCTe (TrTT8a), WcCTf (TrLDOXa), WcCTg (Tr4Cla), WcCTh (Tr4CLb), WcCTi (Tr4Clc), WcCTj (Tr4CLd), WcCTk (TrC4Ha), WcCTl (TrC4Hb) and WcCTm (TrC4Hc) cDNAs under the control of the CaMV 35S promoter with duplicated enhancer region ($35S^2$) is described here in detail. The selection process is shown in FIG. 81.

Preparation of White Clover Cotyledonary Explants

White clover (cv 'Mink') seeds were rinsed for 5 minutes in running tap water and incubated twice, for 5 minutes in 70% v/v ethanol in a 120 ml tissue culture container with gentle shaking. The same container was used to incubate the seeds for 2 minutes in 1% sodium hypochlorite (1:3 ratio of Domestos™ bleach in water) with gentle shaking. The seeds were then rinsed six times in sterile water in a laminar flow hood and incubated for 18 hours at 4° C. in the dark. Cotyledonary explant were extracted using 10 ml syringes attached to 21 G needles (Terumo, Japan) under a dissecting microscope in a laminar flow hood. Both layers of the seed coat were peeled away, the end of the hypocotyl was cut off and the cotyledons with approximately 4 mm of hypocotyl were separated and transferred to a 90×90×20 mm petri dish containing MGL medium.

Preparation of *Agrobacterium*

*Agrobacterium tumefaciens* strain AGL-1 containing each PZP221-derived binary expression vector was streaked on LB medium containing 50 μg/ml rifampicin and 100 μg/ml spectinomycin and grown at 27° C. for 48 hours. A single colony was used to inoculate 5 ml of LB medium containing 50 μg/ml rifampicin and 100 μg/ml spectinomycin and grown over night at 27° C. and 250 rpm on an orbital shaker. The overnight culture was used as an inoculum for 40 ml of YEP medium containing 100 μg/ml spectinomycin and 40 mg/l acetosyringone. Incubation was over night at 27° C. and 250 rpm on an orbital shaker in a 250 ml Erlenmeyer flask.

The overnight cultures were centrifuged for 15 min at 5500×g and the supernatant discarded. The cells were resuspended in MGL media with 40 mg/l acetosyringone to a volume corresponding to an $OD_{600}$ reading of 0.4. The cells were then incubated at 27° C. and 250 rpm until the $OD_{600}$ reading reached 0.8.

Cocultivation and Selection of White Clover Transformants

The MGL medium was removed from the petri dish containing white clover cotyledonary explants and replaced with the prepared *Agrobacterium* suspension using a sterile serological pipette. The petri dish was sealed with laboratory film, covered with aluminium foil and incubated with gentle shaking for 45 min. The dish was opened in the laminar flow hood and the *Agrobacterium* suspension removed with a pipette. The explants were then transferred to plates containing RM73 media with 40 mg/l acetosyringone (Table 4) and incubated for 3 days in a plant tissue culture room at 22° C. with a 16 hour photoperiod. After this, the explants were transferred, with the hypocotyl end in the media, to plates containing RM73 media with 75 mg/l gentamicin and 250 mg/l cefotaxime. The explants were transferred to fresh plates every two weeks for 6-8 weeks. Shoots were then transferred to 120 ml tissue culture vessels containing RIM media (Table 5) with 75 mg/l gentamicin and 250 mg/l cefotaxime. When roots had developed, the plantlets were transferred to pots of soil and after 2 weeks of recovery in a misting bench, were grown under standard glasshouse conditions.

Preparation of Genomic DNA 1-2 leaflets of white clover plants recovered from the transformation process were harvested and freeze-dried. The tissue was homogenised on a Retsch MM300 mixer mill, then centrifuged for 10 min at 1700×g to collect cell debris. Genomic DNA was isolated from the supernatant using Wizard Magnetic 96 DNA Plant System kits (Promega) on a Biomek FX (Beckman Coulter). 5 μl of the sample (50 μl) were then analysed on an agarose gel to check the yield and the quality of the genomic DNA.

Analysis of DNA from Putative Transgenic Lines Using Real-Time PCR

Genomic DNA was analysed for the presence of the transgene by real-time PCR using SYBR Green chemistry. PCR primer pairs were designed to detect the aacC1 gentamycin resistance gene in the transferred T-DNA region using MacVector (Accelrys). The sequences of these primers are as follows:

```
                                      SEQ ID No.: 138
pPZPaacC1-1.f 5'-TCAAGTATGGGCATCATTCGCAC-3'

SEQ ID No.: 139
pPZPaacC1-1.r 5'-TGCTCAAACCGGGCAGAACG-3'
```

2.5 μl of each genomic DNA sample was run in a 25 μl PCR reaction including SYBR Green on an ABI (Applied Biosystems) together with samples containing DNA isolated from wild type white clover plants (cv 'Mink', negative control), samples containing buffer instead of DNA (buffer control) and samples containing the plasmid used for transformation (positive plasmid control).

TABLE 4

Composition of RM73 tissue culture media, pH 5.75

| Component | [Stock] | For 1 litre |
|---|---|---|
| MS Macronutrients | 10x | 100 mL |
| MS Micronutrients | 100x | 10 mL |
| MS Vitamins | 100x | 10 mL |
| TDZ | 100 mM | 50 uL |
| NAA | 1 mM | 0.5 mL |
| Sucrose (BDH Chemicals) | — | 30 g |
| Agar | — | 8 g |

TABLE 5

Composition of root-inducing tissue culture media (RIM73), pH 5.75

| Component | [Stock] | For 1 litre |
|---|---|---|
| MS macronutrients | 10x | 100 mL |
| MS micronutrients | 100x | 10 mL |
| MS vitamins | 100x | 10 mL |
| Indole-3-butyric acid | 1 mM | 1.2 mL |
| Sucrose (BDH Chemicals) | — | 15 g |
| Agar (Becton-Dickinson) | — | 8 g |

EXAMPLE 6

Analysis of Condensed Tannins and Their Monomers in the Leaves of Transgenic White Clover Plants Carrying Chimeric White Clover TT12a, TTG1, TT2a, TT2b, TT8a, LDOXa, 4CLa, 4CLb, 4Clc 4CLd, C4Ha, C4Hb and C4Hc Genes Involved in Flavonoid Biosynthesis Accumulation of condensed tannins and their monomers was analysed qualitatively in leaves of transgenic and wild type (cv 'Mink') white clover plants using 4-dimethylamino-cinnemaldehyde (DMACA) staining. Two mature leaflets from each plant were decolourised in absolute ethanol in 6-well tissue culture plates for 3 hours with gentle shaking. The ethanol was removed and replaced with a 0.01% w/v solution of DMACA (Fluka), freshly made up in absolute ethanol with 2.4% v/v concentrated hydrochloric acid. After 1 hour of incubation with gentle shaking, the leaflets were rinsed with distilled water and mounted in 50% glycerol for analysis with a dissecting microscope. Wild type white clover plants show blue staining in epidermal cells in the floral organs and in trichomes. *Lotus corniculatus* (cv 'Draco'), a forage legume with a 'bloat-safe' level of condensed tannins in the leaves, shows blue staining of approximately 50% of mesophyll cells in leaves (FIG. 82). Achieving a level of condensed tannins in white clover leaves that is comparable to the level seen in leaves of *L. corniculatus* by metabolic engineering would be agronomically valuable.

DMACA staining can detect economically significant levels of condensed tannins and their monomers in the leaves of established bloat-safe forage legumes. However, the condensation of catechin monomers to form condensed tannins and their transport from the cytoplasm to the vacuole is poorly understood. Hence, modifying the regulation of known enzymes and transcription factors in the flavonoid pathway may up-regulate catechin levels but not increase condensed tannin levels, and therefore, bloat-safety. The PVPP-butanol-HCl assay detects only condensed tannins, relying on the ability of condensed tannins, but not their monomers to bind to PVPP. The detailed method is as follows.

Clover leaf and inflorescence (positive control) tissue was snap-frozen and ground to a fine powder in a mortar and pestle under liquid nitrogen. After grinding, 0.75 g of the powder from each sample was transferred to a 14 ml screw-cap centrifuge tube (Falcon), vortex-mixed with 1.5 ml of extraction buffer containing 80% v/v methanol in distilled water with 5.3 mM sodium bisulfite. Samples were mixed for 5 hours on a mixing wheel before centrifugation at 3000×g for 10 minutes. A 1 ml aliquot of each supernatant was transferred to a 1.5 ml microcentrifuge tube and reduced to 0.25 ml in a vacuum centrifuge. Equal volumes of the sample were added to each of two 1.5 ml microcentrifuge tubes containing 25 mg of polyvinyl polypyrrolidone (PVPP). Each mixture was vortex-mixed intermittently for 15 min and centrifuged for 1 min at maximum speed in a microcentrifuge. After removal of the supernatant, the pellet was washed four times with 1 ml of methanol, with a 1 min centrifugation step at maximum speed in a microcentrifuge between each wash. A freshly-made 70:30 (v/v) solution of butanol and concentrated hydrochloric acid was added to each pellet and one tube of the mixture was incubated for 1 hour at 70° C., whereas the other tube was incubated at ambient temperature. The difference in the absorbance (530 nm) between the two tubes from each plant sample was proportional to the level of condensed tannins in the sample. This assay can be quantitated with a condensed tannin of known concentration, although only the relative levels of tannins were measured in this experiment.

EXAMPLE 7

Design of Real Time RT-PCR Primers Based on cDNA Sequences of Clover TT12, TTG1, TT2, TT8, LDOX, 4CL and C4H Genes Real-time RT-PCR is a recently developed technique that allows more quantitative analyses of gene expression than Northern or conventional RT-PCR experiments. Essentially, real-time RT-PCR with SYBR Green chemistry and gene-specific primers involves the automatic measurement of the level of a fluorescent PCR product generated from a cDNA species over each cycle. The abundance of each template is proportional to the amplification rate. Therefore, a threshold corresponding to the start of the exponential phase of PCR allows the relative abundance of target genes to be standardised against a uniformly expressed 'housekeeping' gene in each tissue and compared to a negative control without a template. Real-time RT-PCR with SYBR Green chemistry has been used successfully by others in the field to quantify the expression of four flavonoid-related genes in *Lotus corniculatus* plants exposed to different light regimes (Paolocci et al., 2005)

A Real-Time RT-PCR strategy involving with SYBR Green chemistry and the δδCT method of analysis was used characterise the expression of TT12, TTG1, TT2, TT8, LDOX, 4CL and C4H homologues in white clover tissues containing high and low levels of condensed tannins. This approach aimed to determine which of the genes and isoforms were most likely to be involved in condensed tannin production, or in the production of other flavonoids, and could therefore be targeted for overexpression or downregulation in the metabolic engineering of bloat-safe white clover.

The full-length cDNA sequences of white clover of TT12, TTG1, TT2, TT8, LDOX, 4CL and C4H homologues were used as input data for the Primer Express (Applied Biosystems, Foster City, USA) primer design program, using the default settings, no 3' GC clamp and a predicted amplicon size of 50-150 base pairs. Primers close to the 3' ends of the input sequences were preferred, due to the likelihood of a large number of cDNA molecules derived from clover samples being incomplete at the 5' end. The sequences of the chosen primers are shown in Table 6.

The specificity of the primer sets was tested using 1 ul of plasmid DNA (0.01 ng/ul) from the original cDNA cloned into pGEM-T Easy or autoclaved, purified water, 12.5 μl 2×SYBR Green Master Mix (Applied Biosystems), 0.5 ul each of the forward and reverse primers (10 uM) and 10.5 ul of autoclaved, purified water (Sartorius AG, Goettingen, Germany). Real-time PCR was performed in 96-well optical PCR plates (Applied Biosystems) using the Stratagene MX3000P cycler and the following cycling parameters: 95° C. for 10 min, 40 cycles of 95° C. for 30 sec and 60° C. for 1 min, followed by 55° C. for 1 min and 95° C. for 1 min. All of the primer sets except those designed to amplify clover TT2a amplified a satisfactory level of products from the corresponding cDNA templates with a cycle threshold cut-off of 24 cycles (Table 7). The primer sets were isoform-specific, with the exception of the two sets designed to amplify clover C4H homologues.

It was shown by DMACA staining that the lower half of Mink white clover buds are enriched for condensed tannins. Therefore a preliminary experiment was carried out to test for the expression of clover TT12, TTG1, TT2, TT8, LDOX, 4CL and C4H genes in the buds of white clover (cv Mink), relative to expression of a clover histone control gene. Total RNA was extracted from upper and lower halves of buds as well as whole buds using the RNeasy kit (QIAGEN GmbH, Hilden, Germany) and contaminating genomic DNA was digested on the column using the optional on-column DNAse digestion according to the manufacturers' instructions. Complementary DNA (cDNA) was synthesised from 0.5 ug of total RNA using the Quantitect Reverse Transcriptase Kit (QIAGEN GmbH). Real-time RT-PCR reactions were set up and run as described earlier using 1 ul of cDNA, plasmid control DNA or autoclaved, purified water as the template. The experiment showed that expression of clover LDOX correlated well with condensed tannin production in the lower half of white clover buds (FIG. 83).

TABLE 6

List of primers designed for Real-time RT-PCR analysis of condensed tannin-rich organs of white clover, based on cDNA sequences of clover TT12, TTG1, TT2, TT8, LDOX, 4CL and C4H genes

| Gene name | Clone ID | primer 1 (forward) | primer 2 (reverse) |
|---|---|---|---|
| WcCTa (TrTT12a) | 05wc1CsD12 | GACAGAGAGCATAGCCGAGCA SEQ. ID. NO. 140 | GGTATAAGACCGCGAGCGAA SEQ. ID. NO. 141 |

TABLE 6 -continued

List of primers designed for Real-time RT-PCR analysis of condensed tannin-rich organs of white clover, based on cDNA sequences of clover TT12, TTG1, TT2, TT8, LDOX, 4CL and C4H genes

| Gene name | Clone ID | primer 1 (forward) | primer 2 (reverse) |
|---|---|---|---|
| WcCTb (TrTTG1a) | 10wc1CsD07 | AACTCATGTTCCATCCCGCA SEQ. ID. NO. 142 | CGGAGGAGGTTTTCTGGAGAG SEQ. ID. NO. 143 |
| WcCTc (TrTT2a) | 14wc1LsB05 | GTAATGGCAACTGGCGTGCT SEQ. ID. NO. 144 | CACATCTTAACAAGCCTCGTAGCT SEQ. ID. NO. 145 |
| WcCTd (TrTT2b) | 04wc1EsE11 | CCATTCTAATTGGCGTGCTCT T SEQ. ID. NO. 146 | CCACACCTTAACAACCCAGCTT SEQ. ID. NO. 147 |
| WcCTe (TrTT8a) | 06wc2DsD04 | TGGGAGGCTTCATGTGATCA SEQ. ID. NO. 148 | GCATTAGCTGGTCCTTTGAACTTAG SEQ. ID. NO. 149 |
| WcCTf (TrLDOXa) | 07wc3GsD03 | GCTAGTGGTCAACTTGAATGG GA SEQ. ID. NO. 150 | TCAGGAAAAATACAATGAAAGAAATA ATCT SEQ. ID. NO. 151 |
| WcCTg (Tr4CLa) | 14wc2KsH10 | GCACCCACCGGAAAAGTCTA SEQ. ID. NO. 152 | CCGAGAGGTGAGTTCGACGT SEQ. ID. NO. 153 |
| WcCTh (Tr4CLb) | 13wc1DsH07 | TCATAGTGGATAGGCTTAAAG AATTGAT SEQ. ID. NO. 154 | TGGGATGTGAAAGAATAATGGCTT SEQ. ID. NO. 155 |
| WcCTi (Tr4CLc) | 16wc1NsB11 | GTTGTCCCGCAAAAGGATGT SEQ. ID. NO. 156 | CACAAAGGCAACAGGAACTTCAC SEQ. ID. NO. 157 |
| WcCTj (Tr4CLd) | 12wc1CsA11 | CTTTCCTCGGTGCCTCCTTC SEQ. ID. NO. 158 | AAGGATTTGCGGTGGTGATG SEQ. ID. NO. 159 |
| WcCTk (TrC4Ha) WcCTm (TrC4Hc) | 14wc2CsB09 06wc1OsE12 | CTTGCCGGTTATGACATCCC SEQ. ID. NO. 160 | CCACGCGTTGACCAATATCTT SEQ. ID. NO. 161 |
| WcCTl (TrC4Hb) | 11wc1OsE04 | CGTTGATGAGAGAAAGAAACT TGAAA SEQ. ID. NO. 162 | GAGCATCCAAAATGTGATCAATTG SEQ. ID. NO. 163 |

TABLE 7

Results of testing real-time PCR primer sets on plasmids containing cDNA sequences encoding clover TT12, TTG1, TT2, TT8, LDOX, 4CL and C4H genes

| Template | Primers | | | | | | | | | | | |
|---|---|---|---|---|---|---|---|---|---|---|---|---|
| | TT12a | TTG1a | TT2a | TT2b | TT8a | LDOXa | 4CLa | 4CLb | 4CLc | 4CLd | C4Hac | C4Hb |
| WcCTa (TrTT12) | 26.7 | | | | | | | | | | | |
| WcCTb (TrTTG1a) | | 19.6 | | | | | | | | | | |
| WcCTc (TrTT2a) | | | 27.7 | 0 Ct | | | | | | | | |
| WcCTd (TrTT2b) | | | 36.2 | 20.8 | | | | | | | | |
| WcCTe (TrTT8) | | | | | 20 | | | | | | | |
| WcCTf (TrLDOX) | | | | | | 21.13 | | | | | | |
| WcCTg (Tr4CLa) | | | | | | | 19.5 | no Ct | 37.7 | no Ct | | |
| WcCTh (Tr4CLb) | | | | | | | no Ct | 19.3 | 39.7 | no Ct | | |
| WcCTi (Tr4CLc) | | | | | | | 37.4 | 36.8 | 19.8 | 35.8 | | |
| WcCTj (Tr4CLd) | | | | | | | 31.3 | 31.8 | 32.5 | 20.6 | | |
| WcCTk (TrC4ha) | | | | | | | | | | | 22.44 | 22.9 |

TABLE 7-continued

Results of testing real-time PCR primer sets on plasmids containing cDNA sequences encoding clover TT12, TTG1, TT2, TT8, LDOX, 4CL and C4H genes

| Template | TT12a | TTG1a | TT2a | TT2b | TT8a | LDOXa | 4CLa | 4CLb | 4CLc | 4CLd | C4Hac | C4Hb |
|---|---|---|---|---|---|---|---|---|---|---|---|---|
| WcCTI (TrC4Hb) | | | | | | | | | | | 22.05 | 17.55 |
| WcCTm (TrC4Hc) | | | | | | | | | | | 20.2 | 37.13 |
| ddH2O | 37.2 | 0 Ct | 0 Ct | 38.8 | 35.3 | 0 Ct | 37.6 | 0 Ct | 32.5 | 31.1 | 37.2 | 0 Ct |

REFERENCES

Causier, B. and Davies B. (2002). Analysing protein-protein interactions with the yeast two-hybrid system. *Plant Mol. Biol.* 50: 855-870

Frohman et al., (1988) Rapid production of full-length cDNAs from rare transcripts: amplification using a single gene-specific oligonucleotide primer. *Proc. Natl. Acad Sci. USA* 85:8998

Gish and States (1993) Identification of protein coding regions by database similarity search. *Nature Genetics* 3:266-272

Hink, M A, Bisseling, T. and Visser, A. G. (2002). Imaging protein-protein interactions in living cells. *Plant Mol. Biol.* 50:871-873

Loh, E. Y., Elliott, J. F., Cwirla, S., Lanier, L. L., Davis, M. M. (1989). Polymerase chain reaction with single-sided specificity: Analysis of T-cell receptor delta chain. *Science* 243: 217-220

Ohara, O., Dorit, R. L., Gilbert, W. (1989). One-sided polymerase chain reaction: The amplification of cDNA. *Proc. Natl. Acad Sci USA* 86:5673-5677

Paolocci, F., Bovone, T. Tosti, N., Arcioni, S. and Damiani, F. (2005). Light and an exogenous transcription factor qualitatively and quantitatively affect the biosynthetic pathway of condensed tannins in *Lotus corniculatus* leaves. J. Exp. Bot. 56: 1093-1103

Finally, it is to be understood that various alterations, modifications and/or additions may be made without departing from the spirit of the present invention as outlined herein.

It will also be understood that the term "comprises" (or its grammatical variants) as used in this specification is equivalent to the term "includes" and should not be taken as excluding the presence of other elements or features.

Documents cited in this specification are for reference purposes only and their inclusion is not acknowledgment that they form part of the common general knowledge in the relevant art.

The invention claimed is:

1. A substantially purified or isolated nucleic acid, said nucleic acid being selected from the group consisting of:
   (a) a nucleotide sequence encoding a TRANSPARENT TESTA 2 (TT2) selected from the group consisting of Seq ID Nos. 9, 11, 12, 13, 60, 62 and functionally active fragments thereof;
   (b) a nucleotide sequence which is the full length complement to a sequence selected from the group consisting of Seq ID Nos. 9, 11, 12, 13, 60 and 62; and
   (c) a variant nucleotide sequence encoding a TT2 or TT2-like protein which is a variant of a starting sequence, said starting sequence having a sequence as defined in paragraph (a), wherein the variant nucleotide sequence has at least 90% identity to the starting sequence.

2. The nucleic acid of claim 1, wherein the variant nucleotide sequence has at least 95% identity to the starting sequences.

3. The nucleic acid of claim 1, wherein the variant nucleotide sequence has at least 98% identity to the starting sequence.

4. The nucleic acid of claim 1, wherein the nucleotide sequence encoding a TT2 or TT2-like protein is selected from the group consisting of Seq ID Nos. 9, 11, 12, 13, 60 and 62.

5. A construct comprising a nucleic acid or nucleic acid fragment according to claim 1.

6. A vector comprising a nucleic acid or nucleic acid fragment according to claim 1.

7. A vector according to claim 6, further including a promoter and a terminator, said promoter, nucleic acid or nucleic acid fragment and terminator being operatively linked.

8. A plant cell, plant, plant seed or other plant part, comprising a nucleotide construct or a vector, said construct or vector comprising a nucleic acid or nucleic acid fragment according to claim 1.

9. A plant, plant seed or other plant part derived from a plant cell or plant according to claim 8.

10. A method of modifying a flavonoid-related biological property of a plant comprising introducing into said plant an effective amount of nucleic acid or nucleic fragment according to claim 1, wherein said nucleic acid or nucleic fragment is optionally introduced in a construct or vector.

11. A method according to claim 10 wherein the property of the plant that is modified is flavonoid biosynthesis in a plant, said method comprising introducing into said plant an effective flavonoid biosynthesis-modifying amount of the nucleic acid or nucleic acid fragment.

12. A method according to claim 10 wherein the property of the plant that is modified is protein binding, metal chelation, anti-oxidation, and/or UV-light absorption in a plant, said method comprising introducing into said plant an effective protein binding, metal chelation, anti-oxidation, and/or UV-light absorption modifying amount of the nucleic accord or nucleic acid fragment.

13. A method according to claim 10 wherein the property of the plant that is modified is pigment production in a plant, said method comprising introducing into said plant an effective pigment production-modifying amount of the nucleic acid or nucleic acid fragment.

14. A method according to claim 10 wherein the property of the plant that is modified is plant defense to a biotic stress, said method comprising introducing into said plant an effective defense to biotic stress-modifying amount of the nucleic acid or nucleic acid fragment.

15. A method according to claim 14 wherein said biotic stress is selected from the group consisting of viruses, microorganisms, insects and fungal pathogens.

16. A method according to claim 10 wherein the property of the plant that is modified is forage quality of a plant by disrupting protein foam and/or conferring protection from rumen pasture bloat, said method comprising introducing into said plant an effective forage quality-modifying amount of the nucleic acid or nucleic acid fragment.

17. A substantially purified or isolated polypeptide encoded by a nucleic acid or nucleic fragment according to claim 1.

18. A substantially purified or isolated polypeptide, said polypeptide being selected from the group consisting of:
   (a) an amino acid sequence encoding a TT2 or TT2-like polypeptide selected from the group consisting of Seq ID Nos. 10, 14, 61, 63 and functionally active fragments thereof; and
   (b) a variant amino acid sequence encoding a TT2 or TT2-like polypeptide which is a variant of a sequence recited in (a), wherein the variant sequence has at least 90% identity to the sequence recited in (a).

* * * * *

SEQUENCE LISTING

```
<160> NUMBER OF SEQ ID NOS: 163

<210> SEQ ID NO 1
<211> LENGTH: 694
<212> TYPE: DNA
<213> ORGANISM: Trifolium repens

<400> SEQUENCE: 1
aaaaactagt tgtgaggcat ataactatga gctctataga aaaccaacca ttactattgg      60
ggcttgactc acactcacac attgcaaatc tatcatcaga tactattgaa gaattcttgg     120
aacataggcc tattcagtta agatggtggc ttaaacttgt tgcttgggag tcaagggtcc     180
tatggatact ttctggtgca tctattattg tctacctttt caattacatg ctaagctttg     240
ctaccttaat gtttagtgga catttaggat ctcttgagct tgctggtgca tctatagcta     300
atgttggaat tcaaggtctt gcttatggaa ttatgctagg aatggcaagt gcagtgcaaa     360
ctgtgtgtgg acaagcttat ggagccaaaa aatatgcagt aatgtgcatc acattgcaaa     420
gagcagtaat cttacattta ggagcagcag tgattctcac atttctctat tggttttctg     480
gagattttct aaaagtcata ggacagacag agagcatagc cgagcaaggt caagttttcg     540
ctcgcggtct tatacctcaa ctctatgcat ttgcattgag ttgtccaatg caaaggtttc     600
tccaagcaca gaacattgtt aatcctcttg catatatggc agttggagtg ttcattcttc     660
atgtgcttgt tagttggcta gttatctatg tttt                                 694
```

```
<210> SEQ ID NO 2
<211> LENGTH: 222
<212> TYPE: PRT
<213> ORGANISM: Trifolium repens

<400> SEQUENCE: 2

Met Ser Ser Ile Glu Asn Gln Pro Leu Leu Gly Leu Asp Ser His
1               5                   10                  15

Ser His Ile Ala Asn Leu Ser Ser Asp Thr Ile Glu Glu Phe Leu Glu
            20                  25                  30

His Arg Pro Ile Gln Leu Arg Trp Trp Leu Lys Leu Val Ala Trp Glu
        35                  40                  45

Ser Arg Val Leu Trp Ile Leu Ser Gly Ala Ser Ile Ile Val Tyr Leu
    50                  55                  60

Phe Asn Tyr Met Leu Ser Phe Ala Thr Leu Met Phe Ser Gly His Leu
65                  70                  75                  80

Gly Ser Leu Glu Leu Ala Gly Ala Ser Ile Ala Asn Val Gly Ile Gln
                85                  90                  95

Gly Leu Ala Tyr Gly Ile Met Leu Gly Met Ala Ser Ala Val Gln Thr
            100                 105                 110

Val Cys Gly Gln Ala Tyr Gly Ala Lys Lys Tyr Ala Val Met Cys Ile
        115                 120                 125

Thr Leu Gln Arg Ala Val Ile Leu His Leu Gly Ala Ala Val Ile Leu
    130                 135                 140

Thr Phe Leu Tyr Trp Phe Ser Gly Asp Phe Leu Lys Val Ile Gly Gln
145                 150                 155                 160

Thr Glu Ser Ile Ala Glu Gly Gln Val Phe Ala Arg Gly Leu Ile
                165                 170                 175

Pro Gln Leu Tyr Ala Phe Ala Leu Ser Cys Pro Met Gln Arg Phe Leu
            180                 185                 190

Gln Ala Gln Asn Ile Val Asn Pro Leu Ala Tyr Met Ala Val Gly Val
        195                 200                 205

Phe Ile Leu His Val Leu Val Ser Trp Leu Val Ile Tyr Val
    210                 215                 220

<210> SEQ ID NO 3
<211> LENGTH: 512
<212> TYPE: DNA
<213> ORGANISM: Trifolium repens

<400> SEQUENCE: 3
tgctattggg gcttgactca cactcacaca ttgcaaatct atcatcagat tctattgaag      60
aattcttgga acataggcct attcagttaa gatggtggct taaacttgtt gcttgggagt     120
caagggtcct atggatactt tctggtgcat ctattattgt ctacctttc aattacatgc      180 taagctttgc taccttaatg tttagtggac atttaggatc tcttgagctt gctggtgcat     240
ctatagctaa tgttggaatt caaggtcttg cttatggaat tatgctagga atggcaagtg     300
cagtgcaaac tgtgtgtgga caagcttatg gagccaaaaa atatgcagta atgtgcatca     360
cattgcaaag agcagtaatc ttacatttag gagcagcagt gattctcaca tttctctatt     420
ggttttctgg agattttcta aaagtcatag gacagacaga gagcatagcc gagcaaggtc     480
aagttttcgc tcgcggtctt atacctcaac tc                                   512

<210> SEQ ID NO 4
<211> LENGTH: 553
<212> TYPE: DNA
<213> ORGANISM: Trifolium repens
```

```
<400> SEQUENCE: 4 ataaactat gagctctata gaaaaccaac cattgctatt ggggcttgac tcacactcac      60
acattgcaaa tctatcatca gattctattg aagaattctt ggaacatagg cctattcagt    120
taagatggtg gcttaaactt gttgcttggg agtcaagggt cctatggata ctttctggtg    180
catctattat tgtctacctt ttcaattaca tgctaagctt tgctacctta atgtttagtg    240
gacatttagg atctcttgag cttgctggtg catctatagc taatgttgga attcaaggtc    300
ttgcttatgg aattatgcta ggaatggcaa gtgcagtgca aactgtgtgt ggacaagctt    360
atggagccaa aaatatgca gtaatgtgca tcacattgca aagagcagta atcttacatt     420
taggagcagc agtgattctc acatttctct attggttttc tggagatttt ctaaaagtca    480
taggacagac agagagcata gccgagcaag gtcaagtttt cgctcgcggt cttataccto    540 aactctatgc att                                                       553

<210> SEQ ID NO 5
<211> LENGTH: 593
<212> TYPE: DNA
<213> ORGANISM: Trifolium repens

<400> SEQUENCE: 5
ttgtgaggca tataactatg agctctatag aaaaccacca ttactattgg ggcttgactc     60
acactcacac attgcaaatc tatcatcaga tactattgaa gaattcttgg aacataggcc    120
tattcagtta agatggtggc ttaaacttgt tgcttgggag tcaagggtcc tatggatcct    180
ttctggtgca tctattattg tctaccttt caattacatg ctaagctttg ctaccttaat     240
gtttagtgga catttaggat ctcttgagct tgctggtgca tctatagcta atgttggaat    300
tcaaggtctt gcttatggaa ttatgctagg aatggcaagt gcagtgcaaa ctgtgtgtgg    360
acaagcttat ggagccaaaa atatgcagt aatgtgcatc acattgcaaa gagcagtaat    420
cttacatttt ggagcagcag tgattctcac atttctctat tggttttctg gagattttct    480
aaaagtaata ggacagacag agagcatagc cgagcaaggt caagttttcg ctcgcggtct    540
tatacctcaa ctctatgcat ttgcattgag ttgtccaatg caaaggttc tcc             593

<210> SEQ ID NO 6
<211> LENGTH: 694
<212> TYPE: DNA
<213> ORGANISM: Trifolium repens

<400> SEQUENCE: 6
aaaaactagt tgtgaggcat ataactatga gctctataga aaaccaacca ttactattgg     60
ggcttgactc acactcacac attgcaaatc tatcatcaga tactattgaa gaattcttgg    120
aacataggcc tattcagtta agatggtggc ttaaacttgt tgcttgggag tcaagggtcc    180
tatggatcct ttctggtgca tctattattg tctaccttt caattacatg ctaagctttg     240
ctaccttaat gtttagtgga catttaggat ctctagagct tgctggtgca tctacagcta    300
atgttggaat tcaaggtctt gcttatggaa ttatgctagg aatggcaagt gcagtgcaaa    360
ctgtgtgtgg acaagcttat ggagccaaaa atatgcagt aatgtgcatc acattgcaaa    420
gagcagtaat cttacatttt ggagcagcag tgattctcac atttctctat tggttttctg    480
gagattttct aaaagtcata ggacagacag agagcatagc cgagcaaggc caagttttcg    540
ctcgcggtct tatacctcaa ctctatgcat ttgcattgag ttgtccaatg caaaggtttc    600
tccaagcaca gaacattgtt aatcctcttg catatatggc agttggagtg ttcattcttc    660
```

```
atgtgcttgt tagttggcta gttatctatg tttt                                694
```

<210> SEQ ID NO 7
<211> LENGTH: 482
<212> TYPE: DNA
<213> ORGANISM: Trifolium repens

<400> SEQUENCE: 7

```
ttctctcttg tgttttcat caaacacctt ctctgcataa ttttcttcat caaaaaattc      60
aaacactcaa aaactcaaac acctttcgtg catcaccaaa aatggagaat tcaactcaag    120
aatcacacat ccgatccgaa aactctgtta cctacgattc cccttatcct ctctacgcca    180
tggctctttc tccaaacacc aattcacacc cacaacaacg catcgctgtt ggtagtttca    240
tcgaagaata caccaaccgc atcgatatcc tcaatttcaa ccctgagaat ttatcaatta    300
aacctcaacc ttgactttcc ttggatcatg cttatccacc taccaaactc atgttccatg    360
ccgcaacaaa ttcatctgtg cagaaaacct actacgacct tgtaactact tacggtgact    420
atctacgact ttgggaaggt cacgaaaatt ggggtgaggc tctttctctt tttaacaaca    480
gc                                                                   482
```

<210> SEQ ID NO 8
<211> LENGTH: 70
<212> TYPE: PRT
<213> ORGANISM: Trifolium repens

<400> SEQUENCE: 8

```
Met Glu Asn Ser Thr Gln Glu Ser His Ile Arg Ser Glu Asn Ser Val
1               5                   10                  15
Thr Tyr Asp Ser Pro Tyr Pro Leu Tyr Ala Met Ala Leu Ser Pro Asn
            20                  25                  30
Thr Asn Ser His Pro Gln Gln Arg Ile Ala Val Gly Ser Phe Ile Glu
        35                  40                  45
Glu Tyr Thr Asn Arg Ile Asp Ile Leu Asn Phe Asn Pro Glu Asn Leu
    50                  55                  60
Ser Ile Lys Pro Gln Pro
65                  70
```

<210> SEQ ID NO 9
<211> LENGTH: 537
<212> TYPE: DNA
<213> ORGANISM: Trifolium repens

<400> SEQUENCE: 9

```
atataccaat agtgcattct tcttcctata ttgttattac cataaacatg gtaagagctc      60
cttgttgtga aaaatgggga ttgaagagag gtccttggtc tcttgaggaa gatcaaatcc    120
ttacatctta cattcaaaaa catggtaatg caactggcg tgctctccca aagctagcag     180
gcttgttaag atgtggaaaa agctgtagac ttaggtggat taactatttg agacctgata    240
tcaagagagg aaatttcaca aatgaagaag aggaaaatat cattaagcta catgaaatgc    300
ttgggaacag gtggtcggca attgcagcaa aattaccagg aagaacggac aatgaaataa    360
aaaatgtgtg gcacacgcat ttgaagaaga attattgaa acaaatgaa acaaactcag      420
aaactaagaa aagggtgatc acaaaaacaa aaatcaaacg ttctgattca aattcaagca    480
ctataacaca atcagaatca gtttctgcat gcactactag ttctagtgat ttttcat      537
```

<210> SEQ ID NO 10

```
<211> LENGTH: 163
<212> TYPE: PRT
<213> ORGANISM: Trifolium repens

<400> SEQUENCE: 10

Met Val Arg Ala Pro Cys Cys Glu Lys Met Gly Leu Lys Arg Gly Pro
1               5                   10                  15

Trp Ser Leu Glu Glu Asp Gln Ile Leu Thr Ser Tyr Ile Gln Lys His
            20                  25                  30

Gly Asn Gly Asn Trp Arg Ala Leu Pro Lys Leu Ala Gly Leu Leu Arg
        35                  40                  45

Cys Gly Lys Ser Cys Arg Leu Arg Trp Ile Asn Tyr Leu Arg Pro Asp
50                  55                  60

Ile Lys Arg Gly Asn Phe Thr Asn Glu Glu Glu Asn Ile Ile Lys
65                  70                  75                  80

Leu His Glu Met Leu Gly Asn Arg Trp Ser Ala Ile Ala Ala Lys Leu
                85                  90                  95

Pro Gly Arg Thr Asp Asn Glu Ile Lys Asn Val Trp His Thr His Leu
            100                 105                 110

Lys Lys Lys Leu Leu Lys Thr Asn Glu Thr Asn Ser Glu Thr Lys Lys
        115                 120                 125

Arg Val Ile Thr Lys Thr Lys Ile Lys Arg Ser Asp Ser Asn Ser Ser
    130                 135                 140

Thr Ile Thr Gln Ser Glu Ser Val Ser Ala Cys Thr Thr Ser Ser Ser
145                 150                 155                 160

Asp Phe Ser

<210> SEQ ID NO 11
<211> LENGTH: 531
<212> TYPE: DNA
<213> ORGANISM: Trifolium repens

<400> SEQUENCE: 11
atataccaat agtgcattct tcttcctata ttgttattac cataaacatg gtaagagctc     60
cttgttgtga aaaatggga ttgaagagag gtccttggtc tcttgaggaa gatcaaatcc    120
ttacatctta cattcaaaaa catggtaatg gcaactggcg tgctctccca aagctagcag    180
gcttgttaag atgtggaaaa agctgtagac ttaggtggat taactatttg agacctgata    240
tcaagagagg aaatttcaca aatgaagaag aggaaaatat cattaagcta catgaaatgc    300
ttgggaacag gtggtcggca attgcagcaa aattaccagg aagaacggac aatgaaataa    360
aaaatgtgtg gcacacgcat ttgaagaaga aattattgaa aacaaatgaa acaaactcag    420
aaactaagaa aagggtgatc acaaaaacaa aaatcaaacg ttctgattca aattcaagca    480
ctataacaca atcagaatca gtttctgcat gcactactag ttctagtgat t             531

<210> SEQ ID NO 12
<211> LENGTH: 537
<212> TYPE: DNA
<213> ORGANISM: Trifolium repens

<400> SEQUENCE: 12
atataccaat agtgcattct tcttcctata ttgttattac cataaacatg gtaagagctc     60
cttgttgtga aaaatggga ttgaagagag gtccttggtc tcttgaggaa gatcaaatcc    120
ttacatctta cattcaaaaa catggtaatg gcaactggcg tgctctccca aagctagcag    180
gcttgttaag atgtggaaaa agctgtagac ttaggtggat taactatttg agacctgata    240
```

```
tcaagagagg aaatttcaca aatgaagaag aggaaaatat cattaagcta catgaaatgc      300
ttgggaacag gtggtcggca attgcagcaa aattaccagg aagaacggac aatgaaataa      360
aaaatgtgtg gcacacgcat ttgaagaaga aattattgaa acaaatgaa acaaactcag       420 aaactaagaa aagggtgatc acaaaaacaa aaatcaaacg ttctgattca aattcaagca      480
ctataacaca atcagaatca gtttctgcat gcactactag ttctagtgat ttttcat         537
```

<210> SEQ ID NO 13
<211> LENGTH: 549
<212> TYPE: DNA
<213> ORGANISM: Trifolium repens

<400> SEQUENCE: 13

```
ttggattttt attgcaaaaa tggtgagagc tccatgttgt gaaaaaatgg ggttgaagaa       60
aggtccatgg actcaagaag aagatagaat tctcatcaat cacataaaca cttatggcca     120
ttctaattgc cgtgctcttc caaaacaagc tgggttgtta aggtgtggaa aaagttgtag     180
attgagatgg gcaaattatt tgaaaccaga tatcaaacgg ggtaatttta ctaaagaaga     240
agaggatgca ataatcaatt tgcaccaaat gttgggaaat aggtggtcaa ctatagcagc     300
aagattacca ggacgaacgg acaatgaaat aaaaaatgta tggcacaccc acttgaagaa     360
gaggctgcca caaaccaac aaggccacaa caatagccca aaaagaaata agaaacaaac      420
caatttggac tttgaagcct ccaaatcaga ccaagatatc aaacaagaac aaaataatgt     480
tgatgatatg ccacaatgtt ctagtgacat gtcataccat aataatagta gcaatagcat     540
tgctactac                                                             549
```

<210> SEQ ID NO 14
<211> LENGTH: 176
<212> TYPE: PRT
<213> ORGANISM: Trifolium repens

<400> SEQUENCE: 14

```
Met Val Arg Ala Pro Cys Cys Glu Lys Met Gly Leu Lys Lys Gly Pro
1               5                   10                  15

Trp Thr Gln Glu Glu Asp Arg Ile Leu Ile Asn His Ile Asn Thr Tyr
            20                  25                  30

Gly His Ser Asn Trp Arg Ala Leu Pro Lys Gln Ala Gly Leu Leu Arg
        35                  40                  45

Cys Gly Lys Ser Cys Arg Leu Arg Trp Ala Asn Tyr Leu Lys Pro Asp
    50                  55                  60

Ile Lys Arg Gly Asn Phe Thr Lys Glu Glu Asp Ala Ile Ile Asn
65                  70                  75                  80

Leu His Gln Met Leu Gly Asn Arg Trp Ser Thr Ile Ala Ala Arg Leu
                85                  90                  95

Pro Gly Arg Thr Asp Asn Glu Ile Lys Asn Val Trp His Thr His Leu
            100                 105                 110

Lys Lys Arg Leu Pro Gln Asn Gln Gln Gly His Asn Asn Ser Pro Lys
        115                 120                 125

Arg Asn Lys Lys Gln Thr Asn Leu Asp Phe Glu Ala Ser Lys Ser Asp
    130                 135                 140

Gln Asp Ile Lys Gln Glu Gln Asn Asn Val Asp Asp Met Pro Gln Cys
145                 150                 155                 160

Ser Ser Asp Met Ser Tyr His Asn Asn Ser Asn Ser Ile Ala Thr
                165                 170                 175
```

<210> SEQ ID NO 15
<211> LENGTH: 530
<212> TYPE: DNA
<213> ORGANISM: Trifolium repens

<400> SEQUENCE: 15

```
aagctgatga aggtatgaac catgttttgt cagaaagaag gagaagagca aaacttaatg      60
aaaggttttt aactcttaga tcaatggtcc cttcagatag taaggatgac aaagtttcta     120
tactagatga tgcaattgaa tatcttagca agcttgagaa aaggataaaa gaattagaag     180
ctcaaaaaga accaatagat atagagtcta gaagtaaaaa atcacatcat gatttgttgg     240
agaggacttg tgatgattat ataacaaca aaactaacaa tggcaagaaa ccaatgatga     300
agaagaggga aatatgtgac ataggtgaga caaggagaca gatattttct gatgctttaa     360
aaggaagttc taatagtgat gttactgtca gtatgagtga caatggagtt gtgattgaaa     420
tgaagtgtcc ttctagagaa ggaaggatat tggaaattat ggatgcagtt aacaatctca     480
acatggattt taattcagtt caatctacag attccgatgg gaggcttcat                530
```

<210> SEQ ID NO 16
<211> LENGTH: 176
<212> TYPE: PRT
<213> ORGANISM: Trifolium repens

<400> SEQUENCE: 16

```
Ala Asp Glu Gly Met Asn His Val Leu Ser Glu Arg Arg Arg Arg Ala
1               5                   10                  15

Lys Leu Asn Glu Arg Phe Leu Thr Leu Arg Ser Met Val Pro Ser Asp
            20                  25                  30

Ser Lys Asp Asp Lys Val Ser Ile Leu Asp Asp Ala Ile Glu Tyr Leu
        35                  40                  45

Ser Lys Leu Glu Lys Arg Ile Lys Glu Leu Glu Ala Gln Lys Glu Pro
    50                  55                  60

Ile Asp Ile Glu Ser Arg Ser Lys Lys Ser His His Asp Leu Leu Glu
65                  70                  75                  80

Arg Thr Cys Asp Asp Tyr Tyr Asn Asn Lys Thr Asn Asn Gly Lys Lys
                85                  90                  95

Pro Met Met Lys Lys Arg Glu Ile Cys Asp Ile Gly Glu Thr Arg Arg
            100                 105                 110

Gln Ile Phe Ser Asp Ala Leu Lys Gly Ser Ser Asn Ser Asp Val Thr
        115                 120                 125

Val Ser Met Ser Asp Asn Gly Val Val Ile Glu Met Lys Cys Pro Ser
    130                 135                 140

Arg Glu Gly Arg Ile Leu Glu Ile Met Asp Ala Val Asn Asn Leu Asn
145                 150                 155                 160

Met Asp Phe Asn Ser Val Gln Ser Thr Asp Ser Asp Gly Arg Leu His
                165                 170                 175
```

<210> SEQ ID NO 17
<211> LENGTH: 672
<212> TYPE: DNA
<213> ORGANISM: Trifolium repens

<400> SEQUENCE: 17

```
tagaaactac aaaataaaaa aaaattatca tataataaag atgggaaccg tgcacaaag       60
agttgaaagc ttatctttga gtggaatatc atcaattcca aagaatatg tgagaccaaa     120
agaagagtta acaaacatag gaaacatatt tgatgaagta aaaaaacaag ggccacaagt     180
```

```
tccaacaatt gatataaaag aaataaactc ttcagatgaa attgttagaa gaaaatgtag      240
ggataagctt aagaaagctg cagaggaatg gggtgtgatg aatttggtga accatggtat      300
ttctgatgaa ttacttaatc gacttaaaaa agttggtgaa acttttttg  agttacctgt      360 tgaagaaaaa gaaaaatatg ctaatgatca aagtgatggg aagattcaag ggtatggtag      420
taaattagct aataatgcta gtggtcaact tgaatgggaa gattatttct tcattgtat       480 ttttcctgag gataagcgtg acttatctat atggcctaag actccagctg attatactga      540
ggtcacaaca gaatatgcaa agaactaag  aggcctagct agcaagataa tggaagtgtt      600
atctcttgaa cttggcttag aaggaggaag attagagaaa gaagttggtg gaatggaaga      660
gcttttactt ca                                                         672

<210> SEQ ID NO 18
<211> LENGTH: 210
<212> TYPE: PRT
<213> ORGANISM: Trifolium repens

<400> SEQUENCE: 18

Met Gly Thr Val Ala Gln Arg Val Glu Ser Leu Ser Leu Ser Gly Ile
1               5                   10                  15

Ser Ser Ile Pro Lys Glu Tyr Val Arg Pro Lys Glu Glu Leu Thr Asn
            20                  25                  30

Ile Gly Asn Ile Phe Asp Glu Val Lys Lys Gln Gly Pro Gln Val Pro
        35                  40                  45

Thr Ile Asp Ile Lys Glu Ile Asn Ser Ser Asp Glu Ile Val Arg Arg
    50                  55                  60

Lys Cys Arg Asp Lys Leu Lys Lys Ala Ala Glu Glu Trp Gly Val Met
65                  70                  75                  80

Asn Leu Val Asn His Gly Ile Ser Asp Glu Leu Leu Asn Arg Leu Lys
                85                  90                  95

Lys Val Gly Glu Thr Phe Phe Glu Leu Pro Val Glu Glu Lys Glu Lys
            100                 105                 110

Tyr Ala Asn Asp Gln Ser Asp Gly Lys Ile Gln Gly Tyr Gly Ser Lys
        115                 120                 125

Leu Ala Asn Asn Ala Ser Gly Gln Leu Glu Trp Glu Asp Tyr Phe Phe
    130                 135                 140

His Cys Ile Phe Pro Glu Asp Lys Arg Asp Leu Ser Ile Trp Pro Lys
145                 150                 155                 160

Thr Pro Ala Asp Tyr Thr Glu Val Thr Thr Glu Tyr Ala Lys Glu Leu
                165                 170                 175

Arg Gly Leu Ala Ser Lys Ile Met Glu Val Leu Ser Leu Glu Leu Gly
            180                 185                 190

Leu Glu Gly Gly Arg Leu Glu Lys Glu Val Gly Gly Met Glu Glu Leu
        195                 200                 205

Leu Leu
    210

<210> SEQ ID NO 19
<211> LENGTH: 543
<212> TYPE: DNA
<213> ORGANISM: Trifolium repens

<400> SEQUENCE: 19
aagaagagtt aacaaacata ggaaacatat tgatgaagt  aaaaaaacaa gggccacaag       60
ttccaacaat tgatataaaa gaaataaact cttcagatga aattgttaga agaaaatgta      120
```

```
gggataagct taagaaagct gcagaggaat ggggtgtgat gaatttggtg aaccatggta      180
tttctgatga attacttaat cgacttaaaa aagttggtga acttttttt gagttacctg       240 ttgaagaaaa agaaaatat gctaatgatc aaagtgatgg gaagattcaa gggtatggta      300
gtaaattagc taataatgct agtggtcaac ttgaatggga agattatttc tttcattgta      360 ttttcctga ggataagcgt gacttatcta tatggcctaa gactccagct gattatactg      420
aggtcacaac agaatatgca aaagaactaa gaggcctagc tagcaagata atggaagtgt      480
tatctcttga acttggctta aaggaggaa gattagagaa agaagttggt ggaatggaag      540
agc                                                                   543

<210> SEQ ID NO 20
<211> LENGTH: 517
<212> TYPE: DNA
<213> ORGANISM: Trifolium repens

<400> SEQUENCE: 20
atatgtgaga ccaaaagaag agctaataaa cataggaaac atatttgatg aataaaaaaa       60
acaagggcca aagttccaa caattgatat aaaagaaata aactctacag atgaaattgt      120
tagaagaaaa tgtatggata agcttatttt agctgcagag gaatggggtg tgatgaattt      180
ggtgaatcat ggtatttctg atgaattact taatcgactt aaaaaagttg gtgaaacttt      240
ttttgagtta cctgttgaag aaaagaaaa atatgctaat gatcaaagtg ttgggaagat      300
tcaagggtat ggtagtaaat tagctaataa tgctagtggt caacttgaat gggaagatta      360
tttctttcat tgtatttttc ctgaggataa gcgtgactta tccatatggc ctaagactcc      420
agctgattat actgaggtca caacagaata tgcaaaagaa ctaagaggcc tagctagcaa      480
gataatggaa gtgttatctc ttgaacttgg cttagaa                              517

<210> SEQ ID NO 21
<211> LENGTH: 528
<212> TYPE: DNA
<213> ORGANISM: Trifolium repens

<400> SEQUENCE: 21
aagaatatgt gagaccaaaa gaagagttaa caaacatagg aaacatattt gatgaagtaa       60
aaaaacaagg gccacaagtt ccaacaattg atataaaaga aataaactct tcagatgaaa      120
ttgttagaag aaaatgtagg gataagctta agaaagctgc agaggaatgg ggtgtgatga      180
atttggtgaa ccatggtatt tctgatgaat tacttaatcg acttaaaaaa gttggtgaaa      240 cttttttttga gttacctgtt gaagaaaaag aaaaatatgc taatgatcaa agtgatggga      300
agattcaagg gtatggtagt aaattagcta ataatgctag tggtcaactt gaatgggaag      360
attatttctt tcattgtatt tttcctgagg ataagcgtga cttatctata tggcctaaga      420
ctccagctga ttatactgag gtcacaacag aatatgcaaa agaactaaga ggcctagcta      480
gcaagataat ggaagtgtta tctcttgaac ttggcttaga aggaggaa                  528

<210> SEQ ID NO 22
<211> LENGTH: 576
<212> TYPE: DNA
<213> ORGANISM: Trifolium repens

<400> SEQUENCE: 22
ttccaaagaa tatgtgagac caaaagaaga gttaacaaac ataggaaaca tatttgatga       60
agtaaaaaaa caagggccac aagttccaac aattgatata aagaaataa actcttcaga      120
```

```
tgaaattgtt agaagaaaat gtagggataa gcttaagaaa gctgcagagg aatggggtgt      180
gatgaatttg gtgaaccatg gtatttctga tgaattactt aatcgactta aaaaagttgg      240
tgaaactttt tttgagttac ctgttgaaga aaagaaaaa tatgctaatg atcaaagtga       300
tgggaagatt caagggtatg gtagtaaatt agctaatat gctagtggtc aacttgaatg       360
ggaagattat ttctttcatt gtattttccc tgaggataag cgtgacttat ctatatggcc      420
taagactcca gctgattata ctgaggtcac aacagaatat gcaaaagaac taagaggcct      480
agctagcaag ataatggaag tgttatctct tgaacttggc ttagaaggag gaagattaga     540
gaaagaagtt ggtggaatgg aagagctttt acttca                                576

<210> SEQ ID NO 23
<211> LENGTH: 576
<212> TYPE: DNA
<213> ORGANISM: Trifolium repens

<400> SEQUENCE: 23
tgaaagctta gctttgagtg aatatcatc aattccaaaa gaatatgtga gaccaaaaga       60
agagttaata acataggaa acatatttga tgaagaaaaa aaacaagggc cacaagttcc       120
aacaattgat ataaaagaaa taaactctac agatgaaatt gttagaagaa attgtaggga      180
taagcttaag aaagctgcag aggaatgggg tgtgatgaat ttggtgaatc atggtatttc      240
tgatgaatta cttaatcgac ttaaaaaagt tggtgaaact ttttttgagt tacctgttga      300
agaaaaagaa aaatatgcta atgatcaaag tgttgggaag attcaagggt atggtagtaa      360
attagctaat aatgctagtg gtcaacttga atgggaagat tatttctttc attgtatttt      420
tcctgaggat aagcgtgact tatccatatg gcctaagact ccagctgatt atactgaggt      480
cacaacagaa tatgcaaaag aactaagagg cctagctagc aagataatgg aagtgttatc      540
tcttgaactt ggcttagaag gaggaagatt agagaa                                576

<210> SEQ ID NO 24
<211> LENGTH: 574
<212> TYPE: DNA
<213> ORGANISM: Trifolium repens

<400> SEQUENCE: 24
agatgggaac cgtggcacaa agagttgaaa gcttatcttt gagtggaata tcatcaattc      60
caaaagaata tgtgagacca aaagaagagt taacaaacat aggaaacata tttgatgaag      120
taaaaaaaca agggccacaa gttccaacaa ttgatataaa agaaataaac tcttcagatg      180
aaattgttag aagaaaatgt agggataagc ttaagaaagc tgcagaggaa tggggtgtga      240
tgaatttggt gaaccatggt atttctgatg aattacttaa tcgacttaaa aaagttggtg      300
aaactttttt tgagttacct gttgaagaaa agaaaaata tgctaatgat caaagtgatg       360
ggaagattca agggtatggt agtaaattag ctaataatgc tagtggtcaa cttgaatggg      420
aagattattt ctttcattgt attttcctg aggataagcg tgacttatct atatggccta       480
agactccagc tgattatact gaggtcacaa cagaatatgc aaaagaacta agaggcctag      540
ctagcaagat aatggaagtg ttatctcttg aact                                  574

<210> SEQ ID NO 25
<211> LENGTH: 384
<212> TYPE: DNA
<213> ORGANISM: Trifolium repens

<400> SEQUENCE: 25
```

-continued

```
tatcatataa taaagatggg aaccgtggca caaagagttg aaagcttatc tttgagtgga      60
atatcatcaa ttccaaaaga atatgtgaga ccaaaagaag agttaacaaa cataggaaac     120
atatttgatg aagtaaaaaa acaagggcca caagttccaa caattgatat aaaagaaata     180
aactcttcag atgaaattgt tagaagaaaa tgtagggata agcttaagaa agctgcagag     240
gaatggggtg tgatgaattt ggtgaaccat ggtatttctg atgaattact taatcgactt     300 aaaaagttg gtgaaacttt ttttgagtta cctgttgaag aaaaagaaaa atatgctaat     360
gatcaaagtg atggcaagat tcaa                                            384

<210> SEQ ID NO 26
<211> LENGTH: 572
<212> TYPE: DNA
<213> ORGANISM: Trifolium repens

<400> SEQUENCE: 26
aaaatatata tataataaag atgggaaccg tggcacaaag agttgaaagc ttatctttga      60
gtggaatatc atcaattcca aaagaatatg tgagaccaaa agaagagtta caaacatag     120 gaaacatatt tgatgaagta aaaaacaag gccacaagt tccaacaatt gatataaaag     180
aaataaactc ttcagatgaa attgttagaa gaaaatgtag ggataagctt aagaaagctg     240
cagaggaatg gggtgtgatg aatttggtga accatggtat ttctgatgaa ttacttaatc     300
gacttaaaaa agttggtgaa actttttttg agttacctgt tgaagaaaaa gaaaaatatg     360
ctaatgatca aagtgatggg aagattcaag ggtatggtag taaattagct aataatgcta     420
gtggtcaact tgaatgggaa gattatttct ttcattgtat ttttcctgag gataagcgtg     480
acttatctat atggcctaag actccagctg attatactga ggtcacaaca gaatatgcaa     540
aagaactaag aggcctagct agcaagataa tg                                  572

<210> SEQ ID NO 27
<211> LENGTH: 540
<212> TYPE: DNA
<213> ORGANISM: Trifolium repens

<400> SEQUENCE: 27
attatattca aattaatata atatgggaac cgtggcacaa agagttgaaa gcttagcttt      60
gagtggaata tcatcaattc caaaagaata tgtgagacca aaagaagagt taacaatcat     120
aggaaacata tttgatgaag aaaaaaaaca agggccacaa gttccaacaa ttgatataaa     180
agaaataaac tcttcagatg aaattgttag aagaaaatgt agggataagc ttaagaaagc     240
tgcagaggaa tggggtgtga tgaatttggt gaatcatggt atttctgatg aattacttaa     300
tcgacttaaa aagttggtg aaacttttt tgagttacct gttgaagaaa agaaaaata     360 tgctaatgat caaagtgttg ggaagattca agggtatggt agtaaattag ctaataatgc     420
tagtggtcaa cttgaatggg aagattattt ctttcattgt atttttcctg aggataagcg     480
tgacttatcc atatggccta agactcctgc tgattatact gaggtcacaa cagaatatgc     540

<210> SEQ ID NO 28
<211> LENGTH: 567
<212> TYPE: DNA
<213> ORGANISM: Trifolium repens

<400> SEQUENCE: 28
tagaaaatat atcatatagt aaagatggga accgtggcac aaagagttga agcttatct      60 ttgagtggaa tatcatcaat tccaaaagaa tatgtgagac caaaagaaga gttaacaaac     120
```

| | | |
|---|---|---|
| ataggaaaca tatttgatga agaaaaaaaa caagggccac aagttccaac aattgatata | 180 | |
| aaagaaataa actcttcaga tgaaattgtt agaacaaaat gtagggataa gcttaaaaaa | 240 | |
| gctgcagagg aatggggtgt gatgaatttg gtgaatcatg gtatttctga tgaattactt | 300 | |
| aatcgactta aaaagttggg tgaaactttt tttgaattac tgttgaagaa aaagaaaaa | 360 | |
| tatgctaatg atcaaagtgt tgggaagatt caagggtatg gtagtaaatt agctaataat | 420 | |
| gctagtggtc aacttgaatg ggaagattat ttctttcatt gtattttttcc tgaggataag | 480 | |
| cgtgacttat ccatatggcc taagactcca gctgattata ctgaggtcac aacagaatat | 540 | |
| gcaaaagaac taagaggcct agctagc | 567 | |

<210> SEQ ID NO 29
<211> LENGTH: 565
<212> TYPE: DNA
<213> ORGANISM: Trifolium repens

<400> SEQUENCE: 29

| | | |
|---|---|---|
| ataatagaaa attatcatat agtaaagatg ggaaccgtgg cacaaagagt tgaaagctta | 60 | |
| tctttgagtg gaatatcatc aattccaaaa gaatatgtga gaccaaaaga agagttaaca | 120 | |
| aacataggaa acatatttga tgaagtaaaa aaacaagggc cacaagttcc aacaattgat | 180 | |
| ataaaagaaa taaactcttc agatgaaatt gttagaagaa aatgtaggga taagcttaag | 240 | |
| aaagctgcag aggaatgggg tgtgatgaat ttggtgaacc atggtatttc tgatgaatta | 300 | |
| cttaatcgac ttaaaaaagt tggtgaaact tttttttgagt tacctgttga agaaaagaa | 360 | |
| aaatatgcta atgatcaaag tgatgggaag attcaagggt atggtagtaa attagctaat | 420 | |
| aatgctagtg gtcaacttga atgggaagat tatttctttc attgtatttt tcctgaggat | 480 | |
| aagcgtgact tatctatatg gcctaagact ccagctgatt atactgaggt cacaacagaa | 540 | |
| tatgcaaaag aactaagagg cctag | 565 | |

<210> SEQ ID NO 30
<211> LENGTH: 580
<212> TYPE: DNA
<213> ORGANISM: Trifolium repens

<400> SEQUENCE: 30

| | | |
|---|---|---|
| aataatagaa aatatatata taataaagat gggaaccgtg gcacaaagag ttgaaagctt | 60 | |
| atctttgagt ggaatatcat caattccaaa agaatatgtg agaccaaaag aagagttaac | 120 | |
| aaacatagga acatatttg atgaagtaaa aaaacaaggg ccacaagttc caacaattga | 180 | |
| tataaaagaa ataaactctt cagatgaaat tgttagaaga aaatgtaggg ataagcttaa | 240 | |
| gaaagctgca gaggaatggg gtgtgatgaa tttggtgaac catggtatttt ctgatgaatt | 300 | |
| acttaatcga cttaaaaaag ttggtgaaac ttttttttgag ttacctgttg aagaaaaga | 360 | |
| aaaatatgct aatgatcaaa gtgatgggaa gattcaaggg tatggtagta aattagctaa | 420 | |
| taatgctagt ggtcaacttg aatgggaaga ttatttctttt cattgtatttt tcctgagga | 480 | |
| taagcgtgac ttatctatat ggcctaagac tccagctgat tatactgagg tcacaacaga | 540 | |
| atatgcaaaa gaactaagag gcctagctag caagataatg | 580 | |

<210> SEQ ID NO 31
<211> LENGTH: 218
<212> TYPE: DNA
<213> ORGANISM: Trifolium repens

<400> SEQUENCE: 31

```
ataatagaaa atatatcata tagtaaagat gggaaccgtg gcacaaagag ttgaaagctt    60
atctttgagt ggaatatcat caattccaaa agaatatgtg agaccaaaag aagagttaac   120
aaacatagga aacatatttg atgaagaaaa aaaacaaggg ccacaagttc aacaattga    180 tataaaagaa ataaactctt cagatgaaat tgttagaa                           218

<210> SEQ ID NO 32
<211> LENGTH: 567
<212> TYPE: DNA
<213> ORGANISM: Trifolium repens

<400> SEQUENCE: 32
tagaaactat atatatcata ttatattcca aattaataat atgggaaccg tggcacaaag    60
agttgaaagc ttagctttga gtggaatatc atcaattcca aagaatatg tgagaccaaa   120 agaagagtta ataaacatag gaaacatatt tgatgaagaa aaaaaacaag gccacaagt   180 tccaacaatt gatataaaag aaataaactc tacagatgaa attgttagaa gaaaatgtag   240
ggataagctt aagaaagctg cagaggaatg gggtgtgatg aatttggtga atcatggtat   300
ttctgatgaa ttacttaatc gacttaaaaa agttggtgaa acttttttg agttacctgt    360 tgaagaaaaa gaaaaatatg ctaatgatca aagtgttggg aagattcaag ggtatggtag   420
taaattagct aataatgcta gtggtcaact tgaatgggaa gattatttct ttcattgtat   480
ttttcctgag gataagcgtg acttatccat atggcctaag actccagctg attatactga   540
ggtcacaaca gaatatgcaa aagaact                                       567

<210> SEQ ID NO 33
<211> LENGTH: 553
<212> TYPE: DNA
<213> ORGANISM: Trifolium repens

<400> SEQUENCE: 33
tatatatttc taaataatag aaaattatca tatagtaaag atgggaaccg tggcacaaag    60
agttgaaagc ttatctttga gtggaatatc atcaattcca aagaatatg tgagaccaaa   120 agaagagtta acaaacatag gaaacatatt tgatgaagta aaaaaacaag gccacaagt   180 tccaacaatt gatataaaag aaataaactc ttcagatgaa attgttagaa gaaaatgtag   240
ggataagctt aagaaagctg cagaggaatg gggtgtgatg aatttggtga accatggtat   300
ttctgatgaa ttacttaatc gacttaaaaa agttggtgaa acttttttg agttacctgt    360 tgaagaaaaa gaaaaatatg ctaatgatca aagtgatggg aagattcaag ggtatggtag   420
taaattagct aataatgcta gtggtcaact tgaatgggaa gattatttct ttcattgtat   480
ttttcctgag gataagcgtg acttatctat atggcctaag actccagctg attatactga   540
ggtcacaaca gaa                                                      553

<210> SEQ ID NO 34
<211> LENGTH: 551
<212> TYPE: DNA
<213> ORGANISM: Trifolium repens

<400> SEQUENCE: 34
ataggttgtt tacgaggtgt aatggtattt actcaaatat ttcaaatttt taactagtta    60
gatagaattc tcatcttcct cattctcctt caattcaatt caattcaatg gcagcatcac   120
aacaacaaga gaaataata ttcaggtcta aacttccgga catatacatc ccaaaacacc   180
ttcccctcca ttcttattgc tttgaaaatc tctcccaatt tggttctcgt ccatgtctca   240
```

```
tcaatgcacc caccggaaaa gtctacacct accacgacgt cgaactcacc tctcggaaag    300
ttgcctccgg tctcaacaaa ttgggagtcc aacagggtga tgtgatcatg atcctcctcc    360
ccaattcccc tgaattcgtc ttctcctttc tggcagcttc ttatctcggc gccatagcca    420
cagcagccaa tccttcttc atggccgcgg agattggaaa gcaagcaaaa gcctccaacg    480
ccaagttgat cataacacag gcatgttact acgacaaagt caaggagttg ttgttggaca    540
accacaacaa g                                                         551
```

<210> SEQ ID NO 35
<211> LENGTH: 148
<212> TYPE: PRT
<213> ORGANISM: Trifolium repens

<400> SEQUENCE: 35

```
Met Ala Ala Ser Gln Gln Glu Glu Ile Ile Phe Arg Ser Lys Leu
1               5                   10                  15

Pro Asp Ile Tyr Ile Pro Lys His Leu Pro Leu His Ser Tyr Cys Phe
            20                  25                  30

Glu Asn Leu Ser Gln Phe Gly Ser Arg Pro Cys Leu Ile Asn Ala Pro
        35                  40                  45

Thr Gly Lys Val Tyr Thr Tyr His Asp Val Glu Leu Thr Ser Arg Lys
    50                  55                  60

Val Ala Ser Gly Leu Asn Lys Leu Gly Val Gln Gly Asp Val Ile
65                  70                  75                  80

Met Ile Leu Leu Pro Asn Ser Pro Glu Phe Val Phe Ser Phe Leu Ala
                85                  90                  95

Ala Ser Tyr Leu Gly Ala Ile Ala Thr Ala Ala Asn Pro Phe Phe Met
            100                 105                 110

Ala Ala Glu Ile Gly Lys Gln Ala Lys Ala Ser Asn Ala Lys Leu Ile
        115                 120                 125

Ile Thr Gln Ala Cys Tyr Tyr Asp Lys Val Lys Glu Leu Leu Leu Asp
    130                 135                 140

Asn His Asn Lys
145
```

<210> SEQ ID NO 36
<211> LENGTH: 530
<212> TYPE: DNA
<213> ORGANISM: Trifolium repens

<400> SEQUENCE: 36

```
aggttgttta ctagtcgtgt cggaattcct tccatatttc aactagttag atagaattct     60
catcttcctc attctccttc aattcaatgg cagcatcaca acaacaagaa gaataatat    120 tcaggtctaa acttccggac atatacatcc aaaacacct tcccctccat tcttattgct    180
ttgaaaatct ctcccaattt ggttctcgtc catgtctcat caatgcaccc accggaaaag    240
tctacaccta ccacgacgtc gaactcacct ctcggaaagt tgcctccggt ctcaacaaat    300
tgggagtcca acagggtgat gtgatcatga tcctcctccc caattcccct gaattcgtct    360
tctcctttct ggcagcttct tatctcggcg ccatagccac agcagccaat ccttcttca    420 tggccgcgga gattggaaag caagcaaaag cctccaacgc caagttgatc ataacacagg    480
catgttacta cgacaaagtc aaggagttgt tgttggacaa ccacaacaag                530
```

<210> SEQ ID NO 37
<211> LENGTH: 516
<212> TYPE: DNA

<213> ORGANISM: Trifolium repens

<400> SEQUENCE: 37

```
ggttgtttac tagtcgtgtc gcaattcctt ccatatttca actagttaga tagaattctc      60
atcttcctca ttctccttca attcaattca attcaatggc agcatcacaa caacaagaag     120
aaataatatt caggtctaaa cttccagaca tatacatccc aaaacacctt ccctccatt      180
cttattgctt tgaaaatctc tcccaatttg gttctcgtcc atgtctcatc aatgcaccca     240
ccggaaaagt ctacacctac cacgacgtcg aactcacctc tcggaaagtt gcctccggtc     300
tcaacaaatt gggagtccaa cagggtgatg tgatcatgat cctcctcccc aattcccctg     360
aattcgtctt ctcctttctg gcagcttctt atctcggcgc catagccaca gcagccaatc     420
ctttcttcat ggccgcggag attggaaagc aagcaaaagc tccaacgcc aagttgatca     480
taacacaggc atgttactac gacaaagtca aggagt                               516
```

<210> SEQ ID NO 38
<211> LENGTH: 526
<212> TYPE: DNA
<213> ORGANISM: Trifolium repens

<400> SEQUENCE: 38

```
ataggttgtt tactagttgt gtcggaattc cttccaatat ttcaactagt tagttagata      60
gatagaattc tcatcttcct cgttctcctc caattcaatt caattcaatg gcagcatcag     120
aacaacaaga agaaataata ttcaggtcta aacttccgga catatacatc ccaaaacacc     180
ttcccctcca ttcttattgc tttgaaaatc tctcccaatt tggttctcgt ccatgtctca     240
tcaatgcacc cactggaaaa gtctacacct accacgacgt cgaactcacc tctcggaaag     300
ttgcctccgg tctcaacaaa ttgggagtcc aacagggtga tgtgatcatg atcctcctcc     360
ccaattcccc tgaattcgtc ttctcctttc tggcagcttc ttatctcggc gccatagcca     420
cagcagccaa tccttctt atggccgcgg agattggaaa gcaagcaaaa gcctccaacg     480
ccaagttgat cataacacag gcatgttact acgacaaagt caggag                    526
```

<210> SEQ ID NO 39
<211> LENGTH: 569
<212> TYPE: DNA
<213> ORGANISM: Trifolium repens
<220> FEATURE:
<221> NAME/KEY: misc_feature
<222> LOCATION: (61)..(61)
<223> OTHER INFORMATION: n is a, c, g, or t

<400> SEQUENCE: 39

```
agttaaggat ttggaaaatg tgaagctggt ttttgtggac tcttcaccgg aaggagaaaa      60
ntatatgcat ttccgtgagc tggctcaagc cgatgagaat gaaattgaag aggtaaagat     120
aaaccctgat gatgtggttg ctttgccata ttccttctgga acaacagggc tacctaaagg     180
tgttatgcta acacacaaag gattagtgac aagtgtagca caacaagttg gtggtgaaaa     240
tccaaatcta tattaccatt ctgaggatgt catactatgt gttcttccca tgtttcatat     300
ctattcactc aactctgttt tgctctgtgg tttgagagcc aaagcttcca ttctttttaat     360
gccaaagttt gatattcatt cttttttag ccttgttcat aaatacagag tcactgttgc      420
tcctgttgtg ccaccaattg ttttggctat ttctaagtca cctgaacttg ataactatga     480
tctttcatcc ataaggattt tgaaatctgg tggtgctcca cttggtaagg aacttgagga     540
cactgttagg gccaaatttc caaagcaa                                         569
```

```
<210> SEQ ID NO 40
<211> LENGTH: 189
<212> TYPE: PRT
<213> ORGANISM: Trifolium repens
<220> FEATURE:
<221> NAME/KEY: MISC_FEATURE
<222> LOCATION: (20)..(20)
<223> OTHER INFORMATION: any amino acid

<400> SEQUENCE: 40

Val Lys Asp Leu Glu Asn Val Lys Leu Val Phe Val Asp Ser Ser Pro
1               5                  10                  15

Glu Gly Glu Xaa Tyr Met His Phe Arg Glu Leu Ala Gln Ala Asp Glu
            20                  25                  30

Asn Glu Ile Glu Glu Val Lys Ile Asn Pro Asp Asp Val Val Ala Leu
        35                  40                  45

Pro Tyr Ser Ser Gly Thr Thr Gly Leu Pro Lys Gly Val Met Leu Thr
    50                  55                  60

His Lys Gly Leu Val Thr Ser Val Ala Gln Gln Val Gly Gly Glu Asn
65                  70                  75                  80

Pro Asn Leu Tyr Tyr His Ser Glu Asp Val Ile Leu Cys Val Leu Pro
                85                  90                  95

Met Phe His Ile Tyr Ser Leu Asn Ser Val Leu Leu Cys Gly Leu Arg
            100                 105                 110

Ala Lys Ala Ser Ile Leu Leu Met Pro Lys Phe Asp Ile His Ser Phe
        115                 120                 125

Phe Ser Leu Val His Lys Tyr Arg Val Thr Val Ala Pro Val Val Pro
130                 135                 140

Pro Ile Val Leu Ala Ile Ser Lys Ser Pro Glu Leu Asp Asn Tyr Asp
145                 150                 155                 160

Leu Ser Ser Ile Arg Ile Leu Lys Ser Gly Gly Ala Pro Leu Gly Lys
                165                 170                 175

Glu Leu Glu Asp Thr Val Arg Ala Lys Phe Pro Lys Ala
            180                 185

<210> SEQ ID NO 41
<211> LENGTH: 641
<212> TYPE: DNA
<213> ORGANISM: Trifolium repens

<400> SEQUENCE: 41
cgttgcaaga aatgcagagc tcaaagttct tgactctgaa actggtcgct ctcttggtta      60
taatcaaccc ggtgagattt gcatccgtgg ccaacaaatc atgaaaggat atttgaatga     120
tgaaaatgca acaaaaacta ctattgatga agagggttgg cttcatactg gtgatgttgg     180
ctatatagat gacaatgatg agattttcat tgttgacagg gtgaaggaac tcattaaatt     240
caaaggcttc caagtgcccc tgctgaact  tgaaggcctt ctagtaagcc atccatctat     300
tgcagatgca gctgttgtcc cgcaaaagga tgtggctgct ggtgaagttc ctgttgcctt     360
tgtggtaaga tcaaatggac ttgatctaac tgaagaggct gtaaaggagt ttatagctaa     420
acaggttgta ttttataaga gactgcacaa agtgtatttc attcatgcaa ttcccaagtc     480
tccatcagga aagatactga ggaaagatct cagagcaaag ttagaaagta ccacccaaaa     540
gccttgagat gctagaagct ttttcactta tttttttggg tcaaaatctt cctcatttgt     600
tcatttgtat cctaatatat tctagctact aggtctcatg c                        641

<210> SEQ ID NO 42
```

<211> LENGTH: 181
<212> TYPE: PRT
<213> ORGANISM: Trifolium repens

<400> SEQUENCE: 42

```
Val Ala Arg Asn Ala Glu Leu Lys Val Leu Asp Ser Glu Thr Gly Arg
1               5                   10                  15

Ser Leu Gly Tyr Asn Gln Pro Gly Glu Ile Cys Ile Arg Gly Gln Gln
            20                  25                  30

Ile Met Lys Gly Tyr Leu Asn Asp Glu Asn Ala Thr Lys Thr Thr Ile
        35                  40                  45

Asp Glu Glu Gly Trp Leu His Thr Gly Asp Val Gly Tyr Ile Asp Asp
    50                  55                  60

Asn Asp Glu Ile Phe Ile Val Asp Arg Val Lys Glu Leu Ile Lys Phe
65                  70                  75                  80

Lys Gly Phe Gln Val Pro Pro Ala Glu Leu Glu Gly Leu Leu Val Ser
                85                  90                  95

His Pro Ser Ile Ala Asp Ala Ala Val Val Pro Gln Lys Asp Val Ala
            100                 105                 110

Ala Gly Glu Val Pro Val Ala Phe Val Val Arg Ser Asn Gly Leu Asp
        115                 120                 125

Leu Thr Glu Glu Ala Val Lys Glu Phe Ile Ala Lys Gln Val Val Phe
    130                 135                 140

Tyr Lys Arg Leu His Lys Val Tyr Phe Ile His Ala Ile Pro Lys Ser
145                 150                 155                 160

Pro Ser Gly Lys Ile Leu Arg Lys Asp Leu Arg Ala Lys Leu Glu Ser
                165                 170                 175

Thr Thr Gln Lys Pro
            180
```

<210> SEQ ID NO 43
<211> LENGTH: 524
<212> TYPE: DNA
<213> ORGANISM: Trifolium repens

<400> SEQUENCE: 43

```
acttaaatta atttaaattc cccttattcc taatattctc ctaacattac caaaatgtca      60
ccatttcctc cacagcaaga agaattcata ttccgttcca aactcccaga cattgaaatt     120
ccaacaaatc ttccattaca ctcttattgt ttccaaaacc tctctcaatt ccataaccgt     180
ccatgtctca tcaacggcga ctccggcgaa atcttaacat actccgacgt ccacctcacc     240
gtccgcaaaa tcgccgccgg tttaaacact ctcggaatta atcaaggtga tgtcatcatg     300
ctcgtcctcc gtaactctcc tcaattcgca ctcactttcc tcggtgcctc cttccgtggc     360
gccgtcatca ccaccgcaaa tcctttctac acctcatcgg aactcgcgaa acaagccaca     420
gcaacaaaaa ctaaactcat cgtaactcaa tccgcatatc taagtaaaat caacgatttc     480
gctaaattca acaacatcaa aatcgtctgc atagattcat catc                      524
```

<210> SEQ ID NO 44
<211> LENGTH: 156
<212> TYPE: PRT
<213> ORGANISM: Trifolium repens

<400> SEQUENCE: 44

```
Met Ser Pro Phe Pro Pro Gln Gln Glu Glu Phe Ile Phe Arg Ser Lys
1               5                   10                  15

Leu Pro Asp Ile Glu Ile Pro Thr Asn Leu Pro Leu His Ser Tyr Cys
```

```
                    20                  25                  30
Phe Gln Asn Leu Ser Gln Phe His Asn Arg Pro Cys Leu Ile Asn Gly
                35                  40                  45

Asp Ser Gly Glu Ile Leu Thr Tyr Ser Asp Val His Leu Thr Val Arg
 50                  55                  60

Lys Ile Ala Ala Gly Leu Asn Thr Leu Gly Ile Asn Gln Gly Asp Val
 65                  70                  75                  80

Ile Met Leu Val Leu Arg Asn Ser Pro Gln Phe Ala Leu Thr Phe Leu
                 85                  90                  95

Gly Ala Ser Phe Arg Gly Ala Val Ile Thr Thr Ala Asn Pro Phe Tyr
                100                 105                 110

Thr Ser Ser Glu Leu Ala Lys Gln Ala Thr Ala Thr Lys Thr Lys Leu
                115                 120                 125

Ile Val Thr Gln Ser Ala Tyr Leu Ser Lys Ile Asn Asp Phe Ala Lys
                130                 135                 140

Phe Asn Asn Ile Lys Ile Val Cys Ile Asp Ser Ser
145                 150                 155

<210> SEQ ID NO 45
<211> LENGTH: 599
<212> TYPE: DNA
<213> ORGANISM: Trifolium repens

<400> SEQUENCE: 45
taacaacaat ggatctactc cttcttgaaa agactctttt atccctcttc atcgccgcta     60
taatcgcaat cacaatctca aaactccgtg gaaaacgctt caaacttcca ccaggtccat    120
ttccagttcc aatttttggt aattggcttc aagttggcga tgatctcaac caccgtaatt    180
taactgattt agccaaacgc ttcggcgaaa tcctgcttct ccggatggga caacgaaacc    240
tggtcgttgt ctcatcaccg gagttagcaa agaagtcct tcacacacaa ggtgtcgaat    300
tcggttccag aacacggaac gtcgtattcg acatctttac cggtaaagga caggacatgg    360
ttttcaccgt gtacggtgaa cattggcgta aaatgaggag aattatgaca gtaccatttt    420
tcacaaacaa agttgttcaa caatatagat ttggttggga atctgaagct gaaagtgttg    480
ttaatgatgt taagaaaaat aatgaagcta gtgttggtgg aattgtgatt agaagaagat    540
tacaattgat gatgtataat attatgtata ggattatgtt tgatagaaga tttgaaagt     599

<210> SEQ ID NO 46
<211> LENGTH: 197
<212> TYPE: PRT
<213> ORGANISM: Trifolium repens

<400> SEQUENCE: 46

Met Asp Leu Leu Leu Glu Lys Thr Leu Leu Ser Leu Phe Ile Ala
  1               5                  10                  15

Ala Ile Ile Ala Ile Thr Ile Ser Lys Leu Arg Gly Lys Arg Phe Lys
                 20                  25                  30

Leu Pro Pro Gly Pro Phe Pro Val Pro Ile Phe Gly Asn Trp Leu Gln
                 35                  40                  45

Val Gly Asp Asp Leu Asn His Arg Asn Leu Thr Asp Leu Ala Lys Arg
 50                  55                  60

Phe Gly Glu Ile Leu Leu Leu Arg Met Gly Gln Arg Asn Leu Val Val
 65                  70                  75                  80

Val Ser Ser Pro Glu Leu Ala Lys Glu Val Leu His Thr Gln Gly Val
                 85                  90                  95
```

```
Glu Phe Gly Ser Arg Thr Arg Asn Val Val Phe Asp Ile Phe Thr Gly
            100                 105                 110
Lys Gly Gln Asp Met Val Phe Thr Val Tyr Gly Glu His Trp Arg Lys
        115                 120                 125
Met Arg Arg Ile Met Thr Val Pro Phe Phe Thr Asn Lys Val Val Gln
130                 135                 140
Gln Tyr Arg Phe Gly Trp Glu Ser Glu Ala Glu Ser Val Val Asn Asp
145                 150                 155                 160
Val Lys Lys Asn Asn Glu Ala Ser Val Gly Gly Ile Val Ile Arg Arg
                165                 170                 175
Arg Leu Gln Leu Met Met Tyr Asn Ile Met Tyr Arg Ile Met Phe Asp
            180                 185                 190
Arg Arg Phe Glu Ser
            195

<210> SEQ ID NO 47
<211> LENGTH: 576
<212> TYPE: DNA
<213> ORGANISM: Trifolium repens

<400> SEQUENCE: 47
tggatctact ccttcttgaa aagactcttt tatccctctt catcgccgct ataatcgcaa    60
tcacaatctc aaaactccgt ggaaaacgct caaacttcc accaggtcca tttccagttc   120 caattttgg taattggctt caagttggcg atgatctcaa ccaccgtaat ttaactgatt   180
tagccaaacg cttcggcgaa atcctgcttc tccggatggg acaacgaaac ctggtcgttg   240
tctcatcacc ggagttagca aaagaagtcc ttcacacaca aggtgtcgaa ttcggttcca   300
gaacacggaa cgtcgtattc gacatcttta ccggtaaagg acaggacatg gttttcaccg   360
tgtacggtga acattggcgt aaaatgagga gaattatgac agtaccattt ttcacaaaca   420
aagttgttca acaatataga tttggttggg aatctgaagc tgaaagtgtt gttaatgatg   480
ttaagaaaaa taatgaagct agtgttggtg gaattgtgat tagaagaaga ttacaattga   540
tgatgtataa tattatgtat aggattatgt ttgata                             576

<210> SEQ ID NO 48
<211> LENGTH: 503
<212> TYPE: DNA
<213> ORGANISM: Trifolium repens

<400> SEQUENCE: 48
tggacctact ccttcttgaa aagactcttt tatccctctt catcgcagcc ataattgcaa    60
tcacaatctc aaaactccgt ggaaaacggt caaacttcc accaggtcca tttccagttc   120 caattttgg taattggctt caagtcggtg atgatctcaa ccaccgtaac ttaaccgatt   180
tagccaaacg gtttggcgaa attatgctac tccggatggg acaacgaaac ctggtcgttg   240
tctcatcacc ggagttagca aaagaagtcc ttcacacaca aggtgtcgaa ttcggttcca   300
gaacacggaa cgtcgtattc gacatcttta ctggtaaagg acaggacatg gttttcaccg   360
tgtacggtga acattggcgt aaaatgagga gaattatgac agtaccattt ttcacaaaca   420
aagttgttca acaatataga tttggttggg aatctgaagc agaaagtgtt gttaatgatg   480
ctaacaaaaa taatgaagct agt                                          503

<210> SEQ ID NO 49
<211> LENGTH: 590
<212> TYPE: DNA
<213> ORGANISM: Trifolium repens
```

```
<400> SEQUENCE: 49
tggatctact ccttcttgaa aagactcttt tatccctctt catcgccgct ataatcgcaa      60
tcacaatctc aaaactccgt ggaaaacgct caaacttcc accaggtcca tttccagttc     120
caatttttgg taattggctt caagttggcg atgatctcaa ccaccgtaat ttaactgatt    180
tagccaaacg cttcggcgaa atcctgcttc tccggatggg acaacgaaac ctggtcgttg    240
tctcatcacc ggagttagca aaagaagtcc ttcacacaca aggtgtcgaa ttcggttcca    300
gaacacggaa cgtcgtattc gacatcttta ccggtaaagg acaggacatg gttttcaccg    360
tgtacggtga acattggcgt aaaatgagga gaattatgac agtaccattt ttcacaaaca    420
aagttgttca acaatataga tttggttggg aatctgaagc tgaaagtgtt gttaatgatg    480
ttaagaaaaa taatgaagct agtgttggtg gaattgtgat tagaagaaga ttacaattga    540
tgatgtataa tattatgtat aggattatgt ttgatagaag atttgaaagt                590

<210> SEQ ID NO 50
<211> LENGTH: 569
<212> TYPE: DNA
<213> ORGANISM: Trifolium repens

<400> SEQUENCE: 50
atggatctac tccttcttga aaagactctt ttatccctct tcatcgcagc cataattgca     60
atcacaatct caaaactccg tggaaaacgg ttcaaacttc caccaggtcc atttccagtt   120 ccaattttg gtaattggct tcaagtcggt gatgatctca accaccgtaa cttaaccgat    180
ttagccaaac ggtttggcga attatgcta ctccggatgg gacaacgaaa cctggtcgtt    240
gtctcatcac cggagttagc aaaagaagtc cttcacacac aaggtgtcga attcggttcc    300
agaacacgga acgtcgtatt tgacatcttt actggtaaag gacaggacat ggttttcacc    360
gtgtacggtg aacattggcg taaaatgagg agaattatga cagtaccatt tttcacaaac    420
aaagttgttc aacaatatag atttggttgg gaatctgaag cagaaagtgt tgttaatgat    480
gttaagaaaa ataatgaagc tagtgttggt ggaattgtga ttagaagaag attacaattg    540
atgatgtata atattatgta taggattat                                       569

<210> SEQ ID NO 51
<211> LENGTH: 546
<212> TYPE: DNA
<213> ORGANISM: Trifolium repens

<400> SEQUENCE: 51
taacaacaat ggatctactc cttcttgaaa agactctttt atccctcttc atcgccgcta     60
taatcgcaat cacaatctca aaactccgtg gaaaacgctt caaacttcca ccaggtccat   120
ttccagttcc aatttttggt aattggcttc aagttggcga tgatctcaac caccgtaatt    180
taactgattt agccaaacgc ttcggcgaaa tcctgcttct ccggatggga caacgaaacc    240
tggtcgttgt ctcatcaccg gagttagcaa aagaagtcct tcacacacaa ggtgtcgaat    300
tcggttccag aacacggaac gtcgtattcg acatctttac cggtaaagga caggacatgg    360
ttttcaccgt gtacggtgaa cattggcgta aaatgaggag aattatgaca gtaccattt    420 tcacaaacaa agttgttcaa caatatagat ttggttggga atctgaagct gaaagtgttg    480
ttaatgatgt taagaaaaat aatgaagcta gtgttggtgg aattgtgatt agaagaagat    540
tacaat                                                                546
```

```
<210> SEQ ID NO 52
<211> LENGTH: 443
<212> TYPE: DNA
<213> ORGANISM: Trifolium repens

<400> SEQUENCE: 52
aagttttgag tataattatg gtgattttat tcctattttg agaccttttt tgaaaggtta      60
tttgaaggtt tgtaaagagg ttaaagatcg taggttgcag cttttcaaag actatttcgt     120
tgatgagaga agaaacttg aaagcaccaa gagcaccact agcaatgatg acttaaatg       180 tgcaattgat cacattttgg atgctcaaaa gaagggagag atcaatgatg acaacgttct     240
ttacattgtt gagaacatca aggttgctgc aattgaaaca cactatggt caattgaatg      300 gggaattgct gagctagtga accaccaaga gatccaaaac aaagtaaggg aagagatgga     360
cagagttcta ggaccaggac accaagtaac cgagccggat cttgagaagc taccttacct    420
acaagccgtg atcaaagaga cac                                              443

<210> SEQ ID NO 53
<211> LENGTH: 147
<212> TYPE: PRT
<213> ORGANISM: Trifolium repens

<400> SEQUENCE: 53

Ser Phe Glu Tyr Asn Tyr Gly Asp Phe Ile Pro Ile Leu Arg Pro Phe
1               5                   10                  15

Leu Lys Gly Tyr Leu Lys Val Cys Lys Glu Val Lys Asp Arg Arg Leu
            20                  25                  30

Gln Leu Phe Lys Asp Tyr Phe Val Asp Glu Arg Lys Lys Leu Glu Ser
        35                  40                  45

Thr Lys Ser Thr Thr Ser Asn Asp Gly Leu Lys Cys Ala Ile Asp His
    50                  55                  60

Ile Leu Asp Ala Gln Lys Lys Gly Glu Ile Asn Asp Asp Asn Val Leu
65                  70                  75                  80

Tyr Ile Val Glu Asn Ile Lys Val Ala Ala Ile Glu Thr Thr Leu Trp
                85                  90                  95

Ser Ile Glu Trp Gly Ile Ala Glu Leu Val Asn His Gln Glu Ile Gln
            100                 105                 110

Asn Lys Val Arg Glu Glu Met Asp Arg Val Leu Gly Pro Gly His Gln
        115                 120                 125

Val Thr Glu Pro Asp Leu Glu Lys Leu Pro Tyr Leu Gln Ala Val Ile
    130                 135                 140

Lys Glu Thr
145

<210> SEQ ID NO 54
<211> LENGTH: 295
<212> TYPE: DNA
<213> ORGANISM: Trifolium repens

<400> SEQUENCE: 54
agcttgccgg ttatgacatc ccggccgaga gcaagatatt ggtcaacgcg tggtggcttg      60
caaataaccc ggctctatgg aaaaagccgg aggaatttag gcctgagagg ttcttggagg    120
aagaggcgca tgttgaggct aatggaaatg actttaggta ccttcctttc ggtgtcggta    180
gaaggagttg acctgcaatt attcttgctt tacctatcct tggtattact atcgggcgtc    240
ttgttcaaaa tttccagctt ttgcctgcac ccggacaatc taagattgat acttc         295
```

<210> SEQ ID NO 55
<211> LENGTH: 98
<212> TYPE: PRT
<213> ORGANISM: Trifolium repens

<400> SEQUENCE: 55

Ser Leu Pro Val Met Thr Ser Arg Pro Arg Ala Arg Tyr Trp Ser Thr
1               5                   10                  15
Arg Gly Gly Leu Gln Ile Thr Arg Leu Tyr Gly Lys Ser Arg Arg Asn
            20                  25                  30
Leu Gly Leu Arg Gly Ser Trp Arg Lys Arg Arg Met Leu Arg Leu Met
        35                  40                  45
Glu Met Thr Leu Gly Thr Phe Leu Ser Val Ser Val Glu Gly Val Asp
    50                  55                  60
Leu Gln Leu Phe Leu Leu Tyr Leu Ser Leu Val Leu Ser Gly Val
65                  70                  75                  80
Leu Phe Lys Ile Ser Ser Phe Cys Leu His Pro Asp Asn Leu Arg Leu
                85                  90                  95
Ile Leu

<210> SEQ ID NO 56
<211> LENGTH: 1879
<212> TYPE: DNA
<213> ORGANISM: Trifolium repens

<400> SEQUENCE: 56

```
aaaaactagt tgtgaggcat ataactatga gctctataga aaaccaacca ttactattgg      60
ggcttgactc acactcacac attgcaaatc tatcatcaga tactattgaa gaattcttgg     120
aacataggcc tattcagtta agatggtggc ttaaacttgt tgcttgggag tcaagggtcc     180
tatggatcct ttctggtgca tctattattg tctaccttt caattacatg ctaagctttg     240
ctaccttaat gtttagtgga catttaggat ctctagagct tgctggtgca tctacagcta     300
atgttggaat tcaaggtctt gcttatggaa ttatgctagg aatggcaagt gcagtgcaaa     360
ctgtgtgtgg acaagcttat ggagccaaaa aatatgcagt aatgtgcatc acattgcaaa     420
gagcagtaat cttacatttta ggagcagcag tgattctcac atttctctat ggttttctg     480
gagattttct aaaagtcata ggacagacag agagcatagc cgagcaaggc caagttttcg     540
ctcgcggtct tatacctcaa ctctatgcat ttgcattgag ttgtccaatg caaaggtttc     600
tccaagcaca gaacattgtt aatcctcttg catatatggc agttggagtg ttcattcttc     660
atgtgcttgt tagttggcta gttatctatg ttttagacta tggacttctt ggtgcagccc     720
ttactctcag ctttttcttgg tggaatcttg tcttgttaaa tggattgtac atcattctta     780
gcccaagatg caaggaaact tggactggct ctctcgatcaa agccttttgc ggaatttggc     840
cttacttcaa gctcacagct gcttccgctg tgatgttatg cttggagata tggtacaatc     900
agggactagt actcatatca gggttgctct ccaatcccac agtggccctg gattctattt     960
caatttgcat gaattactta aattgggata tgcaaattgt gttgggtctt ggtgcagcag    1020
ccagtgtgcg agttagcaat gaattaggag cagctcatcc aagagtagca aaattgtcag    1080
tcttcgtagt gaatggaaat agcatccataa ttagtgtagt tctcgctgcg attattatga    1140
tattccgagt tgctttgagc aagcttttca cttctgacac tgtagtcctt gaagctgtat    1200
ctgacttgac cccattgctt gccatctctg tcctcctaaa tggcattcaa cctatactat    1260
ctggtgttgc agttggaagt ggatggcaag ctttggtggc atatgtaaac ttggtttgtt    1320
actatctcat tggtcttcct gttgggtgtg ttcttggctt taaaacttct ttaggagtag    1380
```

-continued

```
ctggtatttg gtggggattg atcctaggag ttttcataca gactgttaca ctaatagttc   1440
tgactgccag aacaaaatgg gaagaagagg ttgaaaaagc tattgttcgt gtcaaaaggg   1500
cttctgaaga tgataccttg gatcaactgg ttgccgacat atgaaggcat ttctcttact   1560 gtaactttc ttgcagaaat agaagaacac tttagcagca gattaatagt ttctgaacta    1620
caaggatagt gatgttgggt ttgttctgat taagctcaac aaataagctg gatagagaag   1680
aattgtatga tgtggcaagg tagttagatt atgggaggga atatagggcc atggaggatt   1740
agagtgagaa acctttttgaa tttgttcagg gattacagga gctagctatt cttctgtcat  1800
agttccttgt tcaatcaata atattatttc ctcttcaaaa aaaaaaaaaa aaaaaaaaa    1860 aaaaaaaaaa aaaaaaaa                                                 1879
```

<210> SEQ ID NO 57
<211> LENGTH: 505
<212> TYPE: PRT
<213> ORGANISM: Trifolium repens

<400> SEQUENCE: 57

```
Met Ser Ser Ile Glu Asn Gln Pro Leu Leu Gly Leu Asp Ser His
1               5                   10                  15

Ser His Ile Ala Asn Leu Ser Ser Asp Thr Ile Glu Glu Phe Leu Glu
            20                  25                  30

His Arg Pro Ile Gln Leu Arg Trp Trp Leu Lys Leu Val Ala Trp Glu
        35                  40                  45

Ser Arg Val Leu Trp Ile Leu Ser Gly Ala Ser Ile Ile Val Tyr Leu
    50                  55                  60

Phe Asn Tyr Met Leu Ser Phe Ala Thr Leu Met Phe Ser Gly His Leu
65                  70                  75                  80

Gly Ser Leu Glu Leu Ala Gly Ala Ser Thr Ala Asn Val Gly Ile Gln
                85                  90                  95

Gly Leu Ala Tyr Gly Ile Met Leu Gly Met Ala Ser Ala Val Gln Thr
            100                 105                 110

Val Cys Gly Gln Ala Tyr Gly Ala Lys Lys Tyr Ala Val Met Cys Ile
        115                 120                 125

Thr Leu Gln Arg Ala Val Ile Leu His Leu Gly Ala Ala Val Ile Leu
    130                 135                 140

Thr Phe Leu Tyr Trp Phe Ser Gly Asp Phe Leu Lys Val Ile Gly Gln
145                 150                 155                 160

Thr Glu Ser Ile Ala Glu Gln Gly Gln Val Phe Ala Arg Gly Leu Ile
                165                 170                 175

Pro Gln Leu Tyr Ala Phe Ala Leu Ser Cys Pro Met Gln Arg Phe Leu
            180                 185                 190

Gln Ala Gln Asn Ile Val Asn Pro Leu Ala Tyr Met Ala Val Gly Val
        195                 200                 205

Phe Ile Leu His Val Leu Val Ser Trp Leu Val Ile Tyr Val Leu Asp
    210                 215                 220

Tyr Gly Leu Leu Gly Ala Ala Leu Thr Leu Ser Phe Ser Trp Trp Asn
225                 230                 235                 240

Leu Val Leu Leu Asn Gly Leu Tyr Ile Ile Leu Ser Pro Arg Cys Lys
                245                 250                 255

Glu Thr Trp Thr Gly Phe Ser Ile Lys Ala Phe Cys Gly Ile Trp Pro
            260                 265                 270

Tyr Phe Lys Leu Thr Ala Ala Ser Ala Val Met Leu Cys Leu Glu Ile
        275                 280                 285
```

```
Trp Tyr Asn Gln Gly Leu Val Leu Ile Ser Gly Leu Leu Ser Asn Pro
    290                 295                 300
Thr Val Ala Leu Asp Ser Ile Ser Ile Cys Met Asn Tyr Leu Asn Trp
305                 310                 315                 320
Asp Met Gln Ile Val Leu Gly Leu Gly Ala Ala Ala Ser Val Arg Val
                325                 330                 335
Ser Asn Glu Leu Gly Ala Ala His Pro Arg Val Ala Lys Leu Ser Val
            340                 345                 350
Phe Val Val Asn Gly Asn Ser Ile Ile Ser Val Val Leu Ala Ala
        355                 360                 365
Ile Ile Met Ile Phe Arg Val Ala Leu Ser Lys Leu Phe Thr Ser Asp
    370                 375                 380
Thr Val Val Leu Glu Ala Val Ser Asp Leu Thr Pro Leu Leu Ala Ile
385                 390                 395                 400
Ser Val Leu Leu Asn Gly Ile Gln Pro Ile Leu Ser Gly Val Ala Val
                405                 410                 415
Gly Ser Gly Trp Gln Ala Leu Val Ala Tyr Val Asn Leu Val Cys Tyr
            420                 425                 430
Tyr Leu Ile Gly Leu Pro Val Gly Cys Val Leu Gly Phe Lys Thr Ser
        435                 440                 445
Leu Gly Val Ala Gly Ile Trp Trp Gly Leu Ile Leu Gly Val Phe Ile
    450                 455                 460
Gln Thr Val Thr Leu Ile Val Leu Thr Ala Arg Thr Lys Trp Glu Glu
465                 470                 475                 480
Glu Val Glu Lys Ala Ile Val Arg Val Lys Arg Ala Ser Glu Asp Asp
                485                 490                 495
Thr Leu Asp Gln Leu Val Ala Asp Ile
            500                 505
```

```
<210> SEQ ID NO 58
<211> LENGTH: 1485
<212> TYPE: DNA
<213> ORGANISM: Trifolium repens
<220> FEATURE:
<221> NAME/KEY: misc_feature
<222> LOCATION: (453)..(453)
<223> OTHER INFORMATION: n is a, c, g, or t

<400> SEQUENCE: 58
atactcaagc tatgcatcca acgcgttggg agctctccca tatggtcgac ctgcaggcgg     60
ccgcgaattc actagtgatt aagcagtggt aacaacgcag agtacgcggg ggttaccacc    120
taacattttc ctttctcagt ttctctcttg tgtttttcat caaacacctt ctctgcataa    180
ttttcttcat caaaaaattc aaacactcaa aaactcaaac acctttcgtg catcaccaaa    240
aatggagaat tcaactcaag aatcacacat ccgatccgaa aactctgtta cctacgattc    300
cccttatcct ctctacgcca tggctctttc tccaaacacc aattcacacc acaacaacg    360 catcgctgtt ggtagtttca tcgaagaata caccaaccgc atcgatatcc tcaatttcaa    420
ccctgagaat ttatcaatta aacctcaacc ttnactttcc ttcgatcatc cttatccacc    480
taccaaactc atgttccatc ccgcaacaaa ttcatctctc cagaaaacct cctccgacct    540
tctagctact tccggtgact atctccgtct ttgggaagtt cgcgaaaatt cggttgaggc    600
tcttctctct tttaacaaca gcaaaacaag tgagttttgt gctccttta cgtcatttga    660 ttggaacgaa attgagccga aacgaattgg tacttcaagc attgatacta cttgcacaat    720 tgggacatt gaaagaggcg ttgttgaaac gcagcttatt gcacatgata agagggttta    780
```

```
tgacattgct tggggtgaat cgagggtttt tgcttcggtt tctgctgatg ggtctgttag    840 gattttttgat ttgagggata aagagcattc aactattatc tatgagagtc ctcaaccaga    900 taccccttttg cttcgtttgg cttggaacaa gaaggatttg aggtatatgg ctacaacttt    960
gatggatagt aataaagttg tgattttgga tattaggtcg ccaactacgc ctgcggcaga   1020
attggagaga catcgtgctg tgttaatgc tattacttgg gctccaagaa gttctaagca    1080
tatttgttct gctggggatg attcacaggc tcttatttgg gagttgccta ctgtggctgg   1140
tccaaatggg attgatccaa tgtctatgta ttctgctggt tatgaaatta atcagcttca   1200
atggtctgct tctcagcctg attggatcgc aattgctttt gctaacaaga tgcagctttt   1260
gcgggtttga gttttaggta agggaataac ttgtagattt ggaaaaccaa ttaagcattg   1320
tggtgttgtg acttgtaact catgagtagt ttattatagt tgaacgggac aaattgtttt   1380
acttccaaaa aaaaaaaaaa aaaaaaaaaa aaaaagtact ctgcgttgtt accactgctt   1440
aatcgaattc ccgcggccgc catggcggcc gggagcatgc gacgt                   1485
```

<210> SEQ ID NO 59
<211> LENGTH: 394
<212> TYPE: PRT
<213> ORGANISM: Trifolium repens

<400> SEQUENCE: 59

```
Ala Val Val Thr Thr Gln Ser Thr Arg Gly Leu Pro Pro Asn Ile Phe
1               5                   10                  15

Leu Ser Gln Phe Leu Ser Cys Val Phe His Gln Thr Pro Ser Leu His
            20                  25                  30

Asn Phe Leu His Gln Lys Ile Gln Thr Leu Lys Asn Ser Asn Thr Phe
        35                  40                  45

Arg Ala Ser Pro Lys Met Glu Asn Ser Thr Gln Glu Ser His Ile Arg
    50                  55                  60

Ser Glu Asn Ser Val Thr Tyr Asp Ser Pro Tyr Pro Leu Tyr Ala Met
65                  70                  75                  80

Ala Leu Ser Pro Asn Thr Asn Ser His Pro Gln Gln Arg Ile Ala Val
                85                  90                  95

Gly Ser Phe Ile Glu Glu Tyr Thr Asn Arg Ile Asp Ile Leu Asn Phe
            100                 105                 110

Asn Pro Glu Asn Leu Ser Ile Lys Pro Gln Pro Leu Ser Phe Asp His
        115                 120                 125

Pro Tyr Pro Pro Thr Lys Leu Met Phe His Pro Ala Thr Asn Ser Ser
    130                 135                 140

Leu Gln Lys Thr Ser Ser Asp Leu Leu Ala Thr Ser Gly Asp Tyr Leu
145                 150                 155                 160

Arg Leu Trp Glu Val Arg Glu Asn Ser Val Glu Ala Leu Ser Leu Phe
                165                 170                 175

Asn Asn Ser Lys Thr Ser Glu Phe Cys Ala Pro Leu Thr Ser Phe Asp
            180                 185                 190

Trp Asn Glu Ile Glu Pro Lys Arg Ile Gly Thr Ser Ser Ile Asp Thr
        195                 200                 205

Thr Cys Thr Ile Trp Asp Ile Glu Arg Gly Val Val Glu Thr Gln Leu
    210                 215                 220

Ile Ala His Asp Lys Glu Val Tyr Asp Ile Ala Trp Gly Glu Ser Arg
225                 230                 235                 240

Val Phe Ala Ser Val Ser Ala Asp Gly Ser Val Arg Ile Phe Asp Leu
                245                 250                 255
```

```
Arg Asp Lys Glu His Ser Thr Ile Ile Tyr Glu Ser Pro Gln Pro Asp
            260                 265                 270

Thr Pro Leu Leu Arg Leu Ala Trp Asn Lys Lys Asp Leu Arg Tyr Met
        275                 280                 285

Ala Thr Thr Leu Met Asp Ser Asn Lys Val Val Ile Leu Asp Ile Arg
    290                 295                 300

Ser Pro Thr Thr Pro Ala Ala Glu Leu Glu Arg His Arg Ala Gly Val
305                 310                 315                 320

Asn Ala Ile Thr Trp Ala Pro Arg Ser Ser Lys His Ile Cys Ser Ala
                325                 330                 335

Gly Asp Asp Ser Gln Ala Leu Ile Trp Glu Leu Pro Thr Val Ala Gly
            340                 345                 350

Pro Asn Gly Ile Asp Pro Met Ser Met Tyr Ser Ala Gly Tyr Glu Ile
        355                 360                 365

Asn Gln Leu Gln Trp Ser Ala Ser Gln Pro Asp Trp Ile Ala Ile Ala
    370                 375                 380

Phe Ala Asn Lys Met Gln Leu Leu Arg Val
385                 390
```

```
<210> SEQ ID NO 60
<211> LENGTH: 1186
<212> TYPE: DNA
<213> ORGANISM: Trifolium repens

<400> SEQUENCE: 60
atataccaat agtgcattct tcttcctata ttgttattac cataaacatg gtaagagctc      60
cttgttgtga aaaatggga ttgaagagag gtccttggtc tcttgaggaa gatcaaatcc     120
ttacatctta cattcaaaaa catggtaatg caactggcg tgctctccca aagctagcag     180
gcttgttaag atgtgaaaaa gctgtagac ttaggtggat taactatttg agacctgata     240
tcaagagagg aaatttcaca atgaagaag aggaaaatat cattaagcta catgaaatgc     300
ttgggaacag gtggtcggca attgcagcaa aattaccagg aagaacggac aatgaaataa     360
aaaatgtgtg gcacacgcat ttgaagaaga aattattgaa acaaatgaa acaaactcag     420 aaactaagaa aagggtgatc acaaaaacaa aaatcaaacg ttctgattca aattcaagca     480
ctataacaca atcagaatca gtttctgcat gcactactag ttctagtgat ttttcatctg     540
ttacggttgg tgaaaaaata gatgtaaaaa gtgaagatat tgagtctatg aagaagagg      600 aaacaatgcc tgaaattgat gagagttttt ggacagaagc agcattggat gaaacttcaa     660
atgatatgaa atcaagttct ttgaatatct caaatgagat aatgccactt caatgccctt     720
taagtaactc tgatgaaatt ttcacacaaa atcatgatga ttataattct aacttagatg     780
atggcatgga tttttggtat gatatattca ttaggactgg agatcaaata gaattgccag     840
agttctaaat ttttccaaaa aaagaagttg atgatttaaa gtttagacga gttgggtatc     900
aaaccatcgt gtaggtctca cggctcaaat agcgataatt ttagactact tactcgacag     960
attgtctcac atggacaatg agattgatat ttacatcttg gatgatatga gttatgtctt    1020
tatcaactga actatctttc attatcgcat tgtaatttcg atttgaaaga aattacaagg    1080
aaagaaaagc agagtattgg gttaatgata tgtaatctat atctatgtaa aaaaggaact    1140
acaagtgaaa cattgatttt tttttaata tgtgtatatt gttcct                   1186

<210> SEQ ID NO 61
<211> LENGTH: 266
<212> TYPE: PRT
```

<213> ORGANISM: Trifolium repens

<400> SEQUENCE: 61

```
Met Val Arg Ala Pro Cys Cys Glu Lys Met Gly Leu Lys Arg Gly Pro
1               5                   10                  15

Trp Ser Leu Glu Glu Asp Gln Ile Leu Thr Ser Tyr Ile Gln Lys His
            20                  25                  30

Gly Asn Gly Asn Trp Arg Ala Leu Pro Lys Leu Ala Gly Leu Leu Arg
        35                  40                  45

Cys Gly Lys Ser Cys Arg Leu Arg Trp Ile Asn Tyr Leu Arg Pro Asp
    50                  55                  60

Ile Lys Arg Gly Asn Phe Thr Asn Glu Glu Glu Asn Ile Ile Lys
65                  70                  75                  80

Leu His Glu Met Leu Gly Asn Arg Trp Ser Ala Ile Ala Ala Lys Leu
                85                  90                  95

Pro Gly Arg Thr Asp Asn Glu Ile Lys Asn Val Trp His Thr His Leu
            100                 105                 110

Lys Lys Lys Leu Leu Lys Thr Asn Glu Thr Asn Ser Glu Thr Lys Lys
        115                 120                 125

Arg Val Ile Thr Lys Thr Lys Ile Lys Arg Ser Asp Ser Asn Ser Ser
    130                 135                 140

Thr Ile Thr Gln Ser Glu Ser Val Ser Ala Cys Thr Thr Ser Ser Ser
145                 150                 155                 160

Asp Phe Ser Ser Val Thr Val Gly Glu Lys Ile Asp Val Lys Ser Glu
                165                 170                 175

Asp Ile Glu Ser Met Glu Glu Glu Thr Met Pro Glu Ile Asp Glu
            180                 185                 190

Ser Phe Trp Thr Glu Ala Ala Leu Asp Glu Thr Ser Asn Asp Met Lys
        195                 200                 205

Ser Ser Ser Leu Asn Ile Ser Asn Glu Ile Met Pro Leu Gln Cys Pro
    210                 215                 220

Leu Ser Asn Ser Asp Glu Ile Phe Thr Gln Asn His Asp Asp Tyr Asn
225                 230                 235                 240

Ser Asn Leu Asp Asp Gly Met Asp Phe Trp Tyr Asp Ile Phe Ile Arg
                245                 250                 255

Thr Gly Asp Gln Ile Glu Leu Pro Glu Phe
            260                 265
```

<210> SEQ ID NO 62
<211> LENGTH: 1206
<212> TYPE: DNA
<213> ORGANISM: Trifolium repens

<400> SEQUENCE: 62

```
ttggattttt attgcaaaaa tggtgagagc tccatgttgt gaaaaaatgg ggttgaagaa      60
aggtccatgg actcaagaag aagatagaat tctcatcaat cacataaaca cttatggcca     120
ttctaattgg cgtgctcttc caaaacaagc tgggttgtta aggtgtggaa aaagttgtag     180
attgagatgg gcaaattatt tgaaaccaga tatcaaacgg ggtaattta ctaaagaaga      240 agaggatgca ataatcaatt tgcaccaaat gttgggaaat aggtggtcaa ctatagcagc     300
aagattacca ggacgaacgg acaatgaaat aaaaaatgta tggcacaccc acttgaagaa     360
gaggctgcca caaaccaac aaggccacaa caatagccca aaagaaata agaaacaaac       420 caatttggac tttgaagcct ccaaatcaga ccaagatatc aaacaagaac aaaataatgt     480
tgatgatatg ccacaatgtt ctagtgacat gtcataccat aataatagta gcaatagcat     540
```

```
tgctactact aatgataata ataataatct tgacatgttc ataaataatg ataaagatga     600
tgttgattca gcagaaaata atcttgcatt ggatgaagat ttttggtctg aagttttgtc     660
atctgataat tctagcaatg agacaagtgg tggttttatg gatattggtg ctgataatta     720
tcaatttcaa gcttcatttt ctccattagg gactgaagaa ggagtgtttg attcaagttc     780
attgagttta tgccaagata tggacttttg catgatgtt tatgcaagag ctgaggaaat      840
tactgagtta cttgaattgt gatcaactta attatcattg ttattcttaa attttgactt     900
gtattgtatg ttcattcaat caatgggacg aaaatcattt attttttcca ttgtttagac     960
aaaaaaaaaa aaaaaaaaa aaaaaaaagt actctgcgtt gttaccactg cttaatcact     1020
agtgaattcg cggccgcctg caggtcgacc atatgggaga ctcccaacg cgttggatgc      1080 atagcttgag tattctatag tgtcacctaa atagcttggc gtaatcatgg tcatagctgt     1140
ttcctgtgtg aaattgttat ccgctcacaa ttccacacaa catacgagcc ggaagcataa     1200
agtgta                                                                1206

<210> SEQ ID NO 63
<211> LENGTH: 280
<212> TYPE: PRT
<213> ORGANISM: Trifolium repens

<400> SEQUENCE: 63

Met Val Arg Ala Pro Cys Cys Glu Lys Met Gly Leu Lys Lys Gly Pro
1               5                   10                  15

Trp Thr Gln Glu Glu Asp Arg Ile Leu Ile Asn His Ile Asn Thr Tyr
            20                  25                  30

Gly His Ser Asn Trp Arg Ala Leu Pro Lys Gln Ala Gly Leu Leu Arg
        35                  40                  45

Cys Gly Lys Ser Cys Arg Leu Arg Trp Ala Asn Tyr Leu Lys Pro Asp
    50                  55                  60

Ile Lys Arg Gly Asn Phe Thr Lys Glu Glu Glu Asp Ala Ile Ile Asn
65                  70                  75                  80

Leu His Gln Met Leu Gly Asn Arg Trp Ser Thr Ile Ala Ala Arg Leu
                85                  90                  95

Pro Gly Arg Thr Asp Asn Glu Ile Lys Asn Val Trp His Thr His Leu
            100                 105                 110

Lys Lys Arg Leu Pro Gln Asn Gln Gln Gly His Asn Asn Ser Pro Lys
        115                 120                 125

Arg Asn Lys Lys Gln Thr Asn Leu Asp Phe Glu Ala Ser Lys Ser Asp
    130                 135                 140

Gln Asp Ile Lys Gln Glu Gln Asn Asn Val Asp Asp Met Pro Gln Cys
145                 150                 155                 160

Ser Ser Asp Met Ser Tyr His Asn Asn Ser Asn Ser Ile Ala Thr
                165                 170                 175

Thr Asn Asp Asn Asn Asn Leu Asp Met Phe Ile Asn Asn Asp Lys
            180                 185                 190

Asp Asp Val Asp Ser Ala Glu Asn Asn Leu Ala Leu Asp Glu Asp Phe
        195                 200                 205

Trp Ser Glu Val Leu Ser Ser Asp Asn Ser Ser Asn Glu Thr Ser Gly
    210                 215                 220

Gly Phe Met Asp Ile Gly Ala Asp Asn Tyr Gln Phe Gln Ala Ser Phe
225                 230                 235                 240

Ser Pro Leu Gly Thr Glu Glu Gly Val Phe Asp Ser Ser Ser Leu Ser
                245                 250                 255
```

```
Leu Cys Gln Asp Met Asp Phe Trp His Asp Val Tyr Ala Arg Ala Glu
            260                 265                 270

Glu Ile Thr Glu Leu Leu Glu Leu
            275                 280
```

<210> SEQ ID NO 64
<211> LENGTH: 956
<212> TYPE: DNA
<213> ORGANISM: Trifolium repens

<400> SEQUENCE: 64

```
aagctgatga aggtatgaac catgttttgt cagaaagaag gagaagagca aaacttaatg      60
aaaggttttt aactcttaga tcaatggtcc cttcagatag taaggatgac aaagtttcta     120
tactagatga tgcaattgaa tatcttagca agcttgagaa aggataaaa gaattagaag      180
ctcaaaaaga accaatagat atagagtcta gaagtaaaaa atcacatcat gatttgttgg    240
agaggacttg tgatgattat ataacaaca aaactaacaa tggcaagaaa ccaatgatga     300
agaagaggga aatatgtgac ataggtgaga caaggagaca gatattttct gatgctttaa    360
aaggaagttc taatagtgat gttactgtca gtatgagtga caatggagtt gtgattgaaa    420
tgaagtgtcc ttctagagaa ggaaggatat tggaaattat ggatgcagtt aacaatctca    480
acatggattt taattcagtt caatctacag attccgatgg gaggcttcat gtgatcatta    540
gatctaagtt caaaggacca gctaatgcaa aacaaaaag gatcaaacaa gccctacaaa     600
aagtggcttc aaagttttga atatttgtat ttccaaaata aataaaaaac atggagatgt    660
tcaaataagt tcctgccaat gcagtgtga cacagagagt tgaggatatt gatttagtca     720
caagtgcaaa ttcttggaga tattttttga agacttcaag ttagtctttg agcaataata    780
actcttggtg atgtaacatg gacatttgtt tcattacttg taaatgggta gatagattta    840
gttgacattt atactcaatt aattagccaa aaaaaaaaaa aaaaaaaaaa aaaaaaaaaa    900
aaaaaaaaaa aaaaaaaaaa aaattaaaaa aaaaaaaaaa aaaaaaaaaa aaaaaa        956
```

<210> SEQ ID NO 65
<211> LENGTH: 201
<212> TYPE: PRT
<213> ORGANISM: Trifolium repens

<400> SEQUENCE: 65

```
Met Asn His Val Leu Ser Glu Arg Arg Arg Ala Lys Leu Asn Glu
1               5                   10                  15

Arg Phe Leu Thr Leu Arg Ser Met Val Pro Ser Asp Ser Lys Asp Asp
            20                  25                  30

Lys Val Ser Ile Leu Asp Asp Ala Ile Glu Tyr Leu Ser Lys Leu Glu
            35                  40                  45

Lys Arg Ile Lys Glu Leu Glu Ala Gln Lys Glu Pro Ile Asp Ile Glu
        50                  55                  60

Ser Arg Ser Lys Lys Ser His His Asp Leu Leu Glu Arg Thr Cys Asp
65                  70                  75                  80

Asp Tyr Tyr Asn Asn Lys Thr Asn Asn Gly Lys Lys Pro Met Met Lys
                85                  90                  95

Lys Arg Glu Ile Cys Asp Ile Gly Glu Thr Arg Arg Gln Ile Phe Ser
            100                 105                 110

Asp Ala Leu Lys Gly Ser Ser Asn Ser Asp Val Thr Val Ser Met Ser
        115                 120                 125

Asp Asn Gly Val Val Ile Glu Met Lys Cys Pro Ser Arg Glu Gly Arg
```

```
                130                 135                 140
Ile Leu Glu Ile Met Asp Ala Val Asn Asn Leu Asn Met Asp Phe Asn
145                 150                 155                 160

Ser Val Gln Ser Thr Asp Ser Asp Gly Arg Leu His Val Ile Ile Arg
                165                 170                 175

Ser Lys Phe Lys Gly Pro Ala Asn Ala Thr Thr Lys Arg Ile Lys Gln
                180                 185                 190

Ala Leu Gln Lys Val Ala Ser Lys Phe
                195                 200

<210> SEQ ID NO 66
<211> LENGTH: 1790
<212> TYPE: DNA
<213> ORGANISM: Trifolium repens

<400> SEQUENCE: 66
cgacgtcgca tgctcccggc cgccatggcg gccgcgggaa ttcgattaag cagtggtaac      60
aacgcagagt acgcggggat gggagccgtg gcacaaagag ttgaaagctt agctttgagt     120
ggaatatcat caattccaaa agaatatgtg agaccaaaag aagagttaat aaacatagga     180
aacatatttg atgaagaaaa aaaacaaggg ccacaagttc aacaattga tataaaagaa      240
ataaactcta cagatgaaat tgttagaaga aaatgtaggg ataagcttaa gaaagctgca     300
gaggaatggg gtgtgatgaa tttggtgaat catggtattt ctgatgaatt acttaatcga     360
cttaaaaaag ttggtgaaac tttttttgag ttacctgttg aagaaaaaga aaatatgct      420
aatgatcaaa gtgttgggaa gattcaaggg tatggtagta aattagctaa taatgctagt     480
ggtcaacttg aatgggaaga ttatttcttt cattgtattt ttcctgagga taagcgtgac     540
ttatccatat ggcctaagac tccagctgat tatactgagg tcacaacaga atatgcaaaa     600
gaactaagag gcctagctag caagataatg gaagtgttat ctcttgaact tggcttagaa     660
ggaggaagat tagagaaaga agttggtgga atggaagagc ttttacttca aatgaaaatc     720
aactattacc caatttgccc tcagccagaa ctagcacttg gagttgaagc tcatacagat     780
ataagttcac ttacttttcct tctccacaac atggtgccag gtttgcaact ttttatgag    840
ggtaaatggg tcacagcaaa atgtgtacct ggttcaattc taatgcatat tggtgataca     900
attgagattc ttagcaatgg aaaatacaaa agtatccttc accgtggatt ggttaataag     960
gaaaaagtta gaatatcttg ggcagtgttt tgtgaaccac ctaaagagaa aattattctt    1020
aagccacttc ctgaacttgt tactgagatc gaaccagcac gttttccgcc tcgtactttt    1080
gctcagcata ttcatcacaa actttttagg aagagtgagg aagagaagaa ggatgatcct    1140
aaaaaatgag tgtctcataa gtcataattc agctgacatt gtatcacatt tttcgtatct    1200
atattagcct atgaactttt gtgtgtgtaa gtggaataat aggctatgca gcctaaattt    1260
gttgtatgtt ttaaaaaaaa ctatgtaagt catgttttta gatttgattt gatttatctt    1320
attcagttgg tatttagagg aagcgagtct tagtaatcgg acgctacatg agaaatggac    1380
ttgaactcta aaaaaaaaaa aaaaaaaaa aaaaaaagt actctgcgtt gttaccactg      1440
cttaatcact agtgaattcg cggccgcctg caggtcgacc atatgggaga gctcccaacg    1500
cgttggatgc atagcttgag tattctatag tgtcacctaa atagcttggc gtaatcatgg    1560
tcatagctgt ttcctgtgtg aaattgttat ccgctcacaa ttccacacaa catacgagcc    1620
ggaagcataa agtgtaaagc ctggggtgcc taatgagtga gctaactcac attaattgcg    1680
ttgcgctcac tgcccgcttt ccagtcggga aacctgtcgt gccagctgca ttaatgaatc    1740
```

```
ggccaacgcg cggggagagg cggtttgcgt attgggcgct cttccgcttc        1790
```

<210> SEQ ID NO 67
<211> LENGTH: 374
<212> TYPE: PRT
<213> ORGANISM: Trifolium repens

<400> SEQUENCE: 67

| | | | | | | | | | | | | | | |
|---|---|---|---|---|---|---|---|---|---|---|---|---|---|---|
| Met | Ala | Ala | Ala | Gly | Ile | Arg | Leu | Ser | Ser | Gly | Asn | Asn | Ala | Glu | Tyr |
| 1 | | | | 5 | | | | | 10 | | | | | 15 | |
| Ala | Gly | Met | Gly | Ala | Val | Ala | Gln | Arg | Val | Glu | Ser | Leu | Ala | Leu | Ser |
| | | | 20 | | | | | 25 | | | | | 30 | | |
| Gly | Ile | Ser | Ser | Ile | Pro | Lys | Glu | Tyr | Val | Arg | Pro | Lys | Glu | Glu | Leu |
| | | | 35 | | | | | 40 | | | | | 45 | | |
| Ile | Asn | Ile | Gly | Asn | Ile | Phe | Asp | Glu | Glu | Lys | Lys | Gln | Gly | Pro | Gln |
| | 50 | | | | | 55 | | | | | 60 | | | | |
| Val | Pro | Thr | Ile | Asp | Ile | Lys | Glu | Ile | Asn | Ser | Thr | Asp | Glu | Ile | Val |
| 65 | | | | | 70 | | | | | 75 | | | | | 80 |
| Arg | Arg | Lys | Cys | Arg | Asp | Lys | Leu | Lys | Lys | Ala | Ala | Glu | Glu | Trp | Gly |
| | | | | 85 | | | | | 90 | | | | | 95 | |
| Val | Met | Asn | Leu | Val | Asn | His | Gly | Ile | Ser | Asp | Glu | Leu | Leu | Asn | Arg |
| | | | | 100 | | | | | 105 | | | | | 110 | |
| Leu | Lys | Lys | Val | Gly | Glu | Thr | Phe | Phe | Glu | Leu | Pro | Val | Glu | Glu | Lys |
| | | | 115 | | | | | 120 | | | | | 125 | | |
| Glu | Lys | Tyr | Ala | Asn | Asp | Gln | Ser | Val | Gly | Lys | Ile | Gln | Gly | Tyr | Gly |
| | 130 | | | | | 135 | | | | | 140 | | | | |
| Ser | Lys | Leu | Ala | Asn | Asn | Ala | Ser | Gly | Gln | Leu | Glu | Trp | Glu | Asp | Tyr |
| 145 | | | | | 150 | | | | | 155 | | | | | 160 |
| Phe | Phe | His | Cys | Ile | Phe | Pro | Glu | Asp | Lys | Arg | Asp | Leu | Ser | Ile | Trp |
| | | | | 165 | | | | | 170 | | | | | 175 | |
| Pro | Lys | Thr | Pro | Ala | Asp | Tyr | Thr | Glu | Val | Thr | Thr | Glu | Tyr | Ala | Lys |
| | | | 180 | | | | | 185 | | | | | 190 | | |
| Glu | Leu | Arg | Gly | Leu | Ala | Ser | Lys | Ile | Met | Glu | Val | Leu | Ser | Leu | Glu |
| | | 195 | | | | | 200 | | | | | 205 | | | |
| Leu | Gly | Leu | Glu | Gly | Gly | Arg | Leu | Glu | Lys | Glu | Val | Gly | Gly | Met | Glu |
| | 210 | | | | | 215 | | | | | 220 | | | | |
| Glu | Leu | Leu | Leu | Gln | Met | Lys | Ile | Asn | Tyr | Tyr | Pro | Ile | Cys | Pro | Gln |
| 225 | | | | | 230 | | | | | 235 | | | | | 240 |
| Pro | Glu | Leu | Ala | Leu | Gly | Val | Glu | Ala | His | Thr | Asp | Ile | Ser | Ser | Leu |
| | | | 245 | | | | | 250 | | | | | 255 | | |
| Thr | Phe | Leu | Leu | His | Asn | Met | Val | Pro | Gly | Leu | Gln | Leu | Phe | Tyr | Glu |
| | | | 260 | | | | | 265 | | | | | 270 | | |
| Gly | Lys | Trp | Val | Thr | Ala | Lys | Cys | Val | Pro | Gly | Ser | Ile | Leu | Met | His |
| | | 275 | | | | | 280 | | | | | 285 | | | |
| Ile | Gly | Asp | Thr | Ile | Glu | Ile | Leu | Ser | Asn | Gly | Lys | Tyr | Lys | Ser | Ile |
| | 290 | | | | | 295 | | | | | 300 | | | | |
| Leu | His | Arg | Gly | Leu | Val | Asn | Lys | Glu | Lys | Val | Arg | Ile | Ser | Trp | Ala |
| 305 | | | | | 310 | | | | | 315 | | | | | 320 |
| Val | Phe | Cys | Glu | Pro | Pro | Lys | Glu | Lys | Ile | Ile | Leu | Lys | Pro | Leu | Pro |
| | | | | 325 | | | | | 330 | | | | | 335 | |
| Glu | Leu | Val | Thr | Glu | Ile | Glu | Pro | Ala | Arg | Phe | Pro | Pro | Arg | Thr | Phe |
| | | | 340 | | | | | 345 | | | | | 350 | | |
| Ala | Gln | His | Ile | His | His | Lys | Leu | Phe | Arg | Lys | Ser | Glu | Glu | Glu | Lys |
| | | 355 | | | | | 360 | | | | | 365 | | | |
| Lys | Asp | Asp | Pro | Lys | Lys | | | | | | | | | | |

370

<210> SEQ ID NO 68
<211> LENGTH: 2090
<212> TYPE: DNA
<213> ORGANISM: Trifolium repens

<400> SEQUENCE: 68

```
aggttgttta ctagtcgtgt cggaattcct tccatatttc aactagttag atagaattct      60
catcttcctc attctccttc aattcaatgg cagcatcaca acaacaagaa gaaataatat     120
tcaggtctaa acttccggac atatacatcc caaaacacct tcccctccat tcttattgct     180
ttgaaaatct ctcccaattt ggttctcgtc catgtctcat caatgcaccc accggaaaag     240
tctacaccta ccacgacgtc gaactcacct tcggaaagt tgcctccggt ctcaacaaat      300
tgggagtcca acagggtgat gtgatcatga tcctcctccc caattcccct gaattcgtct     360
tctcctttct ggcagcttct tatctcggcg ccatagccac agcagccaat cctttcttca     420
tggccgcgga gattggaaag caagcaaaag cctccaacgc caagttgatc ataacacagg     480
catgttacta cgacaaagtc aaggagttgt tgttggacaa ccacaacaag aagaagaaga     540
agttggtgct catagactct ctccctccct ctaccaccac cacagaagaa gaagaagatg     600
gtaatcatgt tcatttctcg acactgatcg atgctgacga aaggaattg ccggcggatg      660
tgaagatcga ccctgaagat gtggtggcac ttccctattc atcggggaca acgggtctgc     720
caaaaggggt gatgttaaca cacaagggat tggtgagcag catagcgcag caggtggatg     780
gagagaatcc aaatctatgt tacagcagtg aagatgtgat actgtgtgtg cttcctctgt     840
ttcacatata ctctctaaat tctgttttgc tatgtggact gagagcgaag gcaagtatac     900
ttttgatgcc aaaattcgac ataaatggtt tcttgagtct tgtgaacaaa catggagtta     960
cagttgcacc ggtagttcct ccgatagtgt tggcgattgc aaagtcgccg gatcttaaca    1020
aatatgatct gccttcaata aggatattga atcaggagg tgctccactc ggcaaagaac     1080
ttgaagacac tgttaggaac aaatttccca agtaatact tggacaggga tacggaatga     1140
ctgaggcagg gccagtgtta acaatgagct tagcatttgc taaagaagca gtgaatgtga    1200
agccgggtgc gtgtggaaca gttgtaagaa atgcagagat gaagattgtg gatcctgaaa    1260
gtggtaattc tttacctaga aaccaatctg gtgaaatctg cataagagga gaccagatca    1320
tgaaaggtta tctaaatgat gtggaggcaa ctgagagaac gattgacaaa gaaggttggt    1380
tgcatacagg tgatattggg tatattgacg atgacgatga ttattcatt gttgatagat     1440
tgaaggaatt gatcaaatac aaaggatttc aagttgctcc agctgaactt gaagctcttc    1500
ttctttctca tcccaaaatc tctgatgctg ctgttgtccc aatgaaggat gaagccgccg    1560
gagaggtacc tgttgcattt gttgtgggat caaatggtca cactgactta accgaggatg    1620
aaattaagca cttatctcc aaacaggtgg tgttttacaa aagaataagt cgagtattct     1680
tcattgatgc aattcccaag tcaccttcag gcaaaatatt gcgtaaggat ctcagagcaa    1740
agttagcagc agaataagct gttccaaatt gatcatcact ttcacatctt atttctcaac    1800
catatgtatt atataagtta caagcttgtg ttgtgtgttc ttttcatctt attttacaat    1860
tattctgtaa aatcattcaa tcccgatcta actttcattt ctatcatcat gtactcaaaa    1920
tattattttt actaaaacaa atgcacttct tgtttttttt tttaaaaaaa aaaaaaaaa     1980
aaaaaaaaaa aaaaaaaaaa aaaaaaaaaa aaaaaaaaaa aaaaaaaaaa aaaaaaaaaa    2040
aaaaaaaaaa aaaatataaa aaaaaaaaaa aaaaaaaaaa aaaaaaaaaa               2090
```

<210> SEQ ID NO 69
<211> LENGTH: 556
<212> TYPE: PRT
<213> ORGANISM: Trifolium repens

<400> SEQUENCE: 69

```
Met Ala Ala Ser Gln Gln Glu Glu Ile Ile Phe Arg Ser Lys Leu
1               5                   10                  15

Pro Asp Ile Tyr Ile Pro Lys His Leu Pro Leu His Ser Tyr Cys Phe
                20                  25                  30

Glu Asn Leu Ser Gln Phe Gly Ser Arg Pro Cys Leu Ile Asn Ala Pro
            35                  40                  45

Thr Gly Lys Val Tyr Thr Tyr His Asp Val Glu Leu Thr Ser Arg Lys
        50                  55                  60

Val Ala Ser Gly Leu Asn Lys Leu Gly Val Gln Gln Gly Asp Val Ile
65                  70                  75                  80

Met Ile Leu Leu Pro Asn Ser Pro Glu Phe Val Phe Ser Phe Leu Ala
                85                  90                  95

Ala Ser Tyr Leu Gly Ala Ile Ala Thr Ala Ala Asn Pro Phe Phe Met
            100                 105                 110

Ala Ala Glu Ile Gly Lys Gln Ala Lys Ala Ser Asn Ala Lys Leu Ile
        115                 120                 125

Ile Thr Gln Ala Cys Tyr Tyr Asp Lys Val Lys Glu Leu Leu Leu Asp
130                 135                 140

Asn His Asn Lys Lys Lys Lys Leu Val Leu Ile Asp Ser Leu Pro
145                 150                 155                 160

Pro Ser Thr Thr Thr Thr Glu Glu Glu Asp Gly Asn His Val His
                165                 170                 175

Phe Ser Thr Leu Ile Asp Ala Asp Glu Lys Glu Leu Pro Ala Asp Val
            180                 185                 190

Lys Ile Asp Pro Glu Asp Val Val Ala Leu Pro Tyr Ser Ser Gly Thr
        195                 200                 205

Thr Gly Leu Pro Lys Gly Val Met Leu Thr His Lys Gly Leu Val Ser
    210                 215                 220

Ser Ile Ala Gln Gln Val Asp Gly Glu Asn Pro Asn Leu Cys Tyr Ser
225                 230                 235                 240

Ser Glu Asp Val Ile Leu Cys Val Leu Pro Leu Phe His Ile Tyr Ser
                245                 250                 255

Leu Asn Ser Val Leu Leu Cys Gly Leu Arg Ala Lys Ala Ser Ile Leu
            260                 265                 270

Leu Met Pro Lys Phe Asp Ile Asn Gly Phe Leu Ser Leu Val Asn Lys
        275                 280                 285

His Gly Val Thr Val Ala Pro Val Pro Pro Ile Val Leu Ala Ile
    290                 295                 300

Ala Lys Ser Pro Asp Leu Asn Lys Tyr Asp Leu Pro Ser Ile Arg Ile
305                 310                 315                 320

Leu Lys Ser Gly Gly Ala Pro Leu Gly Lys Glu Leu Glu Asp Thr Val
                325                 330                 335

Arg Asn Lys Phe Pro Lys Val Ile Leu Gly Gln Gly Tyr Gly Met Thr
            340                 345                 350

Glu Ala Gly Pro Val Leu Thr Met Ser Leu Ala Phe Ala Lys Glu Ala
        355                 360                 365

Val Asn Val Lys Pro Gly Ala Cys Gly Thr Val Arg Asn Ala Glu
    370                 375                 380
```

```
Met Lys Ile Val Asp Pro Glu Ser Gly Asn Ser Leu Pro Arg Asn Gln
385                 390                 395                 400

Ser Gly Glu Ile Cys Ile Arg Gly Asp Gln Ile Met Lys Gly Tyr Leu
            405                 410                 415

Asn Asp Val Glu Ala Thr Glu Arg Thr Ile Asp Lys Glu Gly Trp Leu
        420                 425                 430

His Thr Gly Asp Ile Gly Tyr Ile Asp Asp Asp Glu Leu Phe Ile
    435                 440                 445

Val Asp Arg Leu Lys Glu Leu Ile Lys Tyr Lys Gly Phe Gln Val Ala
    450                 455                 460

Pro Ala Glu Leu Glu Ala Leu Leu Leu Ser His Pro Lys Ile Ser Asp
465                 470                 475                 480

Ala Ala Val Val Pro Met Lys Asp Glu Ala Ala Gly Glu Val Pro Val
                485                 490                 495

Ala Phe Val Val Gly Ser Asn Gly His Thr Asp Leu Thr Glu Asp Glu
                500                 505                 510

Ile Lys His Phe Ile Ser Lys Gln Val Val Phe Tyr Lys Arg Ile Ser
            515                 520                 525

Arg Val Phe Phe Ile Asp Ala Ile Pro Lys Ser Pro Ser Gly Lys Ile
    530                 535                 540

Leu Arg Lys Asp Leu Arg Ala Lys Leu Ala Ala Glu
545                 550                 555

<210> SEQ ID NO 70
<211> LENGTH: 1467
<212> TYPE: DNA
<213> ORGANISM: Trifolium repens

<400> SEQUENCE: 70
ccgacgtcgc atgctcccgg ccgccatggc ggccgcggga attcgattaa gcagtggtaa     60
caacgcagag tacgcgggaa cacaaggttg ttactatgac aaagttaagg atttggaaaa    120
tgtgaagctg gttttgtgg actcttcacc ggaaggagaa atcatatgc atttccgtga     180 gctggctcaa gccgatgaga atgaaattga agaggtaaag ataaaccctg atgatgtggt    240
tgctttgcca tattcttctg aacaacagg gctacctaaa ggtgttatgc taacacacaa    300
aggattagtg acaagtgtag cacaacaagt tggtggtgaa atccaaatc tatattacca    360 ttctgaggat gtcatactat gtgttcttcc catgtttcat atctattcac tcaactctgt    420
tttgctctgt ggtttgagag ccaaagcttc cattcttta atgccaaagt ttgatattca    480 ttctttttt agccttgttc ataaatacag agtcactgtt gctcctgttg tgccaccaat    540
tgttttggct atttctaagt cacctgaact tgataactat gatctttcat ccataaggat    600
tttgaaatct ggtggtgctc cacttggtaa ggaacttgag acactgtta gggccaaatt    660 tccaaaagca aaacttggac aaggatatgg gatgactgag gctggtccag ttttaacaat    720
gtgtttgtca tttgcaaaag tgccaataga tgttaaaccg ggtgcatgtg aactgttgt    780 aagaaatgct cagatcaaaa ttgttgatcc tgaaaatgat tcttctttgc ctcgtaatca    840
acctggtgaa atttgtatta gaggagacca aatcatgaaa ggttatctaa acgacccaga    900
agcaacaggg agaacaatag acaaagaagg ttggttgcac acaggtgaca ttggttacat    960
tgacaatgat gatgaattgt tcatagtgga taggcttaaa gaattgatta aatacaaagg   1020
ttttcaagtt gctccagctg aacttgaagc cattattctt tcacatccca atatctctga   1080
tgttgctgtc gtcccaatgc tggatgaagc tgctggtgag gtcccagttg catttgttgt   1140
gagatcaaat ggaagtatcg acacaactga ggatgaaatt aagaagtttg tctccaaaca   1200
```

-continued

```
ggtggtattt tacaaaagaa taaacagagt attcttcatt gatgccattc ccaagtcacc    1260
ctcaggcaaa atattaagaa aggacctaag ggctaagctt gcagctggtg ttccaacaaa    1320
ttaaacaatc catttattat ttatttttca tgtattttttt tattcacagc ctgttccaaa   1380
ttcaacagct caatcaattt cagaccttat ttttaattat tagaaaaaaa aaaaaaaaaa    1440
aaaaaaaaaa aagtactctg cgtgtgt                                        1467
```

<210> SEQ ID NO 71
<211> LENGTH: 432
<212> TYPE: PRT
<213> ORGANISM: Trifolium repens

<400> SEQUENCE: 71

```
Met Ala Ala Gly Ile Arg Leu Ser Ser Gly Asn Asn Ala Glu Tyr
1               5                   10                  15

Ala Gly Thr Gln Gly Cys Tyr Tyr Asp Lys Val Lys Asp Leu Glu Asn
            20                  25                  30

Val Lys Leu Val Phe Val Asp Ser Ser Pro Glu Gly Glu Asn His Met
        35                  40                  45

His Phe Arg Glu Leu Ala Gln Ala Asp Glu Asn Glu Ile Glu Glu Val
    50                  55                  60

Lys Ile Asn Pro Asp Asp Val Val Ala Leu Pro Tyr Ser Ser Gly Thr
65                  70                  75                  80

Thr Gly Leu Pro Lys Gly Val Met Leu Thr His Lys Gly Leu Val Thr
                85                  90                  95

Ser Val Ala Gln Gln Val Gly Gly Glu Asn Pro Asn Leu Tyr Tyr His
            100                 105                 110

Ser Glu Asp Val Ile Leu Cys Val Leu Pro Met Phe His Ile Tyr Ser
        115                 120                 125

Leu Asn Ser Val Leu Leu Cys Gly Leu Arg Ala Lys Ala Ser Ile Leu
    130                 135                 140

Leu Met Pro Lys Phe Asp Ile His Ser Phe Phe Ser Leu Val His Lys
145                 150                 155                 160

Tyr Arg Val Thr Val Ala Pro Val Val Pro Ile Val Leu Ala Ile
                165                 170                 175

Ser Lys Ser Pro Glu Leu Asp Asn Tyr Asp Leu Ser Ser Ile Arg Ile
            180                 185                 190

Leu Lys Ser Gly Gly Ala Pro Leu Gly Lys Glu Leu Glu Asp Thr Val
        195                 200                 205

Arg Ala Lys Phe Pro Lys Ala Lys Leu Gly Gln Gly Tyr Gly Met Thr
    210                 215                 220

Glu Ala Gly Pro Val Leu Thr Met Cys Leu Ser Phe Ala Lys Val Pro
225                 230                 235                 240

Ile Asp Val Lys Pro Gly Ala Cys Gly Thr Val Val Arg Asn Ala Gln
                245                 250                 255

Ile Lys Ile Val Asp Pro Glu Asn Asp Ser Ser Leu Pro Arg Asn Gln
            260                 265                 270

Pro Gly Glu Ile Cys Ile Arg Gly Asp Gln Ile Met Lys Gly Tyr Leu
        275                 280                 285

Asn Asp Pro Glu Ala Thr Gly Arg Thr Ile Asp Lys Glu Gly Trp Leu
    290                 295                 300

His Thr Gly Asp Ile Gly Tyr Ile Asp Asn Asp Glu Leu Phe Ile
305                 310                 315                 320

Val Asp Arg Leu Lys Glu Leu Ile Lys Tyr Lys Gly Phe Gln Val Ala
```

```
                    325                 330                 335
Pro Ala Glu Leu Glu Ala Ile Ile Leu Ser His Pro Asn Ile Ser Asp
                340                 345                 350

Val Ala Val Val Pro Met Leu Asp Glu Ala Ala Gly Glu Val Pro Val
            355                 360                 365

Ala Phe Val Val Arg Ser Asn Gly Ser Ile Asp Thr Thr Glu Asp Glu
370                 375                 380

Ile Lys Lys Phe Val Ser Lys Gln Val Val Phe Tyr Lys Arg Ile Asn
385                 390                 395                 400

Arg Val Phe Phe Ile Asp Ala Ile Pro Lys Ser Pro Ser Gly Lys Ile
                405                 410                 415

Leu Arg Lys Asp Leu Arg Ala Lys Leu Ala Ala Gly Val Pro Thr Asn
                420                 425                 430
```

<210> SEQ ID NO 72
<211> LENGTH: 991
<212> TYPE: DNA
<213> ORGANISM: Trifolium repens
<220> FEATURE:
<221> NAME/KEY: misc_feature
<222> LOCATION: (78)..(78)
<223> OTHER INFORMATION: n is a, c, g, or t

<400> SEQUENCE: 72

```
cgacgtcgca tgctcccggc cgccatggcg gccgcgggaa ttcgattaag cagtggtaac      60
aacgcagagt acgcgggngg ttcatgtgga accgttgcaa gaaatgcaga gctcaaagtt     120
cttgactctg aaactggtcg ctctcttggt tataatcaac ccggtgagat ttgcatccgt     180
ggccaacaaa tcatgaaagg atatttgaat gatgaaaatg caacaaaaac tactattgat     240
gaagagggtt ggcttcatac tggtgatgtt ggctatatag atgacaatga tgagattttc     300
attgttgaca gggtgaagga actcattaaa ttcaaaggct tccaagtgcc ccctgctgaa     360
cttgaaggcc ttctagtaag ccatccatct attgcagatg cagctgttgt cccgcaaaag     420
gatgtggctg ctggtgaagt tcctgttgcc tttgtggtaa gatcaaatgg acttgatcta     480
actgaagagg ctgtaaagga gtttatagct aaacaggttg tattttataa agactgcac      540 aaagtgtatt tcattcatgc aattcccaag tctccatcag gaaagatact gaggaaagat     600
ctcagagcaa agttagaaag taccacccaa agccttgag atgctagaag ctttttcact      660 tattttttt ggtcaaaatc ttcctcattt gttcatttgt atcctaatat attctagcta     720
ctaggtctca tgcttaattt atgtattgat aatatatata aggtataaag tcaatatatc     780
catggtgaag ttgtatgtac aaatgctcca ttgtgtattt ttaagccaat tgcctaagca     840
gttctctggt ttgttgtgct tgtaatgtga tttgggaaac agtattgtta ctatcaatct     900
atgtagttct tttcatcata taaaaaaaaa aaaaaaaaa aaaaaaaaaa aaaaaaaaaa     960
aaaaaaaaaa aaaaaaaaa aaaaaaaaa a                                     991
```

<210> SEQ ID NO 73
<211> LENGTH: 204
<212> TYPE: PRT
<213> ORGANISM: Trifolium repens
<220> FEATURE:
<221> NAME/KEY: misc_feature
<222> LOCATION: (18)..(18)
<223> OTHER INFORMATION: Xaa can be any naturally occurring amino acid

<400> SEQUENCE: 73

```
Met Ala Ala Ala Gly Ile Arg Leu Ser Ser Gly Asn Asn Ala Glu Tyr
1               5                   10                  15
```

Ala Xaa Gly Ser Cys Gly Thr Val Ala Arg Asn Ala Glu Leu Lys Val
        20                  25                  30

Leu Asp Ser Glu Thr Gly Arg Ser Leu Gly Tyr Asn Gln Pro Gly Glu
            35                  40                  45

Ile Cys Ile Arg Gly Gln Gln Ile Met Lys Gly Tyr Leu Asn Asp Glu
    50                  55                  60

Asn Ala Thr Lys Thr Thr Ile Asp Glu Glu Gly Trp Leu His Thr Gly
65                  70                  75                  80

Asp Val Gly Tyr Ile Asp Asp Asn Asp Glu Ile Phe Ile Val Asp Arg
                85                  90                  95

Val Lys Glu Leu Ile Lys Phe Lys Gly Phe Gln Val Pro Pro Ala Glu
            100                 105                 110

Leu Glu Gly Leu Leu Val Ser His Pro Ser Ile Ala Asp Ala Ala Val
            115                 120                 125

Val Pro Gln Lys Asp Val Ala Ala Gly Glu Val Pro Val Ala Phe Val
130                 135                 140

Val Arg Ser Asn Gly Leu Asp Leu Thr Glu Glu Ala Val Lys Glu Phe
145                 150                 155                 160

Ile Ala Lys Gln Val Val Phe Tyr Lys Arg Leu His Lys Val Tyr Phe
                165                 170                 175

Ile His Ala Ile Pro Lys Ser Pro Ser Gly Lys Ile Leu Arg Lys Asp
            180                 185                 190

Leu Arg Ala Lys Leu Glu Ser Thr Thr Gln Lys Pro
            195                 200

<210> SEQ ID NO 74
<211> LENGTH: 2833
<212> TYPE: DNA
<213> ORGANISM: Trifolium repens

<400> SEQUENCE: 74
cgacgtcgca tgctcccggc cgccatggcg gccgcgggaa ttcgattaag cagtggtaac      60
aacgcagagt acgcggggaa acttagctaa cttaaattaa tttaattccc cttattccta     120
atattctcct aacattacca aaatgtcacc atttcctcca cagcaagaag aattcatatt     180
ccgttccaaa ctcccagaca ttgaaattcc aacaaatctt ccattacact cttattgttt     240
ccaaaacctc tctcaattcc ataaccgtcc atgtctcatc aacggcgact ccggcgaaat     300
cttaacatac tccgacgtcc acctcaccgt ccgcaaaatc gccgccggtt taaacactct     360
cggaattaat caaggtgatg tcatcatgct cgtcctccgt aactctcctc aattcgcact     420
cactttcctc ggtgcctcct tccgtggcgc cgtcatcacc accgcaaatc ctttctacac     480
ctcatcggaa ctcgcgaaac aagccacagc aacaaaaact aaactcatcg taactcaatc     540
cgcatatcta agtaaaatca acgatttcgc taaattcaac aacatcaaaa tcgtctgcat     600
agattcatca tcgtcgccgt cgtcggaaga agatgccacc ggcgttgtgg atttttcagt     660
tttaacaaat gctgatgaaa acgatttacc agatgttaaa ctaacgccta acgacatcgt     720
tgcgttaccg ttttcttcgg aacttcagg acttccaaaa ggcgttatgt taacacatga     780
aaatttagtt acaactatat cacagttagt tgacggtgaa atccacatc aatacactaa     840 cggcgaggat gtgttactct gtgtgttacc tatgtttcat atctatgcac tcaattcaat     900
attactatgt ggaattcgtt gtggtgctgc ggttttaatt gtggaaaaat ttgagattaa     960
aacgttattg gaacttattg aaaagtttaa agtgacggta gcgtcgtttg tgccaccaat    1020
tgttttggcg ttggtaaaaa gtggtgaatc aaataaatat gatttgtcgt ctattagagc    1080

```
gatgattact ggtgcagcac ctatgggaat ggaacttgaa caagctgtaa aggatagatt      1140
gccacataca gtacttggtc agggatacgg catgacagag gcaggaccac tatcaattag      1200
ccttgcattt gcaaaggaac cattcagaac aaaacctggt gcatgtggca ccgtcgtaag      1260
aaacgccgag atgaaaatcg ttgatacaga gactggtgtt tctcttccta gaaacaaagc      1320
tggtgaaatt tgcattagag gcacaaaggt tatgaaagga tacctaaatg atcccgaggc      1380
gacaaagaga actatagacg aagagggatg gctacacacg ggtgacattg gtttgattga      1440
cgatgatgat gaactcttca tcgttgatcg attaaaagaa ttgatcaaat acaaaggata      1500
ccaagtagct cctgctgagc tcgaagcatt gttaatttca cactcgaaca tttctgatgc      1560
tgctgttgta ccattgaaag atgaagttgc tggagaatta ccggttgcat tgttgtaag       1620 atcaaacggt tcaaagatca gtgaagatga atcaagcaa tacatttcac aacaggttgt       1680
attttacaag agaataaaca gagtttattt cacagacaca attcctaaag cggcctctgg      1740
caaaattctc cgaaagaaat taaccgcaag acttaacgaa ggtttggtgg tggccactta     1800
attatgttcg tgtgtgtgac aaagacgaac gaattacact acctgcatat gcaaatgcag     1860
cagcatgaat ggatacaaaa tattcttaaa caatacaagt attgtgtgtt ctgtcacttc     1920
tgtgcaatat ttgtttctct gtgtgcaaat tctttctctg caatgcggct tctgctgtgg     1980
gtattggatc atcaatgcgc gcggcttctt tctgtgatta aaaataata atgccgtgtt     2040 aatcctacta ggtaggccta ttcgttcgct tcttttttagg ggattattca ctacttattg     2100
atagaagatg tttaagacag ccttttcttt ctctataaga aaaaaattca ggtactgtat     2160
taagtctttt ttcgtcaact gtgtaatgtg acatttcatt tttgatgaac aaatgccaca     2220
gaacattaaa tcaagtgtcc aacaaaacaa ttcactgcta tttagatgta atatatagtg    2280
ttcctgcaaa ccgtgtttaa tcaattttt tagtaaaatt gtcaagtctt tgacaatat       2340 tattgcaaat tttaatctat atgtaaaaat cttaagcgat acaatactca ttttaaagct     2400
aagagaatga taataagata agatagaatg aaattcatac aaaaaaaaaa aaaaaaaaa      2460 aaaaaaaag tactctgcgt tgttaccact gcttaatcac tagtgaattc gcggccgcct     2520
gcaggtcgac catatgggag agctcccaac gcgttggatg catagcttga gtattctata    2580
gtgtcaccta aatagcttgg cgtaatcatg gtcatagctg tttcctgtgt gaaattgtta    2640
tccgctcaca attccacaca acatacgagc cggaagcata aagtgtaaag cctggggtgc    2700
ctaatgagtg agctaactca cattaattgc gttgcgctca ctgcccgctt tccagtcggg    2760
aaacctgtcg tgccagctgc attaatgaat cggccaacgc gcggggagag gcggtttgcg    2820
tattgggcgc tct                                                      2833

<210> SEQ ID NO 75
<211> LENGTH: 622
<212> TYPE: PRT
<213> ORGANISM: Trifolium repens

<400> SEQUENCE: 75

Met Ser Pro Phe Pro Gln Gln Glu Glu Phe Ile Phe Arg Ser Lys
1               5                   10                  15

Leu Pro Asp Ile Glu Ile Pro Thr Asn Leu Pro Leu His Ser Tyr Cys
            20                  25                  30

Phe Gln Asn Leu Ser Gln Phe His Asn Arg Pro Cys Leu Ile Asn Gly
        35                  40                  45

Asp Ser Gly Glu Ile Leu Thr Tyr Ser Asp Val His Leu Thr Val Arg
    50                  55                  60
```

```
Lys Ile Ala Ala Gly Leu Asn Thr Leu Gly Ile Asn Gln Gly Asp Val
 65                  70                  75                  80

Ile Met Leu Val Leu Arg Asn Ser Pro Gln Phe Ala Leu Thr Phe Leu
                 85                  90                  95

Gly Ala Ser Phe Arg Gly Ala Val Ile Thr Thr Ala Asn Pro Phe Tyr
            100                 105                 110

Thr Ser Ser Glu Leu Ala Lys Gln Ala Thr Ala Thr Lys Thr Lys Leu
        115                 120                 125

Ile Val Thr Gln Ser Ala Tyr Leu Ser Lys Ile Asn Asp Phe Ala Lys
    130                 135                 140

Phe Asn Asn Ile Lys Ile Val Cys Ile Asp Ser Ser Ser Pro Ser
145                 150                 155                 160

Ser Glu Glu Asp Ala Thr Gly Val Val Asp Phe Ser Val Leu Thr Asn
                165                 170                 175

Ala Asp Glu Asn Asp Leu Pro Asp Val Lys Leu Thr Pro Asn Asp Ile
            180                 185                 190

Val Ala Leu Pro Phe Ser Ser Gly Thr Ser Gly Leu Pro Lys Gly Val
        195                 200                 205

Met Leu Thr His Glu Asn Leu Val Thr Thr Ile Ser Gln Leu Val Asp
    210                 215                 220

Gly Glu Asn Pro His Gln Tyr Thr Asn Gly Glu Asp Val Leu Leu Cys
225                 230                 235                 240

Val Leu Pro Met Phe His Ile Tyr Ala Leu Asn Ser Ile Leu Leu Cys
                245                 250                 255

Gly Ile Arg Cys Gly Ala Ala Val Leu Ile Val Glu Lys Phe Glu Ile
            260                 265                 270

Lys Thr Leu Leu Glu Leu Ile Glu Lys Phe Lys Val Thr Val Ala Ser
        275                 280                 285

Phe Val Pro Pro Ile Val Leu Ala Leu Val Lys Ser Gly Glu Ser Asn
    290                 295                 300

Lys Tyr Asp Leu Ser Ser Ile Arg Ala Met Ile Thr Gly Ala Ala Pro
305                 310                 315                 320

Met Gly Met Glu Leu Glu Gln Ala Val Lys Asp Arg Leu Pro His Thr
                325                 330                 335

Val Leu Gly Gln Gly Tyr Gly Met Thr Glu Ala Gly Pro Leu Ser Ile
            340                 345                 350

Ser Leu Ala Phe Ala Lys Glu Pro Phe Arg Thr Lys Pro Gly Ala Cys
        355                 360                 365

Gly Thr Val Val Arg Asn Ala Glu Met Lys Ile Val Asp Thr Glu Thr
    370                 375                 380

Gly Val Ser Leu Pro Arg Asn Lys Ala Gly Glu Ile Cys Ile Arg Gly
385                 390                 395                 400

Thr Lys Val Met Lys Gly Tyr Leu Asn Asp Pro Glu Ala Thr Lys Arg
                405                 410                 415

Thr Ile Asp Glu Glu Gly Trp Leu His Thr Gly Asp Ile Gly Leu Ile
            420                 425                 430

Asp Asp Asp Asp Glu Leu Phe Ile Val Asp Arg Leu Lys Glu Leu Ile
        435                 440                 445

Lys Tyr Lys Gly Tyr Gln Val Ala Pro Ala Glu Leu Glu Ala Leu Leu
    450                 455                 460

Ile Ser His Ser Asn Ile Ser Asp Ala Ala Val Val Pro Leu Lys Asp
465                 470                 475                 480

Glu Val Ala Gly Glu Leu Pro Val Ala Phe Val Val Arg Ser Asn Gly
```

```
                             485                 490                 495
Ser Lys Ile Ser Glu Asp Glu Ile Lys Gln Tyr Ile Ser Gln Gln Val
                500                 505                 510

Val Phe Tyr Lys Arg Ile Asn Arg Val Tyr Phe Thr Asp Thr Ile Pro
            515                 520                 525

Lys Ala Ala Ser Gly Lys Ile Leu Arg Lys Lys Leu Thr Ala Arg Leu
        530                 535                 540

Asn Glu Gly Leu Val Val Ala Thr Leu Cys Ser Cys Val Gln Arg Arg
545                 550                 555                 560

Thr Asn Tyr Thr Thr Cys Ile Cys Lys Cys Ser Ser Met Asn Gly Tyr
                565                 570                 575

Lys Ile Phe Leu Asn Asn Thr Ser Ile Val Cys Ser Val Thr Ser Val
            580                 585                 590

Gln Tyr Leu Phe Leu Cys Val Gln Ile Leu Ser Leu Gln Cys Gly Phe
                595                 600                 605

Cys Cys Gly Tyr Trp Ile Ile Asn Ala Arg Gly Phe Phe Leu
        610                 615                 620

<210> SEQ ID NO 76
<211> LENGTH: 2152
<212> TYPE: DNA
<213> ORGANISM: Trifolium repens

<400> SEQUENCE: 76
cgtcgcatgc tcccggccgc catggcggcc gcgggaattc gattaagcag tggtaacaac      60
gcagagtacg cggggaatta acatctccac aaccacaata acaataacaa caatggatct     120
actccttctt gaaaagactc ttttatccct cttcatcgcc gctataatcg caatcacaat     180
ctcaaaactc cgtggaaaac gcttcaaact tccaccaggt ccatttccag ttccaatttt     240
tggtaattgg cttcaagttg gcgatgatct caaccaccgt aatttaactg atttagccaa     300
acgcttcggc gaaatcctgc ttctccggat gggacaacga aacctggtcg ttgtctcatc     360
accggagtta gcaaaagaag tccttcacac acaaggtgtc gaattcggtt ccagaacacg     420
gaacgtcgta ttcgacatct ttaccggtaa ggacaggac atggttttca ccgtgtacgg      480
tgaacattgg cgtaaaatga ggagaattat gacagtacca ttttcacaa acaaagttgt      540 tcaacaatat agatttggtt gggaatctga agctgaaagt gttgttaatg atgttaagaa     600
aaataatgaa gctagtgttg gtggaattgt gattagaaga agattacaat tgatgatgta     660
taatattatg tataggatta tgtttgatag aagatttgaa agtgaagaag atcctttgtt     720
tgtgaaattg aaagctttga atggtgaaag gagtcgttta gctcaaagtt ttgagtataa     780
ttatggtgat tttattccaa ttttgagacc ttttttgaaa ggttatttga aggtttgtaa     840
agaggttaag gatcgtaggt tgcagctttt caaagactat ttcgttgatg agagaaagaa     900
gcttgaaagt accaagagca ccactagcaa tgatggactt aaatgtgcta ttgatcacat     960
tttggatgct caaaagaaag gagagatcaa tgatgacaac gttctttaca ttgtcgagaa    1020
catcaatgtt gctgcaattg aaacaacact atggtcaatt gaatggggaa ttgctgagct    1080
agtgaaccac caagggatcc aaaacaaagt aagggaagag atggacagag ttctaggacc    1140
aggacaccaa gtaaccgagc cggatcttca gaagctacct tacctacaag ccgtgatcaa    1200
agagacactt cgtctacgaa tggcaattcc actcctcgtc ccacacatga accttcatga    1260
tgcaaagctt gccggttatg acatcccggc cgagagcaag atattggtca acgcgtggtg    1320
gcttgcaaat aacccggctc tatggaaaaa tccagaggaa tttaggcctg agaggttctt    1380
```

-continued

```
ggaggaagag gcgcatgttg aggctaatgg aaatgacttt aggtaccttc ctttcggtgt   1440
tggtagaagg agttgtcctg gaattattct tgctttacct atccttggta ttactatcgg   1500
gcgtcttgtt cagaatttcg agcttttgcc tccacccgga caatctaaga ttgatacttc   1560
cgagaaagga ggacagttta gtttgcacat actcaaacat tccaccattg ttgctaagcc   1620
aagatcattt taattagtat tcacactaat acccttatt tgttttactt tactttgtgt    1680
aatgcatttt aatgattcat aatgtgggaa tgttattaaa atgtcttagg tgaataatgt    1740
tgttgttttg tgcttgtccc atgtataaat cttttgaact ttaagtaatg gttttgagat    1800
gattttgtaa caacacttgt cccttatatt ctcttgattg attaatagtt tgttgtcctg    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaacaa aaaaaaaaaa aaaaaaaaaa aaaaaaaagt actctgcgtt     2040
gttaccactg cttaatcact agtgaattcg cggccgcctg caggtgggcc atatgggaga    2100
gctcccaacg cgttggatgc atagcttgag tattctatta gtgtcaaccc cc            2152
```

<210> SEQ ID NO 77
<211> LENGTH: 506
<212> TYPE: PRT
<213> ORGANISM: Trifolium repens

<400> SEQUENCE: 77

```
Met Asp Leu Leu Leu Glu Lys Thr Leu Leu Ser Leu Phe Ile Ala
 1               5                  10                  15

Ala Ile Ile Ala Ile Thr Ile Ser Lys Leu Arg Gly Lys Arg Phe Lys
                20                  25                  30

Leu Pro Pro Gly Pro Phe Pro Val Pro Ile Phe Gly Asn Trp Leu Gln
            35                  40                  45

Val Gly Asp Asp Leu Asn His Arg Asn Leu Thr Asp Leu Ala Lys Arg
        50                  55                  60

Phe Gly Glu Ile Leu Leu Leu Arg Met Gly Gln Arg Asn Leu Val Val
 65                  70                  75                  80

Val Ser Ser Pro Glu Leu Ala Lys Glu Val Leu His Thr Gln Gly Val
                    85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Glu His Trp Arg Lys
            115                 120                 125

Met Arg Arg Ile Met Thr Val Pro Phe Phe Thr Asn Lys Val Val Gln
        130                 135                 140

Gln Tyr Arg Phe Gly Trp Glu Ser Glu Ala Glu Ser Val Val Asn Asp
145                 150                 155                 160

Val Lys Lys Asn Asn Glu Ala Ser Val Gly Gly Ile Val Ile Arg Arg
                    165                 170                 175

Arg Leu Gln Leu Met Met Tyr Asn Ile Met Tyr Arg Ile Met Phe Asp
                180                 185                 190

Arg Arg Phe Glu Ser Glu Glu Asp Pro Leu Phe Val Lys Leu Lys Ala
            195                 200                 205

Leu Asn Gly Glu Arg Ser Arg Leu Ala Gln Ser Phe Glu Tyr Asn Tyr
        210                 215                 220

Gly Asp Phe Ile Pro Ile Leu Arg Pro Phe Leu Lys Gly Tyr Leu Lys
225                 230                 235                 240

Val Cys Lys Glu Val Lys Asp Arg Arg Leu Gln Leu Phe Lys Asp Tyr
```

```
                245                 250                 255
Phe Val Asp Glu Arg Lys Lys Leu Glu Ser Thr Lys Ser Thr Thr Ser
            260                 265                 270

Asn Asp Gly Leu Lys Cys Ala Ile Asp His Ile Leu Asp Ala Gln Lys
            275                 280                 285

Lys Gly Glu Ile Asn Asp Asp Asn Val Leu Tyr Ile Val Glu Asn Ile
            290                 295                 300

Asn Val Ala Ala Ile Glu Thr Thr Leu Trp Ser Ile Glu Trp Gly Ile
305                 310                 315                 320

Ala Glu Leu Val Asn His Gln Gly Ile Gln Asn Lys Val Arg Glu Glu
                325                 330                 335

Met Asp Arg Val Leu Gly Pro Gly His Gln Val Thr Glu Pro Asp Leu
            340                 345                 350

Gln Lys Leu Pro Tyr Leu Gln Ala Val Ile Lys Glu Thr Leu Arg Leu
            355                 360                 365

Arg Met Ala Ile Pro Leu Leu Val Pro His Met Asn Leu His Asp Ala
            370                 375                 380

Lys Leu Ala Gly Tyr Asp Ile Pro Ala Glu Ser Lys Ile Leu Val Asn
385                 390                 395                 400

Ala Trp Trp Leu Ala Asn Asn Pro Ala Leu Trp Lys Asn Pro Glu Glu
                405                 410                 415

Phe Arg Pro Glu Arg Phe Leu Glu Glu Ala His Val Glu Ala Asn
            420                 425                 430

Gly Asn Asp Phe Arg Tyr Leu Pro Phe Gly Val Gly Arg Arg Ser Cys
            435                 440                 445

Pro Gly Ile Ile Leu Ala Leu Pro Ile Leu Gly Ile Thr Ile Gly Arg
            450                 455                 460

Leu Val Gln Asn Phe Glu Leu Leu Pro Pro Pro Gly Gln Ser Lys Ile
465                 470                 475                 480

Asp Thr Ser Glu Lys Gly Gly Gln Phe Ser Leu His Ile Leu Lys His
                485                 490                 495

Ser Thr Ile Val Ala Lys Pro Arg Ser Phe
            500                 505

<210> SEQ ID NO 78
<211> LENGTH: 1234
<212> TYPE: DNA
<213> ORGANISM: Trifolium repens

<400> SEQUENCE: 78
tactcaagct atgcatccaa cgcgttggga gctctcccat atggtcgatc tgcaggcggc      60
cgcgaattca ctagtgatta agcagtggta caacgcaga gtacgcgggg gagtcgtttg     120
gcacaaagtt ttgagtataa ttatggtgat tttattccta tttttgagacc tttttttgaaa    180
ggttatttga aggtttgtaa agaggttaaa gatcgtaggt tgcagctttt caaagactat     240
ttcgttgatg agagaaagaa acttgaaagc accaagagca ccactagcaa tgatggactt     300
aaatgtgcaa ttgatcacat tttggatgct caaaagaagg gagagatcaa tgatgacaac     360
gttctttaca ttgttgagaa catcaaggtt gctgcaattg aaacaacact atggtcaatt     420
gaatgggaa ttgctgagct agtgaaccac caagagatcc aaaacaaagt aagggaagag     480
atggacagag ttctaggacc aggacaccaa gtaaccgagc cggatcttca gaagctacct     540
tacctacaag ccgtgatcaa agagacactt cgtcttcgaa tggcaatccc actcctcgtc     600
ccacacatga accttcatga tgcaaagctt gccggttatg acatcccggc cgagagcaag     660
```

```
atattggtca atgcttggtg gcttgcaaat aacccggctt tgtggaaaaa gccggaggaa    720
tttaggccag aggggttctt ggaggaagag gcgcatgttg aggctaatgg aaatgacttt    780
aggtaccttc ctttcggtgt tggtagaagg agttgtcctg gaattattct tgctttacct    840
atccttggta ttactatcgg gcgtcttgtt cagaatttcg agcttttgcc tccacccgga    900
caatctaaga ttgatacttc tgagaaagga ggacagttta gtttgcacat actcaaacat    960
tccaccattg ttgctaagcc aagatcattt taattagtat tcacactaat accctttatt   1020
tgttataaaa aaaaaaaaaa aaaaaaaaaa aaaaaaagt actctgcgtt gttaccactg    1080
cttaatcgaa ttcccgcggc cgccatggcg gccgggagca tgcgacgtcg ggcccaattc    1140
gccctatagt gagtcgtatt acaattcact ggccgtcgtt ttacaacgtc gtgactggga    1200
aaaccctggc gttacccaac ttaatcgcct tgca                                1234
```

<210> SEQ ID NO 79
<211> LENGTH: 303
<212> TYPE: PRT
<213> ORGANISM: Trifolium repens

<400> SEQUENCE: 79

```
Ala Val Val Thr Thr Gln Ser Thr Arg Gly Ser Arg Leu Ala Gln Ser
1               5                   10                  15

Phe Glu Tyr Asn Tyr Gly Asp Phe Ile Pro Ile Leu Arg Pro Phe Leu
            20                  25                  30

Lys Gly Tyr Leu Lys Val Cys Lys Glu Val Lys Asp Arg Arg Leu Gln
        35                  40                  45

Leu Phe Lys Asp Tyr Phe Val Asp Glu Arg Lys Lys Leu Glu Ser Thr
    50                  55                  60

Lys Ser Thr Thr Ser Asn Asp Gly Leu Lys Cys Ala Ile Asp His Ile
65                  70                  75                  80

Leu Asp Ala Gln Lys Lys Gly Glu Ile Asn Asp Asn Val Leu Tyr
                85                  90                  95

Ile Val Glu Asn Ile Lys Val Ala Ala Ile Glu Thr Thr Leu Trp Ser
            100                 105                 110

Ile Glu Trp Gly Ile Ala Glu Leu Val Asn His Gln Glu Ile Gln Asn
        115                 120                 125

Lys Val Arg Glu Glu Met Asp Arg Val Leu Gly Pro Gly His Gln Val
    130                 135                 140

Thr Glu Pro Asp Leu Gln Lys Leu Pro Tyr Leu Gln Ala Val Ile Lys
145                 150                 155                 160

Glu Thr Leu Arg Leu Arg Met Ala Ile Pro Leu Leu Val Pro His Met
                165                 170                 175

Asn Leu His Asp Ala Lys Leu Ala Gly Tyr Asp Ile Pro Ala Glu Ser
            180                 185                 190

Lys Ile Leu Val Asn Ala Trp Trp Leu Ala Asn Asn Pro Ala Leu Trp
        195                 200                 205

Lys Lys Pro Glu Glu Phe Arg Pro Glu Gly Phe Leu Glu Glu Glu Ala
    210                 215                 220

His Val Glu Ala Asn Gly Asn Asp Phe Arg Tyr Leu Pro Phe Gly Val
225                 230                 235                 240

Gly Arg Arg Ser Cys Pro Gly Ile Ile Leu Ala Leu Pro Ile Leu Gly
                245                 250                 255

Ile Thr Ile Gly Arg Leu Val Gln Asn Phe Glu Leu Leu Pro Pro Pro
            260                 265                 270

Gly Gln Ser Lys Ile Asp Thr Ser Glu Lys Gly Gly Gln Phe Ser Leu
```

```
                  275                 280                 285
His Ile Leu Lys His Ser Thr Ile Val Ala Lys Pro Arg Ser Phe
    290                 295                 300

<210> SEQ ID NO 80
<211> LENGTH: 744
<212> TYPE: DNA
<213> ORGANISM: Trifolium repens

<400> SEQUENCE: 80
gcccgacgtc gcatgctccc ggccgccatg gcggccgcgg gaattcgatt aattcagtgg      60
taacaacgca gagtacgcgg gacatgaacc ttcatgatga aaagcttgcc ggttatgaca     120
tcccggccga gagcaagata ttggtcaacg cgtggtggct tgcaaataac ccggctctat     180
ggaaaaagcc ggaggaattt aggcctgaga ggttcttgga ggaagaggcg catgttgagg     240
ctaatggaaa tgactttagg taccttcctt tcggtgttgg tagaaggagt tgtcctggaa     300
ttattcttgc tttacctatc cttggtatta ctatcgggcg tcttgttcag aatttcgagc     360
ttttgcctcc acccggacaa tctaagattg atacttccga gaaggagga caatttagtt      420 tgcacatact caaacattcc accattgttg ctaagccaag atcattttaa ttagtattca     480
cactaatacc ctttatttgt tttactttac tttgtgtaat gcattttaat gattcataat     540
gtgggaatgt tattaaaatg tcttaggtga ataatgttgt tgttttgtgc ttgtcccatg     600
tataaatctt tgaacttttt aagtaatggt tttgagatga ttttgtaaca aaaaaaaaa      660 aaaaaaaaaa aaaaaaaaaa aaaaaaaaaa aaaagaaaa aaaaaaaaaa aaaaaaaaaa      720
aaaaaagtac cctgggttgt tacc                                            744

<210> SEQ ID NO 81
<211> LENGTH: 155
<212> TYPE: PRT
<213> ORGANISM: Trifolium repens

<400> SEQUENCE: 81

Pro Thr Ser His Ala Pro Gly Arg His Gly Gly Arg Gly Asn Ser Ile
1               5                   10                  15

Asn Ser Val Val Thr Thr Gln Ser Thr Arg Asp Met Asn Leu His Asp
            20                  25                  30

Ala Lys Leu Ala Gly Tyr Asp Ile Pro Ala Glu Ser Lys Ile Leu Val
        35                  40                  45

Asn Ala Trp Trp Leu Ala Asn Asn Pro Ala Leu Trp Lys Lys Pro Glu
    50                  55                  60

Glu Phe Arg Pro Glu Arg Phe Leu Glu Glu Glu Ala His Val Glu Ala
65                  70                  75                  80

Asn Gly Asn Asp Phe Arg Tyr Leu Pro Phe Gly Val Gly Arg Arg Ser
                85                  90                  95

Cys Pro Gly Ile Ile Leu Ala Leu Pro Ile Leu Gly Ile Thr Ile Gly
            100                 105                 110

Arg Leu Val Gln Asn Phe Glu Leu Leu Pro Pro Gly Gln Ser Lys
        115                 120                 125

Ile Asp Thr Ser Glu Lys Gly Gly Gln Phe Ser Leu His Ile Leu Lys
    130                 135                 140

His Ser Thr Ile Val Ala Lys Pro Arg Ser Phe
145                 150                 155

<210> SEQ ID NO 82
<211> LENGTH: 19
```

```
<212> TYPE: DNA
<213> ORGANISM: Trifolium repens

<400> SEQUENCE: 82
gcatttgcat tgagttgtc                                              19

<210> SEQ ID NO 83
<211> LENGTH: 18
<212> TYPE: DNA
<213> ORGANISM: Trifolium repens

<400> SEQUENCE: 83
agccagtgtg cgagttag                                               18

<210> SEQ ID NO 84
<211> LENGTH: 20
<212> TYPE: DNA
<213> ORGANISM: Trifolium repens

<400> SEQUENCE: 84
aattgtcagt cttcgtagtg                                             20

<210> SEQ ID NO 85
<211> LENGTH: 20
<212> TYPE: DNA
<213> ORGANISM: Trifolium repens

<400> SEQUENCE: 85
acaacgaagt atgacagaag                                             20

<210> SEQ ID NO 86
<211> LENGTH: 18
<212> TYPE: DNA
<213> ORGANISM: Trifolium repens

<400> SEQUENCE: 86
gcatcgctgt tggtagtt                                               18

<210> SEQ ID NO 87
<211> LENGTH: 19
<212> TYPE: DNA
<213> ORGANISM: Trifolium repens

<400> SEQUENCE: 87
caacgcctct ttcaatgtc                                              19

<210> SEQ ID NO 88
<211> LENGTH: 19
<212> TYPE: DNA
<213> ORGANISM: Trifolium repens

<400> SEQUENCE: 88 taccccttttg cttcgtttg                                             19

<210> SEQ ID NO 89
<211> LENGTH: 18
<212> TYPE: DNA
<213> ORGANISM: Trifolium repens

<400> SEQUENCE: 89
cacacgcatt tgaagaag                                               18

<210> SEQ ID NO 90
<211> LENGTH: 18
```

```
<212> TYPE: DNA
<213> ORGANISM: Trifolium repens

<400> SEQUENCE: 90
aaccaacaag gccacaac                                              18

<210> SEQ ID NO 91
<211> LENGTH: 22
<212> TYPE: DNA
<213> ORGANISM: Trifolium repens

<400> SEQUENCE: 91
ataggtgaga caaggagaca ga                                         22

<210> SEQ ID NO 92
<211> LENGTH: 18
<212> TYPE: DNA
<213> ORGANISM: Trifolium repens

<400> SEQUENCE: 92
gcctaagact ccagctga                                              18

<210> SEQ ID NO 93
<211> LENGTH: 19
<212> TYPE: DNA
<213> ORGANISM: Trifolium repens

<400> SEQUENCE: 93
tcccattcaa gttgaccac                                             19

<210> SEQ ID NO 94
<211> LENGTH: 18
<212> TYPE: DNA
<213> ORGANISM: Trifolium repens

<400> SEQUENCE: 94
aacaagggcc acaagttc                                              18

<210> SEQ ID NO 95
<211> LENGTH: 19
<212> TYPE: DNA
<213> ORGANISM: Trifolium repens

<400> SEQUENCE: 95
tcttgggcag tgttttgtg                                             19

<210> SEQ ID NO 96
<211> LENGTH: 20
<212> TYPE: DNA
<213> ORGANISM: Trifolium repens

<400> SEQUENCE: 96
cagcagccaa tcctttcttc                                            20

<210> SEQ ID NO 97
<211> LENGTH: 18
<212> TYPE: DNA
<213> ORGANISM: Trifolium repens

<400> SEQUENCE: 97
agtccaacag ggtgatgt                                              18

<210> SEQ ID NO 98
<211> LENGTH: 19
```

```
<212> TYPE: DNA
<213> ORGANISM: Trifolium repens

<400> SEQUENCE: 98
gtagttcctc cgatagtgt                                              19

<210> SEQ ID NO 99
<211> LENGTH: 18
<212> TYPE: DNA
<213> ORGANISM: Trifolium repens

<400> SEQUENCE: 99
tctgatgctg ctgttgtc                                               18

<210> SEQ ID NO 100
<211> LENGTH: 21
<212> TYPE: DNA
<213> ORGANISM: Trifolium repens

<400> SEQUENCE: 100
ttggtaagga acttgaggac a                                           21

<210> SEQ ID NO 101
<211> LENGTH: 20
<212> TYPE: DNA
<213> ORGANISM: Trifolium repens

<400> SEQUENCE: 101
caaaagcctc caatgctaag                                             20

<210> SEQ ID NO 102
<211> LENGTH: 18
<212> TYPE: DNA
<213> ORGANISM: Trifolium repens

<400> SEQUENCE: 102
gaagaggctg taaaggag                                               18

<210> SEQ ID NO 103
<211> LENGTH: 19
<212> TYPE: DNA
<213> ORGANISM: Trifolium repens

<400> SEQUENCE: 103
actcatcgta actcaatcc                                              19

<210> SEQ ID NO 104
<211> LENGTH: 19
<212> TYPE: DNA
<213> ORGANISM: Trifolium repens

<400> SEQUENCE: 104
gcgttggtaa aaagtggtg                                              19

<210> SEQ ID NO 105
<211> LENGTH: 18
<212> TYPE: DNA
<213> ORGANISM: Trifolium repens

<400> SEQUENCE: 105
tttcgatgct gctgttgt                                               18

<210> SEQ ID NO 106
<211> LENGTH: 18
```

```
<212> TYPE: DNA
<213> ORGANISM: Trifolium repens

<400> SEQUENCE: 106
gcctattcgt tcgcttct                                               18

<210> SEQ ID NO 107
<211> LENGTH: 18
<212> TYPE: DNA
<213> ORGANISM: Trifolium repens

<400> SEQUENCE: 107
tacggtgaac attggcgt                                               18

<210> SEQ ID NO 108
<211> LENGTH: 21
<212> TYPE: DNA
<213> ORGANISM: Trifolium repens

<400> SEQUENCE: 108
gatgctcaaa agaaaggaga g                                           21

<210> SEQ ID NO 109
<211> LENGTH: 18
<212> TYPE: DNA
<213> ORGANISM: Trifolium repens

<400> SEQUENCE: 109
atcgggcgtc ttgttcag                                               18

<210> SEQ ID NO 110
<211> LENGTH: 19
<212> TYPE: DNA
<213> ORGANISM: Trifolium repens

<400> SEQUENCE: 110
aggaccagga caccaagta                                              19

<210> SEQ ID NO 111
<211> LENGTH: 18
<212> TYPE: DNA
<213> ORGANISM: Trifolium repens

<400> SEQUENCE: 111
taacccggct ctatggaa                                               18

<210> SEQ ID NO 112
<211> LENGTH: 54
<212> TYPE: DNA
<213> ORGANISM: Trifolium repens

<400> SEQUENCE: 112
ggggacaagt ttgtacaaaa aagcaggctt catgagctct atagaaaacc aacc       54

<210> SEQ ID NO 113
<211> LENGTH: 55
<212> TYPE: DNA
<213> ORGANISM: Trifolium repens

<400> SEQUENCE: 113
ggggaccact ttgtacaaga aagctgggtc tcatatgtcg gcaaccagtt gatcc      55

<210> SEQ ID NO 114
<211> LENGTH: 58
```

```
<212> TYPE: DNA
<213> ORGANISM: Trifolium repens

<400> SEQUENCE: 114
ggggacaagt ttgtacaaaa aagcaggctt catggagaat tcaactcaag aatcacac      58

<210> SEQ ID NO 115
<211> LENGTH: 55
<212> TYPE: DNA
<213> ORGANISM: Trifolium repens

<400> SEQUENCE: 115
ggggaccact ttgtacaaga aagctgggtc tcaaacccgc aaaagctgca tcttg          55

<210> SEQ ID NO 116
<211> LENGTH: 54
<212> TYPE: DNA
<213> ORGANISM: Trifolium repens

<400> SEQUENCE: 116
ggggacaagt ttgtacaaaa aagcaggctt catggtaaga gctccttgtt gtga           54

<210> SEQ ID NO 117
<211> LENGTH: 57
<212> TYPE: DNA
<213> ORGANISM: Trifolium repens

<400> SEQUENCE: 117
ggggaccact ttgtacaaga aagctgggtc ttagaactct ggcaattcta tttgatc        57

<210> SEQ ID NO 118
<211> LENGTH: 54
<212> TYPE: DNA
<213> ORGANISM: Trifolium repens

<400> SEQUENCE: 118
ggggacaagt ttgtacaaaa aagcaggctt catggtgaga gctccatgtt gtga           54

<210> SEQ ID NO 119
<211> LENGTH: 58
<212> TYPE: DNA
<213> ORGANISM: Trifolium repens

<400> SEQUENCE: 119
ggggaccact ttgtacaaga aagctgggtc tcacaattca agtaactcag taatttcc      58

<210> SEQ ID NO 120
<211> LENGTH: 58
<212> TYPE: DNA
<213> ORGANISM: Trifolium repens

<400> SEQUENCE: 120
ggggacaagt ttgtacaaaa aagcaggctt catgaaccat gttttgtcag aaagaagg      58

<210> SEQ ID NO 121
<211> LENGTH: 58
<212> TYPE: DNA
<213> ORGANISM: Trifolium repens

<400> SEQUENCE: 121
ggggaccact ttgtacaaga aagctgggtc tcaaaacttt gaagccactt tttgtagg      58

<210> SEQ ID NO 122
<211> LENGTH: 56
```

```
<212> TYPE: DNA
<213> ORGANISM: Trifolium repens

<400> SEQUENCE: 122
ggggacaagt ttgtacaaaa aagcaggctt catgggagcc gtggcacaaa gagttg      56

<210> SEQ ID NO 123
<211> LENGTH: 57
<212> TYPE: DNA
<213> ORGANISM: Trifolium repens

<400> SEQUENCE: 123
ggggaccact ttgtacaaga aagctgggtc tcattttta ggatcatcct tcttctc      57

<210> SEQ ID NO 124
<211> LENGTH: 58
<212> TYPE: DNA
<213> ORGANISM: Trifolium repens

<400> SEQUENCE: 124
ggggacaagt ttgtacaaaa aagcaggctt catggcggcc gcgggaattc gattaagc    58

<210> SEQ ID NO 125
<211> LENGTH: 57
<212> TYPE: DNA
<213> ORGANISM: Trifolium repens

<400> SEQUENCE: 125
ggggaccact ttgtacaaga aagctgggtc ttattctgct gctaactttg ctctgag     57

<210> SEQ ID NO 126
<211> LENGTH: 58
<212> TYPE: DNA
<213> ORGANISM: Trifolium repens

<400> SEQUENCE: 126
ggggacaagt ttgtacaaaa aagcaggctt catggcggcc gcgggaattc gattaagc    58

<210> SEQ ID NO 127
<211> LENGTH: 54
<212> TYPE: DNA
<213> ORGANISM: Trifolium repens

<400> SEQUENCE: 127
ggggaccact ttgtacaaga aagctgggtc ttaatttgtt ggaacaccag ctgc        54

<210> SEQ ID NO 128
<211> LENGTH: 58
<212> TYPE: DNA
<213> ORGANISM: Trifolium repens

<400> SEQUENCE: 128
ggggacaagt ttgtacaaaa aagcaggctt catggcggcc gcgggaattc gattaagc    58

<210> SEQ ID NO 129
<211> LENGTH: 58
<212> TYPE: DNA
<213> ORGANISM: Trifolium repens

<400> SEQUENCE: 129
ggggaccact ttgtacaaga aagctgggtc tcaaggcttt tgggtggtac tttctaac    58

<210> SEQ ID NO 130
<211> LENGTH: 56
```

```
<212> TYPE: DNA
<213> ORGANISM: Trifolium repens

<400> SEQUENCE: 130
ggggacaagt ttgtacaaaa aagcaggctt catgtcacca tttcctccac agcaag      56

<210> SEQ ID NO 131
<211> LENGTH: 55
<212> TYPE: DNA
<213> ORGANISM: Trifolium repens

<400> SEQUENCE: 131
ggggaccact ttgtacaaga aagctgggtc ttaagtggcc accaccaaac cttcg       55

<210> SEQ ID NO 132
<211> LENGTH: 59
<212> TYPE: DNA
<213> ORGANISM: Trifolium repens

<400> SEQUENCE: 132
ggggacaagt ttgtacaaaa aagcaggctt catggatcta ctccttcttg aaaagactc   59

<210> SEQ ID NO 133
<211> LENGTH: 58
<212> TYPE: DNA
<213> ORGANISM: Trifolium repens

<400> SEQUENCE: 133
ggggaccact ttgtacaaga aagctgggtc ttaaaatgat cttggcttag caacaatg    58

<210> SEQ ID NO 134
<211> LENGTH: 56
<212> TYPE: DNA
<213> ORGANISM: Trifolium repens

<400> SEQUENCE: 134
ggggacaagt ttgtacaaaa aagcaggctt cgcagtggta acaacgcaga gtacgc      56

<210> SEQ ID NO 135
<211> LENGTH: 58
<212> TYPE: DNA
<213> ORGANISM: Trifolium repens

<400> SEQUENCE: 135
ggggaccact ttgtacaaga aagctgggtc ttaaaatgat cttggcttag caacaatg    58

<210> SEQ ID NO 136
<211> LENGTH: 52
<212> TYPE: DNA
<213> ORGANISM: Trifolium repens

<400> SEQUENCE: 136
ggggacaagt ttgtacaaaa aagcaggctt cccgacgtcg catgctcccg gc          52

<210> SEQ ID NO 137
<211> LENGTH: 58
<212> TYPE: DNA
<213> ORGANISM: Trifolium repens

<400> SEQUENCE: 137
ggggaccact ttgtacaaga aagctgggtc ttaaaatgat cttggcttag caacaatg    58

<210> SEQ ID NO 138
<211> LENGTH: 23
```

```
<212> TYPE: DNA
<213> ORGANISM: Trifolium repens

<400> SEQUENCE: 138
tcaagtatgg gcatcattcg cac                                        23

<210> SEQ ID NO 139
<211> LENGTH: 20
<212> TYPE: DNA
<213> ORGANISM: Trifolium repens

<400> SEQUENCE: 139
tgctcaaacc gggcagaacg                                            20

<210> SEQ ID NO 140
<211> LENGTH: 21
<212> TYPE: DNA
<213> ORGANISM: Trifolium repens

<400> SEQUENCE: 140
gacagagagc atagccgagc a                                          21

<210> SEQ ID NO 141
<211> LENGTH: 20
<212> TYPE: DNA
<213> ORGANISM: Trifolium repens

<400> SEQUENCE: 141
ggtataagac cgcgagcgaa                                            20

<210> SEQ ID NO 142
<211> LENGTH: 20
<212> TYPE: DNA
<213> ORGANISM: Trifolium repens

<400> SEQUENCE: 142
aactcatgtt ccatcccgca                                            20

<210> SEQ ID NO 143
<211> LENGTH: 21
<212> TYPE: DNA
<213> ORGANISM: Trifolium repens

<400> SEQUENCE: 143
cggaggaggt tttctggaga g                                          21

<210> SEQ ID NO 144
<211> LENGTH: 20
<212> TYPE: DNA
<213> ORGANISM: Trifolium repens

<400> SEQUENCE: 144
gtaatggcaa ctggcgtgct                                            20

<210> SEQ ID NO 145
<211> LENGTH: 24
<212> TYPE: DNA
<213> ORGANISM: Trifolium repens

<400> SEQUENCE: 145
cacatcttaa caagcctcgt agct                                       24

<210> SEQ ID NO 146
<211> LENGTH: 22
```

<212> TYPE: DNA
<213> ORGANISM: Trifolium repens

<400> SEQUENCE: 146
ccattctaat tggcgtgctc tt                                    22

<210> SEQ ID NO 147
<211> LENGTH: 22
<212> TYPE: DNA
<213> ORGANISM: Trifolium repens

<400> SEQUENCE: 147
ccacacctta acaacccagc tt                                    22

<210> SEQ ID NO 148
<211> LENGTH: 20
<212> TYPE: DNA
<213> ORGANISM: Trifolium repens

<400> SEQUENCE: 148
tgggaggctt catgtgatca                                       20

<210> SEQ ID NO 149
<211> LENGTH: 25
<212> TYPE: DNA
<213> ORGANISM: Trifolium repens

<400> SEQUENCE: 149
gcattagctg gtcctttgaa cttag                                 25

<210> SEQ ID NO 150
<211> LENGTH: 23
<212> TYPE: DNA
<213> ORGANISM: Trifolium repens

<400> SEQUENCE: 150
gctagtggtc aacttgaatg gga                                   23

<210> SEQ ID NO 151
<211> LENGTH: 30
<212> TYPE: DNA
<213> ORGANISM: Trifolium repens

<400> SEQUENCE: 151
tcaggaaaaa tacaatgaaa gaaataatct                            30

<210> SEQ ID NO 152
<211> LENGTH: 20
<212> TYPE: DNA
<213> ORGANISM: Trifolium repens

<400> SEQUENCE: 152
gcacccaccg gaaaagtcta                                       20

<210> SEQ ID NO 153
<211> LENGTH: 20
<212> TYPE: DNA
<213> ORGANISM: Trifolium repens

<400> SEQUENCE: 153
ccgagaggtg agttcgacgt                                       20

<210> SEQ ID NO 154
<211> LENGTH: 28

<212> TYPE: DNA
<213> ORGANISM: Trifolium repens

<400> SEQUENCE: 154
tcatagtgga taggcttaaa gaattgat                                28

<210> SEQ ID NO 155
<211> LENGTH: 24
<212> TYPE: DNA
<213> ORGANISM: Trifolium repens

<400> SEQUENCE: 155
tgggatgtga aagaataatg gctt                                    24

<210> SEQ ID NO 156
<211> LENGTH: 20
<212> TYPE: DNA
<213> ORGANISM: Trifolium repens

<400> SEQUENCE: 156
gttgtcccgc aaaaggatgt                                         20

<210> SEQ ID NO 157
<211> LENGTH: 23
<212> TYPE: DNA
<213> ORGANISM: Trifolium repens

<400> SEQUENCE: 157
cacaaaggca acaggaactt cac                                     23

<210> SEQ ID NO 158
<211> LENGTH: 20
<212> TYPE: DNA
<213> ORGANISM: Trifolium repens

<400> SEQUENCE: 158
ctttcctcgg tgcctccttc                                         20

<210> SEQ ID NO 159
<211> LENGTH: 20
<212> TYPE: DNA
<213> ORGANISM: Trifolium repens

<400> SEQUENCE: 159
aaggatttgc ggtggtgatg                                         20

<210> SEQ ID NO 160
<211> LENGTH: 20
<212> TYPE: DNA
<213> ORGANISM: Trifolium repens

<400> SEQUENCE: 160
cttgccggtt atgacatccc                                         20

<210> SEQ ID NO 161
<211> LENGTH: 21
<212> TYPE: DNA
<213> ORGANISM: Trifolium repens

<400> SEQUENCE: 161
ccacgcgttg accaatatct t                                       21

<210> SEQ ID NO 162
<211> LENGTH: 26

```
<212> TYPE: DNA
<213> ORGANISM: Trifolium repens

<400> SEQUENCE: 162
cgttgatgag agaaagaaac ttgaaa                                          26

<210> SEQ ID NO 163
<211> LENGTH: 24
<212> TYPE: DNA
<213> ORGANISM: Trifolium repens

<400> SEQUENCE: 163
gagcatccaa aatgtgatca attg                                            24
```